US011045440B2

(12) United States Patent
Gallotto et al.

(10) Patent No.: US 11,045,440 B2
(45) Date of Patent: *Jun. 29, 2021

(54) ENTERAL FEEDING DEVICES AND RELATED METHODS OF USE

(71) Applicant: Alcresta Therapeutics, Inc., Newton, MA (US)

(72) Inventors: Robert Gallotto, Medway, MA (US); Greta L. Loring, Wakefield, MA (US); Kenneth Gary, Boxborough, MA (US); Edward S. Park, Southborough, MA (US); David J. Brown, Brookline, MA (US); Willem Robert Klaas Schoevaart, Delft (NL); Michiel Christian Alexander van Vliet, Delft (NL)

(73) Assignee: Alcresta Therapeutics, Inc., Newton, MA (US)

( * ) Notice: Subject to any disclaimer, the term of this patent is extended or adjusted under 35 U.S.C. 154(b) by 203 days.

This patent is subject to a terminal disclaimer.

(21) Appl. No.: 16/287,543

(22) Filed: Feb. 27, 2019

(65) Prior Publication Data

US 2019/0224155 A1 Jul. 25, 2019

Related U.S. Application Data

(63) Continuation of application No. 15/291,530, filed on Oct. 12, 2016, now Pat. No. 10,258,590.
(Continued)

(51) Int. Cl.
*A61K 31/202* (2006.01)
*C12N 11/02* (2006.01)
(Continued)

(52) U.S. Cl.
CPC ............ *A61K 31/202* (2013.01); *A23L 33/00* (2016.08); *A23L 33/12* (2016.08); *A23L 33/40* (2016.08);
(Continued)

(58) Field of Classification Search
CPC ......... B65D 1/02; A23D 7/013; A61K 38/465
See application file for complete search history.

(56) References Cited

U.S. PATENT DOCUMENTS

| 4,629,742 A | 12/1986 | Brady et al. |
| 4,944,944 A | 7/1990 | Tang et al. |

(Continued)

FOREIGN PATENT DOCUMENTS

| CN | 101573048 A | 11/2004 |
| CN | 101068565 A | 11/2007 |

(Continued)

OTHER PUBLICATIONS

Comellas et al. Exploration of the One-Bead One-Compound Methodology for the Design of Prolyl Oligopeptidase Substrates PLOS One, vol. 4, Issue 7, pp. 1-12 (2009).*
(Continued)

*Primary Examiner* — Nathan A Bowers
(74) *Attorney, Agent, or Firm* — Bookoff McAndrews, PLLC

(57) ABSTRACT

Embodiments of the disclosure are drawn to an enteral feeding device for hydrolyzing triglycerides in a nutritional formula. The device may include a body housing a chamber, an inlet configured to fluidly couple with a source of nutritional formula, and an outlet configured to fluidly couple with an enteral feeding tube. The device may include a headspace and a plurality of particles contained within the chamber, wherein the lipase is covalently bonded to the plurality of particles. The device may include an inlet filter
(Continued)

located between the inlet and the chamber, wherein the inlet filter contains a first plurality of openings, and an outlet filter located between the chamber and the outlet, wherein the outlet filter has a second plurality of openings smaller than the plurality of particles.

19 Claims, 52 Drawing Sheets

Related U.S. Application Data

(60) Provisional application No. 62/241,608, filed on Oct. 14, 2015.

(51) Int. Cl.
| | | |
|---|---|---|
| A61L 29/04 | (2006.01) | |
| A61M 5/14 | (2006.01) | |
| A61M 5/142 | (2006.01) | |
| C12N 11/06 | (2006.01) | |
| C12N 11/08 | (2020.01) | |
| A61J 15/00 | (2006.01) | |
| A23L 33/00 | (2016.01) | |
| A23L 33/12 | (2016.01) | |
| C12N 9/20 | (2006.01) | |

(52) U.S. Cl.
CPC .......... *A61J 15/0076* (2015.05); *A61L 29/048* (2013.01); *A61M 5/14* (2013.01); *A61M 5/142* (2013.01); *A61M 5/1413* (2013.01); *C12N 9/20* (2013.01); *C12N 11/06* (2013.01); *C12N 11/08* (2013.01)

(56) References Cited

U.S. PATENT DOCUMENTS

| | | | |
|---|---|---|---|
| 5,010,004 | A | 4/1991 | Kosugi et al. |
| 5,902,617 | A | 5/1999 | Pabst |
| 6,346,216 | B1 | 2/2002 | Kent |
| 6,541,606 | B2 | 4/2003 | Margolin et al. |
| 6,635,222 | B2 | 10/2003 | Kent |
| 6,749,851 | B2 | 6/2004 | Mann et al. |
| 8,361,763 | B2 | 1/2013 | Dayton |
| 8,404,470 | B2 | 3/2013 | Thum et al. |
| 8,754,126 | B2 | 6/2014 | Lai et al. |
| 8,877,812 | B2 | 11/2014 | Lai et al. |
| 9,227,777 | B2 | 1/2016 | Steven et al. |
| 2005/0129830 | A1 | 6/2005 | Kolke et al. |
| 2006/0121017 | A1 | 6/2006 | Margolin et al. |
| 2007/0007201 | A1 | 1/2007 | Lupton |
| 2007/0269355 | A1 | 11/2007 | Malmqvist |
| 2009/0123634 | A1 | 5/2009 | Klemann et al. |
| 2010/0075900 | A1 | 3/2010 | Zwijsen et al. |
| 2010/0239559 | A1 | 9/2010 | Freedman et al. |
| 2010/0304357 | A1 | 12/2010 | Meyers |
| 2011/0150944 | A1 | 6/2011 | Rozen et al. |
| 2012/0172434 | A1 | 7/2012 | Lai |
| 2012/0279939 | A1 | 11/2012 | Lee |
| 2014/0249224 | A1 | 9/2014 | Lai et al. |
| 2015/0140161 | A1 | 5/2015 | Lai et al. |
| 2015/0246102 | A1 | 9/2015 | Margolin et al. |
| 2016/0017272 | A1 | 1/2016 | Gjerde |
| 2019/0093103 | A1* | 3/2019 | Vijayan .................. C40B 50/14 |

FOREIGN PATENT DOCUMENTS

| | | |
|---|---|---|
| DE | 2935546 A1 | 3/1981 |
| JP | 54-132291 A | 10/1979 |
| JP | 60-027380 A | 2/1985 |
| JP | 01-231848 A | 9/1989 |
| JP | 01-273579 A | 11/1989 |
| JP | 11-502450 A | 3/1999 |
| JP | 2004-248671 A | 9/2004 |
| JP | 2005-272307 A | 10/2005 |
| JP | 2007-524674 A | 8/2007 |
| JP | 2007-526943 A | 9/2007 |
| JP | 2008-516965 A | 5/2008 |
| JP | 2009-544780 A | 12/2009 |
| WO | WO 96/21480 | 7/1996 |
| WO | WO 97/23190 A1 | 7/1997 |
| WO | WO 2004/052115 A1 | 6/2004 |
| WO | WO 2005/072306 A2 | 8/2005 |
| WO | WO 2005/084129 A | 9/2005 |
| WO | WO 2006/044529 A1 | 4/2006 |
| WO | WO 2006/092622 A1 | 9/2006 |
| WO | WO 2008/054192 A1 | 5/2008 |
| WO | WO 2008/054208 A2 | 5/2008 |
| WO | WO 2011/092299 A1 | 8/2011 |
| WO | WO 2012/01918 A1 | 2/2012 |
| WO | WO 2013/123139 | 8/2013 |
| WO | WO 2015/020943 A2 | 2/2015 |
| WO | WO 2016/120318 A1 | 8/2016 |

OTHER PUBLICATIONS

Abbott Laboratories (2009) "ProSure® Therapeutic Nutrition for People with Cancer" Product Monograph (48 pages).
Anderson and Ma (2009) "Are all n-3 polyunsaturated fatty acids created equal?" *Lipids Health Dis.* 8:33, dol: 10. 1186/1476-511X-8-33 [online], published Aug. 10, 2009 (20 pages).
Arterburn et al. (2006) "Distribution, interconversion, and dose response of n-3 fatty acids in humans" *Am. J. Clin. Nutr.*, 83 (Suppl.): 1467S-76S.
Bengmark and Jeppsson (1995) "Gastrointestinal surface protection and mucosa reconditioning" *JPEN J. Parenter Enterel Nutr.*, 19(5):410-5.
Balanza-Martinez et al. (2011) "Therapeutic use of omega-3 fatty acids in bipolar disorder" *Expert Rev. Neurother.*, 11(7); 1029-47.
Bansi et al. (2000) "Fibrosing colonopathy in an adult owing to over use of pancreatic enzyme supplements" *Gut*, 46(2): 283-85.
Basri et al. (1994) "Immobilization of hydrophobic lipase derivatives on to organic polymer beads" *J. Chem. Tech. Biotechnol.*, 59(1):37-44.
Bhushan et al. (2008) "immobilization of Lipase of Entrapment in Ca-alginate Beads" *J. Bioactive Compatible Polymers*, 23(6):552-62.
Birch et al. (2010) "The DIAMOND (DHA Intake And Measurement Of Neural Development) Study: A double-masked, randomized controlled clinical trial of the maturation of infant visual acuity as a function of the dietary level of docosahexaenoic acid" *Am. J. Clin. Nutr.* 91 (4): 848-59.
Birch et al. (2010) "The impact of early nutrition on incidence of allergic manifestations and common respiratory illnesses in children" *J. Pediatr.*, 156(6): 902-6.
Bolsover et al. *Cell Biology: A Short Course*, $3^{rd}$ Ed., John Wiley & Sons, Inc., 2011; p. 39.
Borowitz et al. (1995) "Use of pancreatic enzyme supplements for patients with cystic fibrosis in the context of fibrosing colonopathy" *J. Pediatr.*, 127(5):681-84.
Brenna et al. (2009) "α-Linolenic acid supplementation and conversion to n-3 long-chain polyunsaturated fatty acids in humans" *Prostaglandins Leukot. Essent. Fatty Acids*, 80(2-3):85-91.
Burgess et al. (2000) "Long-chain polyunsaturated fatty acids in children with attention-deficit hyperactivity disorder" *Am. J. Clin. Nutr.*, 71(suppl.): 327S-30S.
Calder (2009) "Fatty acids and immune function: relevance to inflammatory bowel diseases" *Int. Rev. Immunol.*, 28A(6): 506-34.
Chiou et al. (2007) "Immobilization of Lipase to Chiltosan Beads using a Natural Cross-Linker" *Prep. Biochem. Biotechnol.*, 37(3):265-75.
Chung et al. (2008) "Fish oil supplementation of control and (n-3) fatty acid-deficient male rats enhances reference and working memory performance and increases brain regional docosahexaenoic acid levels" *J. Nutr.* 138(6):1165-71.

(56) References Cited

OTHER PUBLICATIONS

Clandinin et al. (1994) "Relationship between fatty acid accretion, membrane composition, and biologic functions" *J. Pediatr.*, 125:S25-32.

Damerla et al. (2008) "Pancreatic Enzyme Supplementation in Pancreatic Cancer" *J. Support. Oncol.*, 6:393-6.

Davidson et al. (2004) "Weight Stabilization Is Associated with Improved Survival Duration and Quality of Life In Unrespectable Pancreatic Cancer" *Clinical Nutrition*, 23:239-47.

Emi et al. (1994) "Lipoprotein lipase immobilization onto copoly(ethylene/acrylic acid) fiber", *Eur. Polymer J.*, 30(5):589-95.

Elnashar "The Art of Immobilization using Biopolymers, Biomaterials and Nanobiotechnology" Chapter 1 in *Biotechnology of Biopolymers*. Prof. Magdy Elnashar (Ed.), InTech, 2011: pp. 3-32.

Empey et al. (1991) "Fish oil-enriched diet is mucosal protective against acetic acid-induced colitis in rats" *Canadian J. Physiol. Pharma.*, 69(4):480-7.

European Patent Application No. 13749880.4, by Alcresta, Inc.: Extended European Search Report and Opinion, dated Aug. 25, 2015 (9 pages).

Fan et al. (2004) "Dietary docosahexaenoic acid suppresses T cell protein kinase C theta lipid raft recruitment and IL-2 production" *J. Immunol*l, 173:6151-60.

Fernàndez-Lorente et al. (2010) "Hydrolysis of Fish Oil by Lipases Immobilized Inside Porous Supports" *J. Am. Oil Chem. Soc.*, doi:10.1007/s11746-10-1728-1 [online], published Dec. 14, 2010 (8 pages).

Fernàndez-Lorente et al. (2011) "Release of Omega-3 Fatty Acids by the Hydrolysis of Fish Oil Catalyzed by Lipases Immobilized on Hydrophobic Supports" *J. Am. Oil Chem. Soc.*, 88:1173-78.

Forsyth et al. (1999) "A randomized controlled study of the effect of long chain polyunsaturated fatty acid supplementation on stool hardness during formula feeding" *Arch. Dis. Child*, 81:253-6.

Gadek et al. (1999) "Effect of enteral feeding with eicosapentaenoic acid, gamma-linolenic acid, and antioxidants in patients with acute respiratory distress syndrome" *Grit. Care Med.*, 27(8):1409-20.

Graham (1977) "Enzyme replacement therapy of exocrine pancreatic insufficiency in man. Relations between in vitro enzyme activities and in vivo potency in commercial pancreatic extracts" *N. Engl. J. Med.*, 296(23):1314-17.

Greenberger et al. (1966) "Absorption of Medium and Long Chain Triglycerides: Factors Influencing Their Hydrolysis and Transport" *J. Clin. Invest.*, 45(2):217-27.

Gunnlaugsdottir et al. (1998), "Alcoholysis and Glyceride Synthesis with Immobilized Lipase on Controlled-Pore Glass of Varying Hydrophobicity in Supercritical Carbon Dioxide," *Enzyme and Microbial. Tech.*, 22:360-367.

Gustafsson, H. (2012) "Enzyme Immobilization in Mesoporous Silica" Thesis for the Degree of Licentiate of Engineering, Department of Chemical and Biological Engineering, Chalmers University of Technology; Göteborg, Sweden.

Herzig et al. (2011) "Fecal pancreatic elastase-1 levels in older individuals without known gastrointestinal diseases or diabetes mellitus" *BMC Geriatrics*, 11-4, doi:10.1186/1471-2318-11-4 [online], published Jan. 25, 2011 (5 pages).

Horrocks et al. (1999) "Health benefits of docosahexaenoic acid (DHA)" *Pharmacological Res.* 40(3):211-25.

Hudert et al. (2006) "Transgenic mice rich in endogenous omega-3 fatty acids are protected from colitis" *PNAS*, 103(30): 11276-11281.

Innis (2003) "Perinatal biochemistry and physiology of long-chain polyunsaturated fatty acids" *J. Pediatr.*, 143:S1-S8.

International Search Report and Written Opinion dated May 9, 2013, in International Patent Application No. PCT/US2013/026063 (Alcresta, Inc.) (10 pages).

ISSFAL (International Society for the Study of Fatty Acids and Lipids) (Jul. 2, 2014) "Omega-3 Fats May Reduce Risk of Gastrointestinal Diseases" Press Release [online]. Retrieved from: http://www.issfal.org/news/articles/2014/07/02/omega-3-fats-may-reduce-risk-ot-gastrointestinal-diseases (2 pages).

Jensen et al. (1983) "Determination of lipase specificity" *Lipids*, 18(3):239-52.

Jensen et al. (1985) "Specificity of Human Milk Bile Salt-Stimulated Lipase" *J. Pediatr. Gastroentrol. Nutr.*, 4:580-2.

Jensen et al. (1986) "Absorption of individual fatty acids from long chain or medium chain triglycerides in very small infants" *Am. J. Clin. Nutr.*, 43:745-51.

Jicha and Markesbery (2010) "Omega-3 fatty acids: potential role in the management of early Alzheimer's disease" *Clin. Interv. Aging*, 5:45-61.

Kalivianakis et al. (1999) "Fat malabsorption in cystic fibrosis patients receiving enzyme replacement therapy is due to impaired intestinal uptake of long-chain fatty acids" *Am. J. Clin. Nutr.*, 69:127-34.

Koletzo et al. (2008) "The roles of long-chain polyunsaturated fatty acids in pregnancy, lactation and infancy: review of current knowledge and consensus recommendations" *J. Perinat. Med.*, 36(1):5-14.

Kris-Etherton et al. (2002) "Fish consumption, fish oil, omega-3 fatty acids, and cardiovascular disease" *Circulation*, 106:2747-57.

Lapillone et al. (2009) "Reevaluation of the DHA requirement for the premature infant" *Prostaglandins, Leukotrines and Essential Fatty Acids*, 81:143-50.

Last "Lipase and the Fat Metabolism" LIPASE—*The Universal Remedy* [online], http://www.health-science-spirit.com/lipase/html, accessed Jul. 24, 2012 (8 pages).

Lauritzsen et al. (2001) "The essentiality of long chain n-3 fatty acids in relation to development and function of the brain and retina" *Prog. Lipid Res.*, 40:1-94.

Lie et al. (1991) "Hydrolysis and esterification with immobilized lipase on hydrophobic and hydrophilic zeolites" *J. Chem. Tech. Biotechnol*, 50:549-53.

Logan et al. (2004) "Omega-3 fatty acids and major depression: A primer for the mental health professional" *Lipids Health Dis.*, 3:25, doi:10.1186/1476-511X-3-25 [online]; published Nov. 9, 2004 (8 pages).

Malone (2005) "Enteral Formula Selection: A Review of Selected Product Categories" *Pract. Gastr.*, 26(6:44-74) (19 pages).

Mañń et al. (2009) "Partial Replacement of Dietary (n-6) Fatty Acids with Medium-Chain Triglycerides Decreases the Incidence of Spontaneous Colitis in Interleukin-10-Deficient Mice" *J. Nutr.*, 139:603-10.

Martek Press Release (May 4, 2010), "Study Published in Alzheimer's & Dementia: The Journal of the Alzheimer's Association Shows Algal DHA Improved Memory and Learning in Healthy Adults Age 55 and older" [online]. Downloaded from http://www.prweb.com/releases/MIDAS/DHA/prweb.com/releases/MIDAS/DHA/prweb3955084.htm on Jan. 9, 2015 (2 pages).

Martin et al. (2011) "Decreased Postnatal Docosahexaenoic and Arachidonic Acid Blood Levels In Premature Infants Are Associated with Neonatal Morbidities" *J. Pediatr.*, 159(5): 743-49.

Martinez et al. (1992) "Tissue levels of Polyunsaturated Fatty Acids During Early Human Development" *J. Pediatr.*, 120:S129-S138.

McCann et al. (2005) "Is docosahexaenoic acid, an n-3 long-chain polyunsaturated fatty acid, required for development of normal brain function? An overview of evidence from cognitive and behavioral tests in humans and animals" *Am. J. Clin. Nutr.*, 82:281-95.

McDaniel et al. (2011) "Fish oil supplementation alters levels of lipid mediators of inflammation in microenvironment of acute human wounds" *Wound Repair Regen.*, 19(2):189-200.

McNamara et al. (2008) "Deficits in docosahexaenoic acid and associated elevations in the metabolism of arachidonic acid and saturated fatty acids in the postmortem orbitofrontal cortex of patients with bipolar disorder" *Psychiatry Res.*, 160(3):285-99.

McNamara et al. (2010) "Docosahexaenoic acid supplementation increases prefrontal cortex activation during sustained attention in healthy boys: a placebo-controlled, dose-ranging, functional magnetic resonance imaging study" *Am. J. Nutr.*, 91:1060-67.

McNamara et al. (2010) "Selective deficits in erythrocyte docosahexaenoic acid composition in adult patients with bipolar disorder and major depressive disorder" *J. Affect. Disord.*, 126(1-2):303-11.

(56) References Cited

OTHER PUBLICATIONS

Milligan and Bazinet (2008) "Evolutionary modifications of human milk composition: evidence from long-chain polyunsaturated fatty acid composition of anthropoid milks" *J. Human Evol.*, 55:1086-95.
Mu (2008) "Bioavailability of omega-3 long-chain polyunsaturated fatty acids from foods" *AgroFOOD Industry Hi Tech Supplement*, 19(4):24-6.
Murty et al. (2002) "Hydrolysis of Oils Using Immobilized Lipase Enzyme: A Review" *Biotechnol. Bioprocess Eng.*, 7:57-66.
Nestlé (2011) "Gerber® Infant Formulas Nutrient Comparison Chart" (8 pages).
Nieto et al. (1999) "Synthesis of structured triacylglycerols containing medium-chain and long-chain fatty acids by interesterification with a stereospecific lipase from *Mucor miehei*" *Grasas y Aceites*, 50(3):199-202.
Oh et al. (2010) "GPR120 is an omega-3 fatty acid receptor mediating potent anti-inflammatory and insulin-sensitizing effects" *Cell*, 142(5):687-98.
Oksman et al. (2006) "Impact of different saturated fatty acid, polyunsaturated fatty acid and cholesterol containing diets on beta-amyloid accumulation in APP/PS1 transgenic mice" *Neurobiol. Dis.*, 23(3):563-72.
Peretti et al. (2005) "Mechanisms of lipid malabsorption in Cystic Fibrosis: the impact of essential fatty acids deficiency" *Nutrition & Metabolism*, 2:11, doi: 10.1186/1743-7075-2-11 [online]; published May 3, 2005 (18 pages).
Pérez et al. (2011) "A Novel Halophilic Lipase, LipBL, Showing High Efficiency in the Production of Eicosapentaenoic Acid (EPA)" *PLoS One*, 6(8):e23325, doi:10.1371/journal.pone.0023325 [online], published Aug. 10, 2011 (11 pages).
Pointes-Arruda et al. (2006) "Effects of enteral feeding with eicosapentaenoic acid, y-linolenic acid, and antioxidants in mechanically ventilated patients with severe sepsis and septic shock" *Crit. Care Med.*, 34(9):2325-33.
Reisbick et al., (1997) "Visual Attention in infant monkeys: effects of dietary fatty acids and age" *Dev. Psychol.*, 33(3):387-95.

Ren et al. (2011) "Facile, high efficiency immobilization of lipase enzyme on magnetic iron oxide nanoparticles via a biomimetic coating" *BMC Biotechnol.*, 11:63, dol: 10.1186/1472-6750-11-63 [online], published Jun. 8, 2011 (8 pages).
Ruthig and Meckling-Gill (1999) "Both (n-3) and (n-6) fatty acids stimulate wound healing in the rat intestinal epithelial cell line, IEC-6" *J. Nutr.* 129:1791-98.
Sanderson et al. (1997) "Dietary fish oil diminishes the antigen presentation activity of rat dendritic cells" *J. Leukoc. Biol.*, 62:771-7.
Sangiovanni and Chew (2005) "The role of omega-3 long chain polyunsaturated fatty acids in health and disease of the retina" *Progr. Retinal Eye Res.*, 24:87-138.
Sarkadi-Nagy et al. (2004) "Formula feeding potentiates docosahexaenoic and arachidonic acid biosynthesis in term and preterm baboon neonates" *J. Lipid Res.*, 45:71-80.
Scheltens et al. (2012) "Efficacy of Souvenaid in Mild Alzheimer's Disease: Results from a Randomized Controlled Trial" *J. Alzheimer's Dis.*, 31:225-36.
Stark and Holmberg (1989) "Covalent immobilization of lipase in organic solvents" *Biotechnol. Bioeng.*, 34(7):942-50.
Stoll et al. (1999) "Omega 3 Fatty Acids in Bipolar Disorder. A Preliminary Double-blind, Placebo-Controlled Trial" *Arch. Gen Psychiatry*, 56(5):407-12.
Toyo Denka Kogyo Co., Ltd. (Date unknown) "New Inorganic Carriers for Immobilization of Enzymes. *Toyonite*" (12 pages).
Ville et al. (2002) "Physiological study of pH stability and sensitivity to pepsin of human gastric lipase" *Digestion*, 65:73-81.
Yuhas et al. (2006) "Human milk fatty acid composition from nine countries varies most in DHA" *Lipids*, 41(9):851-58.
Fadiloğlu, Sibel et al., "Olive Oil Hydrolysis by Celite-Immobilized Candida rugosa Lipase," J. Agric. Food Chem., 1998, vol. 46 (9), pp. 3411-3414, Department of Food Engineering, Faculty of Engineering, Gaziantep University, Gaziantep, Turkey.
International Search Report and Written Opinion dated Feb. 8, 2017, in International Application No. PCT/US2016/056722 (11 pages).

\* cited by examiner

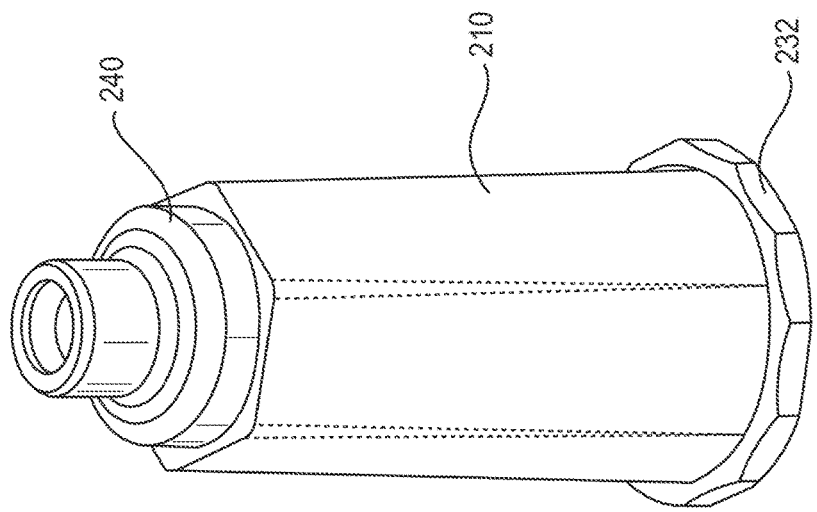
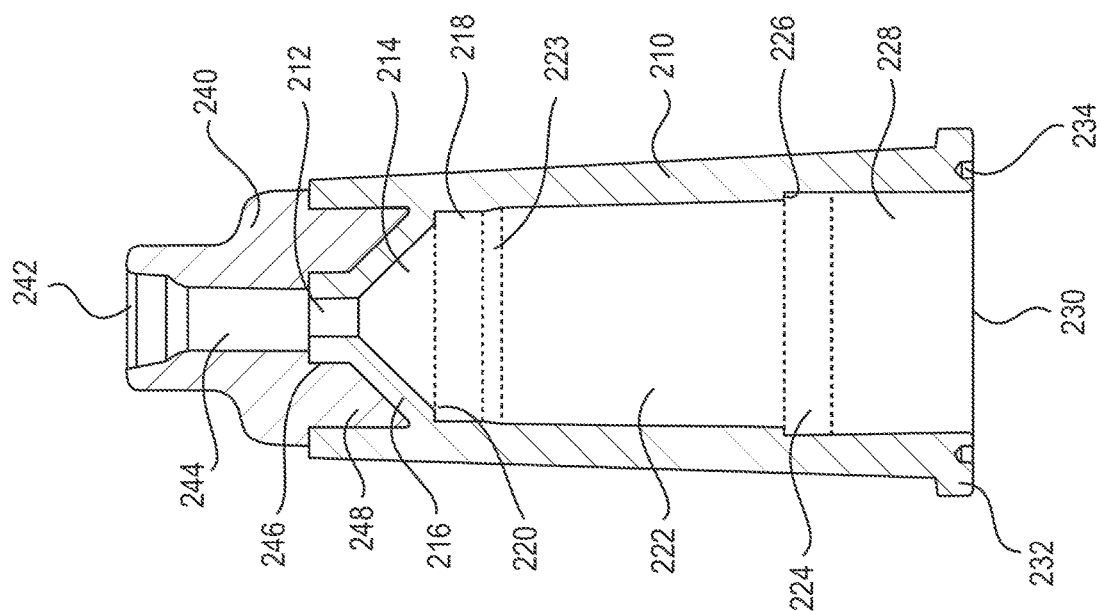
FIG. 3B
FIG. 3A

ENTERAL FEEDING DEVICES AND RELATED METHODS OF USE

CROSS-REFERENCE TO RELATED APPLICATIONS

This application is a continuation application of U.S. patent application Ser. No. 15/291,530, filed on Oct. 12, 2016, which claims the benefits of priority from U.S. Provisional Patent Application No. 62/241,608, filed on Oct. 14, 2015, the entireties of which are incorporated herein by reference.

FIELD OF THE DISCLOSURE

Embodiments of the present disclosure are directed to devices and methods for processing a nutritional formula, and more particularly, to devices and methods for hydrolyzing fats in a nutritional formula into free fatty acids and monoglycerides for ingestion.

BACKGROUND OF THE DISCLOSURE

Long-chain polyunsaturated fatty acids (LC-PUFAs) are lipids having hydrocarbon chains containing two or more carbon-carbon double bonds. LC-PUFAs, such as docosahexaenoic acid (DHA), eicosapentaenoic acid (EPA), and arachidonic acid (AA), are critical for normal human growth, development, and maintaining caloric intake, have important visual, cognitive, cardiovascular, and immunological health benefits throughout a person's life and in medical treatments, and are important for maintaining and/or gaining weight and subsequent survival after medical treatments. The principal source for DHA and EPA is through diet and, to a lesser degree, their precursor, alpha-linolenic acid (ALA), an omega-3 fatty acid. The principal source for AA is through the diet and, to a lesser degree, linoleic acid (LA), an omega-6 fatty acid. Endogenously produced enzymes are highly inefficient at converting ALA to DHA and EPA. According to an official statement by the International Society for the Study of Fatty Acids and Lipids (ISSFAL), the conversion of ALA to DHA is about 1% in infants and is considerably lower in adults. Brenna et al., *Prostaglandins Leukot Essent Fatty Acids*, 80(2-3):85-91 (2009). Thus, adequate absorption of dietary and supplemental nutrient sources of LC-PUFAs, such as DHA and EPA, is important for the health of the human body. Until 2001, direct sources of DHA and AA were not part of the ingredients used in infant formulas in the US.

LC-PUFAs, such as DHA, EPA, and AA, in the diet are primarily in the form of long-chain triglycerides and/or long-chain fatty acid esters. Long-chain polyunsaturated triglycerides are made of three long-chain fatty acids bound to a glycerol molecule via ester linkages. Absorption of long-chain triglycerides by the body first requires the enzymatic action of lipase, e.g., pancreatic lipase, which digest triglycerides through hydrolysis, breaking them down into monoglycerides and free fatty acids. As used herein, the terms triglycerides and fatty acids both may refer to fats found in food or supplemental nutritional formulas. Fatty acids and monoglycerides are found as triglycerides in supplemental nutritional formulas. Free fatty acids or fatty acids not attached to other molecules are used to refer to the byproduct of fat digestion. Free fatty acids or fatty acids not attached to other molecules are unstable, which makes them unsuitable to be packaged in supplemental nutritional formulas.

Additionally, the chain lengths and the number of carbon-carbon double bonds of fatty acids may influence fat absorption. Dietary fatty acids found in food are long-chain fatty acids having at least 12 carbons, for example 16, 18, or 20 carbons, known as C16, C18, and C20 long-chain fatty acids. Medium-chain fatty acids having less than or equal to 12 carbons, for example, 8 and 12 carbons, known as C8 and C12 are rarely found in food (except for coconuts) and are thus less important for digestion and absorption in humans. Short-chain fatty acids having less than or equal to a few carbons, for example, 2, 3, and 4 carbons, known as C2, C3, and C4, are the major anions found in the stool, but they are not found in food. Short-chain fatty acids result from the digestion of fats by the bacteria in the colon and thus often contribute to diarrhea by providing an osmotic gradient. B. Goodman, *Adv. Physiol. Educ.*, 34(2):44-53 (2010).

While all fats provide caloric benefit, they have different impacts on physiological functions. St-Ogne et al., *J. Nutr.*, 132(3): 329-333 (2002). Short-chain triglycerides and medium-chain triglycerides (MCTs) are absorbed directly through the villi of the intestinal mucosa. MCTs can be readily absorbed due to their shorter chain lengths and the residual activity of gastric lipase, even in patients having compromised pancreatic output or pancreatic insufficiency. Long-chain triglycerides (LCTs) have fatty acids with more than 12 carbons, for example C13 to C24. LCTs are not directly absorbed but instead must first be hydrolyzed into free fatty acids and monoglycerides by pancreatic lipase before they are absorbed in the small intestine. Once free fatty acids and monoglycerides are absorbed, they are transported to the liver and ultimately to tissues in the body for various physiological purposes. While both LCTs and MCTs provide calories, only LCTs, specifically LCPUFAs, provide structural components of membranes and biological mediators involved in the regulation of many physiological functions. MCTs, when substituted for LCTs, have been shown to increase energy expenditure and satiety, leading to reduced overall caloric intake and reduced body fat mass. This makes MCTs a poor long-term energy source for patients having compromised pancreatic output or pancreatic insufficiency. M. Clegg, *Int. J. Food Sci. Nutr.*, 61(7): 653-79 (2010). Furthermore, DHA and EPA are commercially available as triglycerides or in esterified form in nutritional supplements, prescription products (e.g., LOVAZA®, OMACOR®, and Vascepa™), and infant formulas. These nutritional supplements or products may be in the form of a powder, liquid beverage, or enteral-feeding formula. Because polyunsaturated fatty acids are unstable and can rapidly degrade, no enteral formula or nutritional supplements containing hydrolyzed fatty acids has been manufactured to date.

Some people, however, are unable to adequately break down or absorb long-chain triglycerides, structured fats, and/or long-chain esters, e.g., patients suffering from compromised pancreatic output or pancreatic insufficiency, preterm infants, people in the ICU, and the elderly, and as a result, they may suffer from inadequate hydrolysis or absorption of long-chain triglycerides and/or long-chain esters and may not benefit from the intake of dietary and/or nutrient supplement sources of LC-PUFAs. Uncorrected fat malabsorption due to compromised pancreatic and/or gastrointestinal or liver dysfunction can lead to malnutrition, failure to gain or maintain weight, decreased ability to recover from infections, decreased growth, and impaired absorptive capacity of the gastrointestinal lumen, despite adequate or exaggerated food intake.

For example, exocrine pancreatic insufficiency (EPI) is one of the conditions that lead to a reduced ability to hydrolyze long-chain triglycerides. EPI may result from diseases that affect and destroy the exocrine function of the pancreas, including cystic fibrosis (CF), chronic pancreatitis (CP), surgery, cancer (in particular pancreatic), developmental immaturity, and pancreatectomy for the treatment of injury or infection. In the course of EPI, lipid malabsorption with resulting steatorrhea typically develops earlier than does the maldigestion of proteins or carbohydrates. Weight loss and steatorrhea are common to all cancers due to the catabolic state of tissues, diversion of nutrients, and malabsorption in advanced stages. Pancreatic cancer is unique compared to other cancers, as weight loss and malabsorption are present in 80%-90% of patients at the time of diagnosis. The vast majority of people with EPI, including CF patients, have significant gastrointestinal manifestations (~90%), leading to fatty acid alterations, imbalances and deficiencies of long-chain fatty acids, e.g., DHA and/or EPA, which may also contribute to the inflammatory characteristics of CF lung disease, such as chronic suppurative lung disease and GI symptoms. In general, EPI may result in decreased pancreatic lipase secretion or efficacy and maldigestion and malabsorption of lipids, leading to reduced caloric intake, significant weight loss, LC-PUFA deficiencies, and GI symptoms, including steatorrhea with bulky, greasy, foul-smelling stools, pain, flatulence, nausea, and thus can have a significant impact on the quality of life.

Current options for treating EPI or to improve the absorption of dietary or supplemental LC-PUFA intake, such as DHA and EPA, include adding lipase supplements to the diet or nutrient supplements to improve hydrolysis of long-chain triglycerides, including pancreatic lipase. However, pancreatic enzymes, and particularly pancreatic lipase present in these supplements, are often sensitive to degradation by gastric acid and pepsin so that only a small fraction of the ingested enzymes reach the duodenum in active form. E. Ville et al., *Digestion*, 65:73-81 (2001). Further, most commercial lipase supplements are made from animal pancreatic lipase, which is known to have significantly reduced stability below a pH of 7. See, e.g., US2010/0239559; D. Kasper et al., *Harrison's Principles of Internal Medicine* 16$^{th}$ Ed. (2004). By the time such lipases pass through the stomach, significant amounts are likely to have been inactivated. Also, not all lipases work to the same degree for hydrolysis of a given long-chain fatty acid, indicating lipase specificity is an important consideration. R. Jensen et al., *Lipids*, 18(3):239-252 (1983). And, in some populations with EPI, nutritional formulas are tightly regulated, such as in pre-term infants or in patients in intensive care units. For these controlled populations, it may not be desirable or feasible to supplement already-approved formulas with additional ingredients.

The current standard of care for treating fat malabsorption and improving dietary fat intake includes porcine enzymatic replacement therapy (PERT) and the use of exaggerated levels of fats delivered as MCTs. In PERT, porcine-derived pancreatic enzyme products are administered orally with meals and snacks. The porcine-derived pancreatic enzymes are typically extracted from pancreas glands harvested from pigs used for food consumption in slaughterhouses certified by the US Department of Agriculture or comparable European authorities. These porcine-derived pancreatic enzymes may contain a mixture of enzymes including lipases, trypsin, chymotrypsin, elastase, proteases, and amylases, and other cellular components. The use and reliance on porcine-sourced material in these products may pose potential risks, including human infection with zoonotic viruses, exposure to endogenous porcine viruses, allergic reactions, and the presentation of hyperuricemia. Moreover, the availability of porcine-derived pancreatic enzymes can be a concern in the event that source herds need to be culled due to diseases or other agricultural imperatives.

Furthermore, lipase supplements, such as the porcine-derived pancreatic enzymes, must be covered with a polymeric resin coating (hydroxypropyl-methylcellulose phthalate or other phthalates) to prevent them from being inactivated in the low-pH environment of the stomach. The polymeric coating approximately constitutes about 30% of the weight of such capsules and is non-digestible, absorbed systemically and excreted by the kidneys. For these reasons, the use of PERTs in immune compromised patients or infants, especially preterm infants, is not practical due to the many potential safety concerns. Moreover, although acid protective coatings have helped, some degree of malabsorption persists, causing patients with EPI to require increasing doses of enzyme supplements. This persistence of fatty acid malabsorption even with use of enterically coated enzymes may be due to the fact that the duodenum and upper jejunum in patients with EPI are often acidic environments, so that the expected raise in pH is not achieved, and the protective coating is not properly dissolved to release the enzyme. D. Graham, *New England J. Med.*, 296(23):1314-1317 (1977). Both of these problems have been addressed by increasing the dose of enzymes administered. It has been observed that large amounts of pancreatic digestive enzymes can damage the large intestine resulting in fibrosing colonopathy. D. Bansi et al., *Gut*, 46:283-285 (2000); D. Borowitz et al., *J. Pediatr.*, 127:681-684 (1995).

In the clinical setting, a number of manufacturers have begun to use structured fats or structured lipids as a dietary source of fats. Structured fats or lipids are created by separating fatty acids from the glycerol backbone of medium- and long-chain triglycerides, a process called de-esterification. The generated fatty acids are then rejoined through re-esterification to create triglycerides containing medium- and long-chain fatty acids on the same glycerol backbone. Structured fats or lipids are limited in their effectiveness as nutrient supplement because the fats or lipids still need to be hydrolyzed by lipases so that the fatty acids and monoglycerides can be absorbed properly by the body. This random re-esterification used to create structured fats or lipids may not produce fats that are easily absorbable by the body, since the re-esterification may occur at the incorrect glycerol backbone, potentially leaving the long-chain poly-unsaturated fats at the incorrect glycerol site.

In clinical practice, the average daily dose of porcine-derived pancreatic enzyme capsules may vary from 17 to 50 capsules per day, which may need to be individualized due to the inherent variability of the porcine-derived pancreatic enzyme, polymeric coating, and food consumption, and for some patients, taking other drugs may significantly affect the quality of life. As the risk of malnutrition from not taking pancreatic enzymes, even with the high doses, is much greater than the potential risk related to phthalates, it is advised that patients with CF continue to take their pancreatic enzymes as prescribed. Unfortunately, as previously noted, high doses of porcine pancreatic enzyme supplements have been found to be associated with fibrosing colonopathy in patients with CF.

To supplement a required caloric intake and absorption of LC-PUFAs, patients with EPI and/or people having inadequate absorption of LC-PUFAs may consume liquid nutritional formula through enteral feeding together with the oral intake of the porcine-derived pancreatic enzyme capsules in PERT. However, a timing gap between the nutritional liquid and the administration of the porcine-derived pancreatic enzyme capsules and/or a lack of synchronization in the small intestine between the availability of the enzymes released from the capsules and the use of enteral formula can exist, which may lead to inefficient enzymatic activity and thus reduced fat hydrolysis and absorption. For at least the above limitations combined, PERT fails to solve the problems of inadequate absorption, maldigestion, and malabsorption of fats, in particular LC-PUFAs, and may limit caloric intake, create fatty acid imbalances and/or deficiencies, exacerbate GI symptoms, require high volumes of nutritional liquid, and thus may significantly affect quality of life.

Accordingly, there exists a need for a device and a method for delivering readily absorbable fats (free fatty acids and monoglycerides), such as LC-PUFAs, to a person in need of the nutrient. In addition, there exists a need for a device and a method capable of efficiently hydrolyzing long-chain triglycerides to deliver absorbable fats in the form of monoglycerides and free fatty acids directly to the gastrointestinal tract. Embodiments of the present disclosure described herein aim to overcome one or more of the limitations of the currently available treatment options and to improve the quality of life for people having impaired ability to adequately hydrolyze dietary fats, for example, LC-PUFAs.

SUMMARY OF THE DISCLOSURE

Embodiments of the present disclosure are directed to devices and methods for hydrolyzing fats in a nutritional formula by exposing the nutritional formula to lipase directly before ingestion. Various embodiments of the disclosure may include one or more of the following aspects.

In accordance with one embodiment, an enteral feeding device for hydrolyzing triglycerides and fatty acid esters in a nutritional formula by exposing the nutritional formula to lipase may include a body housing a chamber. The device may also include an inlet configured to fluidly couple with a source tube, creating a pathway for the nutritional formula to enter the device from the source tube and flow into the chamber. The device may also include an outlet configured to fluidly couple with an enteral feeding tube, creating a pathway for the nutritional formula to exit the chamber and flow into the enteral feeding tube. The device may also include a plurality of particles contained within the chamber, wherein the lipase may be covalently bonded to each of the plurality of particles. The device may also include an inlet filter located between the inlet and the chamber, wherein the inlet filter contains a first plurality of openings configured to broaden a flow path of the nutritional formula as it flows from the inlet and into the chamber. The device may also include an outlet filter located between the chamber and the outlet, wherein the outlet filter has a second plurality of openings, and wherein the second plurality of openings are smaller than the plurality of particles. The triglycerides and fatty acid esters in the nutritional formula may be hydrolyzed as they pass through the plurality of particles contained within the chamber.

Various embodiments of the enteral feeding device may include one or more of the following features: the plurality of particles, when dry, may fill at least 50% of the chamber; the plurality of particles, when dry, may fill at least 80% of the chamber; the plurality of particles, when dry, may fill at least 90% of the chamber; the plurality of particles, when exposed to the nutritional formula, may fill at least 80% of the chamber; the plurality of particles, when exposed to the nutritional formula, may fill at least 90% of the chamber; the plurality of particles, when dry, may fill substantially the same amount of the chamber as when exposed to the nutritional formula; the plurality of particles may swell so that, when dry, the plurality of particles may fill less of the chamber than when exposed to the nutritional formula; an outside surface of at least one of the plurality of particles may be at least partially hydrophobic; the device may be configured so that there is less than a 30% difference between a flow rate set by the pump and a flow rate of the nutritional formula exiting the outlet; at least one of the plurality of particles may be formed of one or more of ethylene glycol dimethacrylate, butyl methacrylate, or glycidyl methacrylate; at least one of the plurality of particles may be formed of between about 50% to about 60% of ethylene glycol dimethacrylate by weight; at least one of the plurality of particles may be formed of between about 30% to about 45% of butyl methacrylate by weight; at least one of the plurality of particles may be formed of between about 0.01% to about 10% of glycidyl methacrylate by weight; at least one of the plurality of particles may have a hydrophilic coating including polyethylene glycol; at least one of the plurality of particles may be formed of between about 0% to about 10% of polyethylene glycol by weight; at least one of the plurality of particles may have a substantially solid cross-section; at least one of the plurality of particles may have a substantially smooth outer surface; at least one of the plurality of particles may have an irregular outer surface; at least one of the plurality of particles may have a porous cross-section forming internal surfaces within the at least one particle; a median or a mean diameter of a pore of the porous cross-section may range from about 1 nm to about 50 nm; a median or a mean diameter of a pore of the porous cross-section may range from about 1 nm to about 50 µm; the lipase may be covalently bonded to the internal surfaces; at least one of an outer surface or an internal surface of at least one of the plurality of particles may include a functional group; the functional group may be an epoxy group; the lipase may be covalently bonded to the epoxy group; the lipase may be selected from at least one of *Chromobacterium viscosum* lipase, *Pseudomonas fluorescens* lipase, or *Rhizopus oryzae* lipase; a median or a mean diameter of the plurality of particles may be between about 100 µm and about 800 µm; a median or a mean diameter of the plurality of particles may be between about 200 µm and about 500 µm; the plurality of particles may include a first group of particles and a second group of particles, wherein the first group of particles has a median or a mean diameter of that is different than a median or a mean diameter of the second group of particles; an amount of the lipase covalently bonded to the plurality of particles may fall within a range of about 5 mg to about 500 mg of lipase per 1 g of the plurality of particles; an average size of at least one of the first plurality of openings or the second plurality of openings may be between about 10% to about 60% smaller than an average diameter of the plurality of particles; at least one of the first plurality of openings or the second plurality of openings may include a plurality of tortuous paths; the inlet filter may be coated with at least one emulsifier configured to emulsify the nutritional formula as it passes through the inlet filter; the inlet filter and the outlet filter each may have a thickness of between about 0.1 mm to about 10 mm; and the device may be further configured to hydrolyze phospholipids.

It is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

The accompanying drawings, which are incorporated in and constitute a part of this specification, illustrate exemplary embodiments of the present disclosure, and together with the description, serve to explain the principles of the disclosure.

FIG. 3A illustrates a cross-section of an exemplary fat hydrolysis device, according to embodiments of the present disclosure.

FIG. 3B illustrates a perspective view of an exemplary fat hydrolysis device, according to embodiments of the present disclosure.

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts.

While the present disclosure is described herein with reference to illustrative embodiments of particular applications, such as devices, methods, and systems for supplying and processing nutritional formulas prior to ingestion, it is understood that the embodiments described herein are not limited thereto. Those having ordinary skill in the art and access to the teachings provided herein will recognize additional modifications, applications, embodiments, and substitution of equivalents that all fall within the scope of the present disclosure. For example, the devices and methods of the present disclosure may be employed for any suitable application, including, but not limited to, supplying fatty acid needs for medical and nutritional purposes for infants, children, or adults, in the hospital, in supportive care institutions, in long-term care facilities, or for home use, or for veterinary use, or for use with livestock. Devices disclosed herein can also be used with other suitable fat-containing liquids. Accordingly, the disclosure is not to be considered as limited by the foregoing or following descriptions.

Figure 1:
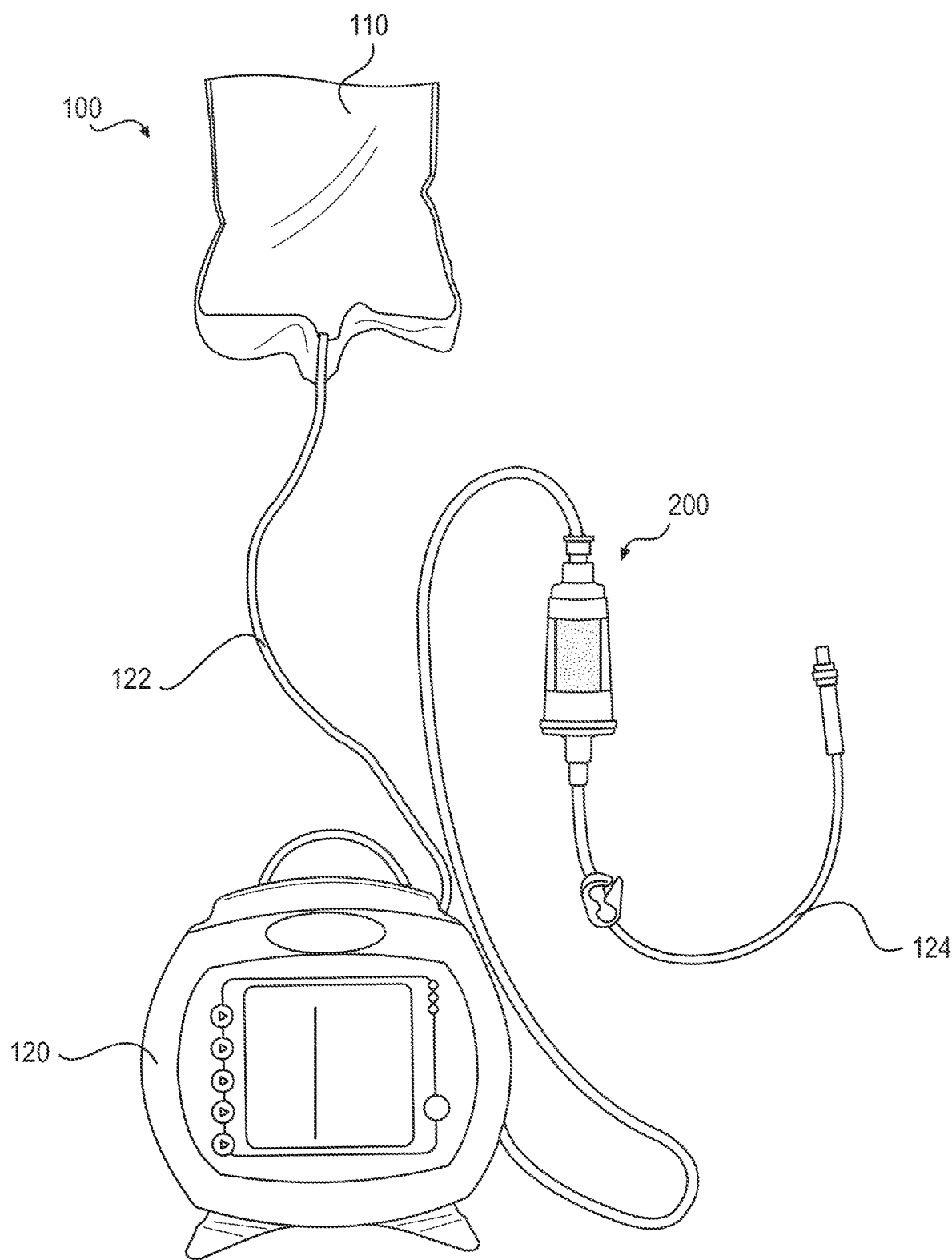
FIG. 1 illustrates an exemplary system for supplying and processing a nutritional formula, according to embodiments of the present disclosure.

FIG. 1 illustrates an exemplary embodiment of an enteral supply system 100 for feeding a nutritional formula 110 to a subject via a feeding tube. System 100 may include a fat hydrolysis device 200, a pump 120, and a first tube 122 fluidly connecting a source of nutritional formula 110 and device 200. Nutritional formula 110 may be contained in a suitable container, such as a feeding bag, a vial, a syringe, or a bottle. Nutritional formula 110 is flowed from the source, through first tube 122, and to device 200 for processing. System 100 also includes a second tube 124 having an end configured to connect to device 200 and an opposite end configured to connect to a patient to deliver processed nutritional formula 110 from device 200 to the patient for ingestion. Second tube 124 may be an enteral feeding tube, for example, a gastric, a nasogastric, a nasoduodenal, a nasojejunal, a gastrostomy, a gastrojejunostomy, a jejunostomy, a PEG tube, or a transjejunal feeding tube to feed nutritional formula 110 to the GI tract of a subject through, for example, the nose, mouth, stomach, or abdomen. System 100 may be used in line with current standard enteral feeding practice.

System 100 is configured to deliver and process nutritional formula 110 at the point of care to allow device 200 to hydrolyze fats contained in nutritional formula 110 right before ingestion. As used herein, the term "nutritional formula" refers to complex mixtures containing, for example, proteins, carbohydrates, fat, water, minerals, and/or vitamins, which may include liquid foods that are specially formulated and processed; liquids used for the partial or exclusive feeding of a person by means of oral intake or feeding by tube; liquids used for the dietary management of a person who, because of therapeutic or medical need, has limited or impaired capacity to ingest, digest, absorb, or metabolize ordinary foodstuffs or certain nutrients; liquids that meet medically determined nutrient requirements; and liquids designed to deliver to a subject nutrients that cannot be provided to the subject via dietary management and modification of the normal diet alone. Nutritional formula 110 may also include formulas intended for the specific dietary management of a disease or condition, for which distinctive nutritional requirements, based on recognized scientific principles, are established by medical evaluation, or may include liquid foods used as part of an overall diet to manage the symptoms or reduce the risk of a disease or condition. In some embodiments, nutritional formula 110 may be delivered to the subject under medical supervision, may be intended only for a person receiving active and ongoing medical supervision, or may be delivered to the subject for home use, either when supervised or unsupervised.

Nutritional formula 110 may be packaged as a dry powder or oil and then mixed with a solvent to form a solution. In other embodiments, nutritional formula 110 may be packaged as a liquid nutritional formula, beverage, or drink. In some embodiments, nutritional formula 110 may be commercially available, or may be prepared by a healthcare professional before feeding. Nutritional formula 110 may be an infant and/or toddler formula as a complete or partial substitute for human milk, may be donor milk or breast milk, or may be designed to supplement or completely replace the diet of an adult or elderly person. In some embodiments, nutritional formula 110 may be a commercially available or a custom-developed formula combined with a commercially available or a custom-developed supplement or fortifier, which may supply additional nutrients including, but not limited to, one or more of LC-PUFAs, vitamin, minerals, or proteins. In some embodiments, nutritional formula 110 may include a combination of MCTs and LCTs. In some embodiments, nutritional formula 110 may be conditioned to make fats contained in it more accessible for hydrolysis. Exemplary conditioning may include one or more of sonication, fat droplet disruption, or emulsification, e.g., by physical or chemical means (e.g. by exposure to a surfactant, surfactant-like substance, or protease). In some embodiments, nutritional formula 110 may be prescribed for a subject in need of additional LC-PUFAs, such as DHA, EPA, and/or AA, a subject having conditions such as maldigestion and malabsorption of lipids, reduced caloric intake, significant weight loss, LC-PUFA deficiencies, and/or a subject having diseases, including cystic fibrosis (CF), chronic pancreatitis (CP), surgery, cancer, liver abnormalities, gastrointestinal dysfunction, and developmental immaturity. In some embodiments, the subject may have exocrine pancreatic insufficiency (EPI) with reduced ability to hydrolyze long-chain triglycerides. In some embodiments, nutritional formula 110 may include at least one medicament prescribed for the subject in need of the medicament and/or nutritional formula 110, or nutritional formula 110 may itself be the prescribed medicament.

Nutritional formula 110 includes at least one fat in triglyceride form, such as MCT and LCT. In some embodiments, nutritional formula 110 may further include at least one nutrient selected from water, maltodextrin, protein, hydrolyzed protein, amino acids, peptides, medium chain triglycerides, diglycerides, monoglycerides, cornstarch, fish oil, soybean oil, rapeseed oil, cottonseed oil, sunflower oil, olive oil (oils may or may not be refined), soluble fiber, lecithin, magnesium chloride, sodium ascorbate, guar gum, calcium phosphate, salt, choline chloride, phosphoric acid, calcium citrate, sodium phosphate, taurine, magnesium oxide, zinc sulfate, potassium chloride, niacinamide, ferrous sulfate, calcium pantothenate, manganese sulfate, pyridoxine hydrochloride, copper sulfate, thiamine mononitrate, beta-carotene, riboflavin, vitamin a palmitate, folic acid, biotin, sodium selenate, chromium chloride, potassium iodide, sodium molybdate, soluble fiber, fructooligosaccharide, probiotic, citric acid, vitamin A, vitamin D, vitamin E, vitamin $B_1$, vitamin $B_2$, vitamin $B_3$, vitamin $B_5$, vitamin $B_6$, vitamin $B_7$, vitamin $B_9$, and vitamin $B_{12}$. Exemplary nutritional formulas and systems are described in International Patent Application No. PCT/US2013/026063, filed Feb. 14, 2013, and U.S. patent application Ser. No. 14/378,856, filed Aug. 14, 2014, both of which are herein incorporated by reference in their entireties.

The flow of nutritional formula 110 to device 200, and ultimately to the subject, is controlled by pump 120 of system 100. In some embodiments, pump 120 may be a peristaltic pump, although any suitable type of infusion pump, e.g., an elastomeric pump, a multi-channel pump, a syringe pump, and/or a smart pump may be used. A flow rate of nutritional formula 110 through the tubes and/or device 200 may be set and/or adjusted by pump 120. In some embodiments, pump 120 may include a processor, a display, and/or actuators (e.g. buttons, knobs, touch screen, etc.) to adjust and control the flow rate of nutritional formula 110 in system 100 and device 200. Pump 120 may be adjusted and set by a healthcare provider and/or the subject receiving nutritional formula 110. Pump 120 may perform continuous feeding, pulsatile feeding, intermittent feeding, bolus feeding, and/or flushing, and delivery of fluids may be set or adjusted automatically, semi-automatically, or manually.

In some embodiments, pump 120 may be a smart pump. Pump 120 may make automatic adjustments to the flow rate based on timing or feedback from system 100. Pump 120 may include user alerts to warn when the user sets parameters for pump 120 that fall outside of specified limits. Pump 120 may send an alert when an actual flow rate of nutritional formula 110 falls outside of set parameters for pump 120. The parameters may be stored in a memory of pump 120, or may be entered and/or adjusted for a specific delivery regime.

In other embodiments, system 100 may not include pump 120 and may instead depend on gravity to flow nutritional formula 110 through device 200. The relative positioning of the source of nutritional formula 110 may allow nutritional formula 110 to flow through the tubes and device 200 under the influence of gravity alone. For example, a container of nutritional formula 110 may be placed above device 200 and/or above the subject, as shown in FIG. 1.

In other embodiments, pump 120 may be replaced with a syringe. The syringe may be filled with nutritional formula 110, and the flow rate of nutritional formula 110 in the tubes or device 200 may be set, and/or adjusted by using the syringe manually, semi-automatically, or automatically. For example, nutritional formula 110 may be pre-packaged in a pre-filled syringe mounted inside of an auto-injector-like device. The pre-packaged formula may also contain a pump 'engine' (e.g., a spring-loaded piston), and may be used to deliver the formula through device 200 and to the feed tube.

In other embodiments, system 100 may use any suitable means, e.g., a balloon or other suitable pressure-generating device, to generate a pressure drop or a flow-driving force that drives nutritional formula 110 through the tubes and/or device 200.

Figure 2:
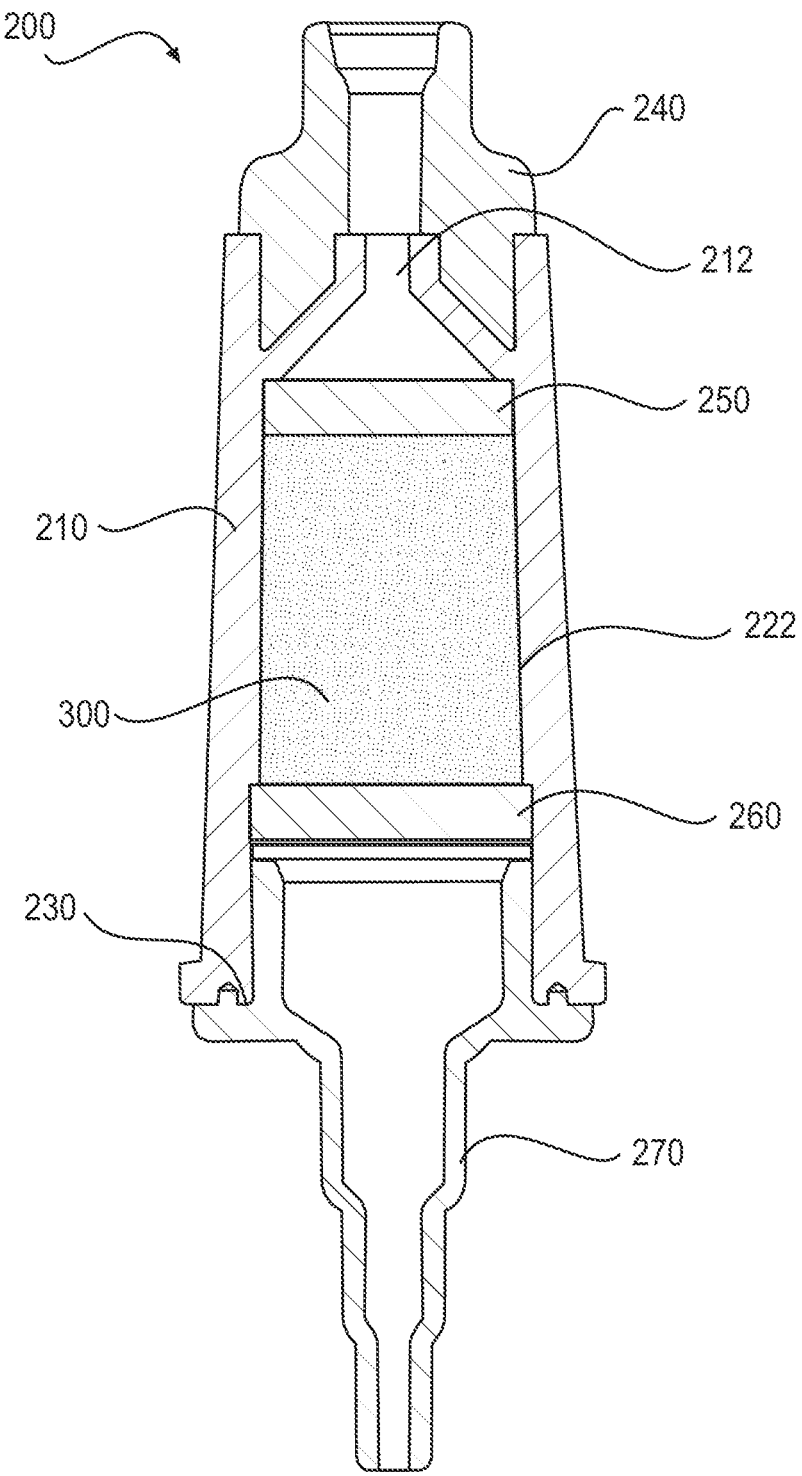
FIG. 2 illustrates a cross-section of an exemplary fat hydrolysis device, according to embodiments of the present disclosure.

FIG. 2 illustrates an exemplary device 200 in accordance with the present disclosure. Device 200 may include a body 210 having an inlet 212, a chamber 222, and an outlet 230. Chamber 222 may contain a plurality of particles 300. Device 200 may further include a first connector 240 and a second connector 270 configured to fluidly connect with first tube 122 and enteral tube 124, respectively. In some embodiments, device 200 may include an inlet filter 250 and an outlet filter 260. For example, inlet filter 250 may be located adjacent inlet 212, and outlet filter 260 may be located adjacent outlet 230. In some embodiments, inlet filter 250 and outlet filter 260 may cooperatively define chamber 222 while in some embodiments, either or both of inlet filter 250 and outlet filter 260 may be located within or outside of chamber 222. For example, there may be a floor and a ceiling that cooperatively define chamber 222. The floor and ceiling may define one or more openings at the top and bottom of chamber 222 and/or they may be porous to allow fluid to pass through into chamber 222. Inlet filter 250 may be located above an opening in the ceiling of chamber 222 adjacent inlet 212 and/or outlet filter 260 may be located below an opening in the floor of chamber 222 adjacent outlet 230. In some embodiments, inlet filter 250 may be located below a ceiling within chamber 222 and/or outlet filter 260 may be located above a floor within chamber 222, or any combination of positions thereof. Inlet filter 250 and outlet filter 260 may prevent particles 300 from exiting device 200. Additionally or alternatively, the filters may prevent foreign objects from entering device 200 and/or enteral tube 124. Particles 300 may be located between inlet filter 250 and outlet filter 260 in chamber 222. Inlet filter 250 and outlet filter 260 may retain particles 300 within chamber 222 as nutritional formula 110 flows through device 200. The smaller pore openings in inlet filter 250 and/or outlet filter 260 may aid in the emulsification and breakdown of fats.

As shown in FIG. 3A, body 210 may include one or more additional chambers. For example, body 210 may include an inlet chamber 214, an inlet filter chamber 218 for holding inlet filter 250, an outlet filter chamber 224 for holding outlet filter 260, and/or an outlet chamber 228. In some embodiments, the perimeter of inlet filter 250 may be about the same shape and size as that of the interior perimeter of inlet filter chamber 218. Inlet filter 250 may be fixed in inlet filter chamber 218 via, e.g., friction fit, press fit, snap fit, twist fit, and/or ultrasonic welding. In some embodiments, the perimeter of inlet filter chamber 218 may be smaller than the interior perimeter of chamber 222. In some embodiments, the perimeter of inlet filter chamber 218 may be larger than that of chamber 222 such that an edge portion may exist to allow inlet filter 250 be held against and/or out of chamber 222. In other embodiments, inlet filter 250 may be placed in inlet chamber 214 or inlet 212. In some embodiments, inlet chamber 214 may be shaped as an upside-down funnel, widening as it extends away from inlet 212. The interior perimeter of the wide end of inlet chamber 214 may be smaller than the perimeter of inlet filter chamber 218 such that an edge 220 may hold inlet filter 250 against inlet chamber 214. In other embodiments, device 200 may not include inlet chamber 214.

The placement of outlet filter 260 may have similar configurations as that of inlet filter 250. For example, in some embodiments, the perimeter of outlet filter 260 may be about the same shape and size as the interior perimeter of outlet filter chamber 224. Outlet filter 260 may be fixed in outlet filter chamber 224 via, e.g., friction fit, press fit, snap fit, twist fit, and/or ultrasonic welding. In some embodiments, the interior perimeter of outlet filter chamber 224 may be larger than that of chamber 222 such that an edge 226 may hold outlet filter 260 against and/or out of chamber 222. In other embodiments, outlet filter 260 may be located in outlet chamber 228. In some embodiments, the interior perimeter of outlet chamber 228 may be smaller than the interior perimeter of outlet filter chamber 224 such that an edge portion may hold outlet filter 260 against and/or out of outlet chamber 228. In other embodiments, body 210 may not include outlet chamber 228.

In one embodiment, the interior region of body 210 may be shaped as a hollow cylinder. In another embodiment, the interior region of body 210 may be shaped as, for example, a hollow truncated cone or a hollow polygonal prism (such as a triangular, rectangular, pentagonal, hexagonal, or decagonal prism). The perimeter may be consistent in size along the length of device 200 or may vary, e.g., taper and/or flare. The walls may be smooth or textured. Different interior portions of device 200 may have different shapes or texturing. In FIG. 3B, the exterior surface of body 210 is shaped as a polygonal prism, although the exterior may have any suitable shape, e.g., cylindrical, polygonal, etc. The exterior surface may have one or more textured areas, surfaces, indentations, or ridges to provide easy handling or gripping by a user. As noted in FIGS. 3A and 3B, the interior and exterior shape may not be the same, although in other embodiments, they may. Body 210 may be any suitable shape and include at least one chamber 222. In exemplary embodiments, chamber 222 may have a circular or elliptical cross-section. In exemplary embodiments, more than one chamber 222 may be included in body 210, arranged in series or in parallel, and may be fluidly connected.

In some embodiments, the interior diameter of a cross-section of body 210 may range from about 0.5 cm to about 1.5 cm, from about 0.5 cm to about 2 cm, from about 1.5 cm to about 1.7 cm, from about 2 cm to about 4 cm, from about 4 cm to about 6 cm, from about 6 cm to about 8 cm, from about 8 cm to about 12 cm, or from about 12 cm to about 15 cm. In some embodiments, the diameter of a cross-section of body 210 may decrease or increase along the length of body 210 by a range from about 1% to about 5%, from about 5% to about 10% from, from about 10% to about 20%, from about 20% to about 30%, from about 30% to about 40%, from about 40% to about 50%, from about 1% to about 10%, from about 1% to about 20%, from about 1% to about 30%, from about 1% to about 40%, or about 1% to about 50%. The length of body 210 may range from about 1 cm to about 5 cm, from about 2 cm to about 6 cm, from about 4 cm to about 6 cm, from about 4 cm to about 8 cm, from about 1 cm to about 6 cm, from about 1 cm to about 8 cm, or from about 1 cm to about 10 cm, and the total length of device 200 may range from about 1.5 cm to about 6.5 cm, from about 2 cm to about 6.5 cm, from about 4.5 cm to about 6.5 cm, from about 4.5 cm to about 8.5 cm, from about 1.5 cm to about 6.5 cm, from about 1.5 cm to about 8.5 cm, from about 1.5 cm to about 12.5 cm, from about 2.5 cm to about 15 cm, from about 4.5 cm to about 15 cm, from about 6.5 cm to about 15 cm, from about 8.5 cm to about 15 cm, from about 10 cm to about 15 cm, or from about 1.5 cm to about 15 cm. In some embodiments, the volume of chamber 222 may range from about 0.5 mL to about 2 mL, from about 2 mL to about 5 mL, from about 4 mL to about 6 mL, from about 5 mL to about 8 mL, from about 5 mL to about 10 mL, from about 10 mL to about 15 mL, from about 15 mL to about 20 mL, from about 25 mL to about 30 mL, from about 0.5 mL to about 4 mL, from about 0.5 mL to about 5 mL, from about 0.5 mL to about 6 mL, from about 0.5 mL to about 8 mL, from about 0.5 mL to about 10 mL, from about 0.5 mL to about 15 mL, from about 0.5 mL to about 20 mL, from about 0.5 mL to about 25 mL, or from about 0.5 mL to about 30 mL.

In some embodiments, inlet filter 250 and outlet filter 260 may form a top end and a bottom end of chamber 222, respectively. In such embodiments, the location of chamber 222 along a longitudinal axis of body 210 and/or the volume of chamber 222 may be adjusted by adjusting the location of inlet filter 250 and/or outlet filter 260 within body 210. In some embodiments, the total volume inside body 210 may range from about 0.5 mL to about 2 mL, from about 2 mL to about 5 mL, from about 5 mL to about 10 mL, from about 10 mL to about 15 mL, from about 15 mL to about 20 mL, from about 25 mL to about 30 mL, from about 0.5 mL to about 10 mL, from about 0.5 mL to about 15 mL, from about 0.5 mL to about 20 mL, from about 0.5 mL to about 25 mL, or from about 0.5 mL to about 30 m L.

In some embodiments, device 200 may include a first connector 240 configured to connect first tube 122 to body 210 to deliver nutritional formula 110 to device 200. First connector 240 may include an inlet 242 to receive nutritional formula 110, an outlet 246, and a channel 244 fluidly connecting the two. First connector 240 may include a fitting portion 248 configured to attach first connector 240 to body 210. In some embodiments, inlet 242 may generally be in the shape of a cylinder, a funnel, or a truncated cone, and may be designed to match any suitable standardized connector, such as an ENFit™ connector. In some embodiments, channel 244 may fluidly connect inlet 242 to inlet 212 of body 210. In some embodiments, inlet 242, or inlet 242 and channel 244, may form a female fitting configured to fit with a male fitting connected to first tube 122. Or, an outer surface of first connector 240 may form a male fitting configured to fit with a female fitting connected to first tube 122. The male and female fittings may fit via any suitable mechanical means, e.g., friction fit, press fit, twist fit, snap fit, overmolding or molding, thermal bonding, adhesive bonding, and/ or welding. Indeed, first connector 240 may have any suitable size and shape for connecting device 200 to tube 122.

In some embodiments, body 210 may comprise a recessed portion 216, and fitting portion 248 of first connector 240 may form a complimentary protrusion, or vice versa, to connect the two parts. First connector 240 may connect to body 210 via friction fit, twist fit, snap fit, clasp, press fit, overmolding or molding, thermal bonding, adhesive bonding, and/or welding. For example, first connector 240 may be pushed and/or twisted against body 210 until fitting portion 248 abuts recessed portion 216. In other embodiments, first connector 240 and body 210 may connect via a screw mechanism. For example, first connector 240 and body 210 may comprise a set of complementary screw threads such that first connector 240 may be fastened to body 210 by screwing first connector 240 into body 210. In some embodiments, the perimeter of an outside wall of inlet 212 may be larger than that of an interior perimeter of channel 244. For example, as shown in FIG. 3A, a rim of inlet 212 may be pushed or may abut an opening of channel 244 when first connector 240 and body 210 are properly fitted and connected. Once inlet 242 and channel 244 of first connector 240 and inlet 212 of body 210 are fluidly connected, nutritional formula 110 may flow from first tube 122, through first connector 240, and into body 210.

Although FIG. 3A depicts a separate first connector 240, in some embodiments, body 210 may connect directly to first tube 122, and a separate first connector 240 may not be needed. Although the fluid path is shown as extending through inlet 242, channel 244, and inlet 212, it is contemplated that this path may also include other portions or may be formed as a single portion in other embodiments.

In some embodiments, the diameter of inlet 242 may range from about 4 mm to about 7 mm, from about 5 mm to about 10 mm, or from about 4 mm to about 10 mm; the diameter of inlet 212 may range from about 1 mm to about 3 mm, from about 2 mm to about 4 mm, from about 3 mm to about 5 mm, or from about 1 mm to about 5 mm; the diameter of inlet filter chamber 214 may range from about 8 mm to about 12 mm, from about 12 mm to about 15 mm, from about 15 mm to about 18 mm, or from about 8 mm to about 18 mm; the diameter of outlet filter chamber 224 may range from about 10 mm to about 14 mm, from about 14 mm to about 17 mm, from about 17 mm to about 20 mm, or from about 10 mm to about 20 mm; the diameter of outlet 230 may range from about 10 mm to about 15 mm, from about 15 mm to about 20 mm, from about 20 mm to about 25 mm, or from about 10 mm to about 25 mm; and the diameter of fitting channel 234 may range from about 12 mm to about 16 mm, from about 16 mm to about 20 mm, from about 20 mm to about 24 mm, from about 24 mm to about 28 mm, or from about 12 mm to about 28 mm.

Figure 4C:
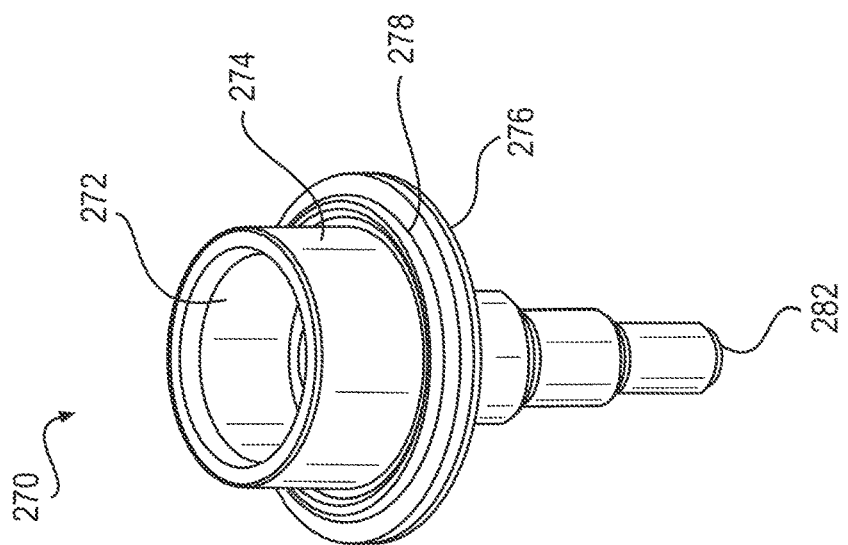
FIG. 4C illustrates a perspective view of the outlet of FIG. 4A.
Figure 4B:
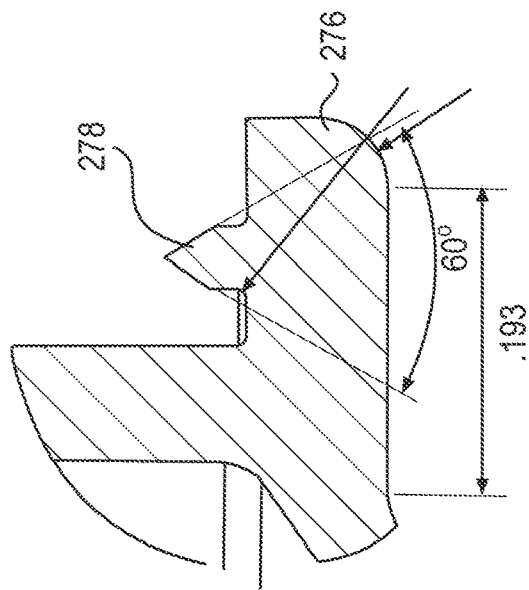
FIG. 4B illustrates a magnified view of a portion of the outlet depicted in FIG. 4A.
Figure 4A:
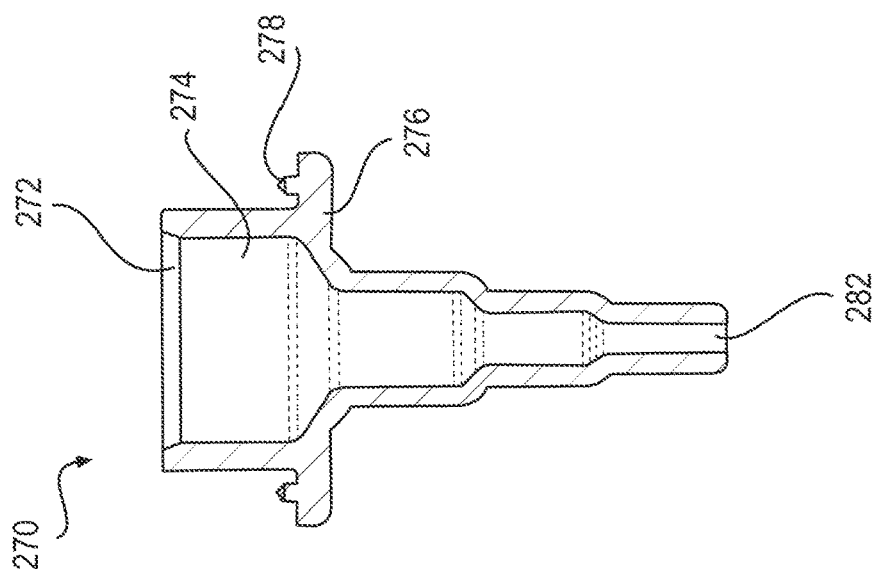
FIG. 4A illustrates a cross-section of an outlet of an exemplary fat hydrolysis device, according to embodiments of the present disclosure.

In some embodiments, a second connector 270 may be used to connect device 200 to enteral tube 124. Body 210 may comprise a rim 232 encircling outlet 230, and rim 232 may have a fitting channel 234 for connecting body 210 to second connector 270. As shown in FIG. 4A, second connector 270 may comprise an inlet 272, an inlet chamber 274, and an outlet 282. In some embodiments, second connector 270 may comprise a brim 276 and a protrusion element 278 projecting up from brim 276 towards inlet 272. In some embodiments, second connector 270 may connect to body 210 via friction fit, press fit, twist fit, clasp, snap fit, overmolding/molding, thermal bonding, adhesive bonding, and/or welding. For example, an outer perimeter of inlet chamber 274 of second connector 270 may correspond in size and shape to an inner perimeter of outlet chamber 228 of body 210 such that inlet chamber 274 of second connector 270 may be pushed, twisted, or otherwise received within outlet chamber 228 of body 210. In some embodiments, brim 276 may be pushed and/or may abut rim 232 of body 210, and protrusion element 278 may fit into fitting channel 234. As shown in FIG. 4B, a cross-section of protrusion element 278 is tapered and complements the tapered shape of fitting channel 234, however, protrusion element 278 may have any suitable shape, for example, rectangular, triangular, semi-circular, polygonal, flared, bulbous, or conical, with predetermined dimensions and angles for mating with fitting channel 234. In some embodiments, the perimeter of the cross-section of fitting channel 234 and protrusion element 278 may be similarly shaped or complementary.

In some embodiments, the perimeter of inlet 272 of second connector 270 and outlet 230 of body 210 may be similarly shaped, for example, circular, elliptical, rectangular, pentagonal, or hexagonal, and may mate with each other. In some embodiments, as shown in FIG. 4C, second connector 270 may be a male connector having one or more stepped tubular portions. The stepped tubular portions may be shaped as hollow cylinders or hollow truncated cones, whose exterior perimeters decrease with each additional step. Second connector 270 may be configured to connect to a female fitting of enteral tube 124. For example, the stepped tubular portions of second connector 270 may fit into a recess of a female connector of enteral tube 124 via, e.g., friction fit, twist fit, snap fit, clasp, and/or press fit. In other embodiments, second connector 270 may have any suitable shape, e.g., a cone, a truncated cone, or a cylinder, and may be designed to match any suitable standardized connector, such as an ENFit™ connector, and may be smooth or may include one or more ridges to facilitate connection to enteral tube 124. In some embodiments, second connector 270 may be a female portion for connecting to a male portion of enteral tube 124. Indeed, second connector 270 may have any suitable size and shape for connecting device 200 to enteral tube 124.

In some embodiments, at least one of first connector 240 and second connector 270 may be any suitable standardized connector, such as an ENFit™ connector.

In some embodiments, the diameter of fitting channel 234 may range from about 12 mm to about 16 mm, from about 16 mm to about 20 mm, from about 20 mm to about 24 mm, from about 24 mm to about 28 mm, or from about 12 mm to about 28 mm; the interior diameters of inlet 272 and inlet chamber 274 may range from about 4.5 mm to about 8 mm, from about 8 mm to about 13 mm, from about 13 mm to about 15 mm, from about 15 mm to about 18 mm, or from about 4.5 mm to about 18 mm, and the exterior diameters of inlet 272 and inlet chamber 274 may range from about 6 mm to about 10 mm, from about 10 mm to about 14 mm, from about 14 mm to about 18 mm, from about 18 mm to about 21 mm, or from about 6 mm to about 21 mm; the diameter of outlet 282 may range from about 0.5 mm to about 1.5, from about 1.5 mm to about 2.5 mm, from about 2.5 mm to about 3.5 mm, or from about 0.5 mm to about 3.5 mm; and the diameter of brim 276 may range from about 7 mm to about 10 mm, from about 10 mm to about 15 mm, from about 15 mm to about 20 mm, from about 20 mm to about 25 mm, from about 22 mm to about 26 mm, from about 25 mm to about 30 mm, or from about 7 mm to about 30 mm.

Although FIGS. 4A-4C depict a separate second connector 270; second connector 270 may not be a separate element of body 210. For example, second connector 270 may be formed integrally as part of body 210 such that body 210 directly connects with enteral tube 124. Although the fluid path is shown as extending through outlet 230, inlet 272, inlet chamber 274, and outlet 282, it is contemplated that this path may also include other portions or may be formed as a single portion in other embodiments.

In some embodiments, the dimensions or sizes of device 200 may be selected based on the particular application of device 200. For example, the diameters of inlet 212, inlet 242, inlet filter 250, chamber 222, outlet filter 260, and outlet 282, and the lengths and sizes of chamber 222 and body 210 may be selected for feeding a nutritional formula 110 to a particular subject. For example, the dimensions or sizes of device 200 for feeding infants may be smaller than those of a device for feeding youths and adults. In some embodiments, the dimensions or sizes of device 200 may be selected based at least in part on the amount of time the device is intended to be used to feed nutritional formula 110 to a subject, a flow rate or a volume of nutritional formula 110 to be fed to a subject, or whether the device is intended to be attached to a pump or not. For example, the dimensions or sizes of device 200 for an overnight enteral feeding procedure may be smaller than those for a shorter or faster enteral feeding procedure of nutritional formula 110, or a larger device may be used for a larger volume or faster intended flow rate of nutritional formula 110.

In some embodiments, more than one device 200 may be connected in series. For example, second connector 270 of a first device 200 may be connected to first connector 240 of a second device 200. For another example, a first end of a tube may be connected to second connector 270 of a first device 200 and connected to first connector 240 of a second device 200, allowing nutritional formula to flow from the first device 200 to the second device 200.

In some embodiments, body 210, first connector 240, and second connector 270 of device 200 may be made of the same material. In some embodiments, body 210, first connector 240, and second connector 270 of device 200 may be made of different materials having different physical, mechanical, or chemical characteristics, such as, for example, flexibility, elasticity, tensile strength, toughness, color, transparency, chemical resistance, and/or thermal resistance, or the parts may be formed of a combination of materials. In some embodiments, the material of device 200 may be a medical grade biocompatible plastic. In some embodiments, device 200 may be sterilizable, and the material of device 200 may be an autoclavable plastic, for example, polyethylene, polypropylene, or polycarbonate. In some embodiments, body 210, first connector 240, and second connector 270, may be manufactured via injection molding or additive manufacturing techniques, such as 3D printing.

In one exemplary embodiment, body 210 of device 200 is made of a clear plastic so that the plurality of particles 300 inside chamber 222 of body 210 are visible to the user. Particles 300 contained in device 200 have lipase immobilized on their surfaces, and as nutritional formula 110 flows through chamber 222 and particles 300, the immobilized lipase hydrolyzes the fats and triglycerides, including triglycerides having LC-PUFAs, in nutritional formula 110, breaking them down into monoglycerides and free fatty acids. Particles 300 contained in chamber 222 are discussed in detail further below.

Figure 5:
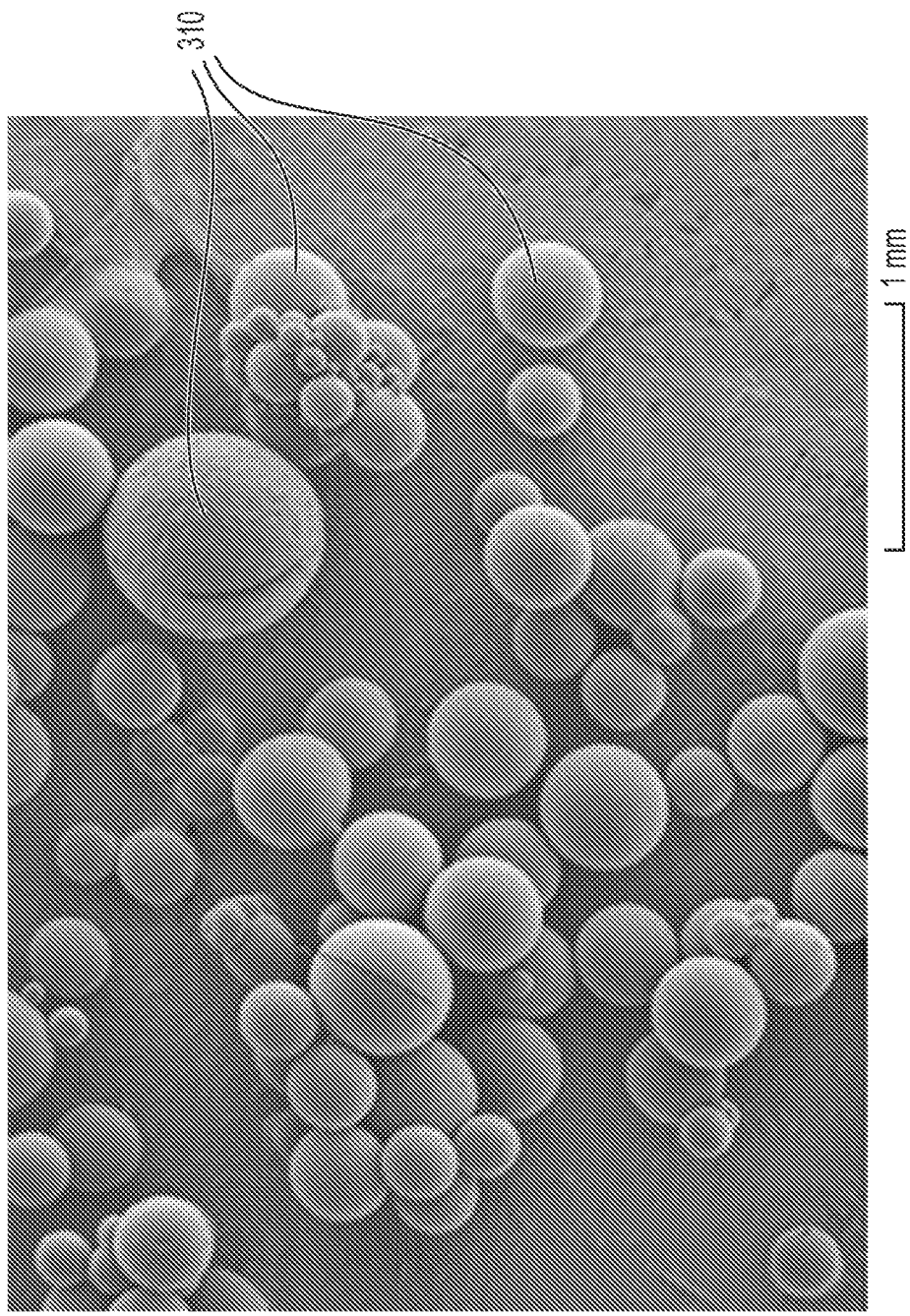
FIG. 5 is a scanning electron microscope image of exemplary particles, according to embodiments of the present disclosure.

As shown in FIG. 5, in some embodiments, an exemplary particle 310 of particles 300 may be formed as a substantially spherical bead. In some embodiments, particle 310 may have a diameter ranging from about 100 μm to about 800 μm, from about 100 μm to about 700 μm, from about 100 µm to about 600 µm, from about 100 µm to about 500 µm, from about 100 µm to about 400 µm, from about 100 µm to about 300 µm, from about 100 µm to about 200 µm, from about 200 µm to about 800 µm, from about 200 µm to about 700 µm, from about 200 µm to about 600 µm, from about 200 µm to about 500 µm, from about 200 µm to about 400 µm, from about 200 µm to about 300 µm, from about 300 µm to about 800 µm, from about 300 µm to about 700 µm, from about 300 µm to about 600 µm, from about 300 µm to about 500 µm, from about 300 µm to about 400 µm, from about 400 µm to about 800 µm, from about 400 µm to about 700 µm, from about 400 µm to about 600 µm, from about 400 µm to about 500 µm, from about 500 µm to about 800 µm, from about 500 µm to about 700 µm, from about 500 µm to about 600 µm, or from about 600 µm to about 800 µm. In other embodiments, particle 310 may be a randomly shaped or irregular particle, or may be elliptical, oblong, donut-shaped, a prism, polygonal, elongated, or any other suitable shape. Particle 310 may have a smooth or a textured surface. Particle 310 may be shaped to increase or decrease its surface area. Particles 300 may be formed of individual particles 310, which may each have substantially the same shape and/or surface or may have two or more different shape and/or surface combinations.

In some embodiments, particles 300 have about the same diameter. Alternatively, particles 300 may have different diameters following a skewed or a normal distribution. In some embodiments, the average diameter of particles 300 may range from about 250 µm to about 500 µm—for example, approximately 260 µm or approximately 460 µm—and may follow a normal distribution. In some embodiments, a skewed distribution of the diameters of particles 300 may have a mean diameter or a median diameter falling between about 100 µm and about 800 µm. In some embodiments, particles 300 may be pre-selected by a sieving process to filter out particles having diameters smaller than a lower size threshold and/or larger than an upper size threshold. Sieving may allow for more control and manipulation of the size and size distribution of particles 300. For example, particles 300 selected from one sieving process may have a narrower distribution of diameters and/or a larger or smaller mean or median diameter compared to those of particles 300 before the sieving process. In some embodiments, a mean or median diameter of particles 300 may be about 100 µm, about 150 µm, about 200 µm, about 250 µm, about 300 µm, about 350 µm, about 400 µm, about 450 µm, or about 500 µm. In some embodiments, fines (much smaller particles, e.g., having diameters of less than approximately 50 µm) may be present, while in others, the fines may be absent from particles 300 included in device 200. Fines may be manufactured or may occur during the manufacture of larger particles 300, e.g., as a result of the recipe or as a result of hydrodynamics of a reactor vessel. Fines may occur while manufacturing larger particles 300 and may be removed or left in the mixture of particles, or fines may be manufactured separately and added to larger particles 300, e.g., to increase the total surface area per unit volume or to allow proper flow rate, which, in some embodiments, may increase hydrolysis efficiency.

In some embodiments, particles 300 may be formed of different sub-portions of particles, and each sub-portion may have a different median or mean diameter or a different distribution of diameters. For example, in such embodiments, particles 300 may have a bimodal or multi-modal distribution.

Particles 300 may be made of any suitable material, e.g., a polymeric material, a metal, etc. In some embodiments, particles 300 may be made of acrylate polymers or acrylics. In some embodiments, particles 300 may be made of a copolymer formed of multiple different monomers. For example, particles 300 may be made of a copolymer having three monomers, such as ethylene glycol dimethacrylate (EGDMA), butyl methacrylate (BMA), and glycidyl methacrylate (GMA). In some embodiments, EGDMA may range from about 25% to about 99% by weight, for example, from about 50% to about 60% by weight, of the composition of the copolymer. In some embodiments, BMA may range from about 1% to about 75% by weight, for example, from about 30% to about 45% by weight, of the composition of the copolymer. Exemplary embodiments may contain EGDMA and BMA levels of 90% and 9%, respectively; 60% and 39%, respectively; or 58% and 41%, respectively. In some embodiments, GMA may range from about 0.01% to about 0.1%, from about 0.1% to about 1%, from about 1% to about 2%, from about 2% to about 5%, from about 5% to about 8%, from about 8% to about 10%, from about 10% to about 15%, from about 15% to about 20%, from about 0.01% to about 10%, from about 0.01% to about 15%, or from about 0.01% to about 20% by weight of the composition of the copolymer. Exemplary embodiments may contain epoxide levels (e.g., GMA) of 0%, 0.25%, 1%, 2%, or 5%.

In some embodiments, particles 300 may be made of styrene polymers or styrenes, caprolactone polymers or caprolactone, polydivinylbenzene polymers or polydivinylbenzene, polyamides polymers or polyamides, polycarbonate polymers or polycarbonates, polypropylene polymers or polypropylene, polyurethane polymers or polyurethane, polyethylene polymers or polyethylene, methacrylate polymers or methacrylates, divinylbenzene (DVB) polymers or divinylbenzene, or of silica. Additional exemplary types of polymers suitable for making particles 300 may include one or more selected from polymethacrylate, polyacrylate, polyurethane, polycarbonate, polydivinylbenzene, caprolactone, polystyrene, polyethylene, polypropylene, polyurethane, polyamides, and polydivinylbenzene monomers, for example.

In some embodiments, particles 300 may be pre-selected and packaged in device 200 during manufacture of device 200. In some embodiments, particles 300 may be packaged under dry conditions and placed in chamber 222 of device 200 before being used in system 100. For example, the size, type, or size distribution of particles 300 may be altered or selected depending on the intended use of device 200, and a user may package the necessary particles 300 in device 200 depending on that specific use. A moisture level of particles 300 upon being manufactured and/or packaged in device 200 may range from about 0.1% to about 1%, from about 1% to about 2%, from about 2% to about 3%, from about 3% to about 4%, from about 4% to about 5%, from about 0.1% to about 2%, from about 0.1% to about 3%, from about 0.1% to about 4%, or from about 0.1% to about 5% of water in the total composition of particles 300.

In some embodiments, the polymeric material of particles 300 may be insoluble in acidic, basic, aqueous, and/or organic solvents. In some embodiments, particles 300 may be dispersed or suspended in an aqueous solvent, an organic solvent, and/or an emulsion, for example, such as an oil-in-water or water-in-oil emulsion. In exemplary embodiments, when nutritional formula 110 is driven by pump 120 or by gravity to flow through chamber 222, particles 300 may be dispersed or suspended in nutritional formula 110, and may move under the influence of the flow dynamics of nutritional formula 110 and/or random Brownian motion.

In some embodiments, particles 300 may swell upon being dispersed or suspended in a solvent. As described herein, swelling of particles 300 may refer to an increase in volume of particles 300, at least in part, due to absorption of the solvent by particles 300. Depending on the composition of particles 300 (e.g., polymeric material), the porosity of particles 300, and/or the composition of the solvent, particles 300 may swell to different degrees when wetted. For example, the amount of swelling may vary depending on solution conditions. Bead swelling may be greater in polar solvents, such as ethanol or acetone, whereas bead swelling may be less in water and water-based solutions. For example, particles 300 may swell by about 1% to about 25% in aqueous solutions and by about 50% to about 100% in organic solvents, such as, for example, ethanol, isopropanol, or acetone. In some embodiments, when particles 300 are dispersed or suspended in nutritional formula 110, the amount of swelling of particles 300 may depend on the composition, such as fat content, protein content, vitamin content, ion content, etc., of nutritional formula 110. In some embodiments, the amount of swelling of particles 300 in nutritional formula 110 may be minimal or none. In some embodiments, the amount of swelling of particles 300 in nutritional formula 110 may be less than about 1%, about 2%, about 5%, about 10%, about 20%, about 30%, about 40%, or about 50% of the original, dry volume.

Figure 6B:
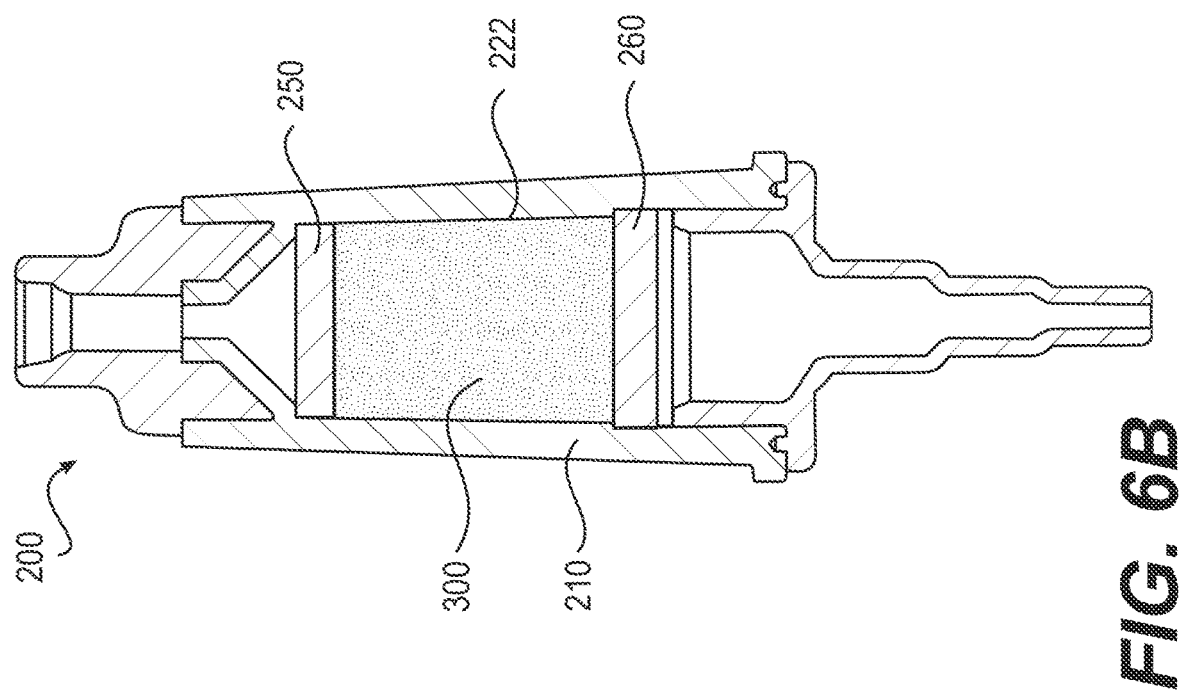
FIG. 6B illustrates a cross-section of an exemplary fat hydrolysis device, according to embodiments of the present disclosure.
Figure 6A:
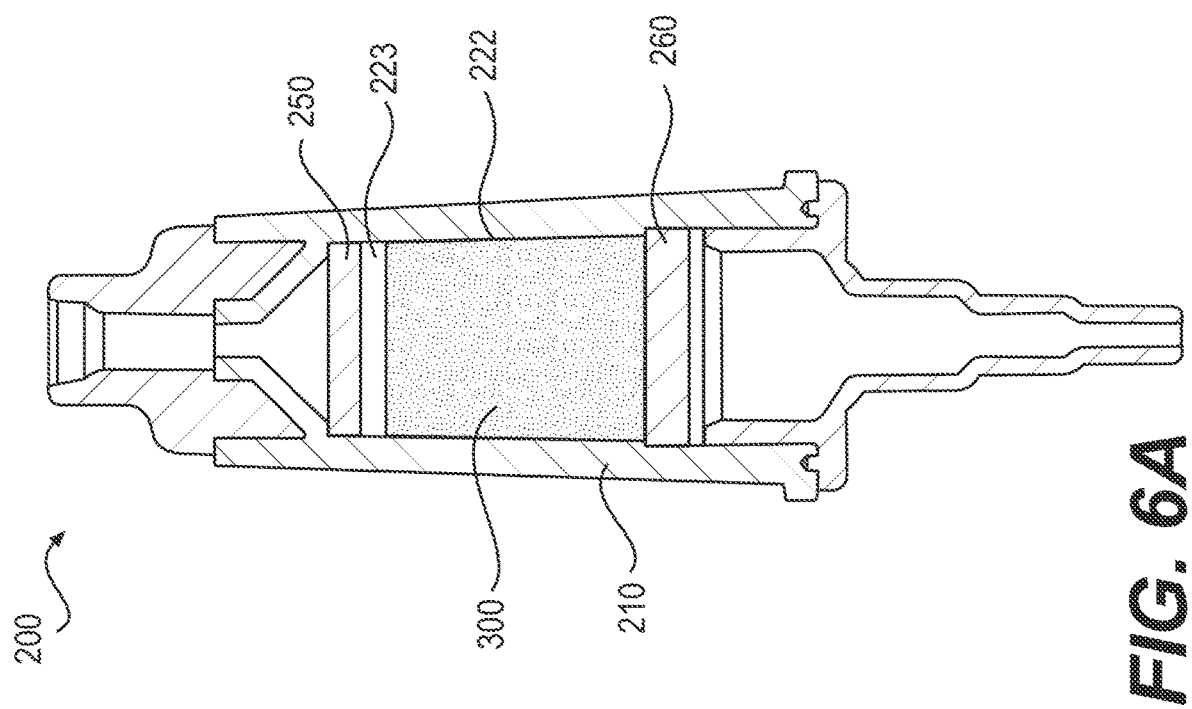
FIG. 6A illustrates a cross-section of an exemplary fat hydrolysis device, according to embodiments of the present disclosure.

As shown in FIG. 6A, in some embodiments, chamber 222 of body 210 may include a headspace 223 that is not occupied by particles 300 under dry conditions. Chamber 222 may be filled with particles 300 when particles 300 are dry, e.g., contain less that 5% water by weight. For example, when particles 300 are dry before nutritional formula 110 is flowed into chamber 222, headspace 223 may take up from about 0 to about 5%, from about 5% to about 10%, from about 5% to about 15%, from about 10% to about 15%, from about 15% to about 20%, from about 20% to about 30%, from about 30% to about 40%, from about 40% to about 50%, from about 5% to about 20%, from about 5% to about 30%, from about 5% to about 40%, from about 5% to about 50%, or from about 0 to about 50% of the volume of chamber 222. The initial, dry volume of headspace 223 depends on the number or volume of particles 300 packaged in chamber 222 and, in some embodiments, may be selected based on the propensity for particles 300 to swell when exposed to liquid.

Swelling may affect the number of particles 300 included in chamber 222 and/or the fill level of chamber 222. In embodiments in which particles 300 have a propensity to swell, adequate head space may be left in chamber 222 when dry particles 300 are loaded into chamber 222 to allow room for swelling to occur once a nutritional formula is introduced into device 200 and particles 300 are wetted. Devices with insufficient headspace above particles 300 in chamber 222 may have increased risk of flow obstruction as particles 300 swell, causing an increase in pressure against inlet and outlet filters 250, 260 that contain particles 300 within chamber 222. Depending on the material used to form particles 300, the propensity for swelling may be higher or lower depending on the type of nutritional formula 110 used. In some embodiments, the volume of headspace 223 prior to use may depend on the composition of nutritional formula 110. And, in some embodiments, the type of particles 300 or volume of headspace 223 may at least in part be selected according to the type of nutritional formula 110 that device 200 will be used with.

As shown in FIG. 6B, in some embodiments, when nutritional formula 110 is flowed through chamber 222, headspace 223 may be occupied by nutritional formula 110 with particles 300 suspended therein. For example, when nutritional formula 110 flows through chamber 222, particles 300 may mix with nutritional formula 110 and may move in nutritional formula 110 so that the volume of headspace 223 that was not occupied by particles 300 under dry conditions may be filled as nutritional formula 110 and particles 300 disperse to fill chamber 222. Incorporating headspace 223 may give particles 300 space in chamber 222 to be mobile and to move and/or mix with nutritional formula 110 under the influence of the flow dynamics of nutritional formula 110. In some embodiments, including headspace 223 may facilitate a reduction in channeling or shunting or facilitate the distribution of nutritional formula 110 through the particles by allowing particles 300 to move, flow, and/or mix, rather than becoming packed against outlet filter 260. Alternatively, including too much headspace 223 may also lead to channeling of nutritional formula 110 around particles 300, particularly when device 200 is oriented horizontally. For example, when device 200 is positioned horizontally, particles 300 may float to the top of nutritional formula 110, leaving a channel beneath particles 300. As a result, nutritional formula 110 may channel and flow under particles 300, potentially reducing hydrolysis efficiency. Additionally, by reducing the amount of particles 300 in device 200 to provide more headspace, the amount of lipase in device 200 is also reduced, since the lipase is bound to particles 300. As a result, too much headspace 223 may cause decreased effective hydrolysis for a given amount of nutritional formula 110, because it is the lipase bound to particles 300 that breaks down nutritional formula 110. Leaving too much headspace 223 means fewer particles 300 are contained within chamber 222, and thus less lipase is contained in chamber 222, leaving too few particles 300 to hydrolyze all of, or a majority of, the triglycerides in nutritional formula 110.

In some embodiments, particles 300 undergo minimal or no swelling when suspended in nutritional formula 110, and thus when nutritional formula 110 flows through chamber 222, the space for particles 300 to move in chamber 222 may be substantially the same as the volume of headspace 223 initially in chamber 222. In some embodiments, particles 300 may swell when exposed to in nutritional formula 110, and thus when nutritional formula 110 flows through chamber 222, the swelling of particles 300 may partially reduce the space for particles 300 to move within chamber 222. For example, if under dry conditions, headspace 223 takes up about 10% of the volume of chamber 222 and particles 300 take up about 90% of the volume of chamber 222, when nutritional formula 110 flows through chamber 222, swelling of particles 300 may cause particles 300 to take up an additional 5% of the volume of chamber 222, reducing the space left for particles 300 to move to about 5% of the volume of chamber 222. Having more space for particles 300 to move may increase the mobility of particles 300 in chamber 222. Thus, in some embodiments, the swelling of particles 300 may reduce the mobility of particles 300 compared to the original, dry volume.

In some embodiments, as shown in FIG. 6B, upon swelling, particles 300 may become packed, resulting in friction between the surfaces of particles 300, which may limit or affect the flow or movement of some or all of particles 300. Insufficient headspace 223 may result in an increase in pressure due to packing of particles 300, which may cause clogging or a reduction in the flow rate of nutritional formula 110 during use. In other embodiments, particles 300 may not swell when suspended in nutritional formula 110. In some embodiments, it may not be necessary for particles 300 to move as much when exposed to nutritional formula 110. In such situations, chamber 222 may not include headspace 223, or may include less of a headspace, if substantially no swelling of particles 300 occurs. In some embodiments, particles 300 may be prone to swelling, and chamber 222 may have a predetermined volume of headspace 223 that becomes substantially filled or partially filled upon swelling of particles 300 during use. In such embodiments, sufficient headspace 223 may be incorporated to allow room for particles 300 to swell when wetted and to allow for sufficient space between particles 300 to allow room for nutritional formula 110 to flow through particles 300 during use.

Preliminary experimentation has demonstrated that overfilling chamber 222 with particles 300—and not leaving enough headspace 223—may result in clogging or flow obstruction when particles 300 swell and pack against each other. In an exemplary test run, 1.2 g of particles 300 was filled into a 3.70 mL chamber 222 having an interior diameter of approximately 1.56 cm, a height of approximately 1.94 cm, and a volume of approximately 3.70 mL. This left a headspace 223 of approximately 1/32 to approximately 2/32 inches above particles 300 in chamber 222. A semi-elemental nutritional formula was flowed through device 200 at a pump setting of 120 mL/hr. Under these conditions, approximately 500 mL of nutritional formula would be expected to be delivered within approximately 4 hrs. and 10 min. At the 1.2 g fill level, a significantly slower flow rate was observed through device 200. In the next runs, the fill weight was reduced to 1.1 g of particles 300 and then 1.0 g of particles 300, incrementally increasing the amount of headspace 223 in chamber 222 to approximately 3/32 inches and to approximately 4/32 inches, respectively. Two runs were performed at each fill level. The results are show below. Reducing the amount of particles 300 in device 200 from 1.2 g to 1.1 g or 1.0 g (providing slightly more headspace) yielded flow rates that were more in line with the expected flow rates, based on the pump setting, indicating reduced or eliminated flow obstruction. The reduced amount of particles 300 did not appear to impact effectiveness.

TABLE 0

Particle fill amount and run time

| Particle fill amount | Run time |
|---|---|
| 1.2 g | 4 hr 32 min |
| 1.2 g | 5 hr 54 min |
| 1.1 g | 4 hr 2 min |
| 1.1 g | 4 hr 0 min |
| 1.0 g | 4 hr 3 min |
| 1.0 g | 4 hr 12 min |

Although the fill-level test described above refers to particle fill amount in terms of weight and describes an amount of headspace provided when chamber 222 is filled with a certain weight of particles, it is understood that if the size of chamber 222 is changed, or if a different size or density of particle is used, then filling chamber 222 with the exemplary weight of particles may yield a different amount of headspace. Headspace depends on the size and volume of the chamber and the size, type, and amount of particles.

The ratio of particle fill weight and headspace also depends on the density of the particles. While direct measurement and observation of headspace amount may be used to fill chamber 222 of device 200, use of weight to fill device 200 may reduce fill variability that may be caused by static on particles 300. Static may cause particles 300 to initially take up more room in chamber 222, but, after particles 300 are allowed to settle and the static is allowed to dissipate, particles 300 may compress and take up less space in chamber 222, ultimately providing more headspace 223 than was intended upon initial visual observation of headspace 223. Using weight to assess fill level may, in some embodiments, help to control for the presence of static. Additionally or alternatively, static-removing measures may be utilized on particles 300 prior to filling.

As alluded to above, however, under-filling devices 200, and leaving too much headspace 223, may result in decreased fat hydrolysis. In a preliminary fill-level test, devices 200 were filled with various amounts of particles 300, ranging from 1.1 g to 0.6 g. The percent hydrolysis for the 1.1 g fill level was calibrated to 100%. The 0.8 g and 0.6 g fill levels displayed decreased hydrolysis of 77% and 65%, respectively, relative to the 1.1 g fill level, which was set at 100%.

As discussed above, the content of the solution to which particles 300 are exposed may affect the swelling of particles 300. Therefore, particles 300 may swell by different amounts, depending on the type and content of the nutritional formula 110 to which particles 300 are exposed. A preliminary study was conducted to assess the swelling of exemplary particles 300 upon exposure to water, to ethanol, and to two different nutritional formulas, Peptamen®, a product of Nestle, and TwoCal® HN, a product of Abbott. In this experiment, approximately 10 to 20 particles 300 were placed onto each of 4 different 100 μm mesh filters. The sample of particles 300 on each filter was measured under a microscope in both the X and Y directions to determine the size of each of the particles 300 in a given sample in a dry state. Then, the filters, with the respective particle sample still on each of them, were carefully placed into their own filter housings. Each of the filters and respective particles was exposed to one of the 4 solutions (water, ethanol, Peptamen®, or TwoCal®). Each solution was pumped through the respective filter for 30 minutes at a pump flow rate of 120 mL/hr. After 30 minutes of exposure, the filters with the respective particles (still on top of the filters) were placed back under the microscope, and each particle on each filter was again measured in both the X and Y directions to determine the size of the particles in the wetted state. Due to the shifting of the particles on the filters during the experiment, the swelling of any individual particle was not tracked. Instead, each particle of the sample of 10-20 particles on each filter was measured before and after exposure to the respective solution, and the average measurements of each particle in a sample before and after wetting were compared for each particle sample. The results are shown below in Table 1. As is demonstrated, different solutions (or different nutritional formulas) may cause different amounts of swelling to occur, even when the same particle type is used.

TABLE 1

Swelling of particles after exposure to solutions

| Wetting agent | Before wetting (average size μm) | After wetting (average size μm) | Average delta (μm) | % Difference |
|---|---|---|---|---|
| Water | 197 | 212 | 15 | 8 |
| TwoCal HN ® | 188 | 210 | 22 | 12 |
| Peptamen ® | 192 | 217 | 25 | 13 |
| Ethanol | 171 | 196 | 25 | 15 |

In some embodiments, particles 300 that swell at or below a certain threshold amount may be used in device 200. For example, particles 300 may be selected that have a percent difference between their dry state and their wetted state of 15% or less, 20% or less, 25% or less, or 30% or less.

In some embodiments, device 200 may be filled with particles 300 so as to accommodate variable amounts of swelling that may occur when different types of nutritional formulas 110 are used with device 200. For example, the fill level, and thus headspace 223, of chamber 222 may be determined based on the amount of swelling that would occur when particles 300 are exposed to a nutritional formula that causes a maximum average amount of swelling of particles 300, compared to other types of nutritional formulas. In such embodiments, the amount of particles 300 or headspace 223 provided may accommodate even this maximum amount of swelling. In other embodiments, chamber 222 may be filled with an amount of particles 300 that provides an amount of headspace 223 to accommodate use with a particular nutritional formula 110 or a particular category of nutritional formulas. That particular nutritional formula 110 or particular category of nutritional formulas may comprise a type of solvent that causes a certain amount of swelling in particles 300, and thus a device 200 tailored for use with this nutritional formula or category of formulas may include an amount of particles 300 and/or headspace 223 able to accommodate the range of swelling that typically occurs with that particular formula or category of formulas. In such embodiments, the device 200 may be packaged with instructions for use with that particular formula or category of formulas. Or, the device may be sold with that particular nutritional formula.

The absolute number of particles 300 in chamber 222 may depend on the diameters, shapes, and size distributions of particles 300 and the volume of chamber 222. In some embodiments, space may exist between particles 300 and particles 300 may be less tightly packed, or, in some embodiments, less space may exist between particles 300 and particles 300 may be closer together. For example, spherical particles 300, when placed together, may have spaces between adjacent particles, and thus particles 300 may not take up all of the space in chamber 222 or the space in chamber 222 available after accounting for headspace 223. For example, the total volume of particles 300 may take up from about 50% to about 100%, from about 90% to about 95%, from about 85% to about 95%, from about 85% to about 90%, from about 80% to about 85%, from about 70% to about 80%, from about 60% to about 70%, from about 50% to about 60%, from about 80% to about 95%, from about 70% to about 95%, from about 60% to about 95%, from about 60% to about 100%, from about 70% to about 100%, from about 80% to about 100%, or from about 90% to about 100% of the space in chamber 222. In some embodiments, the number of particles 300 in chamber 220 may range from about 10,000/mL to about 25,000/mL, from about 25,000/mL to about 50,000/mL, from about 50,000/mL to about 75,000/mL, from about 75,000/mL to about 100,000/mL, from about 100,000/mL to about 200,000/mL, from about 200,000/mL to about 300,000/mL, from about 300,000/mL to about 400,000/mL, from about 400,000/mL to about 500,000/mL, from about 500,000/mL to about 600,000/mL, from about 600,000/mL to about 700,000/mL, from about 700,000/mL to about 800,000/mL, from about 800,000/mL to about 900,000/mL, or from about 10,000/mL to about 1,000,000/mL, depending on the particle size and distribution.

In some embodiments, particles 300 in device 200 may be made up of different groups of particles having different median or mean diameters, and chamber 222 may contain different numbers of particles 300 from each size group. In some embodiments, different groups of particles having different median or mean diameters may be mixed together and/or distributed randomly in chamber 222. In other embodiments, particles 300 of different size groups may be substantially separated in layers, at least in a dry state prior to use.

In some embodiments, the mass density of individual particles 300 may or may not vary. The mass density of particles 300 may be adjusted by adjusting the materials forming particles 300, by modifying the monomer components of the copolymer of particles 300, by adjusting the size and diameters of the pores and/or channels of particles 300, and/or by introducing voids, pores, or a hollow core in particles 300. In some embodiments, particles 300 may have different mass densities. In some embodiments, if device 200 is placed in a vertical position with outlet 230 or outlet 282 pointing down, when nutritional formula 110 flows through chamber 222, particles 300 having a larger mass density than nutritional formula 110 may tend to flow or move towards outlet filter 260 and particles 300 having a smaller mass density than nutritional formula 110 may tend to float or move towards inlet filter 250. In some embodiments, particles 300 with a larger mass density than nutritional formula 110 may collect along outlet filter 260 and may clog some of the pores of outlet filter 260. In some embodiments, particles 300 with a smaller mass density than nutritional formula 110 may collect along inlet filter 250 and may clog some of the pores of inlet filter 250.

In some embodiments, the mass density of particles 300 may be selected to more closely match the density of nutritional formula 110 such that particles 300 may be dispersed or suspended in nutritional formula 110, and may move more with the flow dynamics of nutritional formula 110. In some embodiments, particles 300 may be dispersed or suspended in nutritional formula 110 and may move more with the flow dynamics of nutritional formula 110, depending on the orientation of device 200. This may decrease the propensity of particles 300 to collect at inlet filter 250 or outlet filter 260 and may promote more a centralized or dispersed distribution of particles.

In some embodiments, different groups of particles 300 having different median or mean diameters may have different mass densities. This may reduce the concern for filter clogging by promoting a more-dispersed distribution of particles in nutritional formula 110. In some embodiments, particles 300 may be divided into one or more groups having an average mass density that substantially equals that of nutritional formula 110, that are less than that of nutritional formula 110, and that are more than that of nutritional formula 110. In some embodiments, particles 300 of about the same size, or having about the same median or mean diameters, or whose diameters follow the same distribution, may have about the same or may have different mass densities. In some embodiments, the mass density of particles 300 in chamber 222 may range from about 0.25 g/mL to about 0.36 g/mL, from about 0.25 g/mL to about 0.5 g/mL, from about 0.5 g/mL to about 0.8 g/mL, from about 0.8 g/mL to about 1.0 g/mL, or from about 1.0 g/mL to about 1.5 g/mL, for example.

Figure 7B:
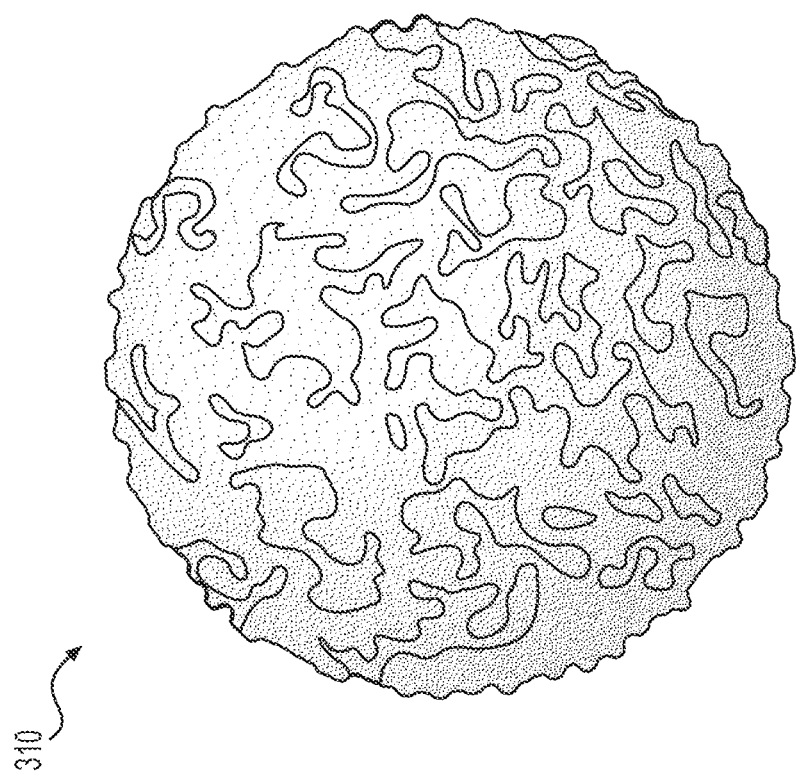
FIG. 7B illustrates a magnified view of a surface of an exemplary particle, according to embodiments of the present disclosure.
Figure 7A:
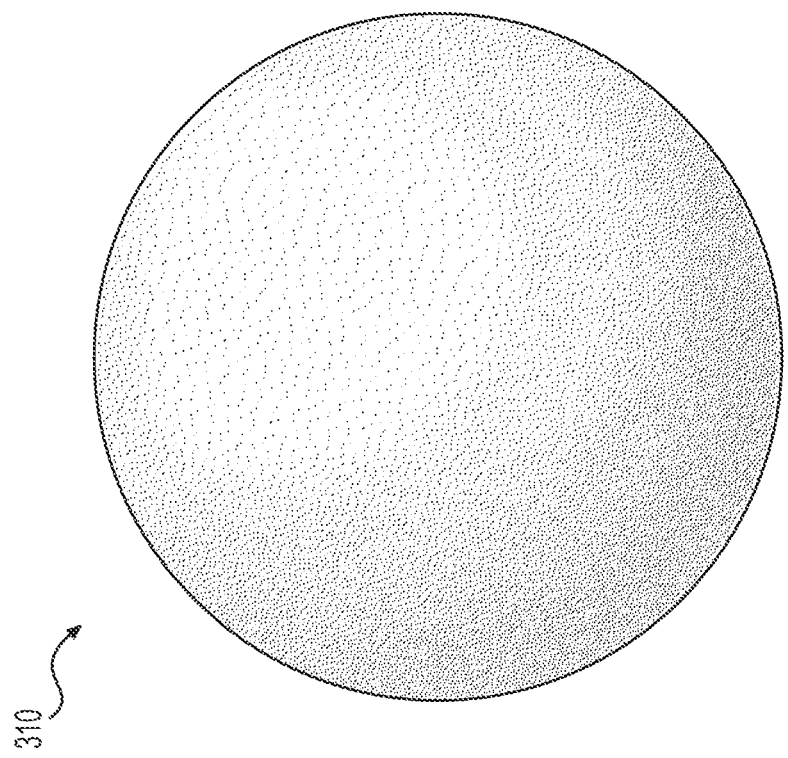
FIG. 7A illustrates a magnified view of a surface of an exemplary particle, according to embodiments of the present disclosure.

As shown in FIG. 7A, the surface of an individual particle 310 may be generally smooth. In another embodiment, as shown in FIG. 7B, the surface of a particle 310 may be uneven, irregular, or textured and may include, for example, grooves, channels, indents, projections, and/or pores. In some embodiments, the depth and/or diameters of the pores and/or grooves on the surface of particle 310 may range from about 1 nm to about 10 nm, from about 10 nm to about 50 nm, from about 50 nm to about 100 nm, from about 100 nm to about 250 nm, from about 250 nm to about 500 nm, from about 500 nm to about 1 μm, from about 1 μm to about 5 μm, from about 5 μm to about 10 μm, from about 10 μm to about 20 μm, from about 20 μm to about 30 μm, from about 30 μm to about 40 μm, from about 40 μm to about 50 μm, from about 10 nm to about 50 μm, or from about 1 nm to about 50 μm. In some embodiments, the grooves and/or pores of particle 310 may form any random geometric shape, may be irregularly distributed on the surface, may be regularly shaped, and/or may be regularly distributed. In some embodiments, the size of the grooves and/or pores may depend on the composition of the polymeric material of particle 310. A non-smooth particle 310 will have a larger surface area than a smooth particle 310 of the same shape having the same diameter.

In some embodiments, particles 300 in chamber 222 may include a plurality of particles 310 shown in FIG. 7A. In some embodiments, particles 300 in chamber 222 may include a plurality of particles 310 shown in FIG. 7B. In other embodiments, particles 300 in chamber 222 may include a mixture of particles 310 shown in FIG. 7A and particles 310 shown in FIG. 7B.

Figure 7D:
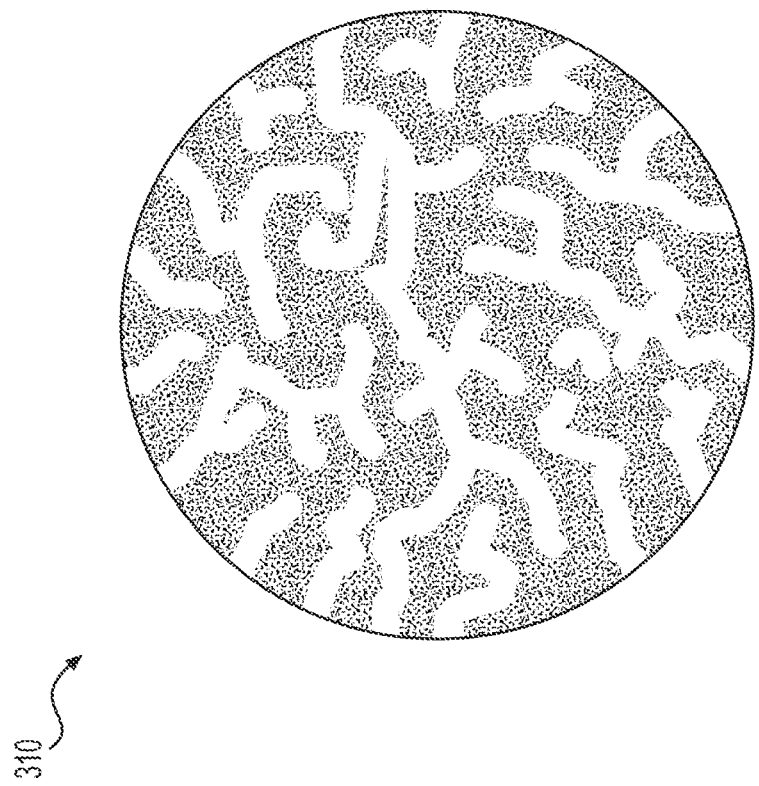
FIG. 7D illustrates a magnified cross-section of an exemplary particle, according to embodiments of the present disclosure.
Figure 7C:
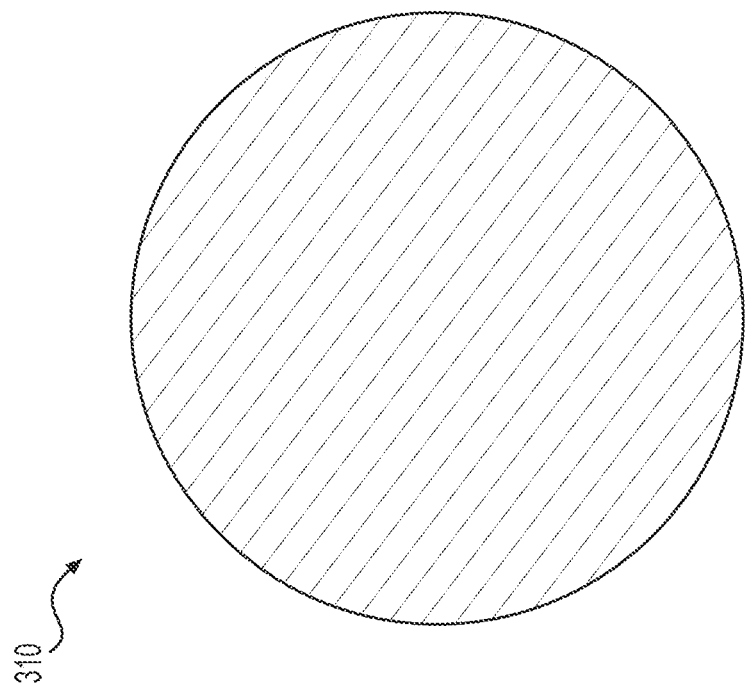
FIG. 7C illustrates a magnified cross-section of an exemplary particle, according to embodiments of the present disclosure.

FIGS. 7C and 7D show exemplary cross-sections of particle 310. In some embodiments, the interior of particle 310 may be generally compact or solid, as shown in FIG. 7C. As shown in FIG. 7D, in some embodiments, the interior of particle 310 may be porous and may have nanoscopic, microscopic, and/or macroscopic structures, such as, for example, pores and/or channels. In some embodiments, the pores and/or cross-sections of the channels may be, for example, generally circular, elliptical, or irregular in geometric shape. In some embodiments, the pores and/or channels may have network-type morphologies that can be either disordered or assembled into ordered arrays. In some embodiments, the surface of the pores and/or channels may be uneven, irregular, or textured, and may be similar to the exterior surface of particle 310. In some embodiments, the dimensions, such as the diameters and/or perimeters, of the pores and/or channels may vary along the length of the pores and/or channels, and may vary depending on the composition of particle 310 and/or the environment particle 310 is suspended in. In some embodiments, the dimensions, such as the diameters and/or perimeters, of the pores or channels, may increase or decrease when particle 310 is suspended in a solvent, such as nutritional formula 110. In some embodiments, the pores and/or channels of particle 310 may or may not connect with the surface of particle 310, may extend through particle 310 from surface to surface, or may extend for discrete lengths within particle 310.

For a porous particle 310, as shown in FIG. 7D, the overall surface area of particle 310 may be increased by the presence of internal pores and/or channels and may depend in part on the sizes, such as the diameters and/or perimeters, of the pores and/or channels. In some embodiments, the diameters of the pores and/or cross-sections of the channels in particle 310 may range from about 1 nm to about 10 nm, from about 10 nm to about 50 nm, from about 50 nm to about 100 nm, from about 100 nm to about 250 nm, from about 250 nm to about 500 nm, from about 500 nm to about 1 μm, from about 1 μm to about 5 μm, from about 5 μm to about 10 μm, from about 10 μm to about 20 μm, from about 20 μm to about 30 μm, from about 30 μm to about 40 μm, from about 40 μm to about 50 μm, from about 10 nm to about 50 μm, or from about 1 nm to about 50 μm. In some embodiments, the sizes of the pores and/or channels of particle 310 may be substantially the same or may vary.

As described herein, reference to the surface of particle 310 may refer to the outside surface of particle 310 and/or the internal surface of the pores and/or channels inside of particle 310. Also, reference to the surface area of particle 310 may refer to the surface area of the outside surface of particle 310 and/or the surface area of the pores and/or channels inside of particle 310 fluidly connected to the outside surface.

Figure 7F:
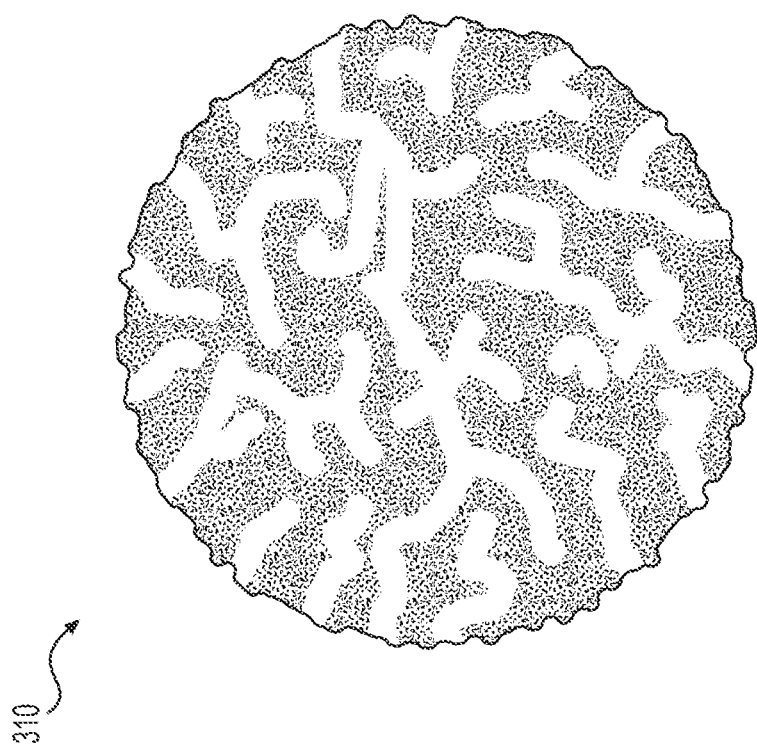
FIG. 7F illustrates a magnified cross-section of an exemplary particle, according to embodiments of the present disclosure.
Figure 7E:
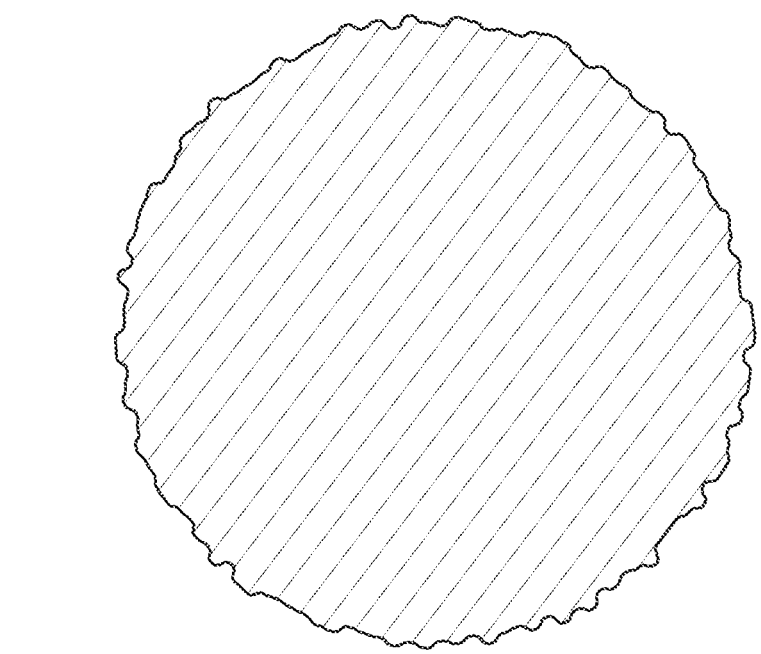
FIG. 7E illustrates a magnified cross-section of an exemplary particle, according to embodiments of the present disclosure.

The characteristics of various embodiments of particles discussed above may be combined in any suitable manner. In some embodiments, as shown FIG. 7C, particle 310 may have a smooth outside surface and a solid core. In some embodiments, as shown FIG. 7D, particle 310 may have a smooth outside surface and a porous core. In some embodiments, as shown FIG. 7E, particle 310 may have an uneven, irregular surface and a compact or solid core. In some embodiments, as shown FIG. 7F, particle 310 may have an uneven, irregular outside surface and a porous core. The combination of an uneven surface and a porous core may provide increased surface area for particle 310 of a given size or diameter compared to its smooth and/or solid counterpart.

Figure 8A:
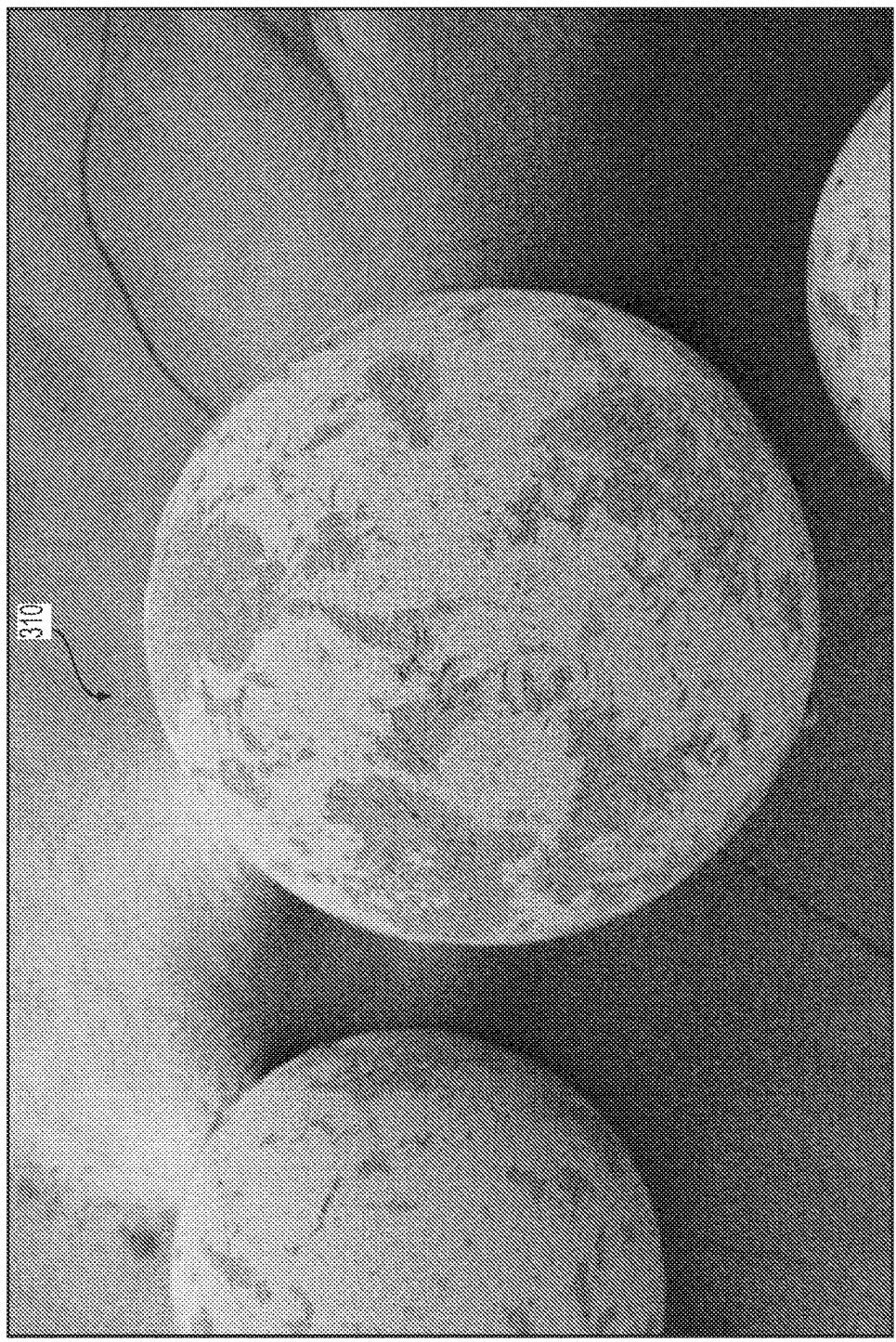
FIG. 8A is a scanning electron microscope image of exemplary particles, according to embodiments of the present disclosure.
Figure 8B:
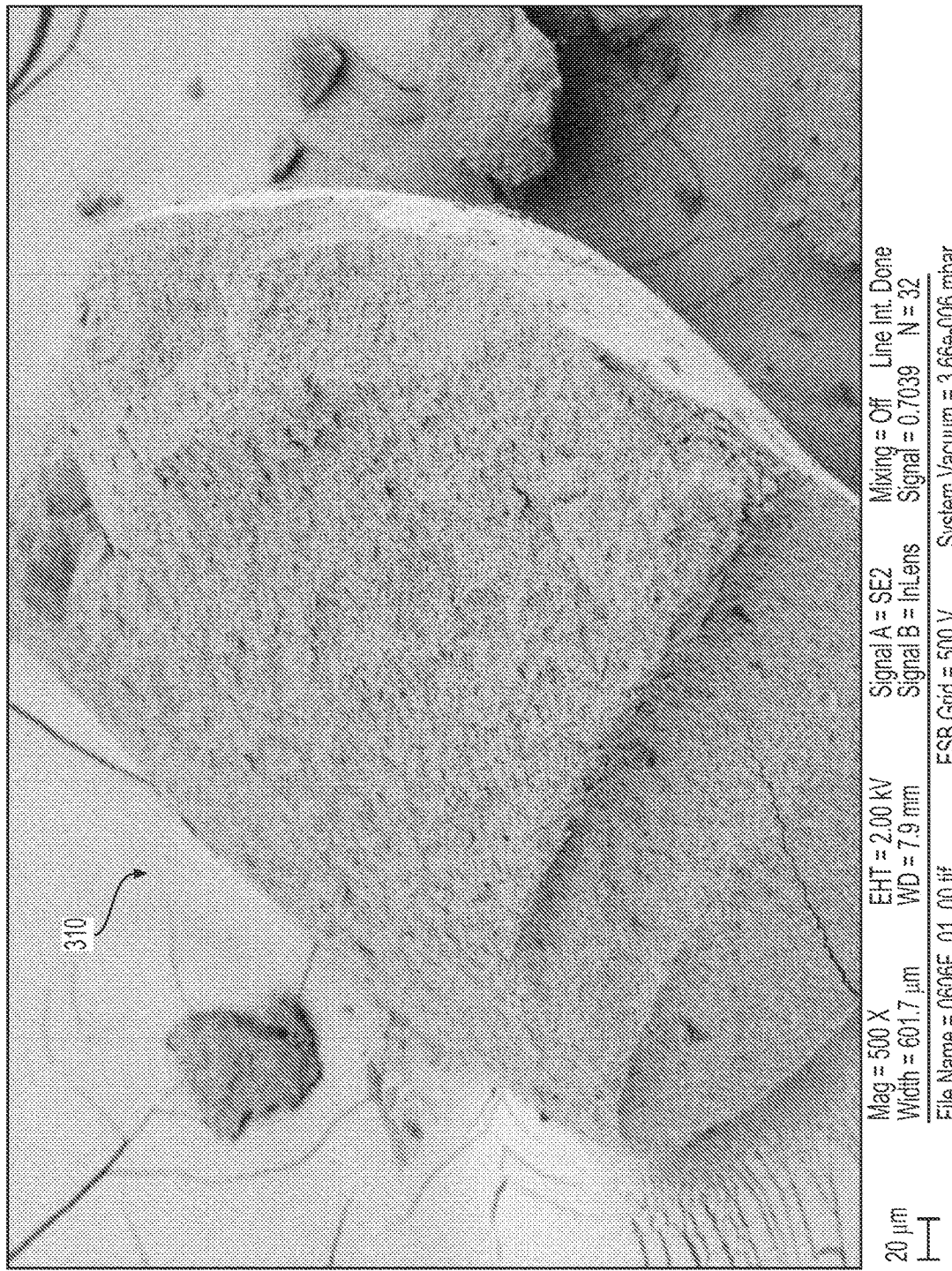
FIG. 8B is a scanning electron microscope image of a cross-section of an exemplary particle, according to embodiments of the present disclosure.
Figure 9:
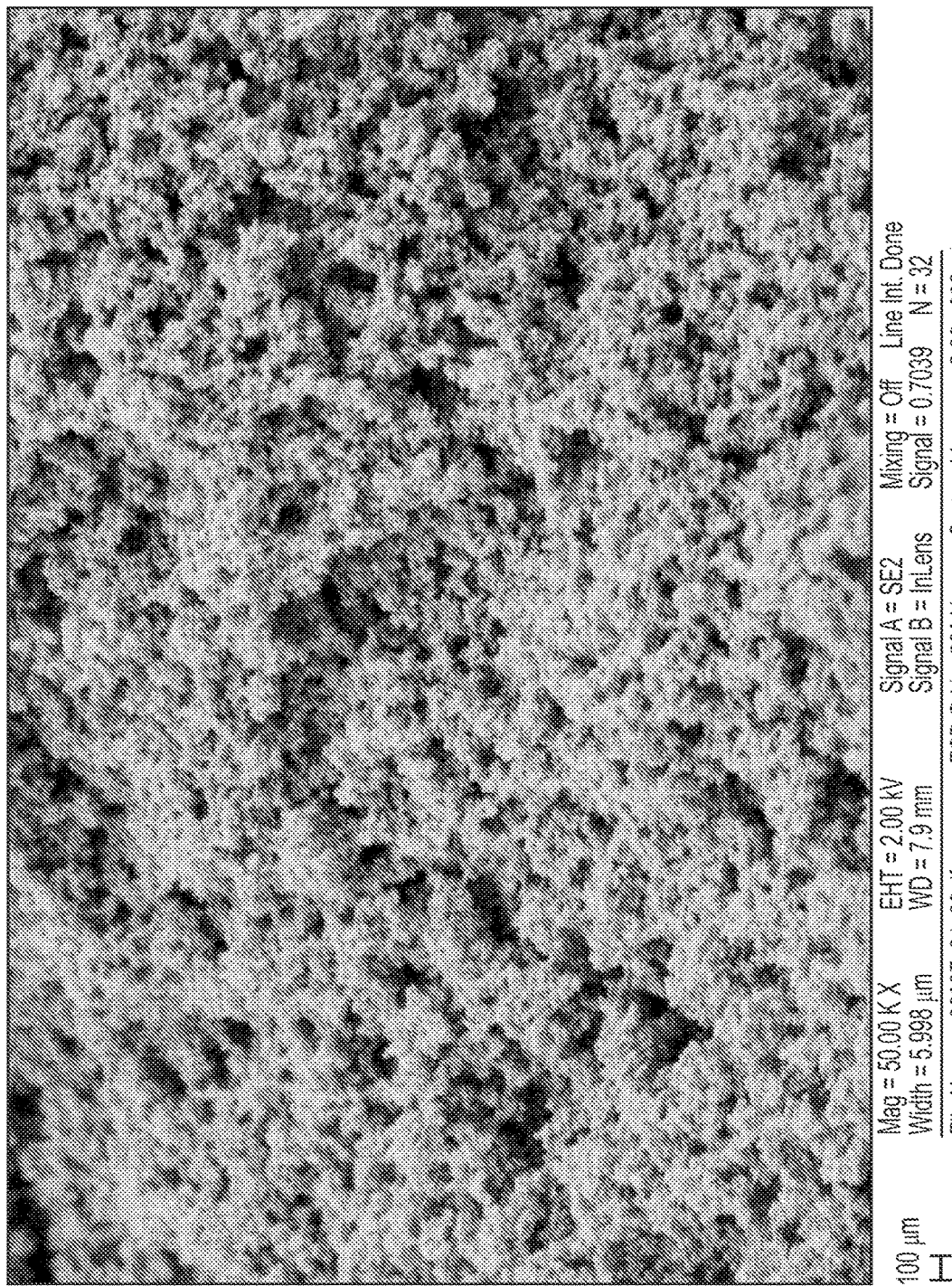
FIG. 9 is a scanning electron microscope image showing inner structures of an exemplary particle, according to embodiments of the present disclosure.

FIG. 8A is a scanning electron microscope image showing an exemplary embodiment of particle 310 magnified 500 times. The scale bar of the image is 10 μm. As shown in FIG. 8A, particle 310 has an uneven outside surface that has varied roughness at different locations. FIG. 8B is a scanning electron microscope image showing a cross-section of an exemplary embodiment of particle 310 magnified 500 times. The scale bar of the image is 20 μm. As shown in FIG. 8B, particle 310 has microscopic pores of varied sizes throughout its interior. FIG. 9 further shows the pores of an exemplary particle 310. FIG. 9 is a scanning electron microscope image showing an exemplary embodiment of the pores and channels inside of particle 310 magnified 50,000 times. The scale bar of the image is 100 nm. As shown in FIG. 9, the pores and channels inside of particle 310 have irregular sizes and shapes that vary at different locations.

In some embodiments, particles 300 may comprise one or more types of particle 310, for example, selected from one or more of the individual particles 310 shown in FIGS. 7A-7F, FIG. 8, and/or FIG. 9, or as discussed above. Different types of individual particles 310 may constitute different numbers of all particles 300 in a given device 200, and may have different distributions of roughness, smoothness, porosity, diameters, materials, densities, and/or swelling properties.

As discussed above, particles 300 contained in device 200 have lipase immobilized on their surfaces. Lipase may be immobilized on exterior surfaces of particles 300, interior surfaces of particles 300, or a combination of exterior and interior surfaces. In some embodiments, functional groups of monomers of the polymeric material of particle 310 may be present on the surface of particle 310 in order to bind lipase to particles 300. Porous particle 310 having inside structures, such as pores and/or channels, may include functional groups located on both the outside surface of particle 310 and the inside surface of the pores and/or channels. For example, the epoxy group of the monomer GMA of a copolymer material of particle 310 may be present on the surface of particle 310. In some embodiments, the epoxy groups may make up from about 0.01% to about 0.1%, from about 0.1% to about 1%, from about 1% to about 2%, from about 2% to about 5%, from about 5% to about 8%, from about 8% to about 10%, from about 10% to about 15%, from about 15% to about 20%, from about 0.01% to about 10%, from about 0.01% to about 15%, from about 0.01% to about 20% of the overall composition of polymeric particle 310 by weight. In some embodiments, the epoxy groups may be located on the outside surface of particle 310. In some embodiments, the epoxy groups may be located on the inside surface of the pores and/or channels or, in some embodiments, both the inside and outside surfaces of particle 310 may include epoxy groups or neither surface may include epoxy groups. In some embodiments, the surface density or concentration of epoxy groups on the outside surface of particle 310 may be higher or lower than that on the inside surface of the pores and/or channels of particle 310. In some embodiments, the amount of epoxy groups on the surface of particle 310 may be capped to limit binding of lipase to an excessive degree.

Figure 10A:
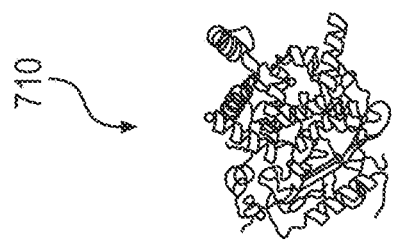
FIG. 10A is a schematic representation of the crystal structure of an exemplary lipase molecule, according to embodiments of the present disclosure.
Figure 10B:
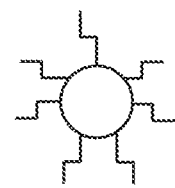
FIG. 10B is a schematic representation of an exemplary particle, according to embodiments of the present disclosure.
Figure 10C:
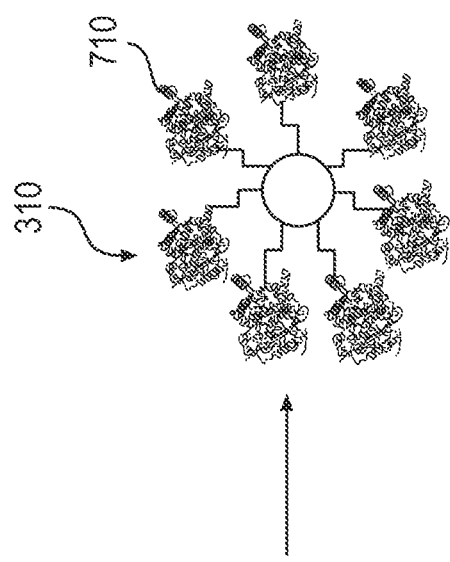
FIG. 10C is a schematic representation of a plurality of lipase molecules from FIG. 10A bound the exemplary particle of FIG. 10B, according to embodiments of the present disclosure.
Figure 10D:
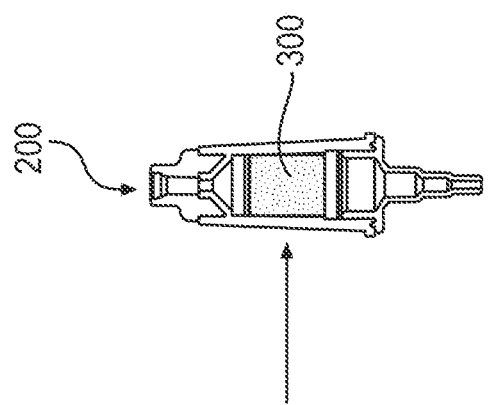
FIG. 10D illustrates a cross-section of an exemplary fat hydrolysis device containing a plurality of the bound particles of FIG. 10C, according to embodiments of the present disclosure.

In some embodiments, the functional groups located on the surface of particle 310 may be used to adsorb or to bind to biomolecules or chemical molecules. In some embodiments, lipase 710 that hydrolyzes fats, including long-chain triglycerides and/or long-chain esters, for example, triglycerides having LC-PUFAs, in nutritional formula 110, may be attached or immobilized to the surface of particle 310 by covalent binding. FIG. 10A shows an exemplary schematic of the crystal structure of lipase 710. FIGS. 10B-10C show exemplary schematics of the attachment of lipase 710 to particle 310. As shown in FIG. 10B, particle 310 may have functional groups on its surface and may function as a carrier of lipase 710. Lipase 710, as shown in FIG. 10C, may covalently bind to the functional groups on the surface of particle 310 in a solution, resulting in a layer of lipase 710 on the surface of particle 310. Additionally, as shown in FIG. 10D, a certain number of individual particles 310 having lipase 710 covalently bound to their surfaces make up particles 300 in device 200.

As known in the art and described herein, cross-linking may refer to a chemical bond that links one polymer chain to another. The chemical bond can be a covalent bond or an ionic bond. In some fields, cross-linking may also refer to the use of a chemical linker to link proteins together. As used herein, "covalent bond" and "covalent binding" refer to a stable, permanent or semi-permanent, irreversible, and/or covalent-like bond for the attachment of lipase 710 to particle 310.

The embodiments of the present disclosure allow lipase 710 immobilized by covalent binding to hydrolyze triglycerides or fatty acid esters in nutritional formula 110 as nutritional formula 110 flows through device 200 directly before ingestion by a subject. By covalently binding lipase 710 to particles 300 and including one or more filters, device 200 is configured so that only a small amount of lipase 710 or substantially no lipase 710 may be included in the nutritional formula 110 ingested by the subject. Although covalent binding is the primary way in which lipase 710 is immobilized on particles 300, it is possible that during the immobilization process, background levels of adsorption may occur. Thus, in some embodiments, lipase 710 may not be solely immobilized by covalent binding. Particles 300 with adsorbed lipase 710 may have lower hydrolysis activity than covalently bound lipase 710 on particles 300.

During the research of the present disclosure, adsorption was tested initially for attaching lipase 710 to particle 310. This is because adsorption is traditionally used for protein immobilization and works via hydrophobic forces. It is a simple and inexpensive means of immobilization. However, when adsorption was initially used for attaching lipase 710 to particles 300 when developing device 200, adsorption did not produce particles capable of effectively hydrolyzing fats in nutritional formula 110. After this initial testing, the inventors looked for other ways to immobilize or attach lipase 710 to particles 300. As has been noted in previous publications, attaching lipase 710 to particle 310 via covalent binding may reduce or limit the enzymatic activity of lipase 710. For example, the enzymatic activity of lipase 710 may be reduced when covalently bound to particle 310 compared to the enzymatic activity of lipase 710 in a soluble state. Thus, it was initially hypothesized that the enzymatic activity of lipase 710 attached to particle 310 by covalent binding may be less than that of lipase 710 attached to particle 310 by adsorption. Yet, the enzymatic activity of lipase 710 attached to particle 310 by covalent binding was greater than that of lipase 710 attached to particle 310 by adsorption. Further, adsorption did not achieve higher performance or efficiency for hydrolyzing fats in nutritional formula 110 when compared to covalent binding. Example 1, described below, compares the enzymatic activities of lipase 710 immobilized to particles 300 by adsorption and by covalent binding and suggests that lipase 710 immobilized to particles 300 by covalent binding has greater enzymatic activity, better performance in hydrolyzing fats, and less release of lipase 710 into nutritional formula 110.

Example 1: Comparison of the Immobilization of Exemplary Lipase 710 to Exemplary Particles 300 Using Adsorption and Using Covalent Binding A total of six test samples of exemplary lipase 710 attached to exemplary particles 300 were prepared. Three test samples, herein referred to as A1, A2, and A3, were prepared by adsorption of exemplary lipase 710 to particles 300 while the other three test samples, herein referred to as C1, C2, and C3, were prepared by covalent attachment of exemplary lipase 710 to particles 300. Exemplary particles 300 for samples A1, A2, and A3 were formed from styrene (A1, A2) or methacrylate (A3) polymer with no reactive groups. Exemplary particles 300 for samples C1, C2, and C3 were formed from methacrylate polymer with reactive (epoxy) groups for covalent bonding. All six test samples were prepared with 125 mg of lipase 710 per gram of particles 300. Covalent attachment of lipase 710 to particles 300 for samples C1, C2, and C3 was achieved by allowing lipase 710 to covalently bind to the epoxy groups on the surface of particles 300. The diameters of particles 300 ranged from 220 µm to 500 µm, and particles 300 were coated with PEG. Three assays were performed to evaluate the six test samples and to compare the immobilization of lipase 710 to particles 300 using adsorption versus using covalent binding.

First, a titration assay was performed for each test sample to evaluate the potency or specific activity of lipase 710 attached to particles 300 in each sample against an emulsified raw fish oil substrate having 40% DHA triglycerides by weight. Second, a lipase release assay was performed to assess the amount of lipase 710 released from particles 300 of each test sample. Third, a fat hydrolysis performance assay was performed to test the fat hydrolysis performance of lipase 710 attached to particles 300 in each sample in an exemplary device 200. The results are discussed in the following.

In the titration assay, for each particle test sample, 12 mg of dry particles 300 were added to an emulsified fish oil substrate. The substrate was equilibrated to 37° C. with stirring. The specific activity of lipase 710 attached to particles 300 was measured in each test sample. The specific activity is defined as the amount of free fatty acids generated per gram of the total lipase 710 attached to particles 300 in a given amount of time under the assay conditions. The amount of free fatty acids generated by each sample was measured by titrating the fish oil substrate with NaOH solution to keep the fish oil substrate at a constant pH. During the hydrolysis reaction, as the immobilized lipase 710 hydrolyzed triglycerides in the raw fish oil substrate, free fatty acids were generated, and NaOH solution was added to neutralize the acids. The moles of NaOH added during the reaction to neutralize the acid equaled the moles of free fatty acids produced by lipase 710 in each sample.

Figure 11:
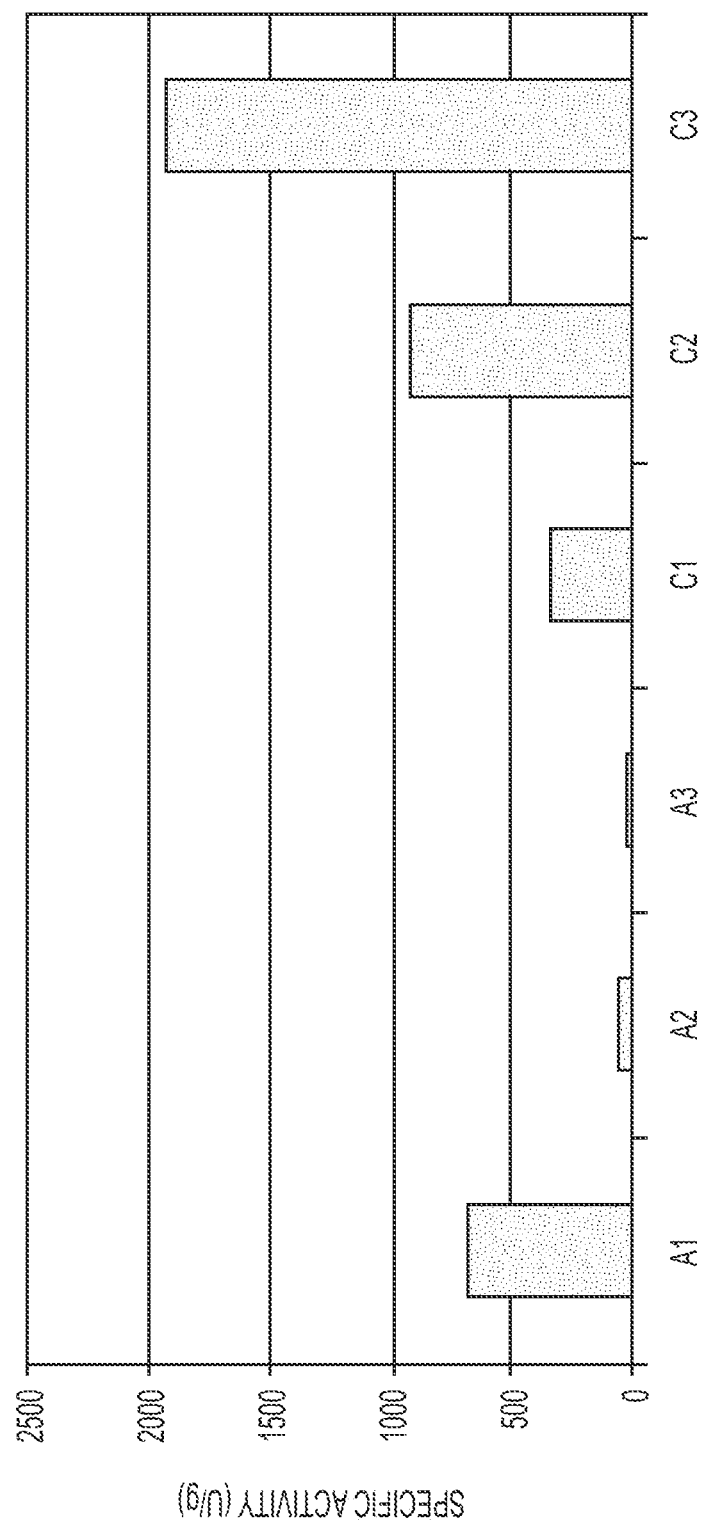
FIG. 11 graphically compares specific activities of lipase attached to exemplary particles, according to embodiments of the present disclosure.

As shown in Table 2 and FIG. 11, the test samples of lipase 710 attached to particles 300 via covalent binding, i.e., C1, C2, and C3, generally had higher specific activities than the test samples of lipase 710 attached to particles 300 via adsorption, i.e., A1, A2, and A3. This result was unexpected from previous publications regarding immobilization using adsorption and using covalent binding. Without being bound to this theory, it is hypothesized that this surprising result may be due to the fact that adsorption is a type of nonspecific binding mechanism that may cause the active site of lipase to be attached to the surface of a particle, reducing the accessibility of the active site of lipase to the fat molecules in the DHA oil substrate. The reduced accessibility may reduce the overall activity of lipase 710 immobilized on particles 300.

TABLE 2

Specific activities of test samples including lipase 710 immobilized to particles 300 via adsorption and covalent binding

| Test sample | Immobilization mode | Specific activity (U/g) |
| --- | --- | --- |
| A1 | Adsorption | 691 |
| A2 | Adsorption | 69 |
| A3 | Adsorption | 24 |
| C1 | Covalent binding | 350 |
| C2 | Covalent binding | 938 |
| C3 | Covalent binding | 1950 |

Figure 12:
FIG. 12 graphically compares release of lipase from exemplary particles, according to embodiments of the present disclosure.

In the lipase release assay, 1 g of each test sample was suspended in 10 mL distilled water in a centrifuge tube. Each centrifuge tube was rotated end over end using an automatic shaker at room temperature for about 12 hours. At 1-hour, 3-hour, and 12-hour time points, each test sample was centrifuged, and a measurement sample from the supernatant of each test sample was collected to obtain a concentration of lipase 710 that had detached from particles 300 at those time points. The concentrations of lipase 710 in the measurement samples were quantified by measuring the absorbance of the measurement samples at a wavelength of 280 nm using a spectrophotometer. As shown in FIG. 12, at all of the time points, the test samples having lipase 710 immobilized to particles 300 via adsorption, A1, A2, and A3, had higher concentrations of lipase 710 in the supernatant than the test samples having lipase 710 immobilized to particles 300 via covalent binding, C1, C2, and C3. Therefore, the results show that the attachment of lipase 710 to particles 300 by covalent binding was stronger and more stable than attachment of lipase 710 to particles 300 by adsorption.

In the fat hydrolysis assay, an exemplary nutritional formula 110, Peptamen AF®, was used. One gram of each test sample was placed in an exemplary device 200. Each exemplary device 200 had a body 210 made of clear polycarbonate and an inlet filter 250 and an outlet filter 260 made using 3-D printing methods. For each exemplary device 200, the diameter of inlet 242 was approximately 6.6 mm; the diameter of inlet filter chamber 214 tapered from 2.6 mm to 15 mm; the diameter of inlet filter 250 was approximately 15 mm and the thickness of inlet filter 250 was approximately 3.2 mm; the diameter of chamber 222 tapered from 15 mm to 17 mm; the diameter of outlet filter chamber 224 was approximately 17 mm; the diameter of outlet filter 260 was approximately 17 mm and the thickness of outlet filter 260 was approximately 3.2 mm; the diameter of outlet 230 was approximately 17 mm; the interior diameters of inlet 272 and inlet chamber 274 were approximately 15 mm; the exterior diameters of inlet 272 and inlet chamber 274 were approximately 17 mm; and the diameter of outlet 282 was approximately 2 mm. Inlet filter 250 and outlet filter 260 were made from polyethylene and had an approximate porosity of 100 μm. Each device 200 was filled with about 1 g to about 1.2 g of particles 300, leaving a headspace 223 of approximately 1 mm above particles 300 in a dry condition.

Figure 13:
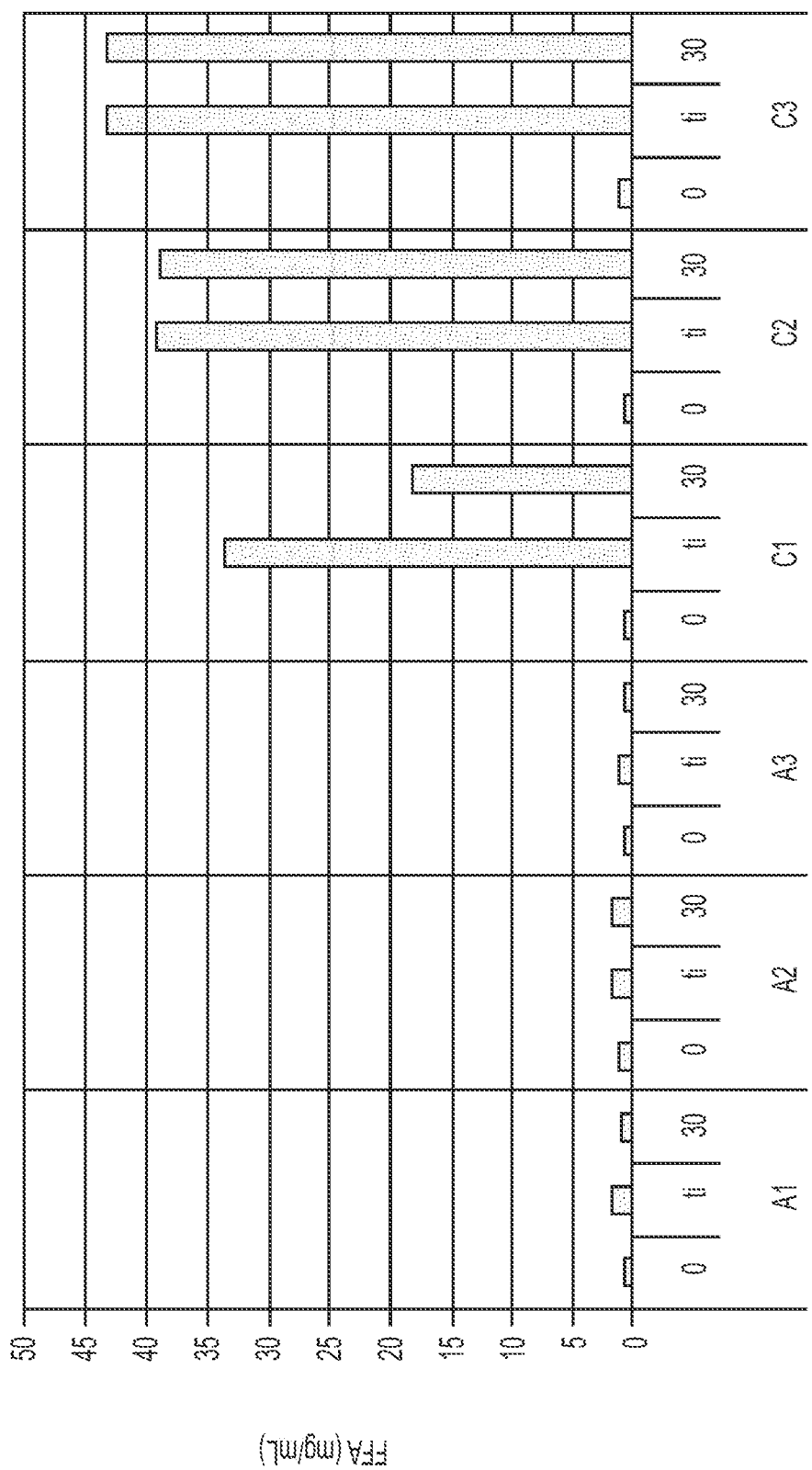
FIG. 13 graphically depicts the amount of free fatty acid generated in a sample of enteral formula Peptamen AF® hydrolyzed by an exemplary fat hydrolysis device, according to embodiments of the present disclosure.

Peptamen AF® solution was driven through device 200 by an exemplary pump 120 at a set flow rate of 2 mL/min. As Peptamen AF® solution passed through each test sample in each device 200, the fat, such as triglycerides, in the Peptamen AF® solution was hydrolyzed by lipase 710 attached to particles 300 of each test sample. During the flow of the Peptamen AF® solution through device 200, for each test sample, three measurement samples were collected. One sample was collected at $t_0$ before Peptamen AF® solution was exposed to particles 300, one sample was collected at $t_i$ just as the Peptamen AF® solution began flowing out of device 200, and one sample was collected at $t_{30}$ 30 minutes after $t_i$. The amount of free fatty acids in each measurement sample collected at each time point was measured using a quantitative colorimetric assay (Abcam® Free Fatty Acid Quantification Kit). Performance of fat hydrolysis by each test sample in device 200 was evaluated based on the amount of free fatty acids generated. FIG. 13 shows the amount of free fatty acids generated by the test samples placed in device 200. The results show that when nutritional formula 110 was flowed though lipase 710 immobilized to particles 300 in device 200, lipase 710 immobilized to particles 300 using covalent binding (C1, C2, and C3) had better performance in hydrolyzing fats in nutritional formula 110 than lipase 710 immobilized to particles 300 using adsorption (A1, A2, and A3).

As shown in Example 1, an advantage of using covalent binding of lipase 710 to particle 310 is the strength of the bond, i.e., the stability and/or strength of the immobilization. Comparatively speaking, adsorption is reversible and has the disadvantage of incomplete attachment, which may allow lipase to detach from a particle. This disadvantage may allow a substantial amount of lipase to mix with a nutritional formula, and if used, may be delivered to the patient as the nutritional formula flows through device 200. This may be undesirable to subjects in need of the fatty nutrients in nutritional formula 110, such as infant populations or immune compromised patients, because excess lipase may negatively affect their GI tracts, as discussed previously.

By contrast, with covalent binding, at least one covalent bond forms between a support material and a functional group on an amino acid on the surface of the lipase. The functional groups that may bind the lipase to the support material include, e.g., amino, carboxyl, sulfhydryl, hydroxyl, imidazole, or phenolic groups, and are not essential for the catalytic activity of the lipase. In some embodiments, the amino groups of the side chains of one or more lysine residues of lipase 710 may react with the epoxy groups on the surface of particle 310 and form covalent bonds. In order to protect the active site, immobilization can be carried out in the presence of a substrate or a competitive inhibitor. For an example of lipase immobilized by covalent binding, see S. Emi et al., *European Polymer Journal* 30(5):589-595 (1994). Supports suitable for covalent binding may include, e.g., Immobead™ (ChiralVision).

As noted above, covalent binding is a stronger and/or a more stable type of interaction between lipase 710 and particle 310, which may result in stronger and/or irreversible binding and reduced detachment of lipase 710 from particles 300. Thus, covalent binding of lipase to particles 300 is used in embodiments of the present disclosure, to reduce or eliminate the amount of lipase 710 that may detach from particles 300 as nutritional formula 110 flows through chamber 222 (and is ultimately delivered to a subject). The covalent binding of lipase 710 to particles 300 may advantageously improve the stability of the attachment, render lipase 710 and particles 300 reusable in some embodiments if desired, and may allow nutritional formula 110 that has been hydrolyzed by lipase 710 attached to particles 300 to have little or substantially no contamination of lipase 710. Purified lipase 710 that is substantially free from non-active lipase and/or non-lipase entities or has reduced amounts of non-active lipase and/or non-lipase entities may allow for improved binding efficiency and hydrolysis efficiency due to improved covalent binding of lipase 710 on particles 300. That said, as mentioned above, even with purified lipase 710, background levels of adsorption may occur during the process of covalently binding the lipase 710 to particles 300, although covalent binding may be the predominant mode of attaching lipase 710 to particles 300.

As described herein, hydrolysis efficiency may be used to describe the performance of device 200 in hydrolyzing the fats (e.g., long-chain fatty acid triglycerides and/or long-chain fatty acid esters) in nutritional formula 110. Hydrolysis efficiency may be defined as the percentage of fat hydrolyzed out of the total amount of fat in nutritional formula 110 after nutritional formula 110 has been flowed through device 200. In addition, lipase 710 used in the devices herein generally cleaves two out of three bonds in a triglyceride, i.e., at the sn-1 and sn-3 positions, leaving an sn-2 monoglyceride. Accordingly, 100% hydrolysis is achieved when two out of three bonds are broken in a given triglyceride. As described in more detail in the following embodiments of the present disclosure, it is recognized that it may be advantageous to maximize the exposure or interaction of lipase 710 attached to particles 300 with the fat molecules in nutritional formula 110 in chamber 222 to improve the hydrolysis efficiency of device 200 in order to supply pre-hydrolyzed free fatty acids and monoglycerides from nutritional formula 110 to a subject in a shorter period of time at the point of care to allow for more effective absorption of free fatty acids and monoglycerides by the body, for example, into plasma and/or tissues. Reducing the exposure time may allow for a reduction in the amount of time needed to provide nutritional formula 110 to a patient, which may allow patients to avoid overnight feeding, if desired, without significantly effecting hydrolysis efficiency.

Lipases can be obtained from animals, plants, and from many natural or genetically engineered microorganisms. Many commercially available lipase products are derived from animals and are particularly susceptible to degradation by digestive enzymes. A less frequently used alternative is microbial lipase, i.e., lipase produced in bacteria or fungus, such as, e.g., yeast. Certain microbial lipases retain activity over a wider pH range than animal or plant lipases, thus eliminating the need for enteric coated tablets. However, microbial enzymes tend to be degraded by trypsin in the small intestine, thereby reducing their availability to breakdown triglycerides and esters in the gut. In some embodiments, lipases 710 used in the present disclosure include bacterial lipases, fungal lipases, or both. Microbial lipases may or may not require a co-lipase or may or may not be affected by bile salts.

Figure 14:
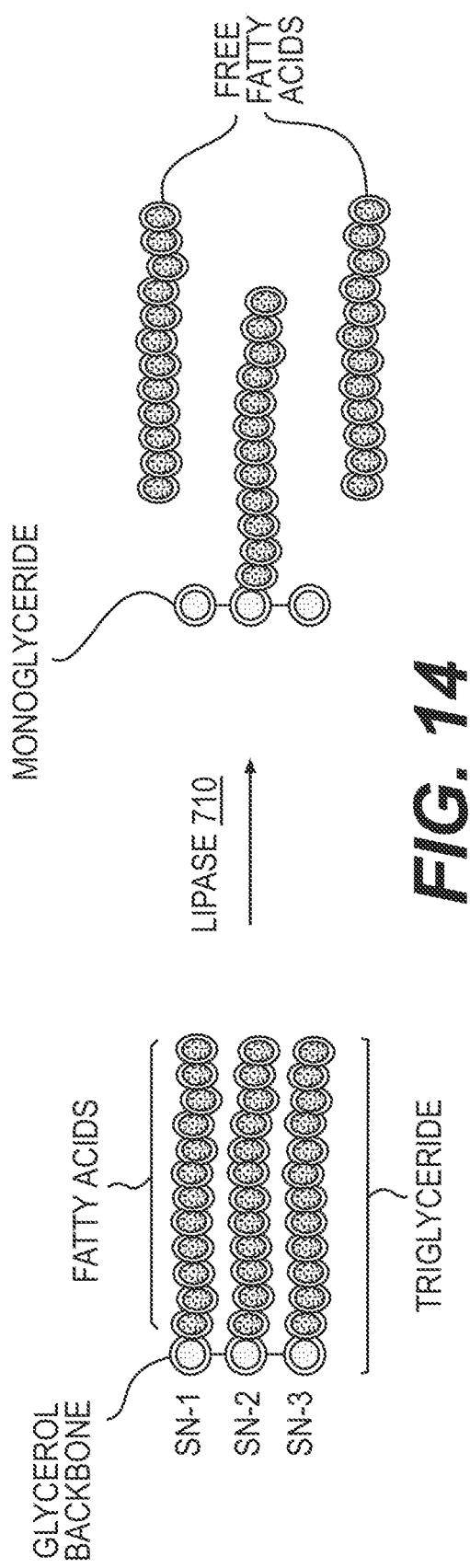
FIG. 14 is a schematic representation of the hydrolysis of a triglyceride molecule by an exemplary lipase molecule, according to embodiments of the present disclosure.

The specificity and kinetics of individual types of lipase can vary significantly. Specificity of lipases is controlled by the molecular properties of the enzyme, structure of the substrate, and factors affecting binding of the enzyme to the substrate. Types of specificity include substrate specificity. In some embodiments, lipase 710 is chosen to selectively hydrolyze triglycerides and/or esters having at least one long-chain and/or medium-chain polyunsaturated fatty acid. In some embodiments, similar to human pancreatic lipase, lipase 710 may specifically hydrolyze the ester bonds at positions 1 and 3 of the glycerol backbone of a triglyceride and generate two free fatty acids and one monoglyceride from the triglyceride, as shown in FIG. 14. In some embodiments, the polyunsaturated fatty acid generated by the hydrolysis of the triglyceride by lipase 710 may include one or more of docosahexaenoic acid (DHA), arachidonic acid (ARA), eicosapentaenoic acid (EPA), and linoleic acid (LA). In some embodiments, lipase 710 may be selected based on assaying its affinity to hydrolyze one or more types of triglycerides having LCTs, such as LC-PUFAs.

It has now been determined that lipase produced by *Chromobacterium viscosum*, *Pseudomonas fluorescens*, *Burkholderia cepacia*, and *Rhizopus oryzae* have greater specificity for DHA, EPA, and ARA than other lipases, such as lipase produced by *Candida rugosa*, *Rhizomucor miehei*, *Penicilium camemberti*, *Aspergillus niger*, and *Aspergiffis oryzae*. Thus, lipase 710 may be a microbial lipase selected from at least one of *Chromobacterium viscosum* lipase, *Pseudomonas fluorescens* lipase, *Burkholderia cepacia* lipase, and/or *Rhizopus oryzae* lipase. In some embodiments, lipase 710 is *Chromobacterium viscosum* lipase, *Pseudomonas fluorescens* lipase, or *Rhizopus oryzae* lipase. In some embodiments, lipase 710 is *Rhizopus oryzae* lipase. In some embodiments, lipase 710 has specific activities for triglycerides having DHA, EPA, and/or ARA that are comparable to the specific activities of one or more of *Chromobacterium viscosum* lipase, *Pseudomonas fluorescens* lipase, or *Rhizopus oryzae* lipase.

Reference to the lipase of certain species, such as *Chromobacterium viscosum* lipase, *Pseudomonas fluorescens* lipase, *Burkholderia cepacia* lipase, and *Rhizopus oryzae* lipase, does not necessarily mean that the lipase was prepared directly from the native host species. For example, the same lipase could be produced recombinantly in another host cell.

In some embodiments, the enzyme may be selected from at least one of *Chromobacterium viscosum* lipase, *Pseudomonas fluorescens* lipase, *Rhizopus oryzae* lipase, *Thermomyces lanuginosus* lipase, *Pseudomonas fluorescens* lipase, *Bacillus subtilis* lipase, *Candida rugosa* lipase, *Mucor javanicus* lipase, Lecitase, *Rhizopus niveus* lipase, *Rhizomucor miehei* lipase, *Aspergillus niger* lipase, *Penicillium camemberti* lipase, *Burkholderia cepacia* lipase, *Aspergillus oryzae* lipase, *Pseudomonas stutzeri* lipase, *Alcaligenes* spp. lipase, *Candida antarctica* lipase, *Hansenula polymorpha* lipase, *Humicola insolens* lipase, *Thermomyces langunosa* phospholipase, lecithinase phospholipase, or a lipase or phospholipase from any recombinant species within any of the above genus, or any suitable lipase or phospholipase or combination thereof.

In some embodiments, at least one type of lipase 710 may be attached to an individual particle 310. In some embodiments, different types of lipase 710 may be attached to the same particle 310 or to different groups of particles that make up particles 300. Different groups of particles may have different lipases, different median or mean diameters, different surface areas, different functional group concentrations or types, and/or may be made with different types of polymeric material, such as solid or porous polymeric materials.

In some embodiments, lipase 710 may be an extract from a microbial population, for example, *Rhizopus oryzae*, and may contain other proteins or enzymes. In some embodiments, lipase 710 may comprise gastric lipase, and/or non-lipase enzymes, such as lecithinase. In some embodiments, lipase 710 may be purified before attachment to a particle 310, and/or may be modified by adding functional chemical groups or chemical linkers. In some embodiments, lipase 710 may hydrolyze more than one type of fat, such as different triglycerides having one or more different long-chain polyunsaturated fatty acids or phospholipids.

In some embodiments, lipase 710 may catalyze hydrolysis of fats or triglycerides at a range of pH values and may have a maximum hydrolysis activity at pH values ranging from about 5 to about 8. The pH of a given nutritional formula 110 may be around a neutral pH, such as from about pH 6 to pH 8, thus a lipase 710 may be selected that hydrolyzes fats efficiently at substantially the same pH range as that of nutritional formula 110. In some embodiments, a lipase 710 may be selected that has a peak activity at the pH of nutritional formula 110. Unlike human pancreatic lipase, lipase 710 may not need co-factors to hydrolyze fats efficiently. In some embodiments, the enzymatic activity of lipase 710 may not be affected by bile salts.

In some embodiments, lipase 710 may be active over temperatures ranging from about 4° C. to about 35° C. In order to prevent nutritional formula 110 from spoilage, nutritional formula 110 may be stored and refrigerated at a temperature ranging from 4° C. to about 10° C. Nutritional formula 110 may be delivered to the patient after being retrieved from refrigerated storage or may be delivered after being warmed to room temperature, e.g., about 20° C. to about 25° C. Thus, the temperature of nutritional formula 110 typically may range from about 4° C. to about 25° C. In some situations, nutritional formula 110 may be warmed, for example, to body temperature, about 36° C. to about 37° C., before delivery. In some embodiments, a lipase 710 may be selected that hydrolyzes fats efficiently at substantially the same temperature range as that of nutritional formula 110. Microbial lipases also generally have an optimal activity level at a certain pH or a certain pH range. In some embodiments, lipase 710 may be suited for use with a neutral pH of nutritional formula in addition to, or instead of, the lower pH range of the stomach environment. In some embodiments, lipase 710 may be less active in the gastrointestinal system, allowing for improved safety. In some embodiments, a lipase 710 may be selected that has a peak activity at the temperature of nutritional formula 110 prior to delivery. In some embodiments, a lipase 710 may be selected that has sufficient activity over the range of temperatures that nutritional formula 110 may be delivered at.

In some embodiments, the density of lipase 710 attached to particle 310 may be controlled by adjusting the concentration of the functional groups, such as the epoxy groups, of the polymeric material of particle 310. A decrease in the concentration of epoxy groups present on the surface of particle 310 may decrease or limit the density of lipase 710 attached to particle 310. In some embodiments, the density of lipase 710 attached to particle 310 may range from about 10 mg to about 100 mg, 100 mg to about 200 mg, from about 100 mg to about 300 mg, from about 100 mg to about 400 mg, from about 100 mg to about 500 mg, from about 200 mg to about 300 mg, from about 200 mg to about 400 mg, from about 200 mg to about 500 mg, from about 300 mg to about 400 mg, from about 300 mg to about 500 mg, or from about 400 mg to about 500 mg per gram of polymeric particle 310.

In some embodiments, the density of lipase 710 attached to the surface of a given particle 310 may be increased to increase the amount of lipase 710 on particles 300 in device 200 to more efficiently hydrolyze fats, such as long-chain fatty acid triglycerides and/or long-chain fatty acid esters, in nutritional formula 110. In some embodiments, increasing the density of lipase 710 attached to the surfaces of particles 300 may allow fewer particles 300 to be used in device 200 without decreasing the amount of lipase 710 in device 200, and thus potentially without substantially affecting the overall hydrolysis efficiency of device 200. In some embodiments, however, increasing the density of lipase 710 attached to the surface of particles 300 may not increase the overall efficiency of lipase 710 on particles 300 or may reach a threshold level of efficiency. For example, although an increased amount of lipase 710 may be bound to an individual particle 310, lipase 710 may be immobilized on the surface of the pores and/or channels inside of particle 310, and, if the sizes of the pores and/or channels are smaller than the fat molecules to be hydrolyzed and/or are substantially hydrophilic, fat molecules in nutritional formula 110 may not come into contact with the pores and/or channels and may not react with lipase 710 bound there. In such situations, increasing the amount of lipase 710 bound inside of particle 310 may not increase the overall hydrolysis efficiency of particles 300 or device 200.

In some embodiments, increasing the density of lipase 710 attached to the surface of particle 310 beyond a threshold may not increase the hydrolysis efficiency of lipase 710 on particle 310 or may even decrease the efficiency in some instances. For example, increasing the density of lipase 710 may affect the orientation of lipase 710 on particle 310 or may increase the steric hindrance between adjacent lipase molecules on particle 310, and/or may reduce the flexibility or accessibility of lipase 710 to the fat molecules in nutritional formula 110. If this occurs, then even through there is more lipase 710 on particle 310, the fats in nutritional formula 110 may not be able to interact with the active site of the lipase, and adjacent lipase molecules may obstruct each other. In some embodiments, the density of lipase 710 attached to the surface of particle 310 may be reduced to allow sufficient flexibility of lipase 710 and/or to reduce steric hindrance between adjacent lipases molecules on particle 310, and thus to preserve and/or increase the overall activity of lipase 710 attached to particle 310 by making it accessible to the fats to be hydrolyzed. In some embodiments, if a threshold efficiency is reached, then an amount of lipase substantially equivalent to that threshold amount may be used, since increasing the amount of lipase may only add cost with no substantial efficiency benefit.

In some embodiments, the purity of lipase 710 may be altered to increase the covalent binding and hydrolysis efficiency of lipase 710 on particle 310. For example, some lipase enzyme preparations may include protein and polysaccharide carryover materials from their isolation or production, or they may contain diluents or inactive lipase. These other materials may interfere with the enzyme active sites of active lipase 710, may compete for covalent binding sites on particles 300, may sterically hinder lipase 710, and/or may prevent the substrate from readily reaching the active site. In some embodiments, these non-active and non-lipase entities may be removed from the enzyme preparation during the process of immobilization, or, in some embodiments, these non-active and non-lipase entities may be removed from the enzyme preparation before immobilization. Removal of non-active and/or non-lipase entities may provide for an increase in the overall activity of lipase 710 attached to particles 300. In some embodiments, the mass ratio of active lipase to enzyme preparation before immobilization may be as low as 5% and as high as essentially 100%.

In some embodiments, the amount of lipase 710 attached to particle 310 may be proportional to the surface area of particle 310. For example, if a first particle 310 has a larger diameter, and thus a larger surface area than a second particle 310, then at an equal density of lipase 710, the first particle 310 will have a larger amount of lipase attached to it than the second particle 310. For particles of the same size, a particle 310 having a porous core may have a larger surface area than a particle 310 having a solid core, thus if the densities of lipase 710 attached to the surface area of the particles are equal, then the amount of lipase 710 attached to the particle with a porous core may be greater than the particle 310 with a solid core. Similarly, for particles of the same size, a particle 310 having an uneven, irregular surface may have a larger surface area than a particle 310 having a smooth surface, thus if the density of lipase 710 attached to the surface of the particles is the same, the amount of lipase 710 attached to the particle 310 with an uneven, irregular surface may be more than that attached to the particle 310 with a smooth surface. Therefore, particles 300 made up of individual particles 310 having a larger surface area, such as particles 310 having uneven surfaces and porous cores, may provide a larger overall surface area and thus a larger amount of lipase 710 than particles 300 made up of individual particles 310 having a smaller surface area and thus a smaller amount of lipase 710, such as particles 310 having smooth surfaces and solid cores.

In some embodiments, the amount of lipase 710 in chamber 222 may be proportional to the total surface area of particles 300 contained in chamber 222. The surface area and volume of individual particles 300 is proportional to the size or diameter of that particle 310. The surface area and volume of a spherical particle having a diameter of D can be calculated as $\pi * D^2$ and $(\pi * D^3)/6$, respectively. In some embodiments, since chamber 222 may have a predetermined volume, there will be a maximum number of particles 300 that can be placed in chamber 222. For example, if chamber 222 has a volume of $V_0$, particles 300 having a median or mean diameter of $D_1$ that can be placed in chamber 222 being $N_1$, and particles 300 having a median or mean diameter of $D_2$ that can be placed in chamber 222 being $N_2$, where $D_1$ is larger than $D_2$, $N_1$ is then smaller than $N_2$. In other words, for a given volume of chamber 222, the number of particles 300 having a larger diameter that are able to fit in chamber 222 will be less than the number of particles 300 having a smaller diameter. In this situation, the total surface area of particles 300 is inversely proportional to the median or mean diameter of particles 300, if all other variables are equal. Thus, given a total volume of particles 300, the total surface area of particles 300 having a larger median or mean diameter is less than the total surface area of particles 300 having a smaller median or mean diameter. Therefore, in some embodiments, to increase the surface area of particles 300, chamber 222 of body 210 may be made in a larger volume to accommodate more particles 300. In other embodiments, to increase the surface area of particles 300, given a certain volume of chamber 222, the median or mean diameter and/or diameters of particles 300 may be selected to be smaller.

In some embodiments, chemical linkers may be used to link the surface of particle 310 to lipase 710. Such chemical linkers may increase the distance between lipase 710 and the particle 310 to which it is attached. For example, a chemical linker may increase the distance of lipase 710 further away from the surface of particle 310 at a range from about 0.1 nm to about 1 nm, from about 1 nm to about 3 nm, from about 3 nm to about 4 nm, from about 4 nm to about 6 nm, from about 6 nm to about 8 nm, from about 8 nm to about 10 nm, from about 12 nm to about 14 nm, from about 14 nm to about 16 nm, from about 16 nm to about 18 nm, from about 18 nm to about 20 nm, from about 0.1 nm to about 3 nm, from about 0.1 nm to about 4 nm, from about 0.1 nm to about 8 nm, from about 0.1 nm to about 10 nm, from about 0.1 nm to about 12 nm, from about 0.1 nm to about 14 nm, from about 0.1 nm to about 16 nm, from about 0.1 nm to about 18 nm, or from about 0.1 nm to about 20 nm. This may increase the mobility or flexibility of lipase 710, reduce steric hindrance of adjacent lipase molecules, and/or orient the active site of lipase 710 to the fat molecules in nutritional formula 110, and thus may preserve or increase the enzymatic activity of lipase 710. In some embodiments, chemical linkers may allow lipase 710 to take a certain orientation on the surface of particle 310 to orient the active site of lipase 710 towards the fat molecules to be hydrolyzed in nutritional formula 110. In some embodiments, spacer molecules may be attached or chemically linked to the surface of particle 310 and may be placed between adjacent lipase molecules to reduce the steric hindrance among adjacent lipase molecules on the surface of particle 310.

In some embodiments, different particles 300 may have a different amount and/or density of lipase 710 attached to their surfaces. As noted herein, particles 300 may include all types of individual particles 310 as described above, or similar particle types may have different sizes, shapes, mass densities, and/or densities of immobilized lipase 710. In some embodiments, each of these different particle types may have a different density of lipase 710, a different surface area, and/or a different amount of immobilized lipase 710, etc.

Increasing the overall surface area of particles 300 and/or the total amount of lipase 710 in chamber 222 may increase the exposure to or interaction between lipase 710 and the fat molecules in nutritional formula 110, which may improve the efficiency of device 200 for hydrolyzing fats, such as long-chain polyunsaturated triglycerides and/or long-chain polyunsaturated esters, in nutritional formula 110.

In some embodiments, the surface of an individual particle 310 may be hydrophobic or partially hydrophobic. For example, the surface of particle 310 may be hydrophobic and thus may have limited wetting ability or no wetted state. In some embodiments, the hydrophobic surface of particle 310 may attract fat molecules from an aqueous solution, an oil-water emulsion, or a complex nutritional liquid, such as nutritional formula 110, through hydrophobic interactions. Such hydrophobic interactions may increase the accessibility of the fat molecules to lipase 710 attached to particle 310 and may facilitate the hydrolysis of the fat molecules in nutritional formula 110 by lipase 710. In some embodiments, the surface of particle 310 may be hydrophilic or partially hydrophilic. For example, the surface of particle 310 may be hydrophilic and may be wetted upon suspension in an aqueous solution, an oil-water liquid, and/or nutritional formula 110. In some embodiments, the polymeric material of particle 310 may be partially hydrophilic and partially hydrophobic, e.g., by including one or more polymers or a copolymer. In such embodiments, particle 310 may be both hydrophilic and hydrophobic on the surface, and may attract fat molecules in nutritional formula 110 and may be wetted in nutritional formula 110. In some embodiments, the outside surface of particle 310 may be hydrophilic, and the surface of the pores and/or channels inside particle 310 may be hydrophobic, or vice versa.

Figure 15:
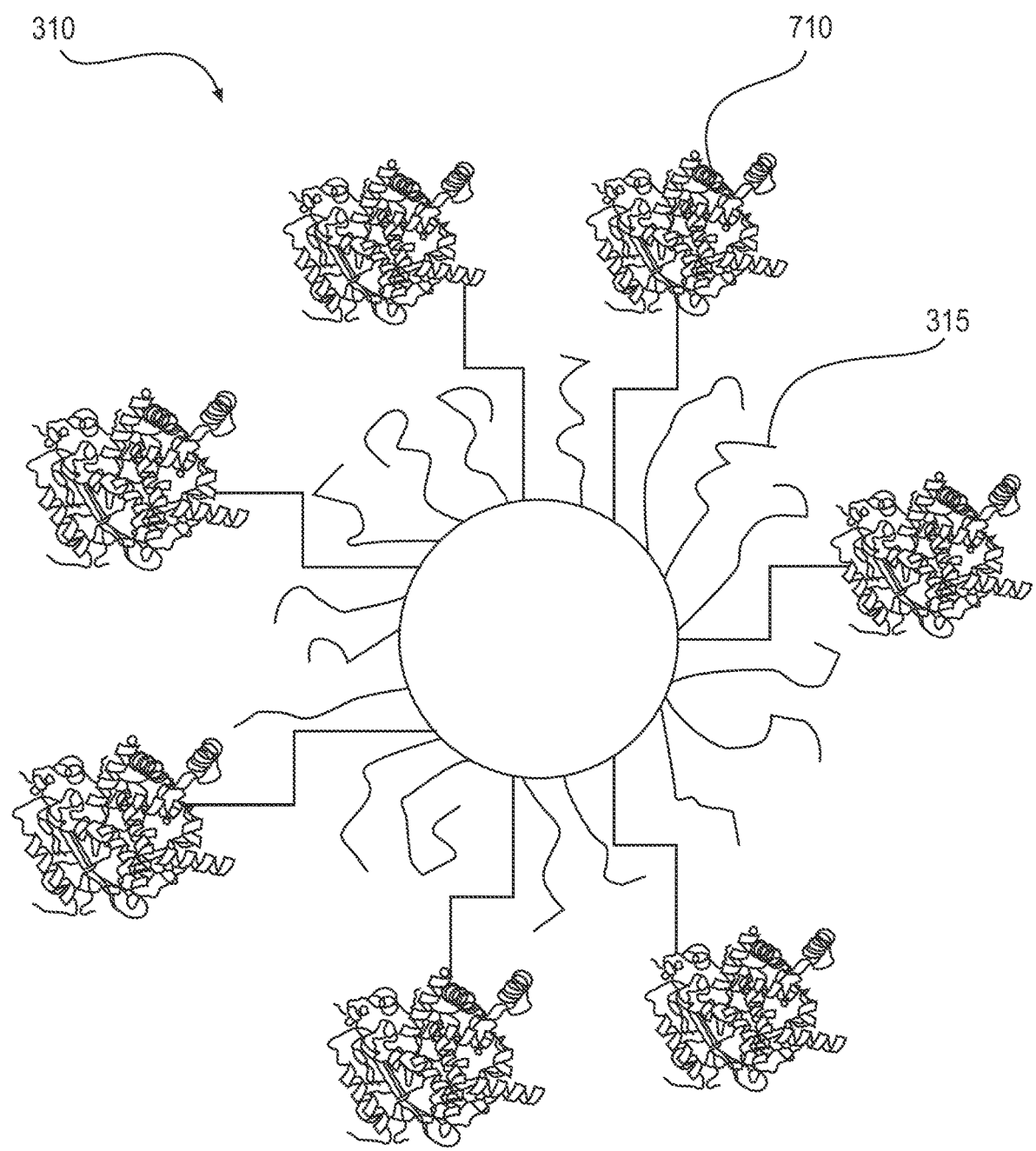
FIG. 15 illustrates a magnified schematic view of an exemplary particle, according to embodiments of the present disclosure.

Having a hydrophilic surface of particle 310 or wetting of particle 310 may be beneficial for the enzymatic activity of lipase 710 attached to the surface of particle 310. In some embodiments, as shown in FIG. 15, particle 310 may have a polyethylene glycol (PEG) coating 315. In some embodiments, PEG coating 315 on the outside surface of particle 310 may improve the wetting ability of particle 310 when particle 310 is suspended in a solvent including water, such as nutritional formula 110, thereby creating a wetted surface environment beneficial for the enzymatic activity of lipase 710. In some embodiments, PEG coating 315 may improve the stability of the attachment of lipase 710 to particle 310. In some embodiments, the amount of PEG coating 315 may range from about 0 to about 2%, from about 2% to about 5%, from about 5% to about 8%, from about 8% to about 10%, from about 5% to about 10%, from about 2% to about 10%, or from about 0 to about 10% of the overall composition of particle 310 by weight. Alternatively, other coatings or combinations of coatings may be used to improve the wetting ability of particle 310 when particle 310 is suspended in a solvent including water. Alternative coatings may include, e.g., a lecithin coating, a polyvynylpyrrolidone coating, a polyvinyl alcohol coating, a non-ionic surfactant coating, an alcohol coating, such as dodecanol, a glycerol coating, a propanediol coating (e.g., 1,2-propanediol), water, or any suitable coating that may improve the wetting ability of particle 310 in nutritional formula 110. In some embodiments, wetting agents may be included in the coating of particle 310 to improve the wetting ability of particle 310 in nutritional formula 110.

In some exemplary embodiments, PEG may be used to provide stability for immobilization of enzymes. In some embodiments, the inclusion of 2% to 10% PEG, by weight, has yielded shelf-life stability of lipase in device 200 of at least approximately 18 months when stored at routine storage conditions (5° C.±3° C. and 25° C.±2° C. at 60% RH±5% RH). In some embodiments, the absence of or reduced levels of PEG on particles 300 may also yield suitable shelf-life stability of lipase on particles 300.

In some embodiments, particle 310 may comprise a polymeric matrix and/or lattice. For example, the polymeric matrix may be made of a porous copolymer having pores and/or channels, and lipase 710 may aggregate and be entrapped in particle 310. In such situations, the active site of the lipase may remain exposed and interact with the fat molecules or micelles. For example, when nutritional formula 110 is flowed through chamber 222 and particles 300, fat molecules of nutritional formula 110 may enter the complex matrix and/or lattice, e.g., by convection and/or diffusion, and then mix with, interact with, or be hydrolyzed by lipase 710 or aggregates of lipase 710 entrapped in the matrix and/or lattice.

Figure 16B:
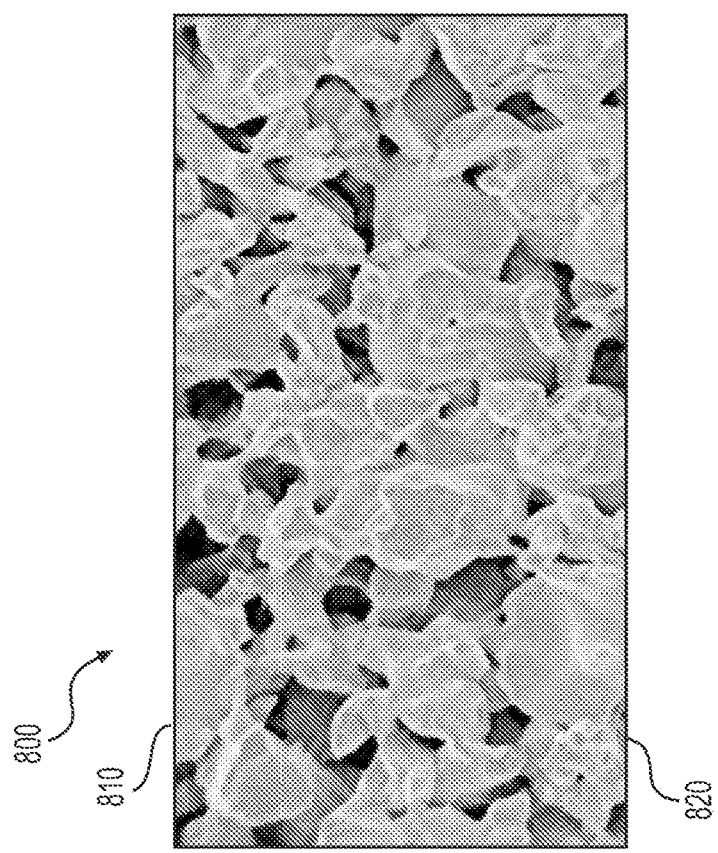
FIG. 16B illustrates a magnified schematic of a cross-section of an exemplary filter mesh material, according to embodiments of the present disclosure.
Figure 16A:
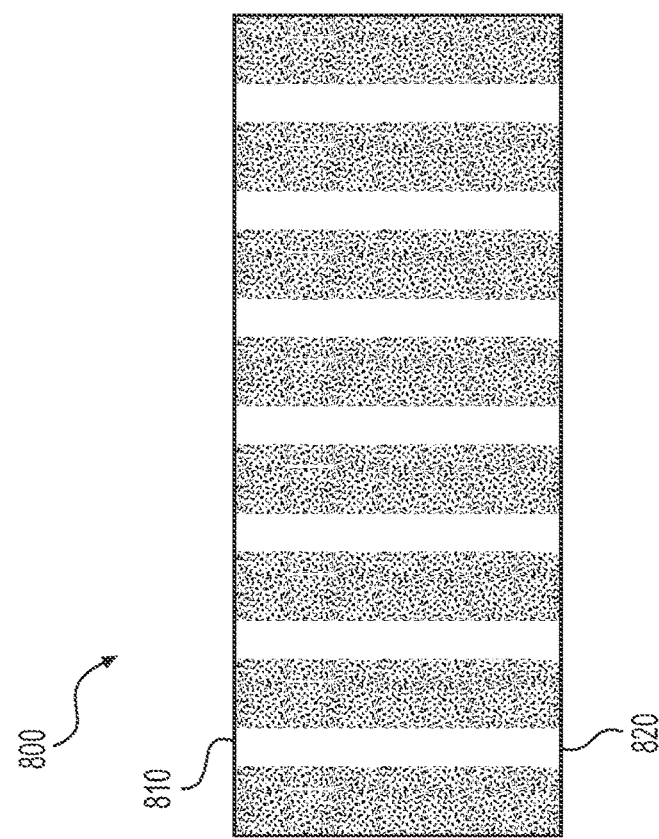
FIG. 16A illustrates a magnified schematic of a cross-section of an exemplary filter mesh material, according to embodiments of the present disclosure.

As discussed previously, one or more filters may be used to retain particles 300 in chamber 222, prevent clogging, and/or direct or affect the flow of a liquid, including nutritional formula 110, through device 200 and particles 300. Inlet filter 250 and outlet filer 260 may include a mesh 800 having an intake surface 810 and an outtake surface 820, as shown in FIGS. 16A and 16B. FIG. 16A shows a cross-section of an exemplary embodiment of mesh 800. As shown in FIG. 16A, in some embodiments, mesh 800 may be a traditional, screen-type mesh 800 having generally ordered channels for passing fluid. Such channels may be patterned, for example, straight, as a comb, e.g., a honeycomb, and/or radially distributed. For example, as shown in FIG. 16A, mesh 800 may have straight paths in its structure to allow nutritional formula 110 to pass through. In some embodiments, nutritional formula 110 may be flowed through the straight paths of mesh 800 directed by pump 120, by gravity feeding, or via use of a syringe. The diameters and/or relative positions of the straight paths may be uniform or may vary across mesh 800.

Mesh 800 may impose hydraulic resistance to the flow of nutritional formula 110, and the magnitude of the hydraulic resistance and the flow of nutritional formula 110 may depend on the diameters and/or locations of the paths of mesh 800. For example, if the diameters or perimeters of the paths of mesh 800 are sufficiently large, nutritional formula 110 may be met with a small magnitude of hydraulic resistance, and may pass through the paths near the middle of mesh 800 more than the paths at the peripheral of mesh 800, resulting in a more focused flow of nutritional formula 110 at an outtake surface 820 of mesh 800. If the diameters of the paths of mesh 800 are sufficiently small and/or the paths are oriented in a manner to distribute flow, nutritional formula 110 may be met with a larger magnitude of hydraulic resistance, and may thus be distributed at intake surface 810 of mesh 800 and may pass more evenly through the paths across mesh 800, resulting in a more distributed flow of nutritional formula 110 at outtake surface 820 of mesh 800. In some embodiments, at least some of the paths of mesh 800 may be angled outwards toward the periphery of mesh 800, directing the flow of nutritional formula 110 to the periphery of chamber 222 and allowing nutritional formula 110 to be distributed across particles 300 in chamber 222. Mesh 800 that provides a more distributed flow of nutritional formula 110 may allow nutritional formula 110 to be exposed to more particles 300, and thus more lipase 710 in chamber 222, potentially increasing the efficiency of device 200 for hydrolyzing fats in nutritional formula 110.

In some embodiments, as shown in FIG. 16B, mesh 800 may be a porous mesh 800 having a plurality of tortuous paths extending through the mesh to allow nutritional formula 110 to pass through. In some embodiments, the tortuous paths may be irregular in size, shape, and/or distribution or may be substantially regular and ordered. In some embodiments, the shapes and locations of the tortuous paths may be randomly generated during the manufacturing of porous mesh 800. In other embodiments, the tortuous paths and the shapes of the cross-sections of the tortuous paths may be predetermined and, for example, designed using computer-aided design packages. For example, the dimensions and the configuration of the tortuous paths of mesh 800 may be first modeled or designed using a computer-aided design (CAD) package and manufactured by using additive manufacturing technologies, such as 3D printing. Such methods of making may also be used for the channels of mesh 800 in FIG. 16A.

As shown in FIG. 16B, tortuous paths of porous mesh 800 may cause nutritional formula 110 to pass through inlet filter 250 while distributing out along porous mesh 800. In this manner, rather than passing only through certain portions of inlet filter 250, e.g., the middle, causing fluid channeling and/or shunting, nutritional formula 110 may be more evenly distributed across outtake surface 820 of mesh 800. Such distribution of nutritional formula 110 may allow nutritional formula 110 to flow through more or substantially all of a cross-section of chamber 222, and thus across a broader cross-section of particles 300, thus reducing the formation of channeling and/or shunting of nutritional formula 110 through particles 300 in chamber 222. Accordingly, nutritional formula 110 would be exposed to more particles 300 and to more lipase 710, potentially increasing the efficiency of device 200 for hydrolyzing fats.

Filters, including tortuous path filters, mesh filters, and depth filters, e.g., may also affect the hydrolysis of fat by breaking up the fat particles in nutritional formulas 110. Packaged nutritional formulas and pasteurized, homogenized human milk have emulsified fat presentations so that the oily and aqueous phases do not separate during room-temperature storage. The emulsified fat particles may vary in size, or may coat the surface of particles 300, which may affect the ability of the immobilized lipase on particles 300 to gain access to the triglyceride backbone for effective hydrolysis of the triglycerides into monoglycerides and free fatty acids. The inclusion of filters may promote hydrolysis by breaking up the particles into smaller, more uniform sizes.

Tortuous filters or depth filters may modify the size of the emulsified fat particles. By varying the filter pore size, filter type, and/or filter depth, the emulsions may be disrupted into smaller particles. In one preliminary study, a first sample of pasteurized, homogenized human milk was passed through a single-layer mesh filter, and a second sample of pasteurized, homogenized human milk was passed through a depth filter. In the initial experiment, passing the milk formula through the mesh filter resulted in disruption of the emulsion into smaller particles or smaller fat globules compared to the milk formula passed through the depth filter. In theory, it may be easier for lipase within device 200 to interact with smaller emulsion particles to hydrolyze fats.

Filters may also act to disrupt proteins or phospholipids surrounding the fats within nutritional formulas. For example, as the nutritional formula passes through a filter, the filter may break up a layer containing phospholipids and proteins that surrounds the fats to allow the lipase within chamber 222 to gain access to the fats more easily. In some embodiments, one or more filters may also be coated with a protease to promote the break-up of proteins.

The sizes and/or diameters of the pores, channels, and/or paths of mesh 800 in inlet filter 250 and/or outlet filter 260 are smaller than the diameters of particles 300, preventing particles 300 from passing through inlet filter 250 and/or outlet filter 260. For example, the median or mean diameter of the pores, channels, and/or paths of porous mesh 800 may be smaller than the smallest diameter of particles 300, for example, by about 10% to about 20%, by about 20% to about 30%, by about 30% to about 40%, by about 40% to about 50%, by about 50% to about 60%, by about 20% to about 60%, by about 30% to about 60%, by about 40% to about 60%, by about 50% to about 60%, by about 10% to about 30%, by about 10% to about 40%, by about 10% to about 50%, or by about 10% to about 60%, to prevent particles 300 from passing through and/or clogging the pores, channels, and/or paths of mesh 800. In some embodiments, the diameters or perimeters of the pores, channels, and/or paths in mesh 800 may range from about 10 µm to about 100 µm, from about 10 µm to about 150 µm, from about 10 µm to about 200 µm, from about 10 µm to about 300 µm, from about 10 µm to about 400 µm, from about 10 µm to about 500 µm, from about 50 µm to about 300 µm, from about 50 µm to about 400 µm, from about 50 µm to about 500 µm, from about 100 µm to about 200 µm, from about 100 µm to about 300 µm, from about 100 µm to about 400 µm, or from about 100 µm to about 500 µm.

In some embodiments, the sizes or diameters of the pores, channels, and/or paths in mesh 800 may depend on the distribution of the diameters of particles 300. As discussed above, in some embodiments, particles 300 may be sieved to filter out particles having diameters smaller than a lower threshold, such as the median or mean diameter of the pores, channels, and/or paths of mesh 800. Such sieving or filtering may reduce the probability of particles 300 having diameters at the smaller end of the distribution that could pass through and/or clog inlet filter 250 and/or outlet filter 260.

In one embodiment, both inlet filter 250 and outlet filter 260 may include a traditional mesh 800, like that shown in FIG. 16A. In another embodiment, both inlet filter 250 and outlet filter 260 may comprise a porous mesh 800 including tortuous paths, like that shown in FIG. 16B. In another embodiment, inlet filter 250 may comprise a traditional mesh 800 and outlet filter 260 may comprise a porous mesh 800. In another embodiment, inlet filter 250 may comprise a porous mesh 800 and outlet filter 260 may comprise a traditional mesh 800. In another embodiment, inlet filter 250 may comprise both a traditional mesh 800 and a porous mesh 800 and outlet filter 260 may comprise a traditional mesh 80 or a porous mesh 800. In another embodiment, inlet filter 250 may comprise a traditional mesh 800 or a porous mesh 800 and outlet filter 260 may comprise a traditional mesh 800 and a porous mesh 800. In another embodiment, both inlet filter 250 and outlet filter 260 may comprise a traditional mesh 800 and a porous mesh 800.

In some embodiments, the thickness of inlet filter 250 and/or outlet filter 260 may range from about 0.1 mm to about 1 mm, from about 0.1 mm to about 2 mm, from about 2 mm to about 4 mm, from about 4 mm to about 6 mm, from about 6 mm to about 8 mm, from about 8 mm to about 10 mm, from about 0.1 mm to about 4 mm, from about 0.1 mm to about 6 mm, from about 0.1 mm to about 8 mm, from about 0.1 mm to about 10 mm. The thickness may or may not affect the flow rate of nutritional formula 110 through device 200 and/or the distribution of nutritional formula 110 across particles 300.

In some embodiments, mesh 800 of inlet filter 250 and/or outlet filter 260 may be made of a biocompatible, inert, and/or medical polymeric material, for example, polyethylene. In some embodiments, inlet filter 250 and/or outlet filter 260 may be a membrane filter. In some embodiments, device 200 may only have outlet filter 260 and may not have inlet filter 250. In some embodiments, device 200 may have more than one outlet filter 260 and/or inlet filter 250. The diameters or perimeters of the channels or tortuous paths in mesh 800 of outlet filter 260 and/or inlet filter 250 may or may not be different from each other.

In some embodiments, inlet filter 250 and/or outlet filter 260 may be coated with at least one emulsifier configured to emulsify nutritional formula 110 as it passes through. Since nutritional formula 110 is composed of a complex mixture that may include, for example, proteins, carbohydrates, fat, water, minerals, and/or vitamins, and may include liquid foods that are specially formulated and processed, the emulsifier may emulsify nutritional formula 110 into an oil-in-liquid emulsion, with fat in nutritional formula 110 in the dispersed phase and liquid as the dispersion medium. For example, fat droplets may be distributed in the liquid medium by the emulsifier. Creating an emulsion of nutritional formula 110 may facilitate the interaction between the fat molecules in nutritional formula 110 and lipase 710 attached to particles 300 in chamber 222. For example, fat droplets may be attracted to a hydrophobic surface of particles 310. The surface of particles 310 may comprise a layer of PEG coating 315 and may be wetted in the liquid medium of the emulsion, and thus lipase 710 may hydrolyze the fat molecules in the emulsion that are attracted to the surface of particle 310. In some embodiments, the type of emulsifier may depend on the composition of nutritional formula 110. In some embodiments, multiple types of emulsifiers may be used to coat the surface of inlet filter 250 and/or outlet filter 260. In some embodiments, nutritional formula 110 may be pre-emulsified or may already be an emulsion before being flowed through device 200. In some embodiments, an internal portion of inlet 212 may be coated with an emulsifier instead of, or in addition to, inlet filter 250.

Alternative suitable emulsifiers may include, for example, proteins, hydrolyzed proteins, lecithin, phospholipids, or polyvinylpyrrylidone, or any suitable combination thereof. Lecithins used as the emulsifier may be mixtures of phospholipids, such as phosphatidyl choline and phosphatidylethanolamine, and may be extracted from sources such as egg yolk and soybeans. Alternative emulsifiers may include diacetyl tartaric acid esters, sodium or calcium stearoyl-2-lactylate, ammonium phosphatide, alginic acid, sodium alginate, potassium alginate, ammonium alginate, calcium alginate, propane-1,2-diol alginate, agar, carrageenan, processed eucheuma seaweed, locust bean gum, carob gum, guar gum, tragacanth, acacia gum; gum arabic, xanthan gum, karaya gum, tara gum, gellan gum, konjac, soybean hemicellulose, cassia gum, polyoxyethylene sorbitan monolaurate, polysorbate 20, polyoxyethylene sorbitan monooleate, polysorbate 80, polyoxyethylene sorbitan monopalmitate, polysorbate 40, polyoxyethylene sorbitan monostearate, polysorbate 60, polyoxyethylene sorbitan tristearate, polysorbate 65, pectins, ammonium phosphatides, sucrose acetate isobutyrate, glycerol esters of wood rosins, cellulose, methyl cellulose, ethyl cellulose, hydroxypropyl cellulose, hydroxypropyl methyl cellulose, ethyl methyl cellulose, carboxy methyl cellulose, crosslinked sodium carboxy methyl cellulose, enzymatically hydrolyzed carboxy methyl cellulose, sodium, potassium, magnesium, and calcium salts of fatty acids, mono- and diglycerides of fatty acids, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyltartaric acid esters of mono- and diglycerides of fatty acids, mixed acetic and tartaric acid esters of mono- and diglycerides of fatty acids, sucrose esters of fatty acids, sucroglycerides, polyglycerol esters of fatty acids, polyglycerol polyricinoleate, propane-1,2-diol esters of fatty acids, thermally oxidized soya bean oil interacted with mono- and diglycerides of fatty acids, sodium stearoyl-2-lactylate, calcium stearoyl-2-lactylate, stearyl tartrate, sorbitan monostearate, sorbitan tristearate, sorbitan monolaurate, sorbitan monooleate, sorbitan monopalmitate, or invertase, for example.

As described above, nutritional formula 110 may be directed through device 200 by pump 120, by gravity feeding, or via use of a syringe. In some embodiments, nutritional formula 110 may be directed through device 200 at a flow rate ranging from about 0.02 mL/min to about 2 mL/min, from about 0.4 mL/min to about 2 mL/min, from about 0.4 mL/min to about 4 mL/min, from about 0.4 mL/min to about 6 mL/min, from about 0.4 mL/min to about 8 mL/min, from about 0.4 mL/min to about 10 mL/min, from about 0.4 mL/min to about 12 mL/min, from about 0.4 mL/min to about 14 mL/min, from about 2 mL/min to about 6 mL/min, from about 2 mL/min to about 8 mL/min, from about 2 mL/min to about 10 mL/min, from about 2 mL/min to about 12 mL/min, from about 2 mL/min to about 14 mL/min, from about 0.02 mL/min to about 4 mL/min, from about 0.02 mL/min to about 6 mL/min, from about 0.02 mL/min to about 8 mL/min, from about 0.02 mL/min to about 10 mL/min, from about 0.02 mL/min to about 12 mL/min, from about 0.02 mL/min to about 14 mL/min, from about 0.4 mL/min to about 14 mL/min, or from about 0.4 mL/min to about 12 mL/min.

In some embodiments, the volume of nutritional formula 110 flowed through device 200 may depend on the need of the subject receiving nutritional formula 110. In some embodiments, the volume of nutritional formula 110 may range from about 1 mL to about 10 mL, from about 10 mL to about 100 mL, from about 100 mL to 250 mL, from about 250 mL to about 500 mL, from about 500 mL to about 750 mL, from about 750 mL to about 1 L, from about 1 L to about 2 L, from about 1 L to about 3 L, from about 2 L to about 3 L, from about 1 mL to about 100 mL, from about 1 mL to about 500 mL, from about 1 mL to about 1 L, from about 100 mL to about 500 mL, from about 100 mL to 750 mL, from about 100 mL to 1 L, from about 500 mL to about 1 L, from about 500 mL to about 2 L, from about 750 mL to about 2 L, or from about 750 mL to about 3 L. In some embodiments, device 200 may be selected to have a volume of chamber 222 to be suitable to deliver nutritional formula 110 of a predetermined volume or at a predetermined flow rate. For example, a device 200 having a higher volume of chamber 222 may be selected to deliver a larger amount of nutritional formula 110 or an amount of nutritional formula 110 at a higher flow rate to an adult than that selected to deliver a smaller amount of nutritional formula 110 or an amount of nutritional formula 110 at a lower flow rate to an infant.

In some embodiments, the time needed to deliver the total amount of nutritional formula 110 through device 200, i.e., a feeding time of nutrient formula 110, may depend on the flow rate, the volume of chamber 222, and/or the total volume of nutritional formula 110 to be delivered to the subject. For example, a faster flow rate and/or a larger volume of chamber 222 may allow a predetermined volume of nutritional formula 110 to flow through device 200 for a shorter feeding time.

In some embodiments, the feeding time may depend on the need or enteral feeding practice suitable to the subject. In some embodiments, the feeding time may range, for example, from about a few seconds to a few minutes, from about a few minutes to about 30 minutes, from about 30 minutes to about an hour, from about an hour to about 4 hours, from about 4 hours to about 10 hours, or from about 10 hours to about 12 hours. In some embodiments, a shorter feeding time may be preferable for subjects in need of nutritional formula 110.

In some embodiments, during a feeding period, nutritional formula 110 flowed through device 200 may be exposed to a substantially consistent amount of particles 300 over time and may be able to react with a substantially consistent amount of lipase 710 on particles 300. It is hypothesized that the amount of exposure of nutritional formula 110 to lipase 710 on particles 300 may be correlated to the opportunity for lipase 710 to interact with the fat molecules in nutritional formula 110, which may be increased as the surface area of particles 300 increase. A greater opportunity for lipase 710 to interact with the fat molecules in nutritional formula 110 may be correlated with a higher hydrolysis efficiency of device 200. Accordingly, increased exposure of nutritional formula 110 to lipase 710 on particles 300 may result in more fat out of the total amount of fat in nutritional formula 110 to be hydrolyzed by device 200.

In some embodiments, a residence time of nutritional formula 110 in chamber 222, i.e., the time that nutritional formula 110 is within chamber 222 and exposed to particles 300, may affect the exposure to or interaction between the fat molecules in nutritional formula 110 and lipase 710 on particles 300. For example, longer residence time may allow the fat molecules to have more dwell time to move around with particles 300 in chamber 222 or to have increased probability to interact with and be hydrolyzed by lipase 710 on particles 300. The flow rate of nutritional formula 110 may affect the residence time of nutritional formula 110 in chamber 222 and may affect the amount of time for the fat molecules in nutritional formula 110 to interact with lipase 710 on particles 300. A faster flow rate may drive nutritional formula 110 through chamber 222 in a shorter amount of time than a slower flow rate.

In some embodiments, the amount of residence time needed may vary based on the composition of nutritional formula 110 or the type of fat in nutritional formula 110. For example, longer residence time may be needed for a nutritional formula 110 having a higher density of fat or a higher viscosity. In some embodiments, recycling loops may be added to the flow of nutritional formula 110 through device 200 or through the tubes of system 100 to increase the overall residence time of nutritional formula 110 in chamber 222. In some embodiments, increasing the diameter of chamber 222 while maintaining the diameter of inlet 212 and/or outlet 272 may increase the residence time of nutritional formula 110 in chamber 222. In some embodiments, the thickness of inlet filter 250 and/or outlet filter 260, and/or the diameters and/or perimeters of the channels and/or tortuous paths of the filters may affect the residence time. For example, greater thickness and/or smaller diameters of the tortuous paths of outlet filter 260 may increase the residence time. In some embodiments, longer residence time of nutritional formula 110 in chamber 222 may allow more exposure to or interaction between the fat molecules and lipase 710, and thus may improve the hydrolysis efficiency of device 200, but the residence time may not be so long so that the free fatty acids generated in nutritional formula 110 spoil.

In some embodiments, increasing the flow rate of nutritional formula 110 may clear chamber 222 of nutritional formula 110 containing hydrolyzed fats and allow new nutritional formula 110 containing unhydrolyzed fat to enter chamber 222. This may free up lipase 710 to react with the new nutritional formula 110, increasing hydrolysis efficiency of device 200. However, as discussed above, increasing the flow rate of nutritional formula 110 through device 200 may decrease the residence time of nutritional formula 110 in device 200 and may reduce the hydrolysis efficiency of device 200. On the other hand, decreasing the flow rate of nutritional formula 110 may increase a residence time of free fatty acids already hydrolyzed by lipase 710 in device 200, which may increase the probability of oxidative degradation of the pre-hydrolyzed free fatty acids before ingestion. Thus, the flow rate of nutritional formula 110 through device 200 may need to be designed to balance the hydrolysis efficiency of device 200, the total feeding time, and the prevention of oxidative degradation of pre-hydrolyzed free fatty acids and monoglycerides, and may need to be individually determined to be suitable for feeding a particular nutritional formula 110 to a subject for a particular feeding regimen.

In some embodiments, higher hydrolysis efficiencies may be achieved even when used with faster flow rates. A higher hydrolysis efficiency and/or a faster flow rate would allow device 200 to deliver a volume of nutritional formula 110 in a shorter amount of feeding time. This may be preferable for patients in need of a large volume of nutritional formula 110 in one or more feeding runs. By achieving higher hydrolysis efficiencies even at faster flow rates, device 200 may be able to efficiently deliver hydrolyzed triglycerides having LCTs, such as LC-PUFAs, to the subject at the time of feeding for point-of-care use, reducing the problem of oxidative degradation of free fatty acids in nutritional formula 110.

In some embodiments, increasing mixing or agitation of nutritional formula 110 in chamber 222 may increase the exposure to, or interaction between, the fat molecules in nutritional formula 110 and lipase 710 on particles 300. For example, particles 300 may move under the influence of the flow dynamics of nutritional formula 110 in chamber 222. In some embodiments, nutritional formula 110 and/or particles 300 may follow a laminar flow, a convective flow, a turbulent flow, an agitated flow, or a combination thereof in chamber 222. The type of flow achieved may also in part be affected by the density and/or viscosity of nutritional formula 110 flowed through device 200. Increasing the mobility and movement of particles 300 may increase the exposure to or interaction between the fat molecules and lipase 710 on particles 300. In some embodiments, headspace 223 may allow room for particles 300 to move and mix with nutritional formula 110. In some embodiments, headspace 223 may facilitate the mixing or may increase the turbulence or agitation of nutritional formula 110 in chamber 222. In some embodiments, adjusting the ratio between the shape or volume of particles 300 and the shape or volume of chamber 222 and/or the volume of headspace 223 may increase the mixing and movement of particles 300, and thus increase the exposure to or interaction between the fat molecules and lipase 710 on particles 300. In some embodiments, device 200 may be agitated during the flow of nutritional formula 110 manually or automatically by a shaking, twisting, tilting, or movement of device 200.

In some embodiments, increasing distribution of nutritional formula 110 in chamber 222 may increase the exposure to or interaction between the fat molecules and lipase 710 on particles 300. For example, as discussed above, the tortuous paths of porous mesh 800, shown in FIG. 16B, of inlet filter 250 may result in a dispersed or a more even distribution of nutritional formula 110 across outtake surface 820 of porous mesh 800. Such distribution of nutritional formula 110 may allow nutritional formula 110 to flow through more or substantially all of a cross-section of chamber 222, and thus more or substantially all of particles 300, and may reduce channeling or shunting of nutritional formula 110 through particles 300 in chamber 222, which could otherwise limit exposure. In some embodiments, headspace 223 may also facilitate a reduction in channeling and/or the dispersion of nutritional formula 110 by allowing particles 300 to move, flow, and/or mix, as discussed above.

In some embodiments, pump 120 may be a peristaltic pump that drives nutritional formula 110 under a peristaltic or inconsistent flow, which may increase the movement and/or mixing of particles 300 in chamber 222, and thus may increase the exposure to or interaction between the fat molecules and lipase 710 on particles 300. Example 2, described below, shows an exemplary distribution of flow of nutritional formula 110 through device 200.

Example 2: Distributed Flow of Nutritional Formula 110 Through Exemplary Device 200

Figure 17:
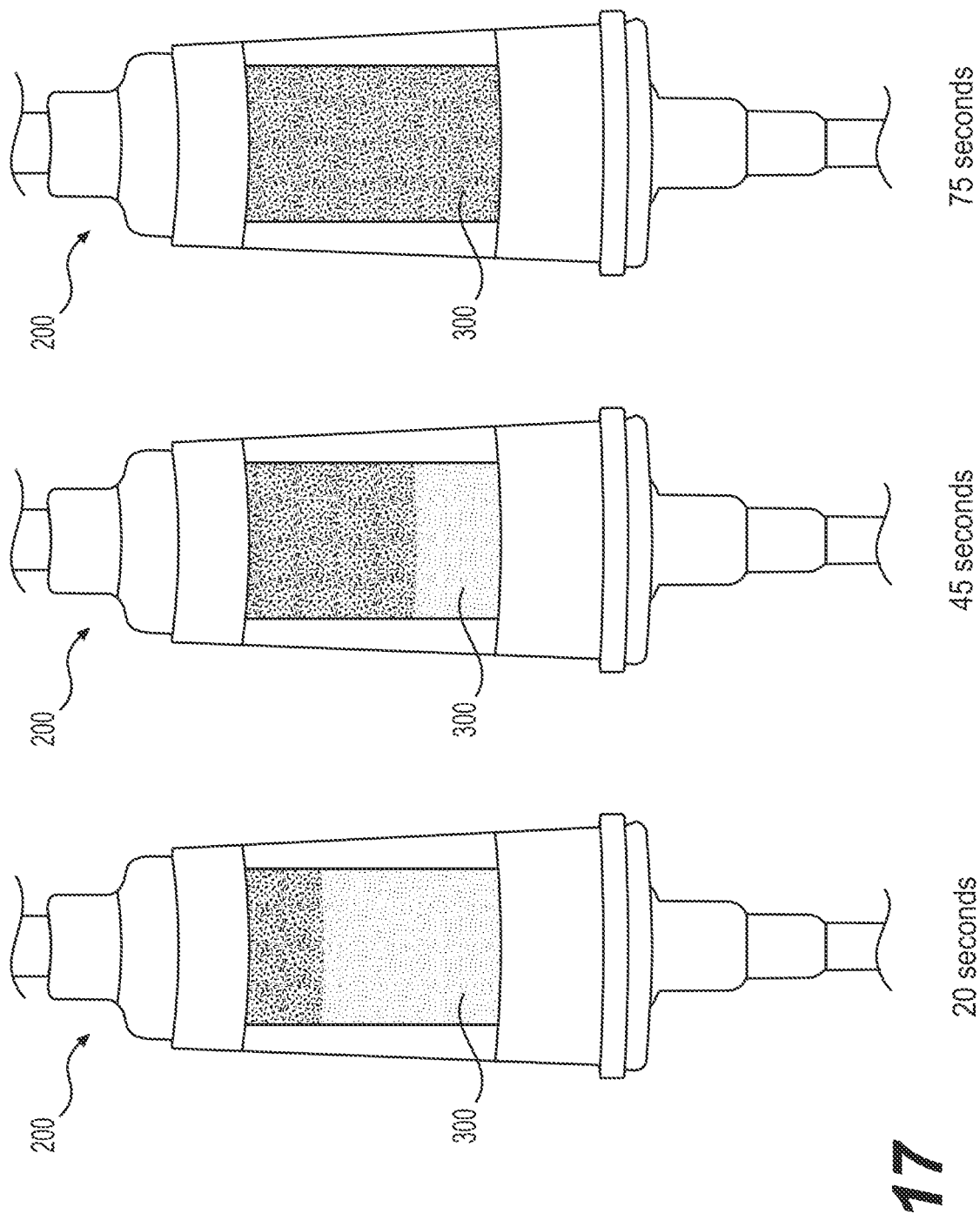
FIG. 17 illustrates the flow of nutritional formula through an exemplary fat hydrolysis device at different time periods, according to embodiments of the present disclosure.

FIG. 17 shows an experiment testing the flow of nutritional formula 110 through an exemplary device 200. Exemplary device 200 used in this experiment was substantially similar to the devices used in Example 1. A digital peristaltic pump 120 was used in this experiment to direct a discontinuous flow of formula sample through exemplary particles 300 in device 200. The formula sample was dyed with a food coloring agent so that the flow of the formula sample could be observed. The left panel, the middle panel, and the right panel of FIG. 17 show the locations of a front of the flow profile of the formula sample at 20 seconds, 45 seconds, and 75 seconds after pump 120 began pumping. As shown in FIG. 17, as the formula sample entered device 200, the front of the flow profile of the formula sample moved substantially evenly across particles 300 in chamber 222. The flow of the formula sample in this experiment was peristaltic and when the pump was not pumping, the front of the flow profile of the formula sample remained substantially in position and did not continue to diffuse throughout particles 300 in chamber 222. When the pump began pumping again, the front of the flow profile of the formula sample continued moving through particles 300 in chamber 222. This discontinuous flow was repeatedly observed during the experiment until the entire chamber 222 of device 200 was filled with the formula sample. The formula sample then began to exit device 200 via outlet 270. The total amount of time used to fill device 200 with the formula sample, as visualized, and determined at the time when the formula sample exit outlet 270 of device 200, was about 1.25 minutes. The flow rate of the formula sample was set at 2 mL/min by setting pump 120, which suggests that it took about 2.5 mL of the formula sample to fill chamber 222 of device 200. No evidence of channeling was observed in this experiment.

This experiment demonstrates that the flow of the formula sample through particles 300 in chamber 222 is distributed approximately evenly across a cross-section of particles 300 in this embodiment of device 200. As discussed above, such even distribution of nutritional formula 110 in device 200 may increase the exposure to and/or interaction between lipase 710 attached to particles 300 and the fat molecules in nutritional formula 110 and thus may improve the hydrolysis efficiency of device 200.

In some embodiments, adjusting the mass density of particles 300 may affect the exposure to or interaction between the fat molecules in nutritional formula 110 and lipase 710 on particles 300. For example, if device 200 is placed in a vertical position, particles 300 having a smaller mass density than nutritional formula 110 may float or move towards inlet filter 250. In such situations, the flow of nutritional formula 110 from inlet filter 250 to outlet filter 260 may agitate particles 300 and/or may facilitate mixing of particles 300 with the flow of nutritional formula 110. In some embodiments, having a mass density of particles 300 that substantially matches that of nutritional formula 110 may allow particles 300 to be dispersed or suspended in nutritional formula 110, and may allow particles 300 to move with the flow dynamics of nutritional formula 110. In some embodiments, a mixture of particles 300 having different densities may be selected so that when nutritional formula 110 is flowed through chamber 222, some particles 300 may move around in a top part of chamber 222, some particles 300 may suspend and may move around in a middle part of chamber 222, and some particles 300 may move around in a bottom part of chamber 222, which may increase the mixing of particles 300 with nutritional formula 110 and may increase the exposure to or interaction between the fat molecules in nutritional formula 110 and lipase 710 on particles 300. In some embodiments, the mass density of particles 300 may not substantially affect the mixing of particles 300 with nutritional formula 110.

In some embodiments, device 200 may be used in a vertical position. In gravity feeding embodiments, device 200 may be orientated in a vertical position for nutritional formula 110 to flow through device 200, as is shown in FIG. 17. In other embodiments, device 200 may be used in a horizontal position. In some embodiments, device 200 may be used in a vertical position with outlet 282 facing upward, or with outlet 282 facing downward, or in a horizontal position.

Example 3: Comparison of Flow Rate of Exemplary Nutritional Formula 110 Through Exemplary Device 200 in Different Orientations In this example, an experiment was performed to test and compare the flow rates of nutritional formula 110 through an exemplary device 200 and the hydrolysis efficiencies of device 200 when device 200 was used in different orientations: a first vertical position with outlet 282 facing upward, a second vertical position with outlet 282 facing downward, and a horizontal position. Exemplary device 200 used in this experiment was substantially similar to those used in Example 1, using inlets made of elastomer and outlets made of polycarbonate. Additionally, an O-ring gasket was used with second connector 270 of device 200 so that second connector 270 could be removably fitted to body 210 of device 200, making device 200 refillable. A total of 6 formula samples, consisting of two types of commercially available nutritional formula 110, Peptamen® and Peptamen AF®, were used for this experiment. Each formula sample was flowed through device 200 in the respective positions driven by pump 120 at a set flow rate of 120 mL/hr. Table 3 shows the average flow rate measured during the flow of each formula sample. Table 4 shows the amount of hydrolyzed free fatty acids delivered in each formula sample.

TABLE 3

Flow rate of nutritional formula 110 with exemplary device 200 positioned in three orientations

| | Flow rate mL/hour | |
|---|---|---|
| | Peptamen ® | Peptamen AF ® |
| Outlet up | 125 | 124 |
| Outlet down | 126 | 125 |
| Horizontal | 125 | 125 |
| Average | 125 | 125 |
| Standard Deviation (SD) | 0.4 | 0.3 |
| % CV | 0.3 | 0.3 |

As shown in Table 3, the average flow rates of the formula samples flowed through device 200 at the three different orientations did not vary more than a CV of 0.3%. As used herein, CV refers to the standard deviation divided by the mean value. Thus, a small CV indicates that the flow rate of the formula samples through device 200 was not substantially affected by the orientation of device 200.

TABLE 4

Amount of free fatty acids produced by exemplary device 200 at different positions

| | grams of Free Fatty Acids (FFA) delivered per serving | |
|---|---|---|
| | Peptamen ® | Peptamen AF ® |
| Outlet up | 6.6 g | 6.6 g |
| Outlet down | 6.2 g | 7.1 g |
| Horizontal | 6.0 g | 6.7 g |
| Average | 6.3 g | 6.8 g |
| SD | 0.3 | 0.3 |
| % CV | 5.3 | 4.2 |

Further, as shown in Table 4, the amount of free fatty acid in the formula samples hydrolyzed and delivered by device 200 did not vary more than a CV of approximately 5%, and thus the hydrolysis of the fats in the formula samples was not substantially affected by the orientation of device 200. The results in Tables 2 and 3 demonstrate the ability of device 200 to operate in different orientations, including vertical and horizontal.

In some embodiments, hydrolysis efficiency of device 200 may vary depending on the composition of nutritional formula 110 and the specificity of lipase 710 to the fat in a particular nutritional formula 110. In some embodiments, the hydrolysis efficiency may increase as the temperature of nutritional formula 110 increases. For example, increasing the temperature of nutritional formula 110 from about 4° C. to about 20° C., from about 4° C. to about 25° C., from about 4° C. to about 37° C., from about 25° C. to about 37° C., or from about 20° C. to about 37° C. may increase the enzymatic activity of lipase 710 and may further increase the thermal dynamic movement of particles 300 and/or fat molecules of nutritional formula 110 in chamber 222, which may increase the exposure to and/or interaction between lipase 710 and fat molecules of nutritional formula 110.

In some embodiments, the hydrolysis efficiency of device 200 may or may not be affected by the type of nutritional formula 110 or the hydraulic resistance of device 200 to the flow of nutritional formula 110. In one embodiment, device 200 may be designed to provide a similar hydrolysis efficiency across a range of different commercially available nutritional formulas 110. In some embodiments, the hydrolysis efficiency of device 200 for commercially available nutritional formulas 110 may range from about 50% to about 60%, from about 60% to about 70%, from about 70% to about 80%, from about 70% to about 90%, from about 70% to about 100%, from about 80% to about 90%, from about 80% to about 100%, from about 90% to about 95%, from about 90% to about 99%, from about 90% to about 100%, or from about 95% to about 100%.

Hydrolysis efficiency has also been tested on pasteurized human milk. Pasteurized human milk may contain up to 20-30% free fatty acids due to hydrolysis of the milk during storage and handling of the milk prior to pasteurization. Usually no further hydrolysis occurs after pasteurization, because the lipase that exists in human milk (bile salt stimulated lipase) is generally inactivated during pasteurization. Device 200 was tested with 30 mL of pasteurized human milk (which is a typical feeding volume used in the neonatal intensive care unit) delivered over 30 minutes (which is the standard feeding duration for preterm infants) to measure the extent of triglyceride hydrolysis. In a preliminary experiment, device 200 was able to increase the free fatty acid content in the pasteurized human milk by approximately 25% or greater.

In some embodiments, device 200 may introduce hydraulic resistance to the flow of nutritional formula 110 as nutritional formula 110 flows through device 200. The magnitude of hydraulic resistance to the flow of nutritional formula 110 may be affected by a number of variables of device 200, including the diameters or shapes of inlet 212 and/or outlet 282; the material, thicknesses, and/or the sizes of the pores, channels, and/or paths of inlet filter 250 and/or outlet filter 260; the number, mass density, swelling, wetting characteristics, and diameters of particles 300; the mixing of particles 300; the volume of headspace 223; and the shape or size of chamber 222. Changing one variable of device 200 or nutritional formula 110 may affect the hydraulic resistance to the flow of nutritional formula 110, and thus may affect the flow rate of nutritional formula 110 through device 200, and may eventually affect the hydrolysis efficiency of device 200.

Accordingly, to achieve a desired hydrolysis efficiency of device 200, a number of different variables of device 200 may need to be designed and manipulated. For example, in some embodiments, increasing the volume of headspace 223 may reduce the hydraulic resistance to or may maintain the hydraulic resistance to the flow of nutritional formula 110 at a lower magnitude as nutritional formula 110 flows through chamber 222. In another example, headspace 223 may facilitate the flow of nutritional formula 110 through particles 300 by allowing particles 300 to move or by increasing the mobility of particles 300. In another example, as nutritional formula 110 flows through particles 300, particles 300 may swell. Headspace 223 may limit or prevent swelled particles 300 from obstructing the pores and/or paths of inlet filter 250, and thus reduce the hydraulic resistance to or maintain a low hydraulic resistance to the flow of nutritional formula 110. Thus, in the embodiments in which particles 300 may swell, headspace 223 may reduce the hydraulic resistance to the flow of nutritional formula 110 and may facilitate the maintenance of a steady flow rate of nutritional formula 110 through device 200.

Examples 4-6, described below, evaluate the effect of materials of inlet filter 250 and/or outlet filter 260, the amount of particles 300, and the diameter of chamber 222 on the flow rate of nutritional formula 110 through exemplary devices 200.

Example 4: Evaluation of Effects of Exemplary Filter Materials on Flow Rates of Nutritional Formula 110 Through Exemplary Devices 200

A series of test runs were performed to evaluate the effects of exemplary materials of mesh 800 for inlet filter 250 and outlet filter 260 on flow rates of nutritional formula 110. Adjustable columns of various diameters were used to mimic exemplary devices 200 having chambers 222 of different diameters. Different materials of inlet filter 250 and outlet filter 260 were also tested, and the different filter types were fitted in the columns. A sample of 1 L Peptamen AF® was flowed through each column using an exemplary pump 120 at a set flow rate of 120 mL/hr.

Porous plastic materials that were authorized for contact with food, compatible with gamma sterilization, and had an approximate porosity of 105 μm were considered for inlet filter 250 and outlet filter 260. Two porous plastic materials from Porex Corporation (Porex X-4906 PE or Porex POR-4744 Hydrophilic PE) were selected. Each of the two porous plastic materials was a customizable polyethylene (PE) sheet and had a thickness of 0.125" and had a porosity range of 90 µm to 130 µm. Another porous plastic material from Applied Separations was initially considered. This material was a hydrophilic PE sheet with a porosity ranging from 20 µm to 70 µm and a thickness of 0.062". In part due to the higher rigidity of the thicker materials, only the two porous plastic materials from Porex Corporation (Porex X-4906 PE or Porex POR-4744 Hydrophilic PE) were tested for use as inlet filter 250 and outlet filter 260.

Each of the selected porous plastic materials was fitted into three empty Omni Fit Adjustable Columns, one having a diameter of 6.6 mm, one having a diameter of 10 mm, and one having a diameter of 15 mm. The effect of each porous material on the flow rate of nutritional formula 110, Peptamen AF®, through the different columns was evaluated. Based on this evaluation, the mesh material was selected and the effects of the density of particles 300 and diameters of chamber 222 on the flow rate of nutritional formula 110 were then evaluated.

Each Porex porous PE sheet was cut into six disks having diameters substantially the same as the diameters of the three columns, i.e., a pair of disks having a diameter of 6.6 mm, a pair of disks having a diameter of 10 mm, and a pair of disks having a diameter of 15 mm. The three columns were cleaned and dried, and each pair of plastic disks having about the same diameter of the corresponding column were inserted into the filter seats of each column's inlet and outlet fittings. The inlet and outlet fittings were then inserted into each column to further mimic device 200. To assess the performance of the filter materials, no particles were placed in the chamber created between the pairs of filter disks. Each column was installed onto an enteral feeding circuit in a horizontal orientation and fluidly connected to a pump set tubing.

Each enteral feeding circuit was then manually primed up to the inlet of the empty adjustable column. The pump was then set to 2 mL/min, and the timer was started. Empty 1.5 mL vials were placed under each column to collect measurement samples for evaluating the flow rate of Peptamen AF® in the columns. The flow rate (mL/min) for each column was measured randomly over 100 minutes by measuring the weight of the formula dispensed from the column and into a respective vial in 30 seconds. The weight of the filled vials at each time point was noted and the net weight of the dispensed formula in the filled vials was obtained by subtracting the weight of the empty vials. The weight of the dispensed formula in each vial was then used to calculate a flow rate.

The filters' effect on the flow rate was assessed. Referring to the user's manual of pump 120, the actual flow rate of pump 120 used should be within about 10% that set by pump 120. For all runs, pump 120 was set at 2 mL/min or 120 mL/hr. Therefore, for each run, the actual flow rate should have been less than about 132 mL/hr and more than about 108 mL/hr. It was desired to identify a filter type that would not cause the actual flow rate of pump 120 to fall out of the 10% variation of the pump setting when not using device 200. The results of the flow rates measured for each column and porous filter combination were shown in Tables 4-9 below.

TABLE 5

Flow rates for an empty 6.6 mm column
with Porex X-4906 filter material
Flow Rate Without Beads
Frit: Porex X-4906 PE 0.125" thick, 90-130 um
Column 6.6 mm Dia
Solution: Peptamen

| Pump Vol (ml) | Time (min) | Flow Rate (ml/min) | Flow Rate (ml/hr) | Percent of Initial Flow Rate (%) | Beaker Vol (ml) |
|---|---|---|---|---|---|
|  | 0 | 1.9 | 112.5 | 100% |  |
|  | 32 | 0.2 | 12 | 11% |  |

TABLE 6

Flow rates for an empty 6.6 mm column
with Porex POR-4744 filter material
Flow Rate Without Beads
Frit: Porex POR-4744 PE Hydrophilic 0.125" thick, 90-130 um
Column 6.6 mm Dia
Solution: Peptamen

| Pump Vol (ml) | Time (min) | Flow Rate (ml/min) | Flow Rate (ml/hr) | Percent of Initial Flow Rate (%) | Beaker Vol (ml) |
|---|---|---|---|---|---|
|  | 5 | 2.4 | 144 | 100% |  |
|  | 18 | 2.2 | 132 | 92% |  |
|  | 32 | 2 | 120 | 83% |  |
|  | 60 | 1.8 | 108 | 75% |  |
| 216 | 103 | 1.4 | 84 | 58% | 175 |

Average flow (ml/hr): 102;
Pump Set Point (ml/hr): 120;
Variance: 15%

TABLE 7

Flow rates for an empty 10 mm column with
Porex X-4906 filter material
Flow Rate Without Beads
Frit: Porex X-4906 PE 0.125" thick, 90-130 um
Column 10 mm Dia
Solution: Peptamen

| Pump Vol (ml) | Time (min) | Flow Rate (ml/min) | Flow Rate (ml/hr) | Percent of Initial Flow Rate (%) | Est. Beaker Vol (ml) |
|---|---|---|---|---|---|
|  | 0 | 1.9 | 144 | 100% |  |
|  | 15 | 1.9 | 132 | 100% |  |
|  | 30 | 2.0 | 120 | 107% |  |
|  | 45 | 2.0 | 108 | 107% |  |
|  | 60 | 1.7 | 104 | 93% |  |
|  | 75 | 1.5 | 88 | 79% |  |
|  | 90 | 1.2 | 72 | 64% |  |
| 200 | 100 | 1.0 | 60 | 54% | 173 |

Average flow (ml/hr): 104;
Pump Set Point (ml/hr): 120;
Variance: 13%

TABLE 8

Flow rates for an empty 10 mm column with
Porex POR-4744 filter material
Flow Rate Without Beads
Frit: Porex POR-4744 Hydrophilic PE 0.125" thick, 90-130 um
Column 10 mm Dia
Solution: Peptamen

| Pump Vol (ml) | Time (min) | Flow Rate (ml/min) | Flow Rate (ml/hr) | Percent of Initial Flow Rate (%) | Est. Beaker Vol (ml) |
|---|---|---|---|---|---|
| | 0 | 2.3 | 136 | 100% | |
| | 15 | 2.0 | 120 | 107% | |
| | 30 | 1.7 | 104 | 93% | |
| | 45 | 1.7 | 104 | 93% | |
| | 60 | 1.7 | 104 | 93% | |
| | 75 | 1.7 | 104 | 93% | |
| | 90 | 1.7 | 104 | 93% | |
| 209 | 105 | 1.7 | 105 | 94% | 208 |

Average flow (ml/hr): 119;
Pump Set Point (ml/hr): 120;
Variance: 1%

TABLE 9

Flow rates for an empty 15 mm column with
Porex X-4906 filter material
Flow Rate Without Beads
Frit: Porex X-4906 PE 0.125" thick, 90-130 um
Column 15 mm Dia
Solution: Peptamen

| Pump Vol (ml) | Time (min) | Flow Rate (ml/min) | Flow Rate (ml/hr) | Percent of Initial Flow Rate (%) | Est. Beaker Vol (ml) |
|---|---|---|---|---|---|
| | 0 | 1.9 | 112 | 100% | |
| | 12 | 2.0 | 120 | 107% | |
| | 25 | 2.1 | 128 | 114% | |
| | 40 | 1.9 | 112 | 100% | |
| | 55 | 1.9 | 112 | 100% | |
| | 70 | 2.1 | 128 | 114% | |
| | 85 | 1.3 | 80 | 71% | |
| 200 | 100 | 1.9 | 112 | 100% | 197 |

Average flow (ml/hr): 118;
Pump Set Point (ml/hr): 120;
Variance: 1%

TABLE 10

Flow rates for an empty 15 mm column with
Porex POR-4744 filter material
Flow Rate Without Beads
Frit: Porex POR-4744 Hydrophilic PE 0.125" thick, 90-130 um
Column 15 mm Dia
Solution: Peptamen

| Pump Vol (ml) | Time (min) | Flow Rate (ml/min) | Flow Rate (ml/hr) | Percent of Initial Flow Rate (%) | Est. Beaker Vol (ml) |
|---|---|---|---|---|---|
| | 0 | 2.0 | 120 | 100% | |
| | 15 | 1.9 | 112 | 100% | |
| | 30 | 2.1 | 128 | 114% | |
| | 45 | 1.9 | 112 | 100% | |
| | 60 | 2.1 | 128 | 114% | |
| | 75 | 1.7 | 104 | 93% | |
| 179 | 90 | 1.9 | 112 | 100% | 176 |

Average flow (ml/hr): 118;
Pump Set Point (ml/hr): 120;
Variance: 2%

As shown in Tables 4 and 5, the flow rates for both 6.6 mm column runs went below the lower limit. The 6.6 mm column with Porex X-4906 filter material experienced a flow rate below the lower limit at the 32 minutes test point and pump 120 went into alarm due to no flow. The 6.6 mm column with Porex POR-4744 filter material experienced a flow rate below the lower limit at the 103 minutes test point and a flow rate above the upper limit at the 5 minutes test point.

As shown in Tables 6 and 7, the flow rates for both 10 mm column runs went below the lower limit. The 10 mm column with Porex X-4906 filter material experienced a flow rate below the lower limit at the 60 minutes test point and a flow rate above the upper limit at the 5 minutes test point. The 10 mm column with Porex POR-4744 filter material experienced a flow rate below the lower limit at the 30 minutes test point.

As shown in Tables 8 and 9, the flow rates for both 15 mm column runs went below the lower limit at one test point. However, both runs recovered and finished within the tolerance of pump 120. The 15 mm column with Porex X-4906 filter material experienced a flow rate below the lower limit at the 85 minutes test point. The 15 mm column with Porex POR-4744 filter material experienced a flow rate below the lower limit at the 75 minutes test point. Neither went above the upper limit.

The results in Tables 4-9 show that the flow rate appeared to improve as the column diameter increased. The 6.6 mm columns experienced failures early in the evaluation. The components of larger diameter columns were also found to be easier to install and handle compared to the components of the smaller diameter columns. The Porex POR-4744 hydrophilic PE filter material appeared to provide more consistent flow rates than the Porex X-4906 PE filter material. The results indicate that a larger diameter column with Porex POR-4744 hydrophilic PE filter material may be advantageous due to more consistent flow rates of the nutritional formula and ease of handling. The materials for inlet filter 250 and outlet filter 260 may have properties that are consistent with the Porex POR-4744 hydrophilic PE filter material.

Example 5: Evaluation of Effects of Exemplary Diameters of Chamber 222 and Amount of Particles 300 on Flow Rates of Nutritional Formula 110 Through Exemplary Devices 200

A series of test runs were performed to evaluate the effects of diameters of chamber 222 and amount of particles 300 on flow rates of nutritional formula 110 in exemplary devices 200. Adjustable columns were again used to substantially mimic exemplary devices 200 having chambers 222 of different diameters, and the columns were filled with different amounts of particles 300. Based on the evaluation of the porous filter materials in Example 4, Porex POR-4744 hydrophilic PE filter material was used for this experiment. Additionally, due to early enteral feeding circuit failures for the columns having a diameter of 6.6 mm, this experiment was limited to two groups of adjustable columns, one group having 3 columns with diameters of 10 mm, and the other group having 3 columns with diameters of 15 mm. Pairs of disks of the selected hydrophilic PE filter material having diameters substantially the same as the diameters of the columns were inserted into the filter seats of each column's inlet and outlet fittings. Additionally, one of the three columns in each group was filled with 1 g, one of the three columns in each group was filled with 2 g, and one of the three columns in each group was filled with 4 g of exemplary particles 300, covalently bound with lipase 710, between the two filter disks inside each respective column. When the columns containing particles 300 were placed in a vertical orientation, the positions of the adjustable fittings of each column were adjusted so that there was approximately a length of 2 mm of headspace 223 above particles 300 in each column.

Each column with a particular diameter and a particle amount combination was installed in a horizontal orientation onto an enteral feeding circuit and fluidly connected to a pump set tubing. One-liter samples of Peptamen AF® of were flowed through each of the columns for about 100 minutes using an exemplary pump 120 (Covidien Kangaroo EPump) set at a flow rate of 2 mL/min or 120 mL/hr. Each column was run 3 times. During each fun, five measurement samples were collected at 0 minutes, 25 minutes, 50 minutes, 75 minutes, and 100 minutes, and were used to obtain the flow rate of Peptamen AF® sample through each column. The flow rates were obtained gravimetrically from the measurement samples for each run of each column as described in Example 4. The results of the obtained flow rates are shown in FIGS. 18-23.

Figure 18:
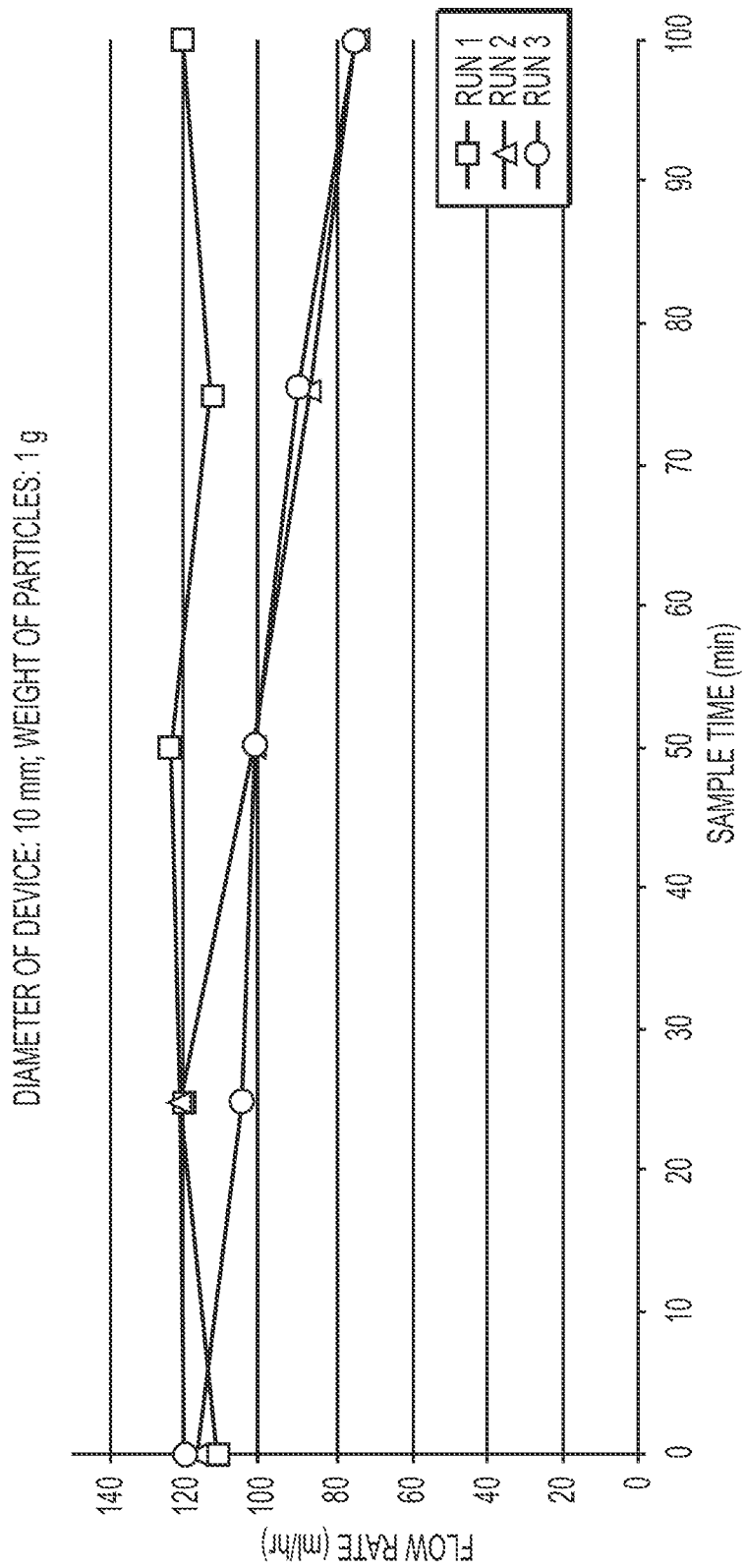
FIG. 18 graphically depicts the flow rates of an exemplary nutritional formula through an exemplary fat hydrolysis device in three test runs, according to embodiments of the present disclosure.
Figure 19:
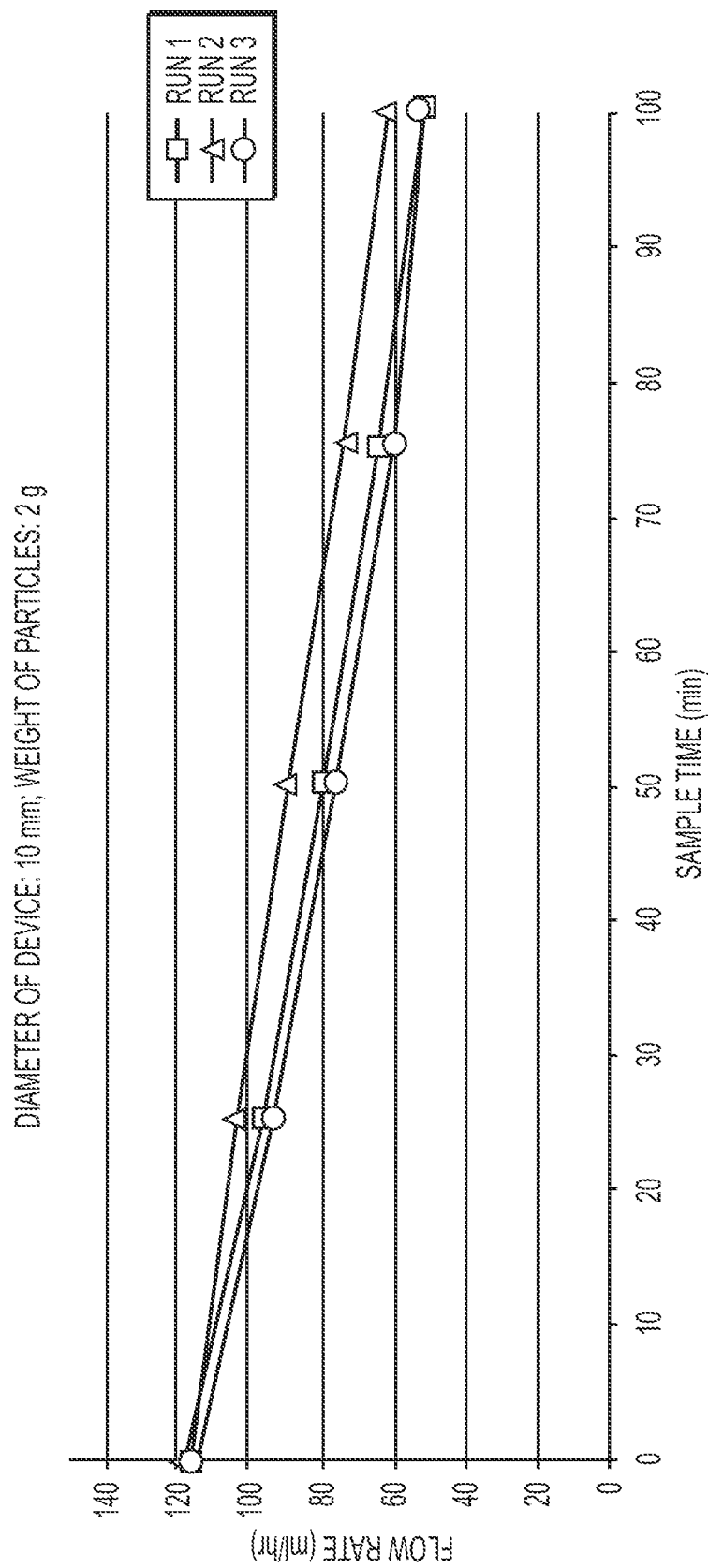
FIG. 19 graphically depicts the flow rates of an exemplary nutritional formula through an exemplary fat hydrolysis device in three test runs, according to embodiments of the present disclosure.
Figure 20:
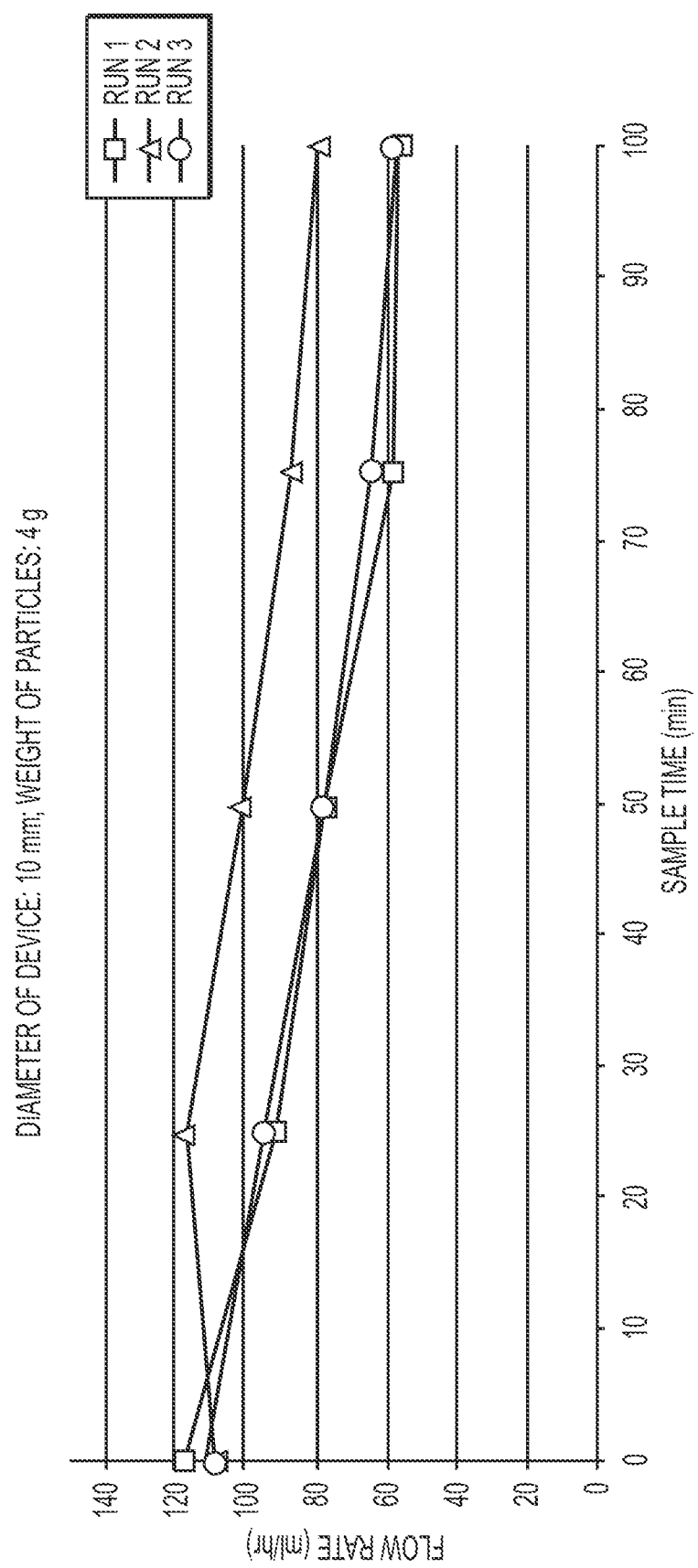
FIG. 20 graphically depicts the flow rates of an exemplary nutritional formula through an exemplary fat hydrolysis device in three test runs, according to embodiments of the present disclosure.

As shown in FIG. 18, in two runs, the flow rates of the 10 mm columns filled with 1 g of particles 300 fell below pump 120's lower limit (108 mL/hr) at the 50 minute time point. These flow rates continued downward for the remainder of the runs. As shown in FIGS. 19 and 20, the flow rates of the 10 mm columns filled with 2 g and 4 g of particles 300, respectively, fell below pump 120's lower limit (108 mL/hr) when tested at the 25 minutes time point. The only exception was the second run of the column filled with 4 g of particles 300, which fell below the limit when measured at the next 50 minutes time point. These flow rates continued downward for the remainder of the runs.

Figure 21:
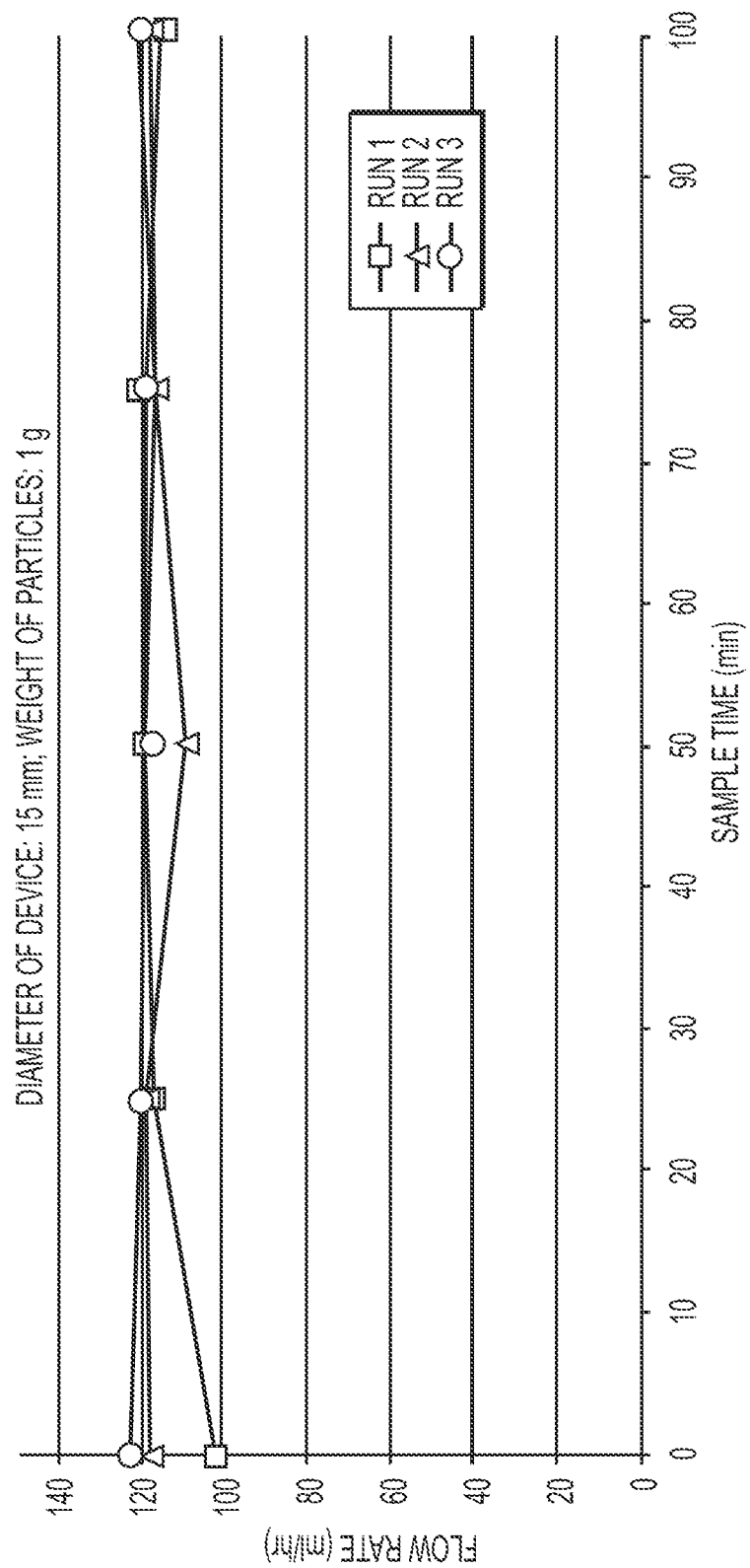
FIG. 21 graphically depicts the flow rates of an exemplary nutritional formula through an exemplary fat hydrolysis device in three test runs, according to embodiments of the present disclosure.
Figure 22:
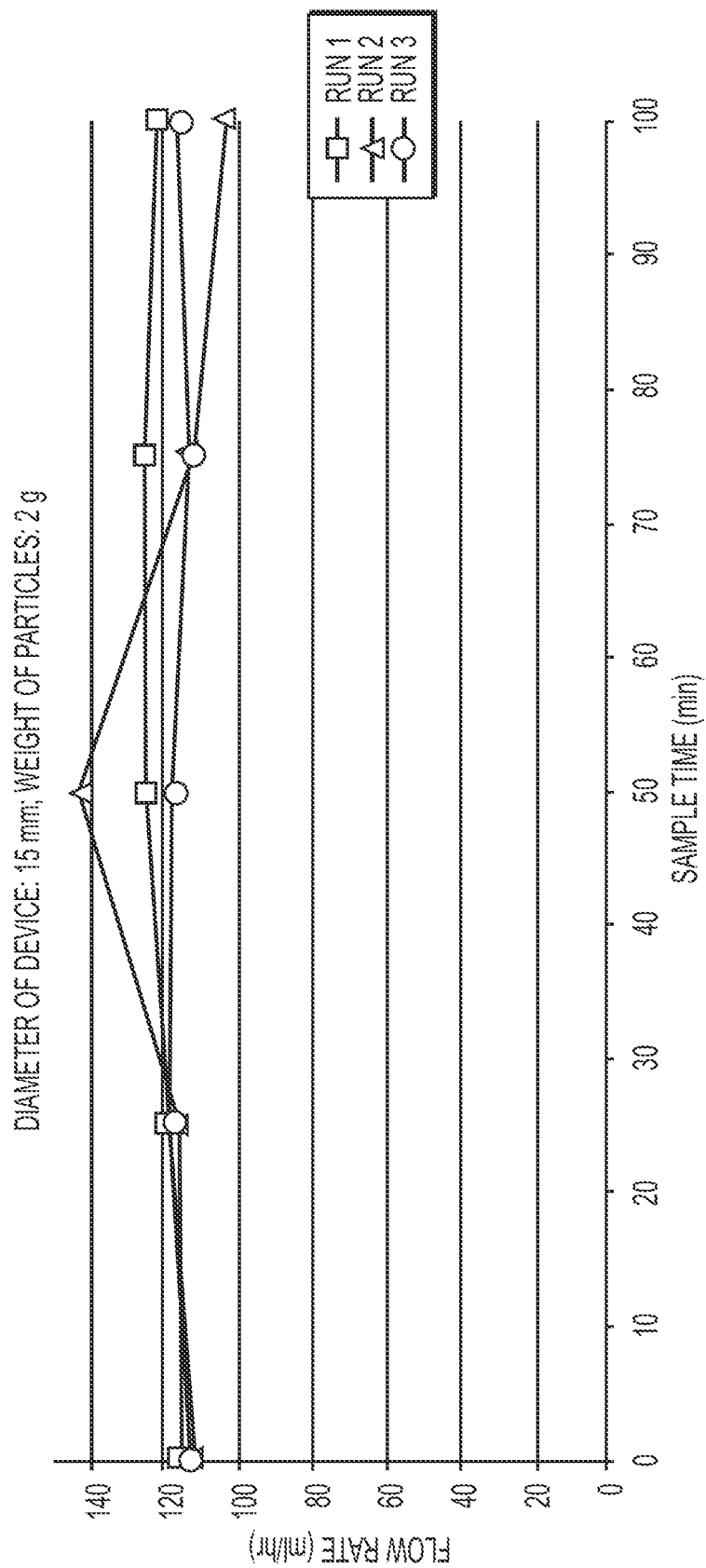
FIG. 22 graphically depicts the flow rates of an exemplary nutritional formula through an exemplary fat hydrolysis device in three test runs, according to embodiments of the present disclosure.
Figure 23:
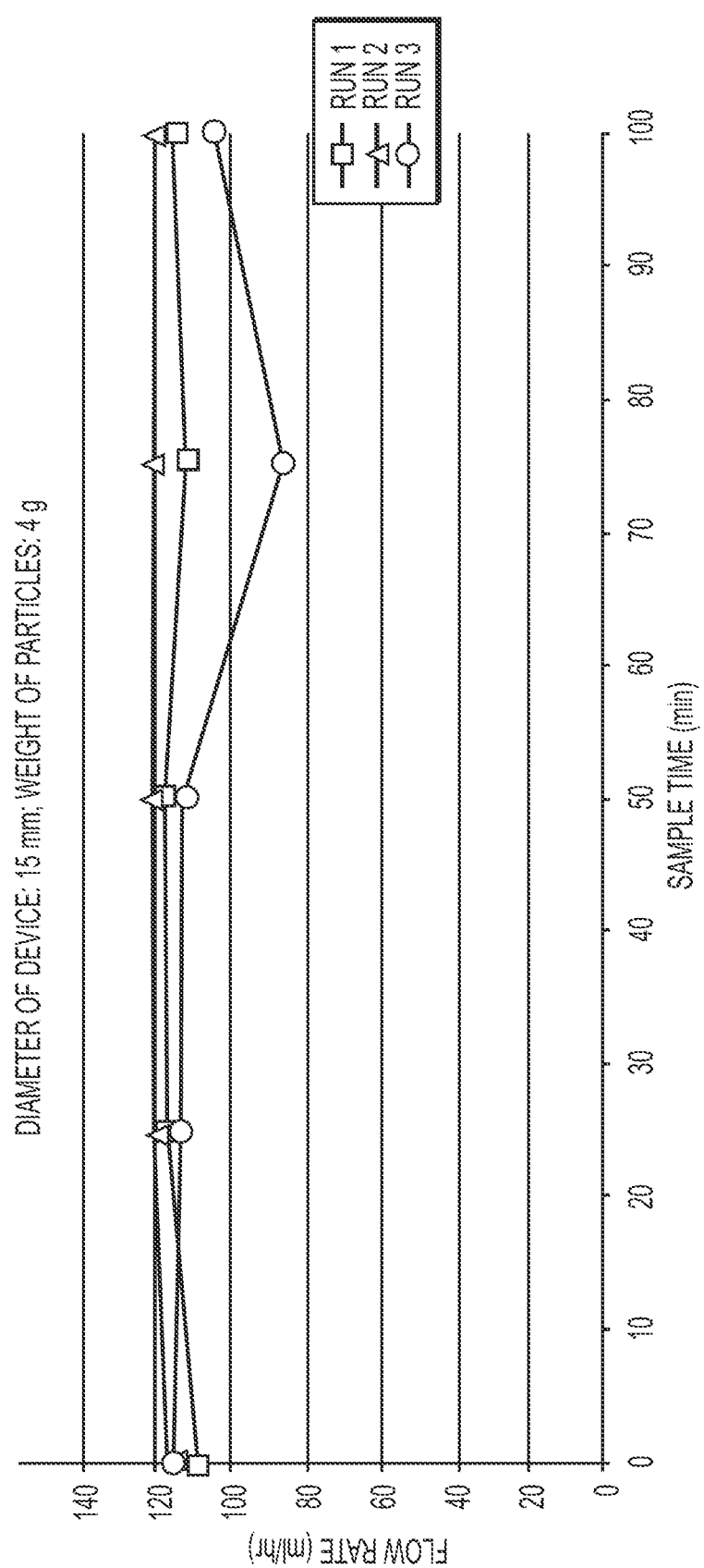
FIG. 23 graphically depicts the flow rates of an exemplary nutritional formula through an exemplary fat hydrolysis device in three test runs, according to embodiments of the present disclosure.

As shown in FIG. 21, the flow rates of the runs of columns with a diameter of 15 mm and filled with 1 g of particles 300 stayed within pump 120's tolerance (i.e., 120 mL/hr+/− 10%) for the duration of the runs. The only exception was the 0 minutes test point for the first run, which then evened out by the next time point and remained within the threshold. As shown in FIG. 22, the flow rates of the 15 mm column filled with 2 g of particles 300 generally fell within the tolerance range, but in run 2, the flow rate increased above pump 120's upper limit (132 mL/hr) at the 50 minutes test point and fell below the lower limit at the 100 minutes test point. All other data points were within tolerance of pump 120 during the runs. As shown in FIG. 23, flow rates of the 15 mm column filled with 4 g of particles 300 generally fell within the tolerance range, but in run 3, the flow rate fell below pump 120's lower limit (108 mL/hr) at the 75 minutes test point and fell just below the lower limit at the 100 minutes test point. All other data points were within tolerance of pump 120 during the runs.

As shown in FIGS. 18-23, the 10 mm columns showed downward flow rate trends, while the 15 mm columns showed more consistent flow rates. These results indicate that a larger diameter of chamber 222 of device 200 was preferable in this embodiment to maintain a stable flow rate. This conclusion was further supported by previous issues maintaining the flow rates in the 6.6 mm columns in Example 4. Additionally, the downward flow rate trend for the 10 mm columns and the 15 mm columns filled with 2 g or 4 g of particles 300 indicates that, for this embodiment, a lower total weight of particles 300 or amount of particles 300 may be preferable to maintain a stable flow rate. This is further supported by the more consistent flow rates of the 15 mm columns filled with 1 g of particles 300.

Although a chamber with a 15 mm diameter was shown as most-efficient in this experiment, changes to particle type, size, or distribution may cause other chamber sizes to be more efficient. Additionally, changes to the inlet and outlet may affect the optimal chamber size, as may changes to the filters or the amount of headspace provided.

Example 6: Evaluation of Effects of Exemplary Devices 200 on Flow Rates of Nutritional Formula 110

Figure 25:
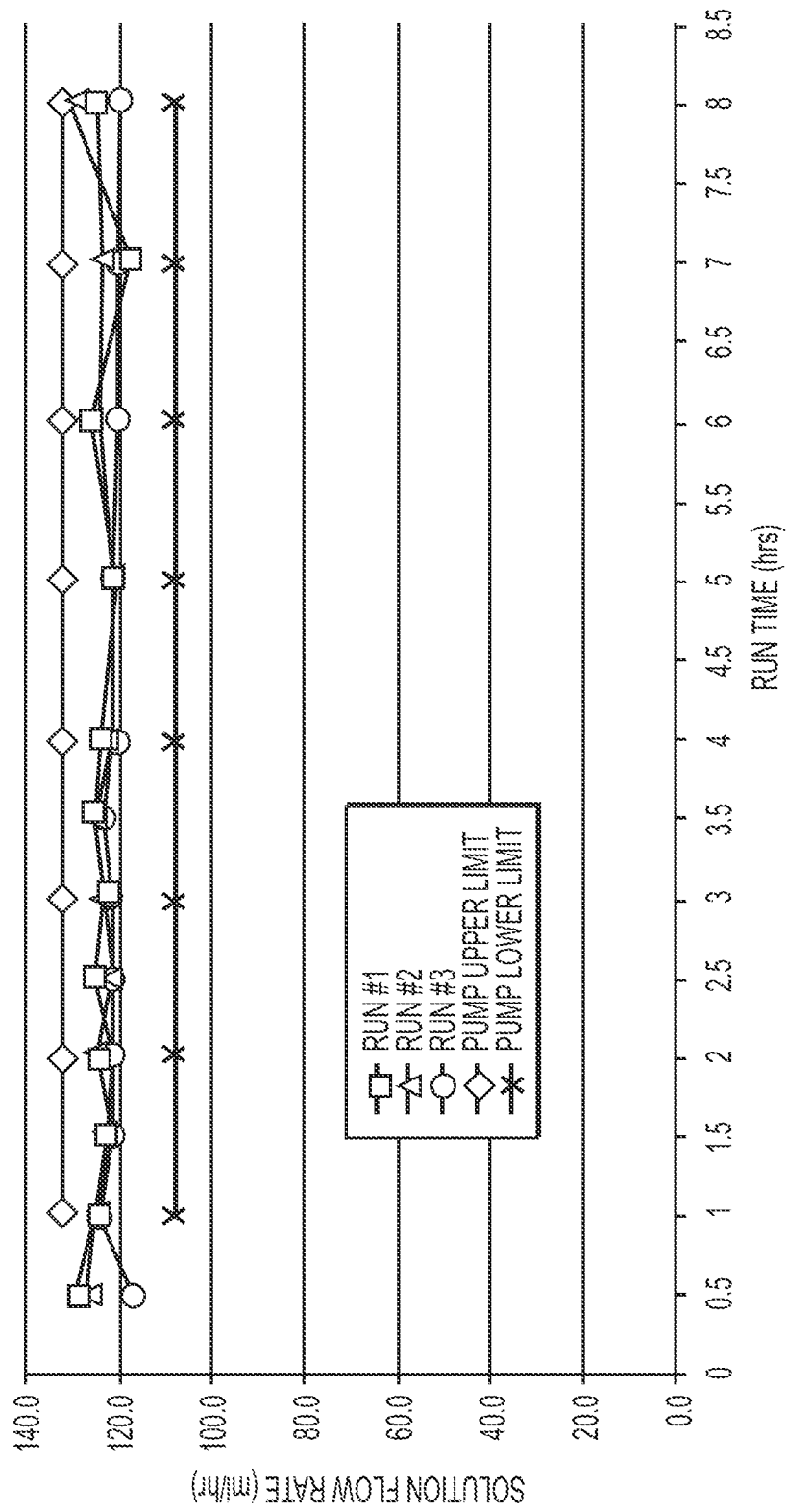
FIG. 25 graphically depicts the flow rates of an exemplary nutritional formula through an exemplary fat hydrolysis device in three test runs, according to embodiments of the present disclosure.
Figure 26:
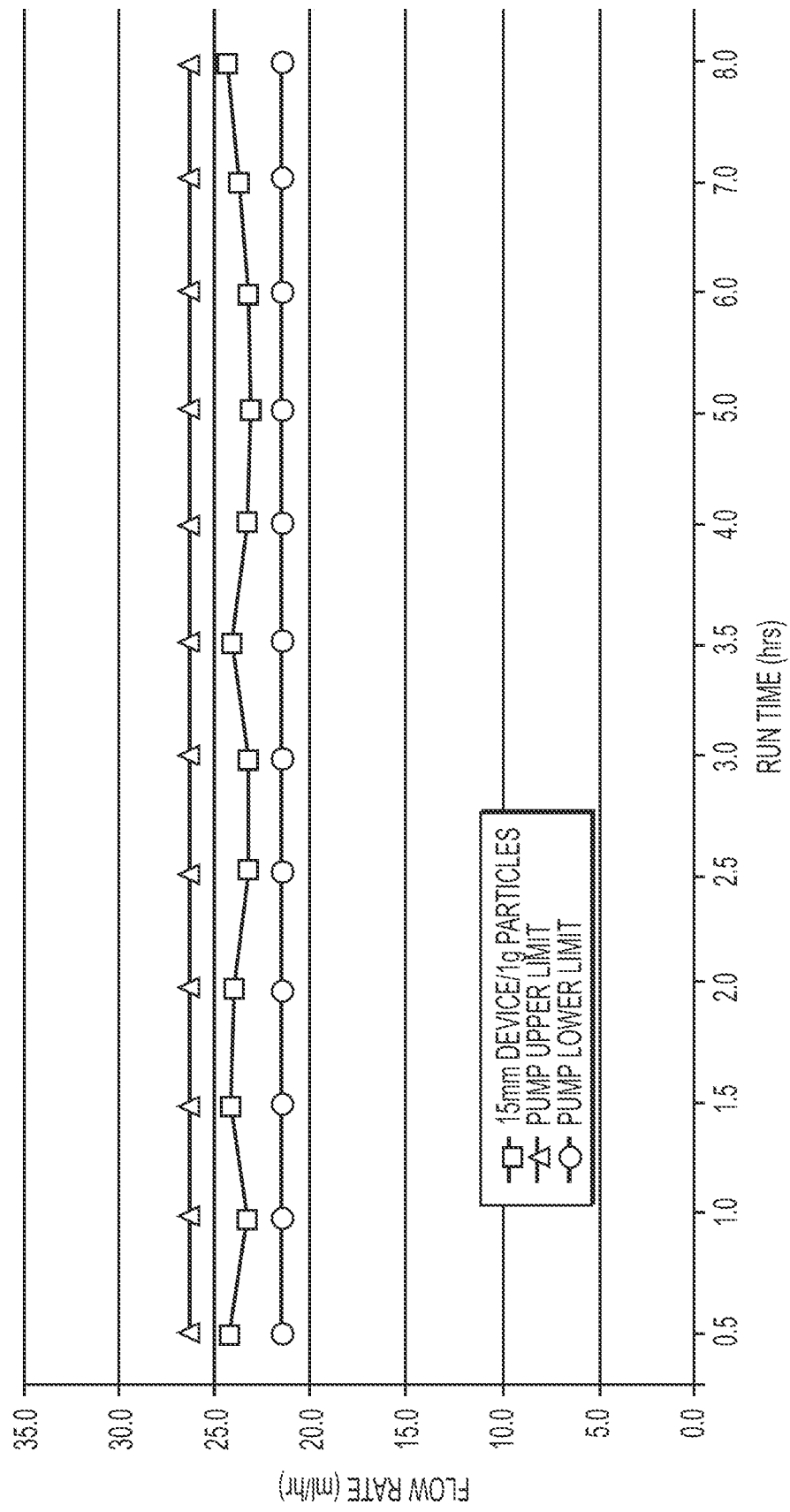
FIG. 26 graphically depicts the flow rate of an exemplary nutritional formula through an exemplary fat hydrolysis device, according to embodiments of the present disclosure.

A series of test runs were performed to evaluate the effects of exemplary devices 200 on the flow rates of nutritional formula 110 by comparing the flow rates of enteral feeding circuits without device 200, with an empty device 200 that did not include particles 300, and with device 200 containing particles 300. Exemplary device 200 used in this experiment was substantially similar to the devices used in Example 1. Based on the consistent flow rate of the 15 mm columns filled with 1 g of particles 300, exemplary devices 200 were assembled from polycarbonate tubing with an interior diameter of 15 mm and custom stereolithographic (e.g., 3D printing) exemplary inlet filters 250 and outlet filters 260, substantially similar to the selected porous filter in Example 5. Enteral feeding circuits were assembled with a device 200 filled with 1 g of particles 300, with an empty device 200 without particles 300, and with no device 200 (i.e., just the tubing of the feeding circuit). One-liter samples of Peptamen AF® were flowed through the enteral feeding circuits using an exemplary pump 120 set at a flow rate of 0.4 mL/min (24 mL/hr) and a flow rate of 2 mL/min (120 mL/hr). The flow rates of these enteral feeding circuits were measured gravimetrically as described in Examples 4 and 5 at 30-minute intervals for 4 hours or until the formula ran out or the pump was stopped. The results of the observed flow rates compared to the upper limit and lower limit of tolerance (±10% variation) of pump 120 are shown in FIGS. 24-26.

Figure 24:
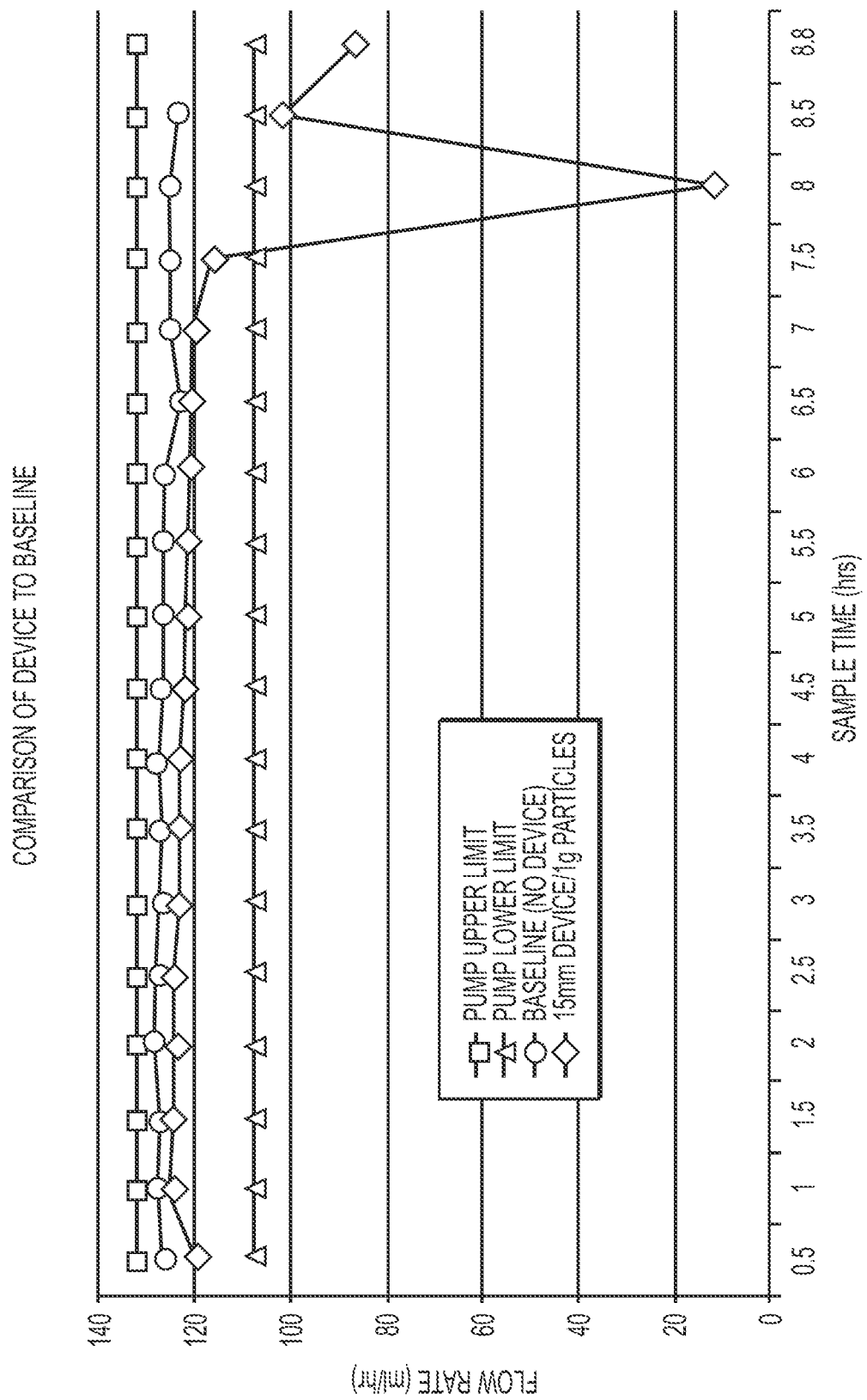
FIG. 24 graphically compares the flow rates of an exemplary nutritional formula through exemplary enteral feeding circuits, according to embodiments of the present disclosure.

FIG. 24 compares the test runs without device 200 and with device 200 containing 1 g of particles 300. Pump 120 was set at a flow rate of 2 mL/min (120 mL/hr). FIG. 25 shows three test runs with device 200 that did not contain particles 300. Pump 120 was set at a flow rate of at 2 mL/min (120 mL/hr). FIG. 26 shows a test run with device 200 containing 1 g of particles 300. Pump 120 was set at a flow rate of 0.4 mL/min (24 mL/hr).

All test runs exceeded the targeted minimum run time of 4 hours and ran until the 1 L sample formula bags were emptied. No circuit failures or pump alarms were observed during any of the test runs. During the targeted minimum run time (4 hours), device 200 containing 1 g of particles 300 showed consistent flow rate performance with the pump set at 2 mL/min and 0.4 mL/min. Flow rate degradation was observed after 7 hours during the 2 mL/min run. No flow rate degradation was observed during the 0.4 mL/min run. The consistent flow rates of device 200 with and without particles 300 indicate that device 200 does not significantly impact flow rate.

In some embodiments, when inlet filter 250 and/or outlet filter 260 include tortuous paths or channels, the tortuous paths or channels may be designed to reduce the hydraulic resistance to the flow of nutritional formula 110 as it passes through. As discussed previously, the tortuous paths may allow nutritional formula 110 to be distributed cross chamber 222, and thus may affect the hydraulic resistance to the flow of nutritional formula 110. In some embodiments, increasing the sizes or diameters, numbers, distribution, and/or adjusting the shapes of the pores, channels, and/or paths of porous mesh 800 may further affect the hydraulic resistance to the flow of nutritional formula 110. In some embodiments, using additional inlet filter 250 or outlet filter 260 or not using inlet filter 250 or outlet filter 260 may affect the overall hydraulic resistance to the flow of nutritional formula 110. Accordingly, variations in filter design may affect the flow rate of nutritional formula 110 through device 200, and it may be possible to offset these effects by adjusting other components of device 200.

In some embodiments, reducing the diameters of particles 300 may increase the overall surface area of particles 300, as discussed previously, but may also increase the hydraulic resistance to the flow of nutritional formula 110. For example, in a given chamber 222, particles 300 having a smaller median or mean diameter may create a higher density of polymeric material in chamber 222, and may create more packing of particles 300, and thus may result in a higher hydraulic resistance to the flow of nutritional formula 110. Increasing the number of particles 300 in chamber 222 may increase the hydraulic resistance. For example, for a given volume of chamber 222, a larger number of particles 300 may have less space to move and less mobility and/or may crowd at the top or bottom of chamber 222, which may lead to a greater hydraulic resistance to the flow of nutritional formula 110 and/or clogging of inlet filter 250 and/or outlet filter 260. Thus, maximizing the overall surface area of particles 300 may need to be balanced with the possibility of clogging of the filters and/or packing of particles 300 and subsequent effect on the hydraulic resistance to the flow of nutritional formula 110 through particles 300. In some embodiments, inert particles may be mixed with smaller particles 300 to disrupt the packing of particles 300.

In some embodiments, particles 300 may swell when suspended in nutritional formula 110 and may pack against each other due to swelling, and thus may have reduced mobility as nutritional formula 110 flows through chamber 222. In some embodiments, a skewed, varied, bi-modal, multi-modal, or narrower distribution of the diameters of particles 300 may promote the packing of particles 300 upon swelling. For example, particles having smaller diameters may fill the space between particles having larger diameters, which may further reduce the mobility or movement of particles 300 during the flow of nutritional formula 110. In such situations, channeling of nutritional formula 110 may occur. For example, nutritional formula 110 may follow a path of least resistance and may flow through a channel among particles 300 that has the least amount of packing or hydraulic resistance. In this case, only lipase 710 attached to particles 300 along the channel may be substantially exposed to nutritional formula 110, reducing hydrolysis efficiency. To reduce this channeling effect and/or packing of particles 300, particles 300 may be made of a polymeric material that has less of a propensity for swelling, for example, swelling of less than about 1%, about 2%, about 5%, about 10%, about 15%, or about 20% of the original dry particle size.

In some embodiments, pump 120 may be a peristaltic pump that drives nutritional formula 110 under a peristaltic, pulsatile, or discontinuous flow, which may reduce or inhibit the packing of particles 300. For example, nutritional formula 110 directed into chamber 222 under a peristaltic flow may increase the movement and/or mixing of particles 300 in chamber 222, and thus may reduce or eliminate packing of particles 300. It may also allow particles 300 to pack less by not applying a constant force on particles 300 towards outlet filter 260 and instead introducing breaks.

Hydraulic resistance of device 200 to nutritional formula 110 may depend on the composition, density, and/or viscosity of nutritional formula 110. In some embodiments, a higher viscosity and/or mass density of nutritional formula 110 may lead to a greater hydraulic resistance to the flow of nutritional formula 110. For example, nutritional formula 110 with a higher viscosity may have more resistance to a driving force from pump 120 to nutritional formula 110 and/or may have more friction within tubes 122, 124, and particles 300 as nutritional formula 110 flows through system 100 and particles 300. Such resistance may or may not substantially affect the flow rate of nutritional formula 110 through device 200.

In some embodiments, the flow rate selected for pump 120 or other device may be adjusted by a healthcare professional based on the composition, density, and/or viscosity of nutritional formula 110 before feeding. For example, the flow rate of nutritional formula 110 may be reduced from a typical setting to increase the residence time of nutritional formula 110 in chamber 222 to increase the exposure to and interaction between the fat molecules in nutritional formula 110 with lipase 710 on particles 300. In another example, the flow rate of nutritional formula 110 may be increased from a typical setting to reduce the total amount of feeding time to a patient in need of a large volume of nutritional formula 110. In some embodiments, the flow rate of nutritional formula 110 may be set by inputting a desired flow rate into pump 120. As describe above, a number of different variables of device 200 may be designed and manipulated. Thus, device 200 may be designed to not substantially affect the flow rate of nutritional formula 110 set by pump 120. In some embodiments, an initial wetting resistance may exist as particles 300 become wetted when nutritional formula 110 initially enters chamber 222. In such situations, the flow rate of nutritional formula 110 may be affected initially but then the effect may decrease over time.

In exemplary embodiments, the flow rate of nutritional formula 110 may be substantially stable and/or predictable over the feeding time of nutritional formula 110. For example, as demonstrated in Example 6, the flow rate of nutritional formula 110 may not vary more than an allowable deviation or tolerance (e.g., about 5%, 10%, 15%, 20%, or 30% deviation from a set flow rate) of pump 120 or other flow driver, such as a gravity feed. Example 7, described below, further demonstrates a substantially stable flow rate of nutritional formula 110 flowed through an exemplary device 200.

Example 7: Stability of Flow Rate of Nutritional Formula 110 Flowed Through Exemplary Device 200

Figure 27:
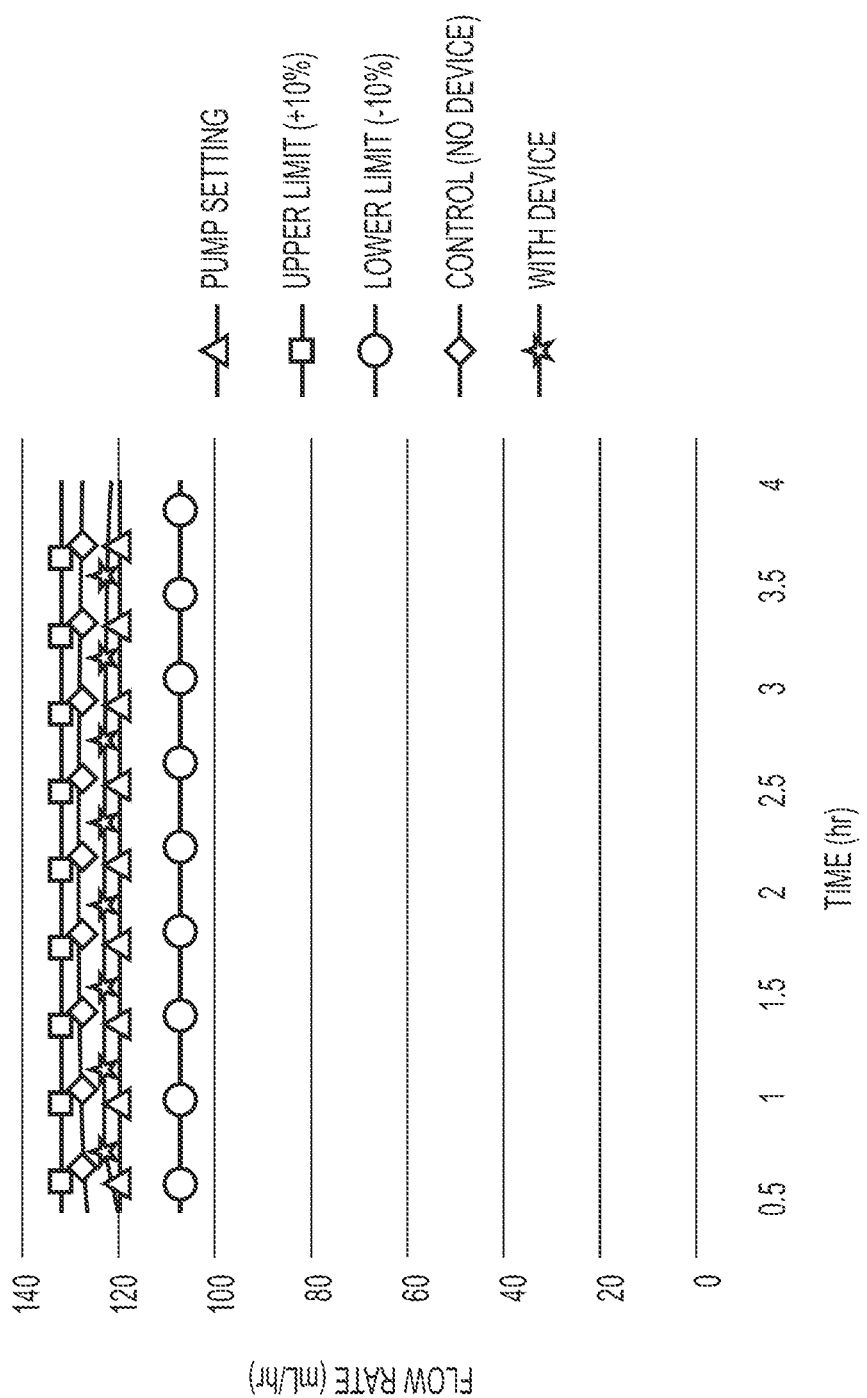
FIG. 27 graphically depicts the flow rate of an exemplary nutritional formula through an exemplary fat hydrolysis device over a 4-hour simulated feeding period.

The flow rate of nutritional formula 110 in an exemplary device 200 directed by a peristaltic pump 120 was monitored over 4 hours. Exemplary device 200 used in this experiment was substantially similar to those described in Example 1. Pump 120 was set to deliver a formula sample at a flow rate of 120 mL/hr or 2 mL/min. As shown in FIG. 27, the flow rate of nutritional formula 110 was maintained at a substantially stable level between about 120 mL/hr to about 125 mL/hr over a 4-hour simulated feeding period. The flow rate of a control in which nutritional formula 110 was flowed without passing through device 200 was also monitored as a comparison to the flow rate of nutritional formula 110 flowed through device 200. As shown in FIG. 27, the flow rate of nutritional formula 110 flowed through device 200 was maintained between the upper limit and lower limit of the tolerance (e.g., 10% variation) of pump 120 over the 4-hour simulated feeding period. Neither pump alarm or clogging of device 200 was observed. This simulated feeding period of nutritional formula 110 shows that the flow rate of nutritional formula 110 flowed through device 200 can be consistently maintained within the tolerance of pump 120.

Various components of device 200, including those pertaining to body 210, chamber 222, headspace 223, particles 300, inlet filter 250 and/or outlet filter 260, lipase 710 attached to particles 300, and parameters of these components, such as sizes, shapes, densities, and other properties discussed above, may vary and be designed for particular applications. For example, the size of chamber 222, the size of the inlets and/or outlets, and/or number of particles 300 may be reduced for devices intended for use with infants. Either individual component may be modified or the proportion of the device may be shrunk or enlarged, according to use. For example, device 200 may come in infant, youth, and/or adult sizes. In some embodiments, the components of device 200 may be adjusted based on the intended length of feeding time, the amount of nutritional formula 110 intended to be delivered, the amount of LCPUFA to be delivered, or the intended flow rate of delivering nutritional formula 110. For example, the size of chamber 222 and/or number of particles 300 of device 200 for an overnight enteral feeding procedure may be different than those for a two-hour enteral feeding procedure. A faster flow-rate device or a total nutrition device may be larger than a slower flow-rate device or one that is intended for use to supplement a patient's diet. In some embodiments, the size of chamber 222 and/or number of particles 300 of device 200 may depend on the type of nutritional formula 110 to be hydrolyzed and processed.

The interplay of the various components of device 200, including those pertaining to body 210, chamber 222, headspace 223, particles 300, inlet filter 250 and/or outlet filter 260, lipase 710 attached to particles 300, and parameters of these components, such as sizes, shapes, densities, and other properties discussed above, may contribute to the overall exposure to and interaction between lipase 710 in chamber 222 and fat molecules in nutritional formula 110, and thus may affect the hydrolysis efficiency and/or performance of device 200. The design of the components of device 200 and their parameters may be adjusted to increase the exposure to and interaction between lipase 710 in chamber 222 and the fat molecules in nutritional formula 110. In some embodiments, device 200 may be designed so that the hydrolysis efficiency or performance of device 200 may not be significantly affected by the type or composition of nutritional formula 110. Device 200 may be configured to work across a broad spectrum of formula types. In other embodiments, the design of various components of device 200 may be selected based on the use of one particular formula type. Example 8, described below, demonstrates an exemplary range of commercial enteral formulas capable of being hydrolyzed by an exemplary device 200.

Example 8: Landscape of Enteral Formulas Tested by an Exemplary Device 200

Figure 28:
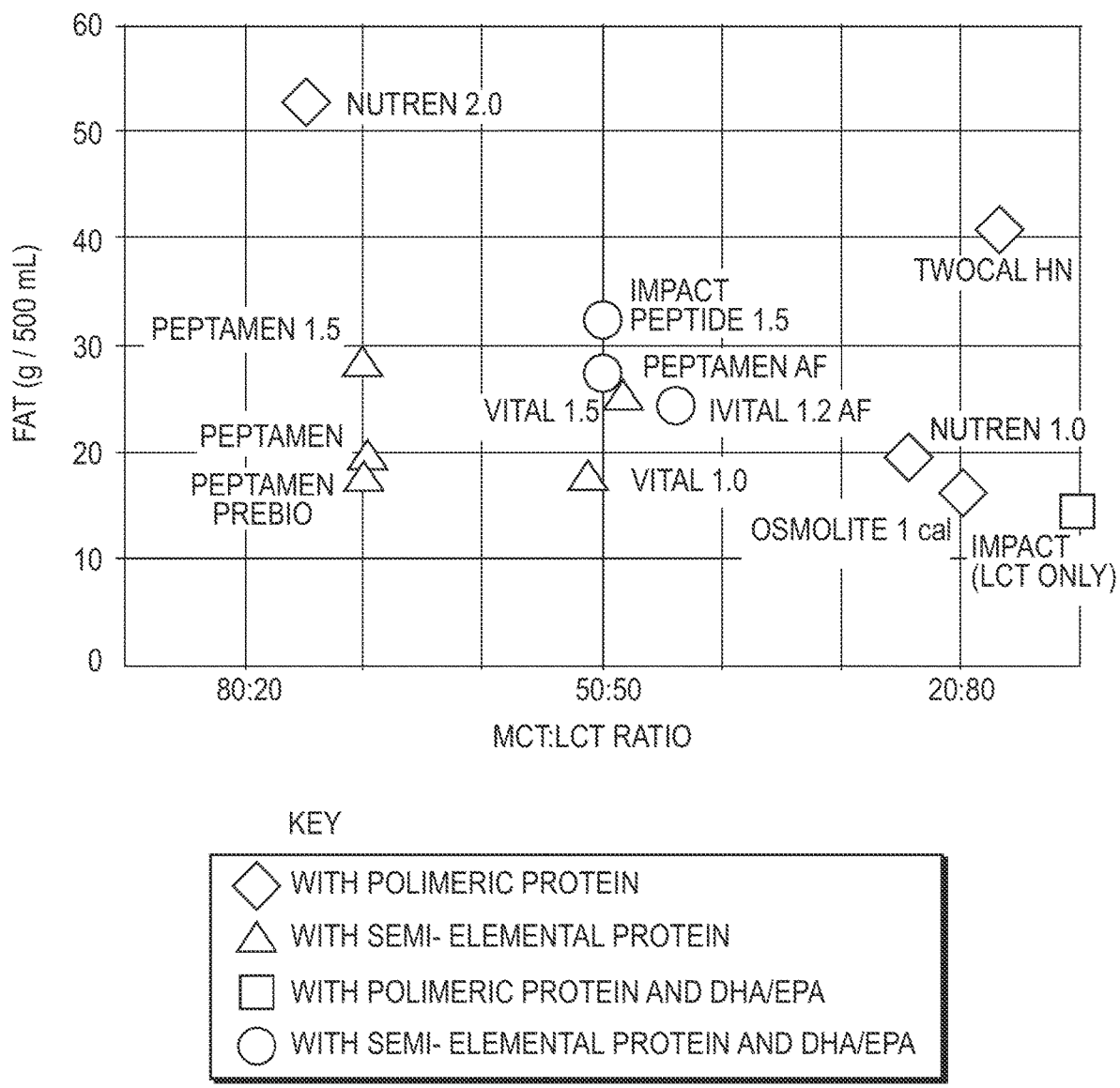
FIG. 28 graphically depicts the fat content and types of fat of commercially available enteral formulas, according to embodiments of the present disclosure.

FIG. 28 shows a number of commercially available enteral formulas hydrolyzed using an exemplary device 200. Exemplary device 200 used in this experiment was substantially similar to that used in Example 3. As described herein, commercially available nutritional formulas differ in their protein and fat content and may be classified as elemental, semi-elemental, and polymeric. Elemental formulas, for example, may contain individual amino acids, glucose polymers, and may have a lower fat content offering a smaller amount of calories derived from long-chain triglycerides. Semi-elemental formulas, for example, may contain peptides of varying chain length, simple sugars, glucose polymers or starch, and fat. Polymeric formulas, for example, may contain intact proteins, complex carbohydrates, and varying types of fats. In this experiment, five commercially available polymeric formulas and eight commercially available semi-elemental formulas were tested with device 200. The volume of each formula used was 500 mL. The content of each formula tested is depicted in FIG. 28, which shows the ratio of medium-chain triglycerides to long-chain triglycerides along the x-axis and shows the fat content along the y-axis.

An exemplary system 100, as shown in FIG. 1, was used to hydrolyze fats, such as long-chain triglycerides, in these nutritional formulas during simulated enteral feedings. Each nutritional formula was directed through an exemplary device 200 at a flow rate of 120 mL/hr for approximately 4 hours. Each nutritional formula was collected at the end of the simulated enteral feeding, and the amount of hydrolyzed free fatty acid was analyzed using a quantitative colorimetric assay (Abcam® Free Fatty Acid Quantification Kit). Each nutritional formula was tested in duplicate simulated enteral feeding runs.

Figure 29:
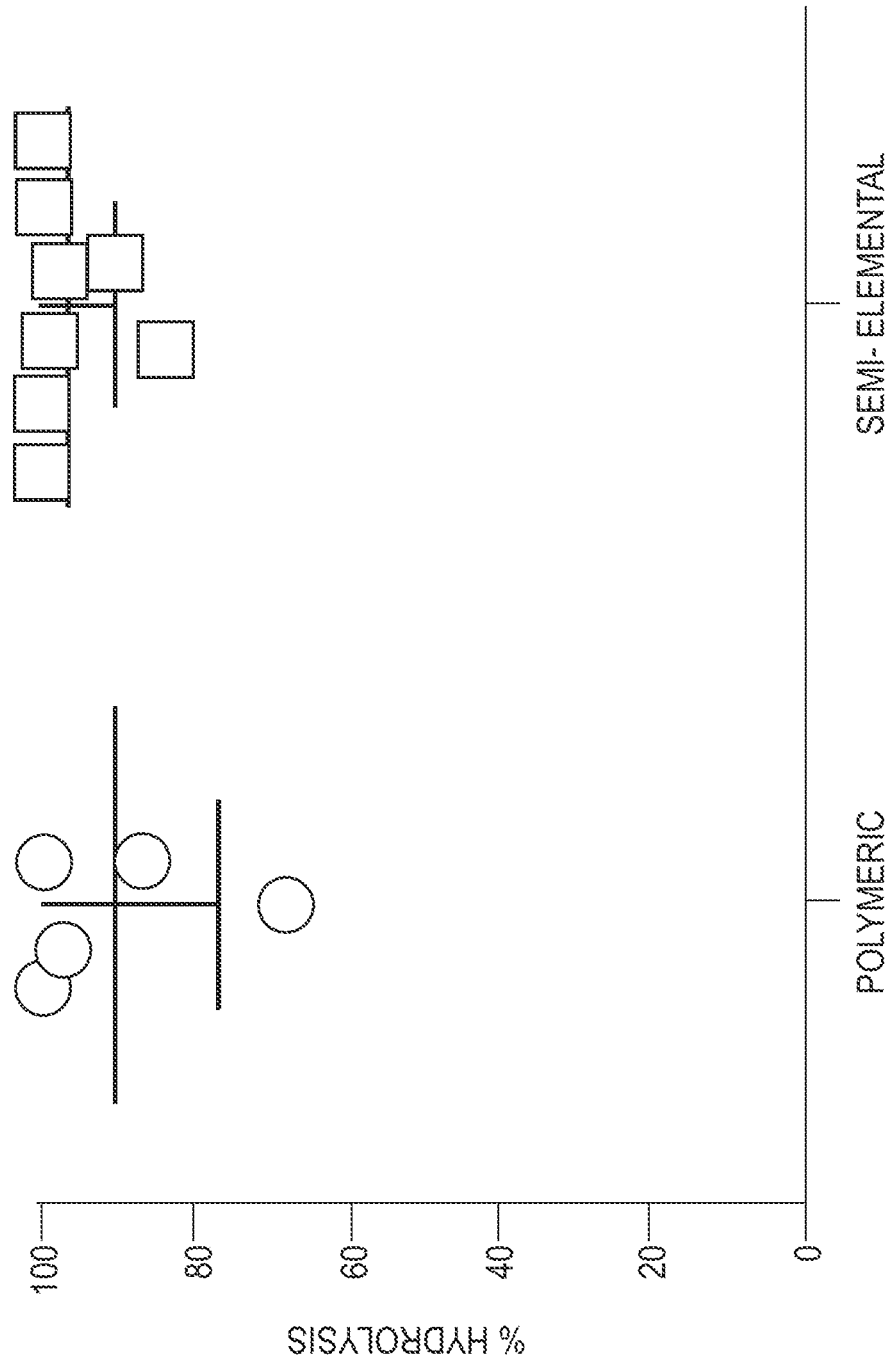
FIG. 29 graphically depicts the percentage of fat hydrolyzed out of the exemplary enteral formulas of FIG. 16 using an exemplary fat hydrolysis device, according to embodiments of the present disclosure.

FIG. 29 shows the hydrolysis efficiency of device 200 when used with the nutritional formulas tested in this experiment, grouped by formula type. The polymeric formulas include Nutren® 2.0, TwoCal HN®, Nutren® 1.0, Osmolite® 1 cal, and Impact®. The semi-elemental formulas include Peptamen® 1.5, Peptamen AF®, Peptamen®, Peptamen Prebio®, Vital® 1.5, Vital 1.2 AF™, Vital® 1.0, and Impact Peptide® 1.5. As shown in FIG. 29, device 200 hydrolyzed over 80% of the fat in all of the nutritional formulas but one. This 80% hydrolysis is remarkable given the differences in formula content, the fact that lipase 710 was covalently bound to particles 300 in device 200, and the fact that the exposure time was relatively short compared to industrial uses of lipase, particularly in light of the reduced activity of covalently bound lipase noted in previous publications.

In some embodiments, device 200 may not significantly affect other non-fat nutrients in nutritional formula 110, such as, for example, proteins, amino acids, carbohydrates, and/or vitamins. For example, lipase 710 attached to particles 300 may be highly specific to hydrolyzing fats in nutritional formula 110 and may not substantially interact with or affect other nutrient components in nutritional formula 110. In some embodiments, lipase 710 attached to particles 300 may have a high degree of purity, such that there are minimal or no other proteins or enzymes, e.g., proteases, mixed with lipase 710, and thus there are no other substances present in the lipase that could interact with or affect other nutrient components in nutritional formula 110. In some embodiments, lipase 710 may be purified over one or more rounds of a purification process prior to binding with particles 300, or one or more rounds of purification after binding with particles 300, to reduce or substantially eliminate other molecules or chemicals in lipase 710. In some embodiments, lipase 710 may be purified to 5%, 25%, 75%, or essentially 100% purity before or after immobilization. In some embodiments, the polymeric material of particles 300 may be inert and may not interact with the nutrient components in nutritional formula 110. Example 9, described below, further demonstrates a comparative analysis of the nutrients in sample nutritional formulas (i) having passed through an exemplary device 200 or (ii) not having passed through device 200. The data shows that this embodiment of device 200 did not substantially affect other nutrients in nutritional formula 110.

Example 9: Comparative Analysis of Nutritional Formulas that Passed Through Exemplary Device 200 or Did not Pass Through Device 200

This study was designed to assess the overall nutritional content of nutritional formula after (i) having passed through an enteral feeding circuit with an exemplary device 200 installed in-line (test) and (ii) having passed through an enteral feeding circuit without any device 200 installed in-line (control). Exemplary device 200 used in this experiment was substantially similar to those described in Example 3, except that outlet 270 was permanently attached to body 210 (i.e., no O-ring was used, making the device 300 in Example 9 single-use). A comprehensive analysis of nutrients was completed for two enteral formulas, Prosure® and TwoCal HN®. The nutrients analyzed are summarized below in Table 11. Prosure® represents a formula with a less fat content that is lower in calories, while TwoCal HN® represents a formula with a higher fat content that is higher in calories.

All samples (control and test) for nutrient analysis were flowed at the slowest recommended flow rate (0.4 mL/min), as it was hypothesized that the impact of device 200 on the formula samples may be greatest when the formula is in direct contact with the device 200 for the longest duration of time.

Triplicate sampling was performed to assess variation between the nutrients of the test and the control samples and variation within each test and control sample. A statistical analysis of the data was performed using an unpaired t-test. The nutrients of the test and the control samples are shown in Table 11.

The test and control data sets were evaluated for each nutrient based on % relative standard deviation (% RSD). For observed % RSD in these experiments, the nutritional values determined were within expected assay precision. Test and control data sets for most of the nutrients tested were generally comparable, and any differences between the test and control data sets were accounted for or expected from the variability of the assay performance. Any differences observed did not exceed variability that would be expected for standard test assays applied to such complex matrices, i.e., nutritional formulas, used in this testing. There were no nutrient differences observed consistently between test and control samples across the two tested formulas.

For the nutrient tests for which a difference (p-value of larger than 0.05) may were detected (indicated by an asterisk in Table 11), (i) there was no evidence of nutrient degradation, since the measured amount of nutrient in the test sample value was higher than in the control sample, such as, for vitamin $B_6$ and calcium, or (ii) the difference in nutrient levels between test and control samples were small when comparing their amounts with each other and with the formula label claim, such as, for vitamins A, E, and C.

Thus, nutrient analysis of formulas that have passed through the device 200 under simulated use conditions in comparison with a no-device control identified no significant differences between the test and control samples for the effect of the feeding system on non-fat nutrients.

TABLE 11

Nutrients analyzed for comparative analysis of nutritional formulas that passed through exemplary device 200 or did not pass through device 200

Nutrient

Energy, kcal
Calories from fat, Cal
Protein, g
Total fatty acids, g
EPA, g
DHA, g
Omega-3 fatty acids, g
Omega-6 fatty acids, g
Carbohydrates, g
Dietary fiber, g
Fructooligosaccharide, g
L-carnitine, mg
Vitamin A, IU*
Vitamin D, IU
Vitamin E, IU*
Vitamin C, mg*
Vitamin $B_6$, mg (Pyridoxine)*
Vitamin $B_{12}$, mcg
Folic acid, mcg
Pantothenic acid, mg
Biotin, mcg
Sodium, mg
Potassium, mg
Chloride, mg
Calcium, mg*
Phosphorus, mg
Magnesium, mg
Riboflavin, mg (Vitamin $B_2$)
Ash, g
Moisture (Water, mL)

Device 200 may be designed for point-of-care use. For example, device 200 may be designed to be used with standard enteral feeding devices for delivering nutritional formula 100 to a subject in need of fatty acid nutrients in a clinic or a hospital. In some embodiments, device 200 may be used in non-clinical settings, such as at the subject's home, long-term or short-term care facility, or at a place the subject visits regularly. The fat, including triglycerides having LC-PUFAs, in nutritional formula 110 is "digested" or pre-hydrolyzed by device 200 right before feeding and is delivered in a form ready for absorption in individuals who lack pancreatic lipase or the physiological capacity to digest or absorb fat. Such delivery of pre-hydrolyzed nutritional formula 100 using device 200 prior to ingestion may provide direct delivery of hydrolyzed and absorbable fatty acids to the GI tract of the subject, leading to improved delivery and absorption efficiency.

The use of device 200 may also prevent the problem of oxidative degradation of free fatty acids in a pre-hydrolyzed nutritional formula 110 and thus may prevent the development of a rancid taste, odor, or texture in the nutritional formula after hydrolysis. Specifically, it is the hydrolysis of fats into short-chain aldehydes and ketones that are objectionable in taste and odor.

Industrial-scale utilization of immobilized lipase for fat hydrolysis requires a water-oil interface to release free fatty acids. The free fatty acids are then re-esterified to form triglycerides since the free fatty acids themselves are unstable for any substantial period of time. Industrial-scale immobilization tends to be time-consuming, inefficient, and requires significant operator manipulation. The use of device 200 is generally with complex mixtures containing, for example, proteins, carbohydrates, fat, water, minerals, and/or vitamins, which may include liquid foods that are specially formulated and processed.

By delivering pre-hydrolyzed absorbable free fatty acids at the point of care, device 200 may also reduce or eliminate the need and/or risks of taking of porcine-derived pancreatic enzyme or microbial enzyme products during the feeding of nutritional formula 110. Further, as discussed above, the amount of residence time of nutritional formula 110 in device 200 may be adjusted and may be balanced with the hydrolysis efficiency of device 200 by adjusting the flow rate to reduce or prevent oxidative degradation of pre-hydrolyzed free fatty acid in nutritional formula 110. Exemplary timespans between the exposure of nutritional formula 110 to lipase and ingestion of the pre-hydrolyzed formula by a patient are discussed in International Patent Application No. PCT/US2013/026063, filed Feb. 14, 2013, and U.S. patent application Ser. No. 14/378,856, filed Aug. 14, 2014, both of which are herein incorporated by reference in their entireties.

System 100 and device 200 allow fats in nutritional formula 110 to be pre-hydrolyzed ex vivo, prior to ingestion, and to match the time of hydrolysis of fat with enteral feeding, leading to reliable, efficient, and consistent delivery of absorbable beneficial fats to the subject. System 100 and device 200 may provide healthcare professionals an advantageous option for feeding patients in need of additional calories and essential fatty acids, such as DHA and EPA.

In some embodiments, device 200 may be disposable and intended for a single use. In other embodiments, device 200 may be reusable for a number of feeding runs before disposal. In such embodiments, device 200 and/or the tubes, e.g., first tube 122 and enteral tube 124, may be cleaned before a new feeding run by flushing or purging a solution through device 200 and/or the tubes. For example, pump 120 may operate on an automatic mode to flush or purge a solution through device 200 and/or the tubes to adequately empty nutritional formula 110 left in device 200 and/or the tubes from a previous feeding run. This flushing or purging would allow device 200 and/or the tubes to be used more than once before disposal.

In some embodiments, particles 300 may be disposable. For example, after a feeding run of nutritional formula 110, used particles 300 may be disposed of and device 200 may be sterilized and/or cleaned, and for a next feeding run of nutritional formula 110, new, unused particles 300 may be packaged under dry conditions in chamber 222 of device 200. In such embodiments, the remainder of device 200 may be sterilizable.

Patients suffering from EPI (insufficient production of exocrine pancreatic enzymes) and/or gastrointestinal or liver dysfunction have a reduced ability to hydrolyze and/or absorb long-chain triglycerides. As a result, they might have maldigestion and malabsorption of lipids, which may lead to reduced caloric intake, significant weight loss, LC-PUFAs deficiencies, and/or GI symptoms, and may be deprived of the benefits associated with ingestion of LC-PUFAs, such as DHA, EPA, AA, etc. System 100 and device 200 may be used for feeding nutritional formula 110 having pre-hydrolyzed triglycerides of DHA, EPA, and/or AA, to patients having compromised pancreatic output. For example, system 100 and device 200 may be used to increase the intake of DHA, EPA, and AA in the plasma of these patients. In some embodiments, since healthy subjects may also benefit from increased absorption of LC-PUFAs, e.g., by reducing the risk of cardiovascular disease, system 100 and device 200 may be used for feeding a healthy subject nutritional formula 110. In some embodiments, system 100 and device 200 may be used to increase the intake of DHA, EPA, and AA in the plasma of infants, aging adults, or people with acute or chronic conditions that may impact fat hydrolysis and/or absorption.

In some embodiments, system 100 and device 200 may be used to increase the intake of hydrolyzed fatty acids for patients having one or more diseases, including for example, Alzheimer's disease (AD), bipolar disorder (BP), depression, major depressive disorder (MDD), post-partem depression, sepsis, acute respiratory stress, wound healing, cancer, cardiovascular disease, stroke, Parkinson's disease, schizophrenia, diabetes, multiple sclerosis, and chronic inflammatory diseases, such as rheumatoid arthritis, systemic lupus erythematosus, and inflammatory bowel disease. In some embodiments, system 100 and device 200 may be used for feeding patients who cannot obtain nutrition by mouth, are unable to swallow safely, or otherwise need nutritional supplementation. In some embodiments, system 100 and device 200 may be used to reduce the need for parenteral nutrition. The use of enteral nutrition may be preferred when possible, as it reduces the risk of generating infection, undesirable immune response, and/or atrophy of the GI tract. In some embodiments, system 100 and device 200 may be used for feeding patients with prematurity, failure to thrive, malnutrition, neurologic and neuromuscular disorders, inability to swallow, anatomical and post-surgical malformations of the mouth and esophagus, cancer, digestive, and/or metabolism disorders. In some embodiments, system 100 and device 200 may be used for improving and/or supporting the therapies of other diseases, such as cancer, by providing fatty nutrient to patients.

Additional advantages and benefits of system 100 and device 200 may also include delivering pre-hydrolyzed fats at a high efficiency. For example, about 70% to over about 90% of fats in nutritional formula 110 may be hydrolyzed after passing through device 200, as shown in FIG. 29. The hydrolysis efficiency of system 100 and device 200 may be maintained for very complex nutritional formulas having various nutrients. Such high hydrolysis efficiency of device 200 may reduce the total volume of nutritional formula 110 that needs to be delivered to the patient. Further, as discussed previously, nutritional formula 110 may be delivered at a flow rate, for example, ranging from 0.4 mL/min to about 8 mL/min or higher. Under such flow rates, device 200 may allow the delivery of a typical volume, e.g., ranging from about 1 mL to about 10 mL, from about 10 mL to about 100 mL, from about 100 mL to 250 mL, from about 250 mL to about 500 mL, from about 500 mL to about 750 mL, from about 750 mL to about 1 L, from about 1 L to about 2 L, from about 1 L to about 3 L, from about 2 L to about 3 L, from about 1 mL to about 100 mL, from about 1 mL to about 500 mL, from about 1 mL to about 1 L, from about 100 mL to 500 mL, from about 100 mL to 750 mL, from about 100 mL to 1 L, from about 500 mL to about 1 L, from about 500 mL to about 2 L, from about 750 mL to about 2 L, from about 750 mL to about 3 L, or from about 3 mL to about 1 L of nutritional formula 110 containing substantially pre-hydrolyzed fat within seconds, minutes, or hours. Such high efficiency of delivering nutritional formula 110 is preferable to improve the quality of life for patients, especially for patients in need of large volumes of nutritional formula 110. Examples 10-12, discussed further below, demonstrate the high hydrolysis and delivery efficiencies of system 100 and device 200 for a wide range of enteral formulas.

In some embodiments, delivering pre-hydrolyzed nutritional formula 110 by using system 100 and device 200 may allow normalization of the caloric intake and fatty acid balance and absorption of a patient, such as the most difficult to digest and absorb LC-PUFAs, for example DHA, EPA, and AA. This may advantageously provide a more controlled option for healthcare providers to improve their management and treatment of people with compromised pancreatic output or lipid malabsorption. Examples 13-15 demonstrating the use of system 100 and device 200 for improving the free fatty acid intake and balance are discussed further below.

Additional Examples of System 100 and Device 200

Example 10: In Vitro Hydrolysis of Enteral Formula Fats Using Exemplary Device 200, Showing Substantially Steady Hydrolysis Efficiency Two experiments on the hydrolysis of triglycerides in two samples of enteral formula Peptamen AF® were performed using an exemplary device 200. Exemplary devices 200 used in this experiment was substantially similar to those described in Example 1. Each experiment simulated an enteral feeding over a period of time. The first experiment tested a first sample of 250 mL of Peptamen AF® over a feeding period of 2 hours. The second experiment tested a second sample of 500 mL of Peptamen AF® over a feeding period of 4 hours. The flow rate of the enteral formula in the two experiments was maintained at 2 mL/min. Testing samples were collected at a plurality of time points during the feeding period of each experiment, and the amount of fatty acid was analyzed using ultra performance liquid chromatography-tandem mass spectrometer (UPLC MS) at each time point.

Figure 30:
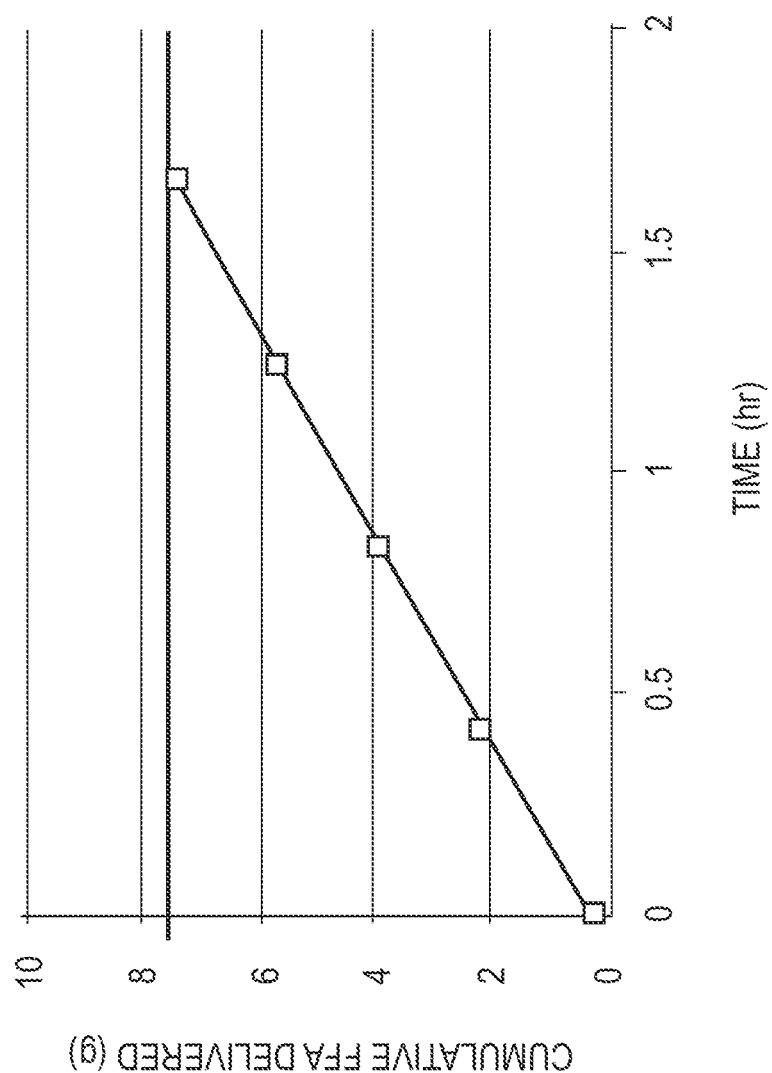
FIG. 30 graphically depicts accumulation of the amount of free fatty acid in a sample of enteral formula Peptamen AF® hydrolyzed by an exemplary fat hydrolysis device, according to embodiments of the present disclosure.

As shown in FIG. 30, for the first experiment, the cumulative amount of free fatty acid in the sample increased almost linearly over the feeding period of the experiment, as shown by the approximately diagonal line, indicating a substantially steady hydrolysis efficiency. The amount of free fatty acids delivered by the end of the experiment was about 7.3 g out of the total amount of 7.7 g of free fatty acids (shown as a horizontal line in FIG. 30) that could have possibly been generated from the amount of triglycerides in the nutritional formula flowed through device 200. This demonstrates a hydrolysis efficiency of about 95%, as is demonstrated graphically with the diagonal line nearly intersecting the total horizontal line by the end of the experiment. The result in FIG. 30 shows that device 200 can efficiently hydrolyze triglycerides in 250 mL enteral formula for a shorter period of feeding time of about 2 hours or less at a substantially steady rate.

Figure 31:
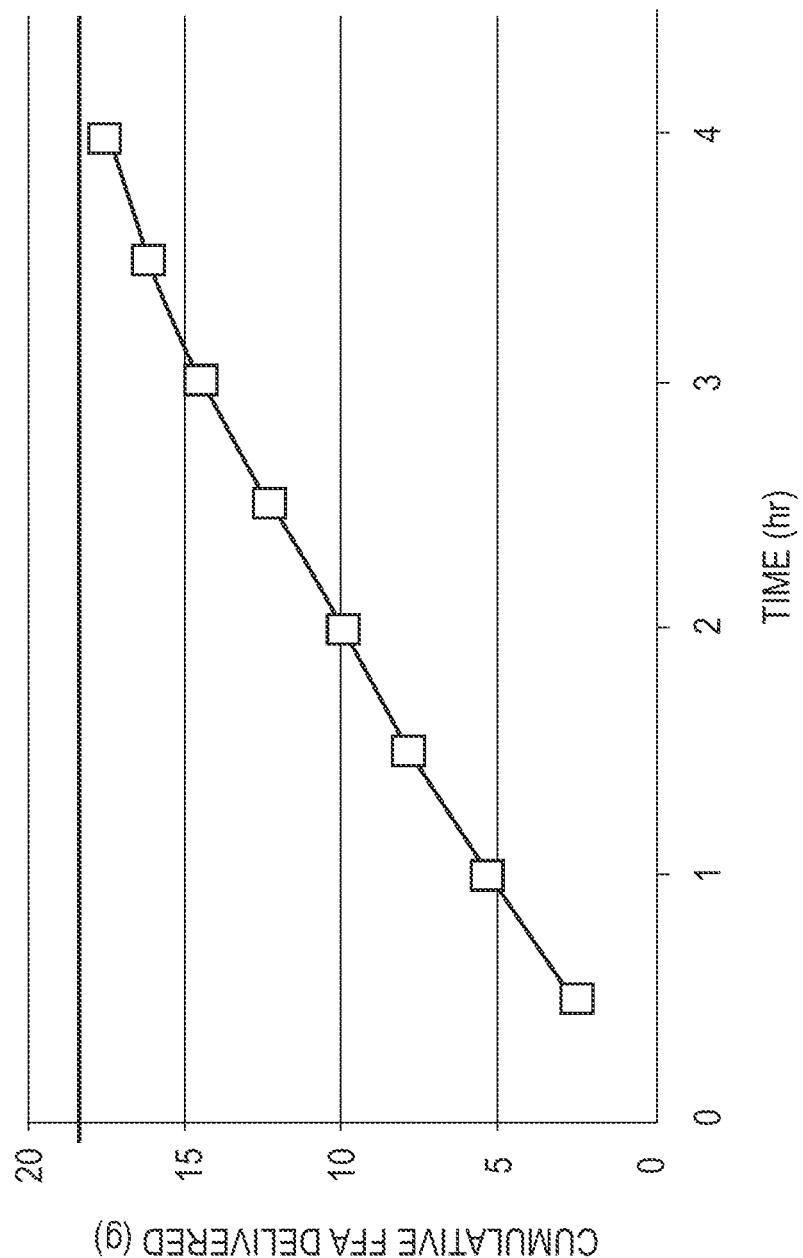
FIG. 31 graphically depicts accumulation of the amount of free fatty acid in a sample of enteral formula Peptamen AF® hydrolyzed by an exemplary fat hydrolysis device, according to embodiments of the present disclosure.

As shown in FIG. 31, for the second experiment, the cumulative amount of free fatty acid in the sample also increased almost linearly over the period of the experiment, again showing a substantially steady hydrolysis efficiency. The amount of free fatty acids delivered at the end of the experiment was about 17.5 g out of the total amount of 18.2 g free fatty acids (shown again as a horizontal line in FIG. 31) that could have possibly been generated from the amount of triglycerides in the nutritional formula flowed through device 200, rendering a hydrolysis efficiency of about 96%. The result in FIG. 31 shows that device 200 can efficiently hydrolyze triglycerides in 500 mL enteral formula for a slightly longer period of feeding time of about 4 hours or less at a substantially steady hydrolysis efficiency.

Example 11: Comparison of Ex Vivo Hydrolysis Efficiency of Exemplary Device 200 with Porcine-Derived Pancreatic Enzyme Capsules (PERT Capsules)

Hydrolysis of fats in three samples of Peptamen AF® by an exemplary device 200 and PERT products was performed and compared. Exemplary devices 200 used in this experiment were substantially similar to those described in Example 1. PERT products are a combination of various lipase, protease, and amylase enzymes. For the first sample, device 200 was used for the hydrolysis of 237 mL of Peptamen AF® for a simulated enteral feeding of about 2 hours. A flow rate of 2 mL/min was used throughout the feeding. No alarm from pump 120 or clogging was observed during the feeding for device 200.

For the second and third samples, two types of commercially available PERT capsules were used for the hydrolysis. The second sample was hydrolyzed using 4 capsules of ZenPep® (80,000 units lipase; 272,000 units protease; 436,000 units amylase; Aptalis), which is an enterically coated product. The third sample was hydrolyzed using 3 tablets of Viokace® (62,640 units lipase; 234,900 units protease; 234,900 units amylase; Aptalis). The PERT capsules were added directly into the second and third sample enteral formula bags, in order to maximize exposure time of the PERT products to the enteral formula, each of which contained one can of 250 mL of Peptamen AF®. In contrast to device 200, where the enteral formula passed through the device, the PERT products were mixed into the formula bags in order to maximize exposure and potential hydrolytic capacity of the PERT enzymes to the enteral formula.

Figure 32:
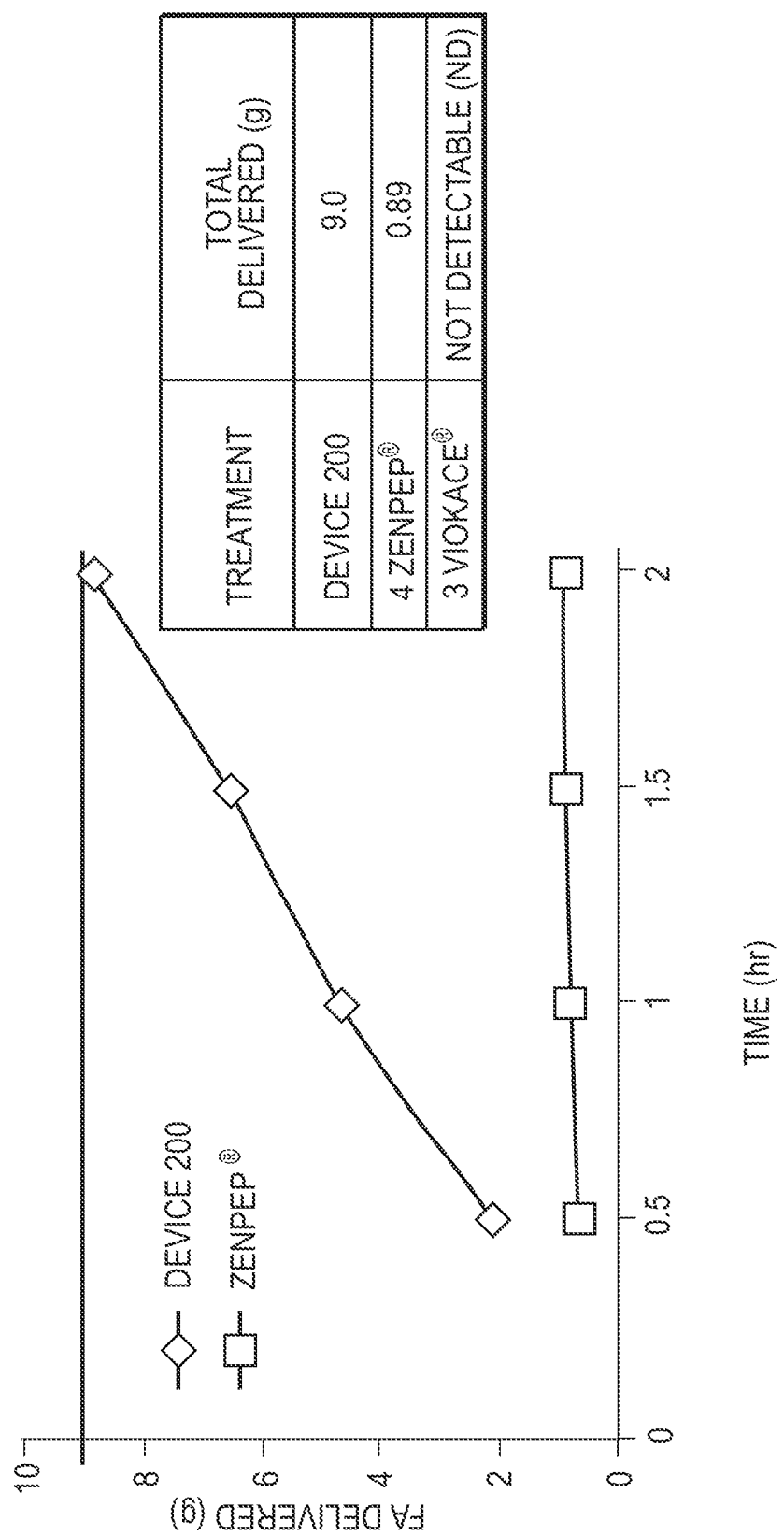
FIG. 32 graphically compares accumulation of the amount of free fatty acid in an exemplary nutritional formula achieved when using commercially available lipase supplements versus an exemplary fat hydrolysis device, according to embodiments of the present disclosure.

Samples of each formula hydrolyzed using device 200 were collected at 0, 30, 60, 90, and 120 minutes during the hydrolysis process, and fat hydrolysis in each sample was evaluated at each time point using a quantitative colorimetric assay (Abcam® Free Fatty Acid Quantification Kit) to measure the amount of free fatty acids. FIG. 32 shows the amount of free fatty acid detected in each formula sample at each time point. As shown in FIG. 32, the cumulative amount of free fatty acid delivered by exemplary device 200 by the end of the experiment almost equaled the amount of free fatty acids that could have possibly been generated if all of the triglycerides in the formula sample had been hydrolyzed. This result agrees with the results depicted in FIGS. 30 and 31 and shows near-complete hydrolysis of the triglycerides available in the nutritional formula. The free fatty acid in the second formula sample generated using ZenPep® capsules remained at less than 1 gram (less than 10% hydrolysis) over the course of the experiment. The amount of free fatty acid in the third formula sample generated using Viokace® was undetectable using the assay and thus does not appear in FIG. 32.

Figure 33:
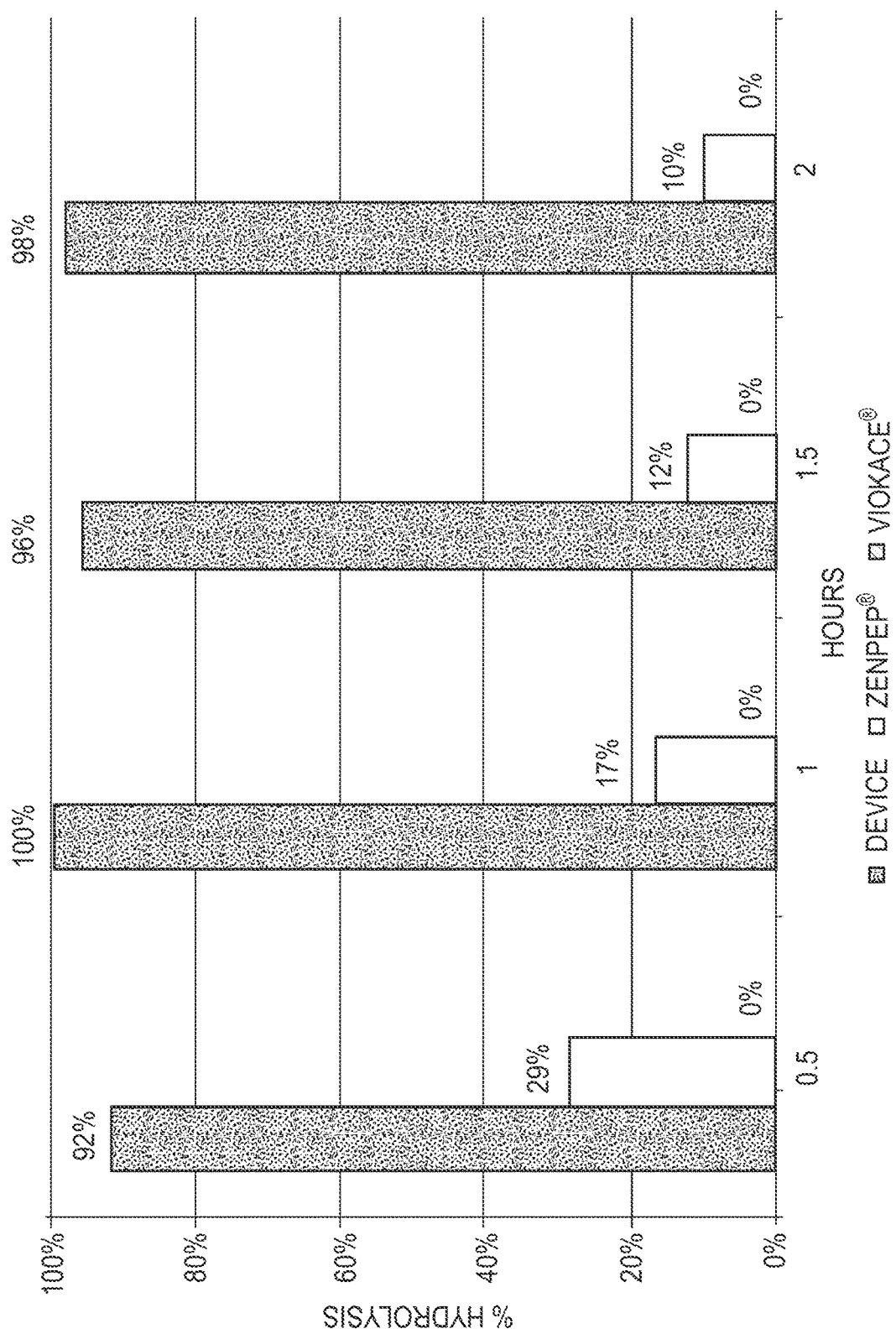
FIG. 33 graphically compares calculated hydrolysis efficiencies of fats in the three samples shown in FIG. 32.

FIG. 33 shows calculated hydrolysis efficiencies in the three formula samples discussed in regards to FIG. 32. As shown in FIG. 33, in the first formula sample, exemplary device 200 hydrolyzed over 90% of the fat starting at the 30-minute time point. In the second formula sample, ZenPep® capsules only hydrolyzed about 10% of the fat by the end of the experiment, reaching only a high of 29% at the 30 minutes time point. In the third formula sample, hydrolysis of fat by Viokace® capsules was undetectable. The results demonstrate that device 200 has superior efficiency in hydrolyzing fat in enteral formulas compared to PERT capsules.

Example 12: Hydrolyzing Fat in Nutritional Formulas of Different Volumes Using Exemplary Device 200

A series of experiments on the hydrolysis of triglycerides in enteral formula Peptamen AF® were performed using an exemplary device 200. Exemplary device 200 used in this experiment was substantially similar to that used in Example 3. Peptamen AF® formula contains an equal amount of triglycerides with MCT and triglycerides with LCT. A 500 mL Peptamen AF® solution contains a total of 27.4 g fat, including 1.2 g EPA and DHA from the triglycerides. One experiment simulated an enteral feeding run of 500 mL Peptamen AF® over 1 hour at a flow rate of 8 mL/min, one experiment simulated an enteral feeding run of 500 mL Peptamen AF® over 2 hours at a flow rate of 4 mL/min, one experiment simulated an enteral feeding run of 500 mL Peptamen AF® over 4 hours at a flow rate of 2 mL/min, one experiment simulated an enteral feeding run of 250 mL Peptamen AF® over 10 hours at a flow rate of 0.4 mL/min, and one experiment simulated an enteral feeding of 1 L Peptamen AF® over 8 hours at a flow rate of 2 mL/min. The flow rate of the formula samples was maintained throughout the simulated feedings with no alarms detected.

Figure 34:
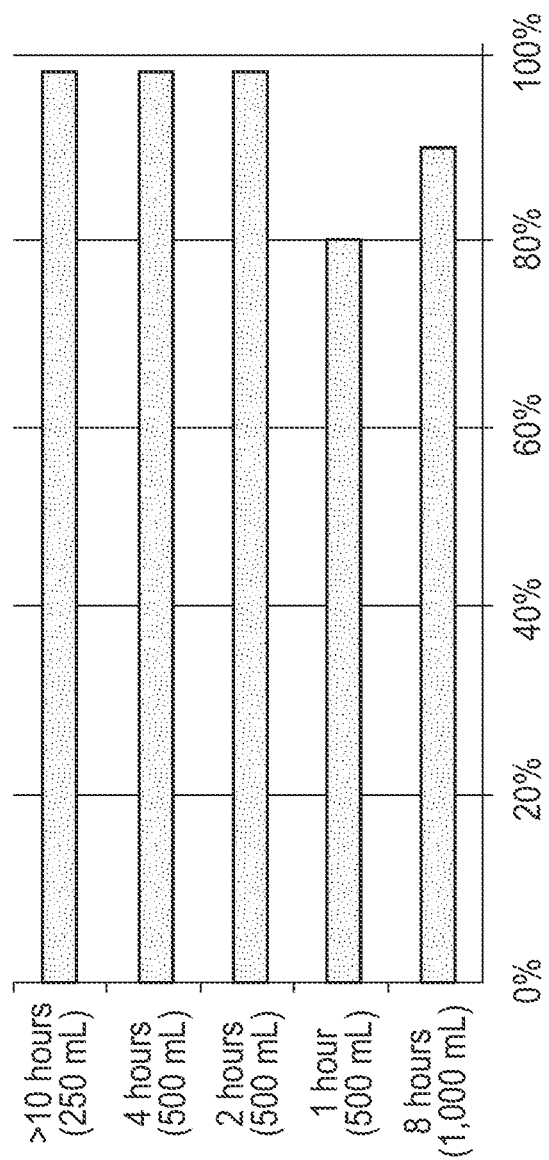
FIG. 34 graphically depicts hydrolysis of fats from a representative complex nutritional formula during simulated feedings using an exemplary fat hydrolysis device, according to embodiments of the present disclosure.

As shown in FIG. 34, device 200 efficiently hydrolyzed over 90% of fat in 500 mL Peptamen AF® over the course of 2 and 4 hours, over 90% of fat in 250 mL Peptamen AF® over the course of 10 hours, and about 90% of fat in 1 L Peptamen AF® over the course of 8 hours. The hydrolysis of fat in 500 mL Peptamen AF® delivered over the course of 1 hour also showed high efficiency. The results show that device 200 may hydrolyze and deliver a substantial percentage of fats in nutritional formula 110 even over a shorter 1 to 2 hour feeding under a faster flow rate, which could potentially reduce the need for longer, overnight enteral feedings.

Example 13: Testing the Efficacy of Lipase 710 Attached to Particles 300 for Digestion of Long-Chain Polyunsaturated Fatty Acid (LC-PUFA) in Young Pigs with Total Pancreatic Insufficiency This experiment evaluated whether the absorption of total fats and long-chain polyunsaturated fatty acids (LC-PUFAs) from infant formula was enhanced when the formula was pre-hydrolyzed with *Rhizopus oryzae* lipase immobilized on acrylic beads (an exemplary lipase 710 covalently attached to exemplary particles 300, substantially similar to the particles 300 described in Example 1), herein referred to as iRO, just before consumption. This experiment was performed in a porcine model of pancreatic insufficiency (young pigs with total pancreatic insufficiency). The porcine model was chosen since at the functional and developmental level, humans and pigs share many similarities with regard to the gastrointestinal tract, genitourinary structures, and development of the brain and pancreas. Surgical ligation of pancreatic ducts in young pigs causes impaired excretion of pancreatic enzyme, including bile salt stimulated lipase, and thus mimics conditions in pre-term and/or full term human babies or individuals with chronic malfunction of exocrine pancreas, such as CF patients, patients after oncology surgery, or elderly subjects. As used herein, EPI pigs are used to refer to this porcine model.

Pancreatic duct ligation was performed on 20 pigs to create exocrine pancreatic inefficiency (EPI) for this experiment. EPI typically fully develops three to four weeks after the surgery. Development of complete pancreatic insufficiency was confirmed by arrested growth and development of steatorrhea. However, out of 20 operated pigs, only 17 EPI pigs developed complete pancreatic insufficiency and were used in this experiment. The 17 EPI pigs (male) and 6 healthy pigs (male) were maintained on a 12-hour day-night cycle, with light from 6 AM to 6 PM and darkness from 6 PM to 6 AM.

Nutritional formula having fat pre-hydrolyzed with iRO was divided into 4 daily feedings, and its efficacy was tested in young, growing EPI pigs that would be developmentally comparable to human babies 3-6 months of age.

Figure 35:
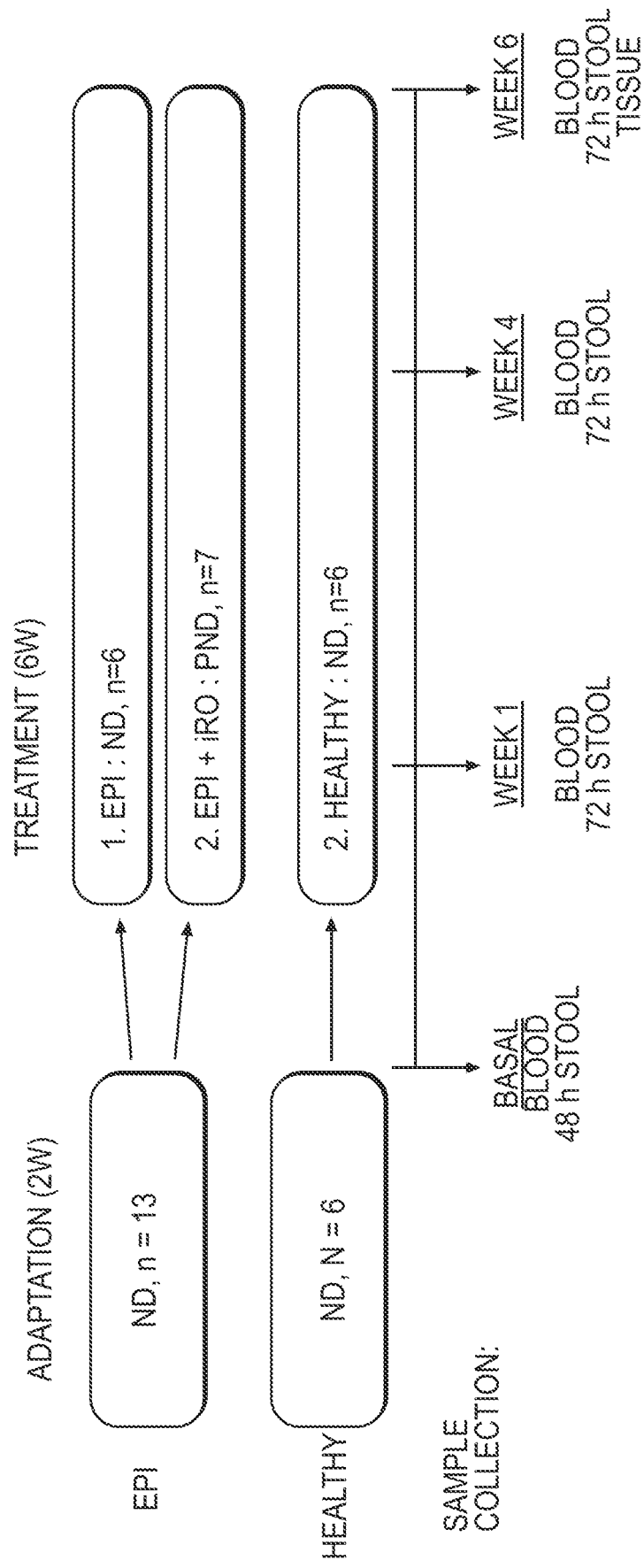
FIG. 35 schematically depicts the study design and procedures for the 6-week pig study described in Example 13.

As shown in FIG. 35, the 6-week treatment study was proceeded by an initial adaptation period of two weeks. Prior to pancreatic duct ligation surgery, following surgery, and prior to the initial adaptation period of this experiment, all pigs were fed a standard pig diet that contained 17.5% crude protein, 3.9% crude fibre, 3.5% crude fat, 5.2% ash, together with 5000 IE/kg vitamin A, 500 IE/kg vitamin D, 85 mg/kg vitamin E. Feeding was done twice daily (2.0% body mass per meal) from 9 AM to 10 AM and from 5 PM to 6 PM.

During the adaptation period, all pigs were fed NAN Pro 1 Gold (Nestle) formula (NAN formula) enriched with long-chain polyunsaturated triglycerides (TG-LCPUFA): 1% docosahexaenoic acid (DHA) and 2% arachidonic acid (AA) from fish oil. Thereafter, in this experiment, the formula was enriched with 1% TG-DHA and 2% TG-AA from fish oil, resulting in a final fat content of about 31%.

A 6-week treatment period followed the initial adaptation period. During the 6-week treatment period, EPI pigs were randomized into 2 groups. In the control group, EPI pigs were fed with enriched formula only, referred to as non-hydrolyzed drink (ND, n=6). In the treatment group, EPI pigs were fed formula pre-hydrolyzed with iRO, referred to as pre-hydrolyzed drink (PND, n=7). In a second control group, healthy pigs with intact function of the exocrine pancreas were enrolled and fed with LC-PUFA enriched formula only (ND, n=6).

To generate the PND, a mesh bag filled with iRO was placed into the enriched infant formula (ND) and mixed with an automatic stirrer for up to 15 minutes at a temperature range from about 30° C. to about 37° C. to allow substantially complete fat hydrolysis. For a single meal for an EPI pig (100 g formula powder diluted in 300 mL water), one mesh bag with 1 g of iRO was used. When hydrolysis was finished, the mesh bags were removed from the bucket and discarded. The size specification of iRO ensured that the beads could not migrate outside of the mesh bag, and the mesh bag prevented any leakage of iRO to the formula. When pre-hydrolysis was complete, the mesh bag was removed, and the PND was ready for consumption.

The action of the iRO was intended to mimic pancreatic lipase and to generate free fatty acids and monoglycerides, similar to those that would be found after the action of endogenously secreted pancreatic lipase in the small intestine. The point-of-care approach in which PND was generated and supplied right before ingestion also addressed the free radical oxidation of free fatty acids from ND and prevented development of a rancid taste or odor. Thus, the benefit of the point-of-care approach was that fats, including triglycerides having LC-PUFAs were "digested" or pre-hydrolyzed just before drinking and thus were made available for absorption by the GI tract that would otherwise lack the physiological capacity to digest fat.

The effect of pre-hydrolysis of dietary fat was monitored by assessing reduction of total and polyunsaturated fatty acids (PUFA) in fecal fats, together with increases in the absorption of AA and DHA expressed as changes from the control group in the plasma, visceral tissue (liver, fat), heart, and neuronal tissues (hippocampus) in the pigs. Presence of fats in fecal matter was interpreted as an indication that the fats had failed to be absorbed by the pigs.

The results of this study demonstrated no mortality, adverse clinical signs, or pathologic macroscopic or microscopic findings along the gut or in the liver following the six-week administration of pre-hydrolyzed formula, including administration of monoglycerides and free fatty acids instead of triglycerides.

13.1 Testing Design and Procedures:

13.1.1 Pre-Treatment Period (7-10 Days)

Approximately 7 days before the adaptation period, 23 pigs were transitioned from regular food to formula feeding. Through the course of this experiment, 4 EPI pigs were eliminated: one due to sickness, one due to improper gavage, and two due to pancreatic double duct development. No loss was recorded in the healthy group of pigs. Thus, the total number of pigs included in final study analysis was 13 EPI pigs and 6 healthy pigs.

13.1.2 Adaptation Period (14 Days)

During this period, all EPI pigs and healthy pigs were given warm liquid ND enriched with 1% triglyceride having DHA (TG-DHA) and 2% triglyceride having AA (TG-AA) 4 times per day. The total daily formula consumption was measured every day and during the entire experiment. On day 1 (1st day of the experiment) of the Adaptation period, body weights were recorded before the morning meal. Stool and blood samples were collected on the last two days of this period.

13.1.3 Treatment Period (6 Weeks)

During this period, EPI pigs were randomized into two groups, based on the body weight and willingness to consume formula:

1) Control EPI group (EPI): six EPI pigs were fed with enriched non-hydrolyzed formula.
2) iRO group (EPI+iRO): seven EPI pigs were fed with formula pre-hydrolyzed with iRO.
3) Healthy control group (Healthy): six healthy pigs of the same age and breed were fed enriched formula only.

On day 1 of the each week of the 6-week treatment period, pigs were weighed before the morning meal. Three 24-hour stool collections were performed during the last three days of the week 1, week 4, and week 6 of the treatment period. On days 7, 28, and 42 of the treatment period, pre-prandial blood samples after an overnight fast were collected.

Weights of collected 24-hour stool samples were recorded, and a small fraction from each sample was measured for total fat and LC-PUFAs.

For measurement of LC-PUFAs, fecal, plasma, and tissue samples were analyzed using a gas chromatography-mass spectrometry (GC-MS) method.

Five mL blood samples were collected on the respective days before feeding. The samples were analyzed for LC-PUFA, triglyceride (TG), cholesterol, low-density lipoproteins (LDL), high-density lipoproteins (HDL), and non-esterified fatty acids (NEFA) content.

At the end of the experiment, the pancreatic area and the involuted pancreas of each pig was examined for pathological changes, together with the gastrointestinal tract and liver, kidney, and heart.

Statistical analysis was performed on the data generated from this study using the ANOVA analysis of variance of the SAS program and ordinary one way ANOVA and ANOVA paired t-test using Prism Graph program. Differences were considered significant if $p \leq 0.05$. All data are expressed as a mean±standard deviation (±SD).

13.2 Results

Figure 36B:
FIG. 36B shows stool appearance of EPI pigs fed with formula pre-hydrolyzed by an exemplary *Rhizopus oryzae* lipase attached to particles ("EPI+iRO").
Figure 36A:
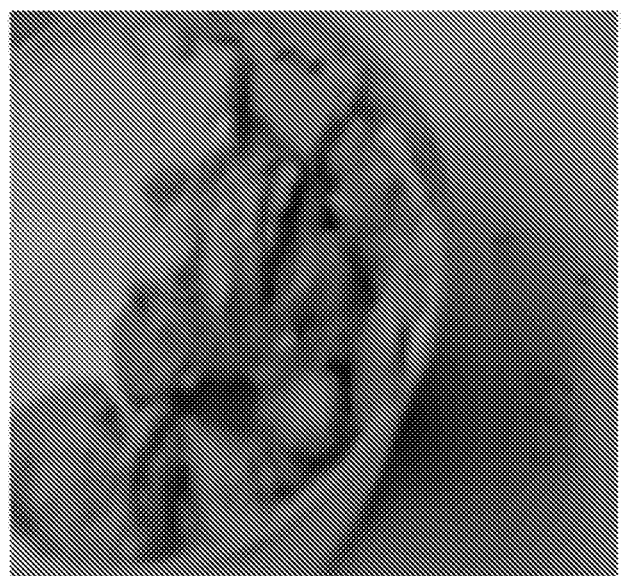
FIG. 36A shows stool appearance of pigs having exocrine pancreatic insufficiency (EPI pigs) fed with non-hydrolyzed formula ("EPI").

13.2.1 Effect of the Consumption of PND on Stool Weight, Appearance, and Total Fat Content Destruction of exocrine pancreatic function in EPI pigs resulted in maldigestion and malabsorption that caused pronounced steatorrhea and voluminous feces with an increased number of stools. FIG. 36A shows an exemplary stool sample of EPI pigs fed with ND, and FIG. 36B shows an exemplary stool sample of EPI pigs fed with PND. As shown in FIG. 36A and FIG. 36B, in EPI pigs fed with PND, absorption of fat was improved based on visible changes in stool appearance (fatty stool disappearance) and also a decrease in weight.

Figure 37:
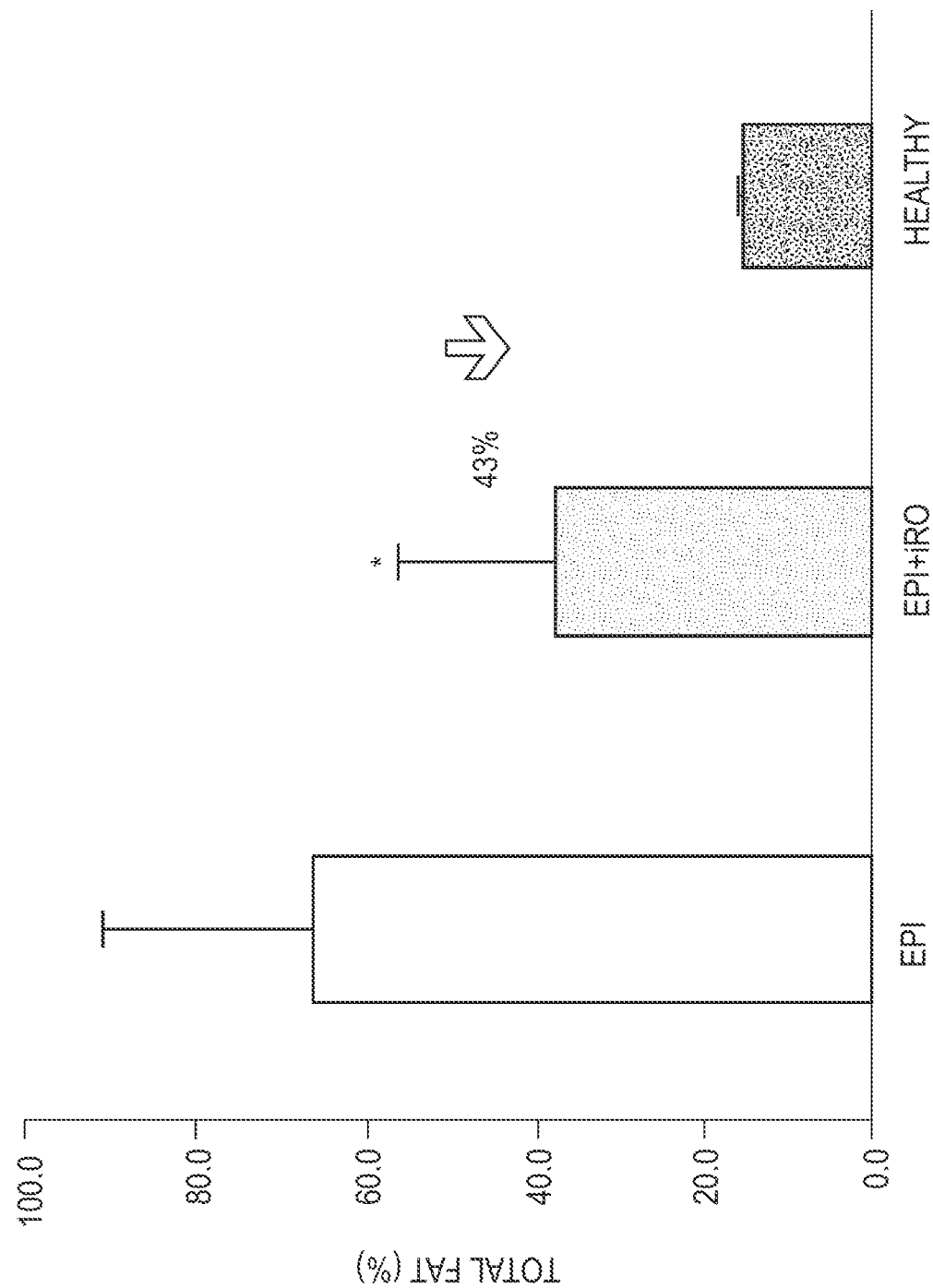
FIG. 37 graphically compares fat measured in stool samples of healthy ("Healthy"), EPI, and EPI+iRO pigs.

As shown in FIG. 37, when total fat was measured in stool dry matter samples, the difference between EPI pigs that were consuming PND vs. ND was more pronounced (EPI: 66.7±24.6% vs. EPI+iRO: 37.9±18.6 g/24 h; n=6-7; p<0.02; mean of three 24 h collections during the last 3 days of the study). There was 43% less fat in the stool samples from the EPI+iRO group compared to the EPI group, suggesting improved absorption of fat that resulted in approximately an additional 243 calories consumed per day. In healthy control pigs, fat content was 13.83±2.4%.

Figure 38B:
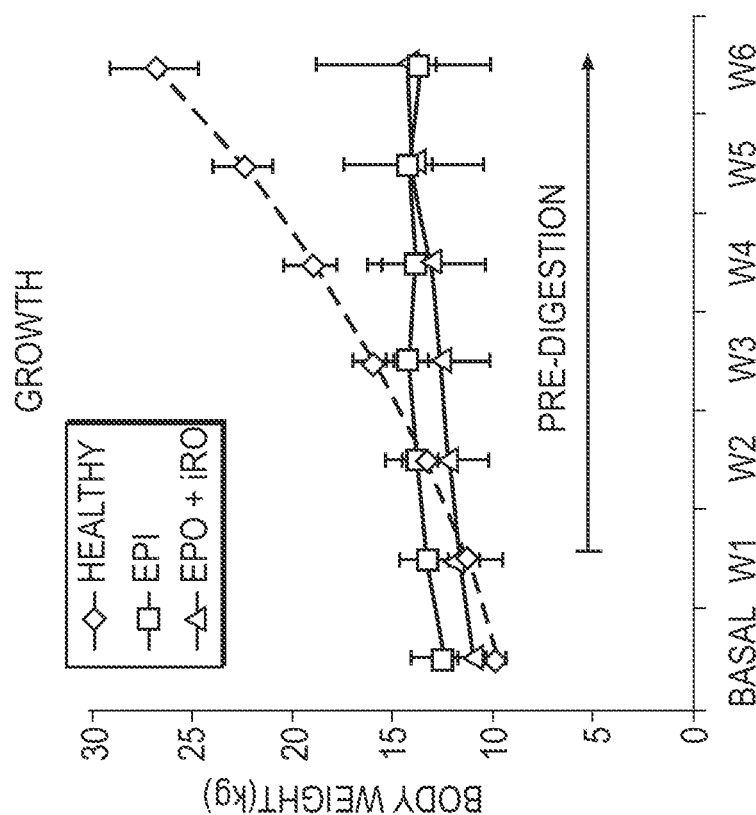
FIG. 38B graphically compares mean of body weight of Healthy, EPI, and EPI+iRO pigs.
Figure 38A:
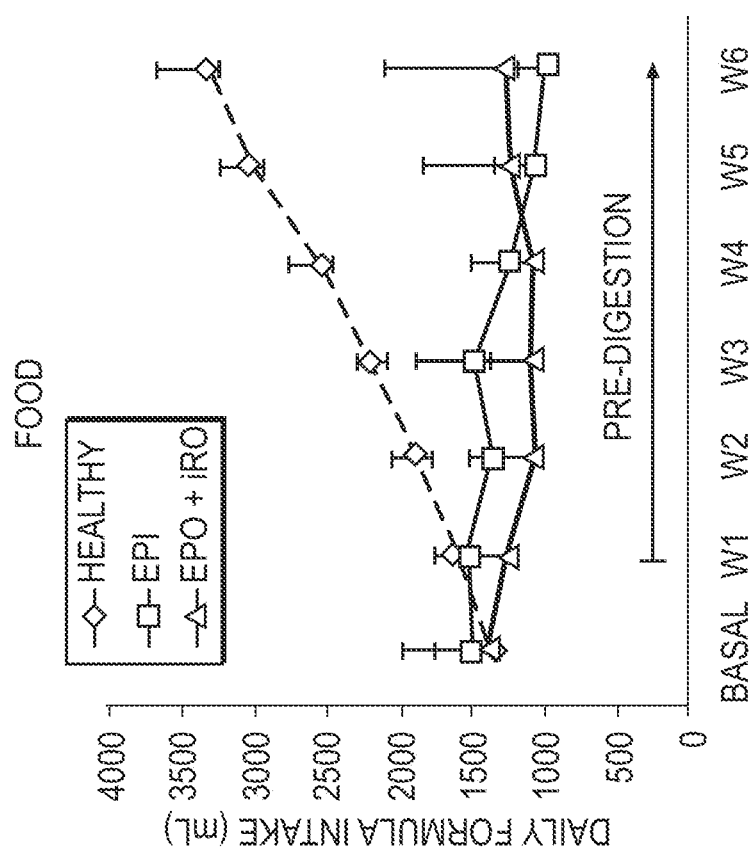
FIG. 38A graphically compares mean of formula intake of Healthy, EPI, and EPI+iRO pigs.

As shown in FIG. 38A and FIG. 38B, formula intake and body weight were substantially the same in EPI group and EPI+iRO group. As expected, the EPI pigs didn't grow, since the formula had only pre-hydrolyzed fat and not the proteins that are necessary for growth and increased body mass. Healthy pigs with intact function of exocrine pancreas were growing 2-4 kg/week.

For estimation of LC-PUFA fat content, stool was collected on days 5, 6, and 7 on the 6th week of treatment, and individual LC-PUFA content was measured. A summary of the results is shown in Table 12.

TABLE 12

Summary of fecal LC-PUFA levels in pigs from EPI group fed with ND or PND and healthy pigs fed with ND.

| n | EPI fed ND g/100 g FA | EPI + iRO fed PND g/100 g FA | % Change EPI vs. EPI + iRO | Healthy fed ND g/100 g FA |
|---|---|---|---|---|
| LA | 0.467 ± 1.01 | 0.126 ± 0.07* | ↓73 | 0.047 ± 0.02** |
| ALA | 0.028 ± 0.06 | 0.046 ± 0.08 | — | 0.033 ± 0.02 |
| AA | 0.674 ± 0.56 | 0.295 ± 0.41* | ↓66 | 0.114 ± 0.08** |
| EPA | 0.012 ± 0.01 | 0.008 ± 0.01 | ↓44 | 0.006 ± 0.01 |
| DHA | 0.734 ± 0.19 | 0.364 ± 0.31* | ↓50 | 0.194 ± 0.07** |
| Σ (n-3) | 2.585 ± 0.20 | 1.605 ± 0.34* | ↓38 | 0.853 ± 0.16** |
| Σ (n-6) | 4.321 ± 1.20 | 2.024 ± 0.58* | ↓53 | 0.961 ± 0.23** |

The data shown in Table 12 is the mean±SD of LC-PUFA levels in stool samples collected on the last 3 days of the last, week 6 of the treatment (n=6-7/group) (* p<0.05 EPI vs. EPI+iRO; ** p<0.05 EPI vs. Healthy). As shown in Table 12, significant reduction of 38% and 53% in fecal omega-3 and omega-6 LC-PUFA was demonstrated in the EPI+iRO group fed with pre-hydrolyzed formula when compared with the EPI group fed with non-hydrolyzed formula. Similarly, 66% and 50% reductions in fecal AA and DHA levels, respectively, were recorded in the EPI+iRO group compared to the EPI group. These data indicate that the inability of EPI pigs to absorb fat was at least partially reversed by feeding with formula pre-hydrolyzed with iRO.

13.2.2 Effect of Pre-Hydrolysis on Blood Lipid Profile

An important finding of this study was that the blood lipid profile in the treatment group fed with PND for 6 weeks was substantially normalized to that of healthy pigs, as shown in Table 13. This result suggests not only increased absorption of fat, but also proper metabolism of fat that resulted in substantially normal blood levels of TG, cholesterol, HDL, and LDL. All EPI pigs had normal blood glucose that was substantially the same as in healthy pigs, confirming that endocrine pancreatic function was preserved and not affected by surgery.

TABLE 13

Triglycerides, cholesterol, HDL, and LDL plasma levels following 6 weeks of feeding of EPI pigs with ND/PND and healthy pigs with ND

| Groups | TG mmol/L | Cholesterol mmol/L | HDL mmol/L | LDL mmol/L | HDL/LDL |
|---|---|---|---|---|---|
| Healthy | 0.51 ± 0.25 | 4.13 ± 0.68 | 2.04 ± 0.31 | 1.27 ± 0.33 | 1.66 ± 0.33 |
| EPI (fed ND) | 0.22 ± 0.07 | 2.69 ± 0.56 | 1.46 ± 0.41 | 0.69 ± 0.35 | 2.63 ± 1.34 |
| EPI + iRO (fed PND) | 0.45 ± 0.17* | 4.13 ± 1.35* | 1.92 ± 0.42* | 1.12 ± 0.51* | 1.82 ± 0.70 |

Data shown in Table 13 is the mean±SD, in cohorts: healthy pigs n=6, EPI n=6, EPI+iRO n=7, for TG, cholesterol, HDL, and LDL collected from pre-prandial samples after 6 weeks of feeding of with ND or PND. Healthy pigs were fed with ND. The p-value is *p<0.05 for difference between EPI and EPI+iRO groups, unpaired t-test. HDL=high-density lipoproteins; LDL=low-density lipoproteins; TG=triglycerides.

Figure 39:
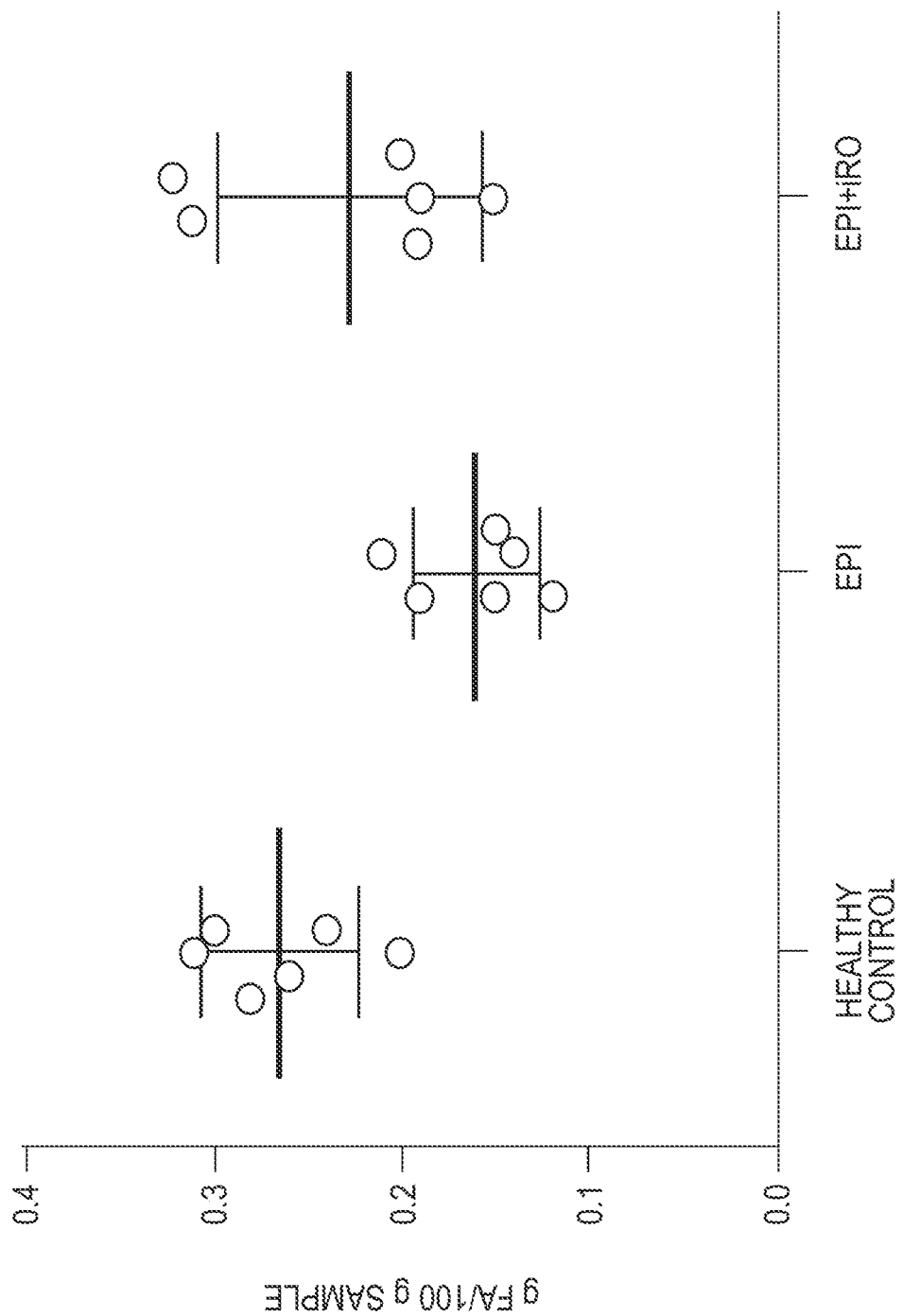
FIG. 39 graphically compares plasma polyunsaturated free fatty acid levels of Healthy, EPI, and EPI+iRO pigs, measured in pre-prandial blood samples.

13.2.3 Plasma and Tissue Changes in LC-PUFA Levels 13.2.3.1 Changes in Plasma and RCB LC-PUFA Levels Feeding with formula containing pre-hydrolyzed fat resulted in positive changes in plasma PUFA levels, as shown in FIG. 39 and Table 14.

TABLE 14

Plasma LC-PUFA concentration upon consumption of pre-hydrolyzed formula for 6 weeks.

| Groups | Sum FA g FA/100 g | LA g FA/100 g | ALA g FA/100 g | AA g FA/100 g | EPA g FA/100 g | DHA g FA/100 g |
|---|---|---|---|---|---|---|
| Healthy (Control) | 0.27 ± 0.04* | 59 ± 9.8* | 1.9 ± 0.5* | 35.0 ± 4.0* | 0.7 ± 0.1 | 10.5 ± 1.2* |
| EPI | 0.16 ± 0.03 | 35.9 ± 7.7 | 1.0 ± 0.3 | 17.0 ± 4.0 | 0.7 ± 0.4 | 3.2 ± 0.7 |
| EPI + iRO | 0.23 ± 0.07* | 47.6 ± 14.8* | 1.4 ± 0.5* | 27.4 ± 12.5* | 0.7 ± 0.5 | 4.7 ± 2.2 |

Data shown in Table 14 is a sum of the polyunsaturated free fatty acid concentration (mean±SD) in healthy pigs (n=6, EPI n=6, and EPI+iRO n=6) for sum of all FA, measured in pre-prandial blood samples collected after 6 weeks of feeding of EPI pigs with ND or PND. Healthy pigs were fed with ND. The p-value is *p<0.05 for difference between groups, ANOVA paired t-test (p=0.091).

As shown in FIG. 39 and Table 14, the concentration of total free fatty acid in circulation was significantly higher in EPI pigs fed for 6 weeks with formula pre-hydrolyzed with iRO than in EPI pigs fed formula only. Similarly, measured individual PUFAs, such as LA, ALA, and AA, were significantly higher in EPI pigs fed with formula pre-hydrolyzed with iRO than in EPI pigs fed with ND only. A trend increase in DHA free fatty acid concentration was also recorded.

Figures 40A, 40B:
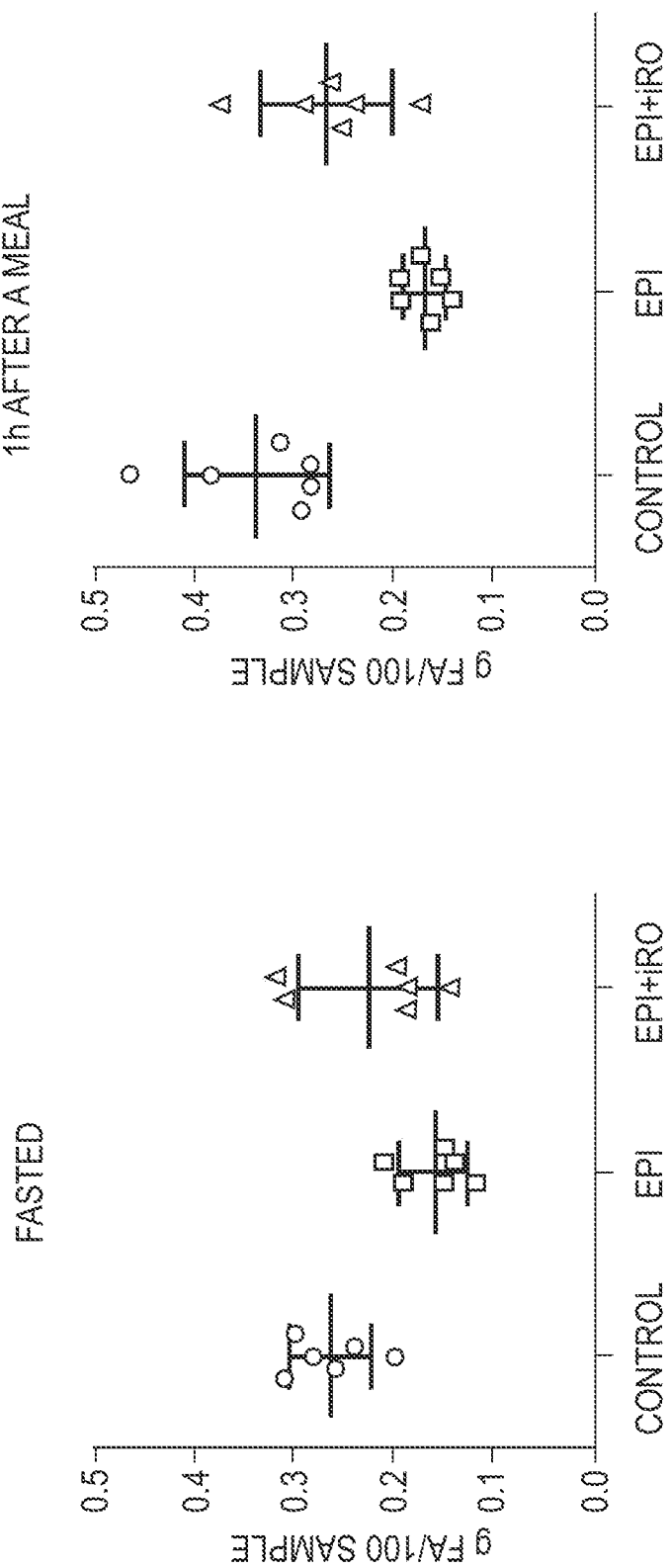
FIG. 40A graphically compares plasma polyunsaturated free fatty acid concentration (mean±SD) in Healthy, EPI, and EPI+iRO pigs.
FIG. 40B graphically compares polyunsaturated free fatty acid concentration (mean±SD) in Healthy, EPI, and EPI+iRO pigs, measured in post-prandial samples.

FIG. 40A and FIG. 40B show the sum of polyunsaturated free fatty acid concentration (mean±SD) in the healthy control group (n=6), EPI group (n=6), and EPI+iRO group (n=6) measured in pre-prandial blood samples and post-prandial 1 h samples collected after 6 weeks of feeding of EPI pigs with ND or PND. Healthy pigs were fed with ND. There was a statistically significant p-value of *p<0.05 for the difference between the groups using ordinary one-way ANOVA (p=0.0007 and p=0.0091, for the difference between the groups for pre-prandial samples and 1 h post-prandial samples, respectively).

As shown in FIG. 40A, FIG. 40B, and Table 15, post-prandial levels of LC-PUFAs from the samples collected 1 h after a meal show increased concentration of free fatty acids in plasma collected from EPI pigs fed with PND when compared to EPI pigs fed with ND. For example, the post-prandial level of LA in EPI pigs fed with PND increased by approximately 10% while the post-prandial level of LA in EPI pigs fed with ND only increased by approximately 3%; the post-prandial level of ALA in EPI pigs fed with PND increased by approximately 35% while the post-prandial level of LA in EPI pigs fed with ND only increased by approximately 10%; and the post-prandial level of EPA in EPI pigs fed with PND increased by approximately 3 folds while the post-prandial level of EPA in EPI pigs fed with ND only increased by approximately 1 fold. This result again suggests enhanced absorption and effectiveness of the point-of-care approach. This result was encouraging, since the plasma concentrations of specific LC-PUFAs, such as LA, ALA, and EPA, were elevated 1 h after feeding with PND, which is usually the time when plasma LC-PUFA levels begin elevating in the healthy pigs. Presumably due to the complex hydrolysis and absorption process, mean LC-PUFA levels were reaching maximal concentration in the plasma approximately about 4 to about 6 hours after a meal.

TABLE 15

Comparison of the total and individual plasma free fatty acid PUFA concentration before and 1 h after a meal

| Groups | | Sum FA g FA/100 g sample | LA µg FA/ 100 g sample | ALA µg FA/ 100 g Sample | AA µg FA/ 100 g sample | EPA µg FA/ 100 g sample | DHA µg FA/ 100 g sample |
|---|---|---|---|---|---|---|---|
| Healthy (Control) | ON fast | 0.27 ± 0.04 | 59.0 ± 9.8* | 1.9 ± 0.5* | 35.0 ± 4.0* | 0.7 ± 0.1 | 10.5 ± 1.2* |
| | 1 h | 0.33 ± 0.07* | 71.6 ± 17.1 | 3.2 ± 1.5* | 37.0 ± 4.5* | 1.7 ± 1 | 10.2 ± 1.2* |
| EPI | ON fast | 0.16 ± 0.03 | 35.9 ± 7.7 | 1.0 ± 0.3 | 17.0 ± 4.0 | 0.7 ± 0.4 | 3.2 ± 0.7 |
| | 1 h | 0.17 ± 0.02 | 37.1 ± 6.2 | 1.1 ± 0.3 | 18.0 ± 3.04 | 1.4 ± 0.7 | 3.0 ± 0.6 |
| EPI + iRO | ON fast | 0.23 ± 0.07 | 47.6 ± 14.8 | 1.4 ± 0.5* | 27.4 ± 12.5 | 0.7 ± 0.5 | 4.7 ± 2.2 |
| | 1 h | 0.26 ± 0.07* | 52.4 ± 14.8 | 1.9 ± 0.6* | 26.3 ± 14 | 2.5 ± 1.3* | 4.4 ± 2.2 |

Data shown in Table 15 is a sum of polyunsaturated free fatty acid concentration (mean±SD) in healthy pigs (n=6, EPI n=6, and EPI+iRO n=6) for sum of all FA, but also LA, ALA, AA, EPA, and DHA measured in pre-prandial blood samples and post-prandial 1 h samples collected after 6 weeks of feeding of EPI pigs with ND or PND. Healthy pigs were fed with ND. The p-value is *p<0.05 for the difference between groups, ANOVA paired t-test.

Benefit of the consumption of PND was also demonstrated based on the general increase of the total amount of free fatty acids in the plasma of EPI+iRO pigs, whether on or off fast, compared to EPI pigs.

13.2.3.2 Tissue Accretion of LC-PUFA

Improved LC-PUFA absorption upon feeding with pre-hydrolized formula for 6 weeks resulted in increased levels of AA and DHA in visceral tissue, as measured in the fat, liver, and heart, and neuronal tissue, as measured in the hippocampus. A summary of the results are shown in Table 16.

Furthermore, the visual cortex was analyzed, and no difference between EPI pigs fed with ND or PND or healthy pigs was found (AA: Healthy: 8.64±0.2, EPI: 8.74±0.4, and EPI+iRO: 8.45±0.24 g/100 g FA, p=NS; DHA: Healthy: 13.19±0.4, EPI: 12.76±10.52, and EPI+iRO: 12.32±0.8 g/100 g FA; p=NS for difference between EPI and EPI+iRO groups). This result is, to that extent, in agreement with the work from C. Tyburczy et al. 85:335-343 (2011), who looked at omega-3 and omega-6 changes in peripheral and central tissue in newborn pigs fed with milk replacers enriched with different amounts of TG-DHA and TG-AA during the first 28 days of life. The sensitivity of different parts of the central nervous tissue to dietary DHA has been previously shown in numerous studies with term and pre-

TABLE 16

Selected LC-PUFA from fat, heart, liver, hippocampus from EPI and healthy pigs fed ND or PND for 6 weeks

| | Groups | | | p-Values | | |
|---|---|---|---|---|---|---|
| Tissues | Healthy | EPI FA (%) g FA/100 g FA | EPI + IRO | Healthy vs. EPI + IRO | Healthy vs. EPI | EPI + IRO vs. EPI |
| Fat | | | | | | |
| AA | 1.09 ± 0.05 | 0.46 ± 0.08 | 0.60 ± 0.18 | <0.001 | <0.001 | 0.0121 |
| DHA | 0.82 ± 0.04 | 0.30 ± 0.05 | 0.46 ± 0.11 | <0.001 | <0.001 | <0.001 |
| Σ Ω-3 | 2.38 ± 0.10 | 1.70 ± 0.28 | 1.90 ± 0.23 | <0.001 | <0.001 | 0.0353 |
| Σ Ω-6 | 14.34 ± 0.52 | 10.66 ± 1.70 | 12.04 ± 2.05 | <0.001 | <0.001 | 0.0363 |
| Heart | | | | | | |
| AA | 19.97 ± 3.25 | 15.62 ± 4.91 | 19.74 ± 3.08 | 0.43129 | 0.0103 | 0.0114 |
| DHA | 5.35 ± 1.06 | 2.44 ± 0.69 | 3.33 ± 1.33 | <0.001 | <0.001 | 0.0205 |
| Σ Ω-3 | 7.18 ± 1.17 | 4.79 ± 1.12 | 5.24 ± 1.21 | <0.001 | <0.001 | 0.1661 |
| Σ Ω-6 | 35.52 ± 6.95 | 36.93 ± 6.96 | 38.73 ± 6.15 | 0.11415 | 0.3119 | 0.2473 |
| Liver | | | | | | |
| AA | 13.51 ± 1.11 | 4.33 ± 1.37 | 6.73 ± 4.90 | <0.001 | <0.001 | 0.0504 |
| DHA | 5.79 ± 0.31 | 1.25 ± 0.33 | 2.05 ± 1.26 | <0.001 | <0.001 | 0.0192 |
| Σ Ω-3 | 7.19 ± 0.46 | 2.65 ± 0.73 | 3.88 ± 1.20 | <0.001 | <0.001 | 0.0020 |
| Σ Ω-6 | 26.59 ± 1.39 | 18.38 ± 2.38 | 22.29 ± 3.69 | <0.001 | <0.001 | 0.0018 |
| Hippocampus | | | | | | |
| AA | 9.06 ± 1.05 | 7.94 ± 1.02 | 8.68 ± 0.81 | 0.1097 | 0.0013 | 0.0090 |
| DHA | 8.33 ± 1.31 | 6.88 ± 1.27 | 7.65 ± 0.84 | 0.0353 | 0.0009 | 0.0175 |
| Σ Ω-3 | 9.44 ± 1.27 | 8.57 ± 1.36 | 8.82 ± 0.83 | 0.0430 | 0.0283 | 0.2559 |
| Σ Ω-6 | 17.59 ± 1.47 | 16.78 ± 1.74 | 17.35 ± 2.09 | 0.3406 | 0.0706 | 0.1784 |

Data shown in Table 16 represents mean±SD levels of LC-PUFA from healthy pigs (n=6, EPI n=6, and EPI+iRO n=7) collected from liver, fat, heart, and hippocampus tissue at the end of the study. EPI pigs were fed either with ND or PND. Healthy pigs were fed with ND. The p-value is *p<0.05 for the difference between groups, ANOVA paired t-test.

Figure 41:
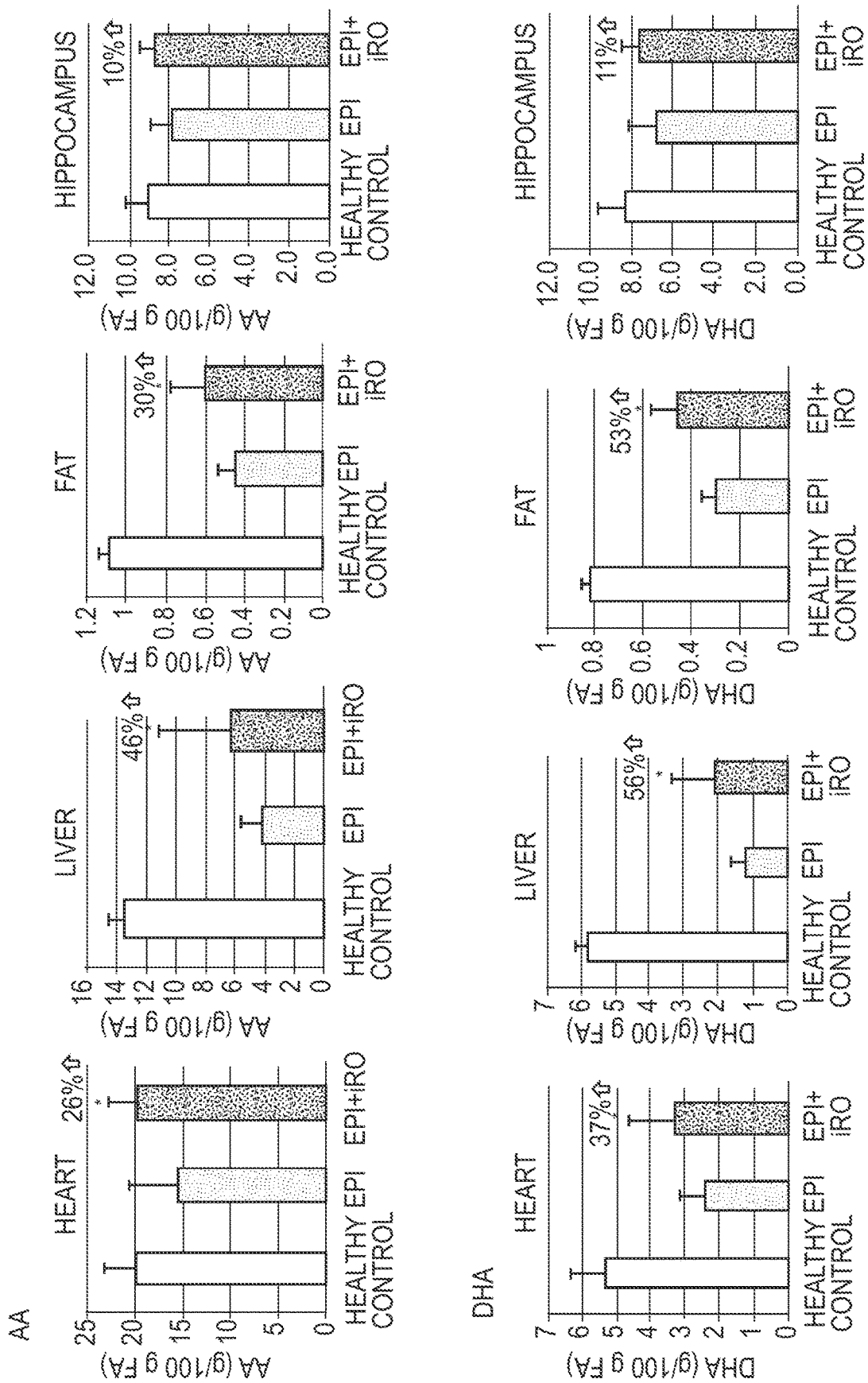
FIG. 41 graphically compares mean accretion of AA and DHA in the heart, liver, fat, and hippocampus of Healthy, EPI, and EPI+iRO pigs.

Improved absorption of LC-PUFA was demonstrated by reduced fecal fats, and increased concentration of total LC-PUFAs was reflected in liver, heart, and fat tissue accretion of AA and DHA. Lung tissue was also examined, and no difference in AA levels was seen between groups (Healthy: 10.12±0.9, EPI: 10.07±1.4, and EPI+iRO: 10.17±1.33 g/100 g FA; p=NS); however, a slight increase in DHA levels in healthy pigs was seen when compared to EPI pigs (Healthy: 2.52±0.2, EPI: 1.68±0.2, and EPI+iRO: 1.72±0.4 g/100 g FA; p<0.05). For neuronal tissue, hippocampus and visual cortex were examined. As shown in Table 16 and FIG. 41, statistically significant positive changes were demonstrated for both DHA and AA levels in the hippocampus.

term neonatal non-human primates. The brain consistently shows increased region-specific DHA accretion related to the level and duration of performed DHA feeding. In our study, pigs were fed a formula enriched with TG-DHA and TG-AA in the ratio of 2:1 (AA/DHA) for 6 weeks, which favored accretion of AA, which can explain why composition of DHA in the majority of the tested peripheral or central tissues were increased to a lesser extent when compared to AA levels. In addition, it is well known that the very same enzymes are involved in metabolism of omega-6 and omega-3 PUFA and therefore different accumulation rates in plasma and tissues can be expected.

13.2.4 Enhanced Absorption of Vitamin A and Vitamin E

Improvement in the absorption in fat-soluble vitamins A and E was also demonstrated in the study (vitamin E: EPI 0.8±0.4 vs. EPI+iRO: 1.5±0.9, p<0.5; vitamin A: EPI: 0.18±0.06 vs. EPI+iRO: 0.26±0.17, p=NS). Most NDs are supplemented with vitamin A and vitamin E acetyl ester stable forms that need to be digested by pancreatic carboxy ester hydrolase before absorption. It is known that pre-term babies, newborn babies, kids, and adults with impaired pancreatic function have deficiency in these fat-soluble vitamins. Thus, enhanced absorption of vitamin A and vitamin E in this study suggests that iRO can cleave respective acetyl ester forms and enhance their absorption (vitamin E: EPI 0.8±0.4 vs. EPI+iRO: 1.5±0.9, p<0.5; vitamin A: EPI: 0.18±0.0.06 vs. EPI+iRO: 0.26±0.17, p=NS).

13.3 Summary

In summary, consumption of pre-hydrolyzed infant formula with iRO, i.e., Rhizopus oryzae lipase attached to beads, was safe and led to improved fat absorption, resulting in reduced total fat and LC-PUFA fat in the stool, reduced steatorrhea, normalized blood lipid profile, and increased composition of LC-PUFA in cell membranes of heart, liver, fat, and hippocampus. Together, data from this nonclinical study suggests that consumption of a pre-hydrolyzed nutritional drink may be an effective treatment for people with compromised pancreatic output not only to simply increase caloric intake, but also to increase intake of "essential" free fatty acids, such as DHA and AA.

Example 14: 12-Day Efficacy Study of Exemplary Device 200 on EPI Pigs Fed Via G-Tube This 12-day study tested the use of an exemplary device 200 during nightly enteral (G-tube) feedings. Exemplary device 200 used in this experiment was substantially similar to that used in Example 3. The study assessed the safety of device 200 during nightly G-tube feeding and whether prehydrolyzed fat enhances the absorption of total fat and long-chain polyunsaturated fatty acids (omega-3) from complete nutritional formula Peptamen AF® (Nestle Nutrition, EU). The efficacy and safety of device 200 in enteral feeding was tested in the porcine model of EPI disease, as described in Example 13.

This 12-day study was used to mimic the effects of device 200 for nightly supplemental G-tube feeding. Pancreatic duct ligation surgery, as described in Example 13, was performed on 14 pigs to create exocrine pancreatic inefficiency in this experiment. Out of the 14 operated pigs, only 11 pigs developed complete pancreatic insufficiency and were used in this study.

Prior to pancreatic duct ligation surgery, following the surgery, and during a pre-study period, pigs were orally fed a standard pig diet that contained 17.5% crude protein, 3.9% crude fiber, and 3.5% crude fat, 5.2%, 5000 IE/kg vitamin A, 500 IE/kg vitamin D, and 85 mg/kg vitamin E. Feeding was done twice daily (2.0% body mass per meal) at 7 AM and 3 PM.

During the 12-day study, five EPI pigs in a control group were fed with non-hydrolyzed Peptamen AF® via a G-tube, and six EPI pigs in a test group were fed Peptamen AF® pre-hydrolyzed using device 200 via a G-tube. Pigs were fed during the day with a standard solid feed similar to the mean human high-fat diet (about 1400 kcal/day/pig). In order to mimic nighttime enteral feeding, which would be a common use for device 200 in EPI patients, the EPI pigs were supplemented with an additional 750 calories (500 mL; 1.8 g Ω-3, Peptamen AF®, Nestlé Nutrition, EU) nightly at a flow rate of 2 mL/min over 4 hours via G-tube feeding. Device 200 used in the study was manually filled with 1 g of lipase 710 attached to particles 300. Peptamen AF® is a semi-elemental enteral formula that provides pre-hydrolyzed protein. The use of PERT capsules for protein digestion was not provided, since Peptamen AF® contains pre-hydrolyzed protein and the use of device 200 would efficiently hydrolyze the fat. Pre-hydrolyzed proteins are stable in pre-packaged enteral formulas in contrast to free fatty acids and monoglycerides, which oxidize and quickly become rancid.

14.1 Study Design and Procedures

Figure 42:
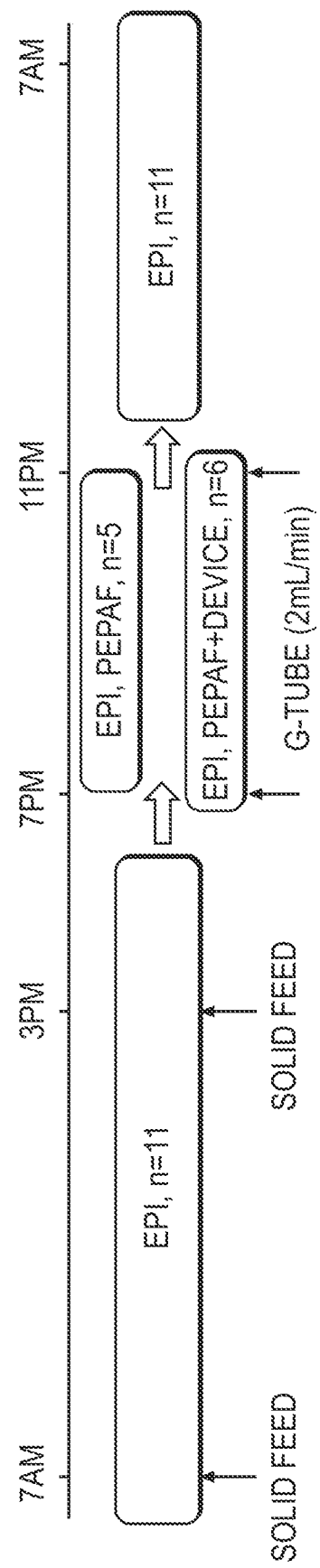
FIG. 42 schematically depicts the study design and procedures for the 12-day pig study described in Example 14.

During this 12-day study period, EPI pigs were randomized into two groups, control group ("PepAF") and test group ("PepAF+Device"), based on the body weight and health status, as shown in FIG. 42:

1) Control group: Five EPI pigs were enrolled and fed with solid feed twice during the day at 7 AM and 3 PM. During the night from 7 PM to 11 PM, 500 mL of non-hydrolyzed Peptamen AF® was provided using G-tube feeding during the 4-hour period.

2) Test group: Six EPI pigs were enrolled and fed with solid feed twice during the day at 7 AM and 3 PM. During the night from 7 PM to 11 PM, 500 mL of Peptamen AF® formula pre-hydrolyzed using device 200 was provided during the 4-hour period of enteral feeding.

The experiment lasted 12 days, and the G-tube feeding was performed every evening during the study. On the last 3 days of the study, three 24 h stool and urine samples were collected. On the last day of the study, just before sacrificing, fasting morning blood samples were collected for taking protein and fat profile and measurements of DHA and EPA levels in the blood as markers of LC-PUFA absorption.

Measurement of Fat and Protein Content in Food and Stool Samples

Stool samples were collected during the last 3 days (3×24 h) of the 12-day study and weights were recorded. A small fraction from each sample was measured for coefficient of protein absorption (% CPA) and total LC-PUFA.

Protein stool measurement was estimated based on the nitrogen fecal losses. Nitrogen levels were measured in food samples and in collected fecal samples using a standard Kjedhal method. The coefficient of protein absorption (% CPA) was calculated as:

$$CPA = \frac{\left[\text{nitrogen intake}\left(\frac{g}{24\,h}\right) - \text{nitrogen in feces (g/24 h)}\right]}{\text{nitrogen intake (g/24 h)}} \times 100\%$$

Plasma lipid profile was estimated based on Lipaemic Index (LI). Lipaemic Index was calculated by:

Lipaemic Index=(OD 660 nm−OD 700 nm)×100%

Each plasma sample was measured in duplicate.

14.2 Results

All pigs had normal behavior, and no adverse events were recorded that related to G-tube feeding through device 200. As shown in Table 17, food consumption was normal and similar between the EPI control group ("PepAF") and test group ("PepAF+Device") fed pre-hydrolyzed formula. Steatorrhea is a common symptom seen in people with compromised pancreatic function (lipid malabsorption due to poor hydrolysis of fat) and was reduced in the test group when compared to the control group, shown by 72-hour stool weight.

There was a positive correlation between % CFA and plasma levels of EPA (rs=0.81; p=0.003), DHA (rs=0.672; p=0.027) and PUFA ($r_s$=0.736; p=0.013).

TABLE 17

Mean food intake and stool weight

| Groups | Food intake (g) | Stool Weight (g)* |
|---|---|---|
| PepAF | 388 ± 81 | 386.7 ± 77.3 |
| PepAF + Device | 363 ± 125 | 316.7 ± 97.7 |

*p = 0.014

One of the safety parameters considered important for this study was growth. It should be noted that this was only a 12-day study using nightly G-tube enteral feeding using device 200. Even with this short duration using device 200, improved growth was observed in the PepAF+Device group (6.7% increase with test group vs. 5.3% increase for the control group, p=NS). Body weight changes are shown in Table 18.

TABLE 18

Body weight change after 12 days of nighttime G-tube feeding

| | BW (kg) | | Difference | |
|---|---|---|---|---|
| Group | day 1 | day 12 | (kg) | % Change |
| Pep AF (n = 5) | 15.7 ± 0.9 | 16.5 ± 0.6 | 0.8 ± 0.7 | 5.3 ± 4.8 |
| Pep AF + Device (n = 6) | 15.2 ± 2.6 | 16.2 ± 2.6 | 1.0 ± 0.3 | 6.7 ± 2.2 |

At the end of the study, blood samples were collected for estimation of blood fat profile and levels of omega-3 fatty acids. As shown in Table 19, plasma TG levels were normal and the same between the groups, but cholesterol and HDL were increased in the pigs fed pre-hydrolyzed Peptamen AF®, suggesting improved fat absorption and a trend towards normalization of cholesterol levels (normal cholesterol range in healthy pigs is 3-4 mmol/L). The p-value is *p<0.05 for the difference between the control and the PepAF+Device group in total cholesterol and HDL levels. TG was within the normal range.

TABLE 19

Blood fat profile

| Group (n = 5-6) | TG (mmol/L) | Cholesterol (mmol/L) | HDL (mmol/L) | LDL (mmol/L) |
|---|---|---|---|---|
| PepAF | 0.59 ± 0.25 | 2.47 ± 0.15 | 0.92 ± 0.15 | 1.17 ± 0.13 |
| PepAF + Device | 0.50 ± 0.22 | 2.81 ± 0.35* | 1.27 ± 0.36* | 1.25 ± 0.09 |

As a part of the safety tests, the morphometric structure (mucosal thickness and epithelial structure) of the small intestine after 12 days of consecutive feeding with pre-hydrolyzed Peptamen AF® by device 200 was observed and compared with the structure of pigs fed non-hydrolyzed Peptamen AF®. As a control, a group of healthy pigs and a group of EPI pigs fed the same solid high-fat diet feed (EPI pigs fed solid feed only, no supplemental enteral G-tube feeding) were included.

The small intestine was chosen as one of the most vulnerable sites in the GI and the part where most of the nutrients from food are absorbed into circulation. In this study, the middle portion of the small intestine was analyzed.

Figure 43:
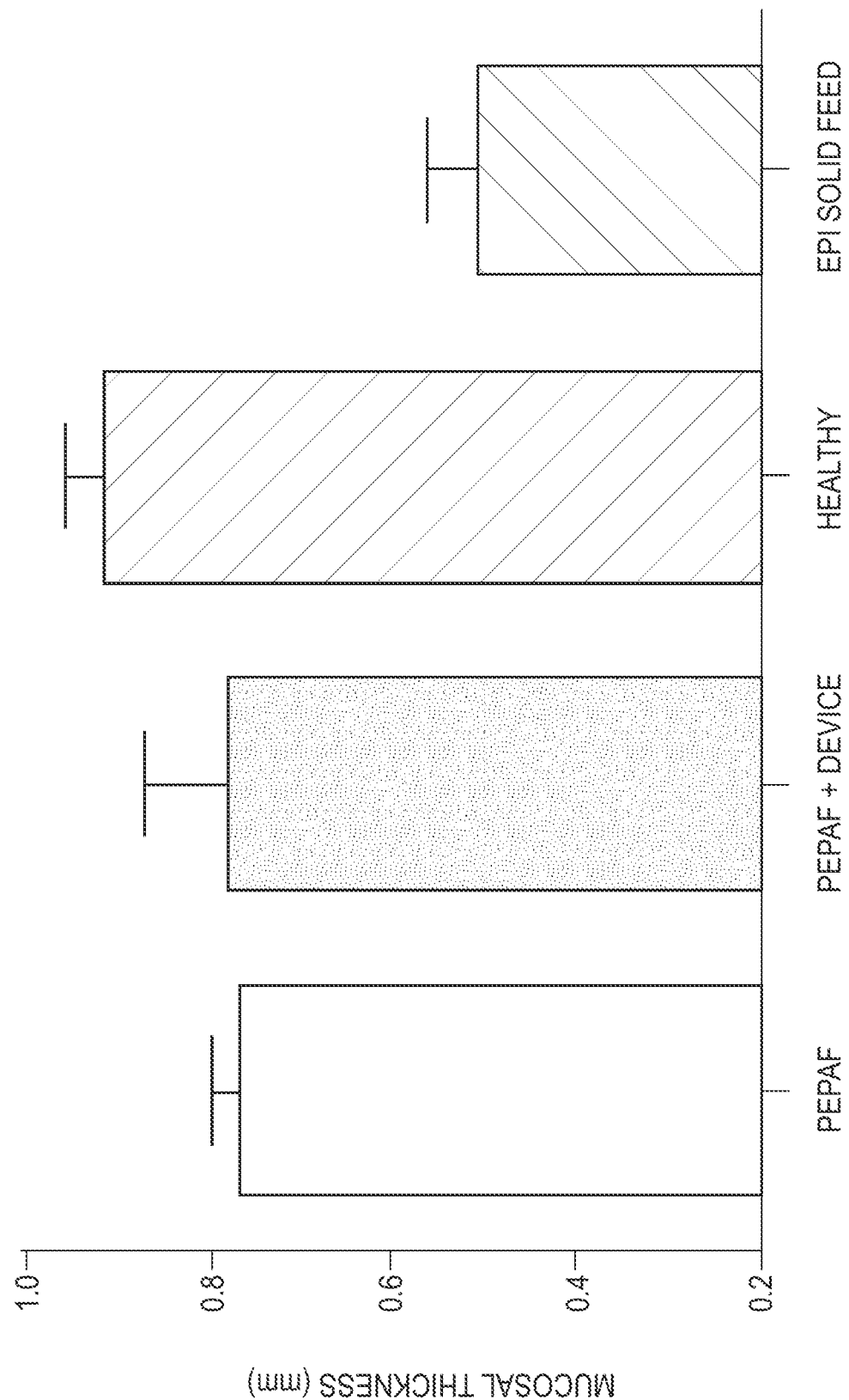
FIG. 43 graphically compares the mean mucosal thickness of the small intestine of the control group and the test group described in Example 14.

As shown in FIG. 43, results of the histopathological examination and morphometry analysis of the samples from the small intestine demonstrate again that consumption of pre-hydrolyzed formula by device 200 is safe, demonstrated by:

1) No pathological changes in the middle portion of the small intestine independent of the use of pre-hydrolyzed or non-hydrolyzed Peptamen AF®.
2) Slight trend increase in the mucosal thickness in PepAF+Device group after only 12 days of pre-hydrolyzed G-tube feeding when compared to control group fed non-hydrolyzed formula.

Overall mucosal thickness was reduced in both EPI groups due to EPI disease in pigs, independent of feeding with either pre-hydrolyzed or non-hydrolyzed Peptamen AF® when compared to healthy pigs fed solid feed. Interestingly, the mucosal thickness was improved in both Peptamen AF® G-tube fed groups when compared to EPI pigs fed only a solid high-fat diet, indicating remodelling capacity of the small intestine.

Figure 44:
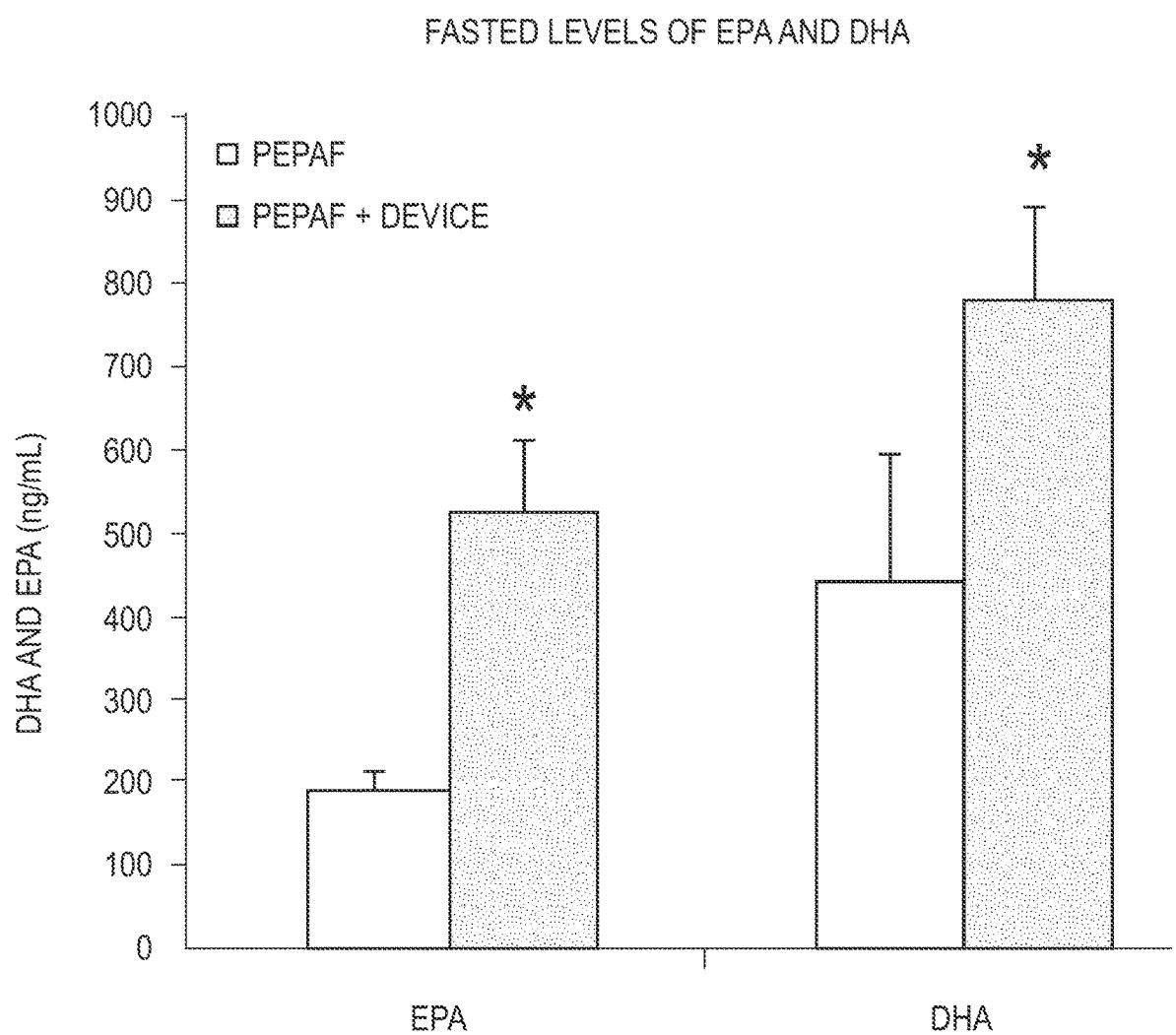
FIG. 44 graphically compares the mean changes in DHA and EPA fasting plasma levels of the control group and the test group described in Example 12.

After only 12 days of nightly G-tube feeding, basal fatty acid DHA and EPA fasting blood levels in EPI pigs fed pre-hydrolyzed formula (PepAF+Device) increased to 727.6±164.9 ng/mL for DHA (p=0.008) and to 512.6±81.6 ng/mL for EPA (p<0.001) when compared to the control group (PepAF) fed non-hydrolyzed formula, whose DHA level was 442.8±154.1 ng/mL and EPA level was 190.8±23.1 ng/mL. FIG. 44 and Table 20 show the mean change over time from baseline to day 12.

TABLE 20

Mean changes in DHA and EPA plasma levels after 12 days of nightly feeding using device 200 in an exocrine pancreatic insufficiency (EPI) porcine model

| Group | DHA (ng/mL) | | | EPA (ng/mL) | | |
|---|---|---|---|---|---|---|
| (n = 5-6) | Baseline | Day 12 | Change | Baseline | Day 12 | Change |
| PepAF + Device | 214.2 ± 141.4 | 727.6 ± 164.9 | 513.4* | 43.3 ± 23.5 | 512.6 ± 81.6 | 469.3* |
| PepAF | 268.7 ± 129.2 | 442.8 ± 154.1 | 174.1 | 81.5 ± 84.0 | 190.8 ± 23.1 | 109.3 |

Results are shown as a mean of group ± SD. DHA and EPA measured as ng/ml.
*p = 0.008 for difference between Pep AF + Device vs. PepAF for DHA.
**p = 0.001 for difference between Pep AF + Device vs. PepAF for EPA.

Results in Table 20 are shown as a mean of the group±SD. DHA and EPA were measured as ng/ml. The p-value is *p=0.008 for the difference between Pep AF+Device vs. PepAF for DHA; **p=0.001 for difference between Pep AF+Device vs. PepAF for EPA.

The healthy control group had a mean baseline level of 753.3±102.2 ng/mL for DHA and 138.1±10.0 ng/mL for EPA. This is indicative of the efficiency of device 200 to hydrolyze fats, including the most complex fats (longer carbon chains and double bonds), such as DHA and EPA triglycerides, providing them in an easily absorbable form of free fatty acids and monoglycerides. Peptamen AF® has a total of 1.8 g of omega-3 fat based on the label claim, primarily in the form of EPA and DHA triglycerides. Since DHA and EPA levels are deficient in people with cystic fibrosis and developmental immature infants, this improvement in physiologically relevant LC-PUFA fats in only 12 days of nightly G-tube feeding using device 200 is an important finding with potential beneficial clinical implications.

In addition, total fatty acid changes in plasma were assessed at the end of 12 days of feeding for the test group fed with pre-hydrolyzed formula compared to the control group fed with non-hydrolyzed formula. As shown in Table 21, increased uptake of specific long-chain polyunsaturated fatty acids with the use of device 200 resulted in a statistically significant reduction in the omega-6 to omega-3 ratio. The healthy control group had a mean baseline omega-6 to omega-3 ratio of $8.7 \pm 0.8$. DHA and EPA measured as grams of DHA or EPA over 100 g of total fatty acids. The p-value is $*p<0.05$ for the difference between baseline and day 12.

TABLE 21

Change in omega-6 to omega-3 ratio after 12 days in an exocrine pancreatic insufficiency (EPI) porcine model

| Group (n = 5-6) | Baseline | Day 12 |
|---|---|---|
| PepAF + Device (pre-hydrolyzed) | 10.5 ± 0.7 | 2.4 ± 0.3* |
| PepAF (non-hydrolyzed) | 10.6 ± 0.6 | 4.2 ± 0.6 |

To assess the effect of improved fat absorption and LC-PUFA absorption, bioavailability analysis of fatty acid content in the lung, retina, heart, liver, small intestine, and the erythrocytes (red blood cells (RBC)) of each pig was performed. Results of DHA and EPA accretion in the respective tissues are shown in Table 22 and Table 23.

TABLE 22

DHA (g/100 g total fatty acids)

| Group (n = 5-6) | Lung | Retina | Heart | Liver | Small Intestine | Erythrocytes (RBC) |
|---|---|---|---|---|---|---|
| PepAF + Device | 5.1 ± 0.3* | 9.6 ± 3.4* | 1.8 ± 0.5 | 5.4 ± 0.3* | 3.4 ± 0.3* | 1.8 ± 0.3 |
| PepAF | 4.5 ± 0.5 | 8.2 ± 2.7 | 1.8 ± 0.5 | 4.7 ± 0.4 | 1.4 ± 0.1 | 1.8 ± 0.2 |

TABLE 23

EPA (g/100 g total fatty acids)

| Group (n = 5-6) | Lung | Retina | Heart | Liver | Small Intestine | Erythrocytes (RBC) |
|---|---|---|---|---|---|---|
| PepAF + Device | 5.8 ± 0.5* | 1.2 ± 0.3* | 1.7 ± 0.4* | 6.2 ± 0.6* | 3.3 ± 0.7* | 1.2 ± 0.4* |
| PepAF | 3.3 ± 0.4 | 0.8 ± 0.4 | 1.3 ± 0.2 | 3.4 ± 0.3 | 2.4 ± 0.9 | 0.87 ± 0.1 |

Results are shown as a mean of group±SD, *p<0.05 for the difference between PepAF+Device vs. PepAF on day 12.

In all tested tissues, a significant increase in the levels of EPA was demonstrated in the test group fed with formula pre-hydrolyzed using device 200 compared with the control group fed with non-hydrolyzed formula. Interestingly, even in RBCs that have a half-life of around 100 days, a significant increase of 37% in EPA levels was observed. Measured levels of DHA were significantly elevated in all analyzed tissues with the exception of the heart and RBCs.

Patients with compromised pancreatic output and/or fat malabsorption have a higher risk of fatty acid deficiencies in plasma and tissue, which may be related to a variety of adverse physiological effects, such as altered membrane and cellular functions, as well reduced tolerability of formula due to poor hydrolysis of fats. Thus, enteral feeding using device 200 may help in reducing such deficiencies and/or may normalize mucosal thickness, indicating a remodelling capacity of the small intestine, as well as improving gastrointestinal symptoms.

To demonstrate changes in blood lipid profile after G-tube feeding, blood samples were collected on the last day of the study before solid meals, 4 hours after the solid meals, and before and after enteral G-tube feeding. LI is a simple turbidometry method that is used to measure postprandial changes in total blood fat.

Figure 45:
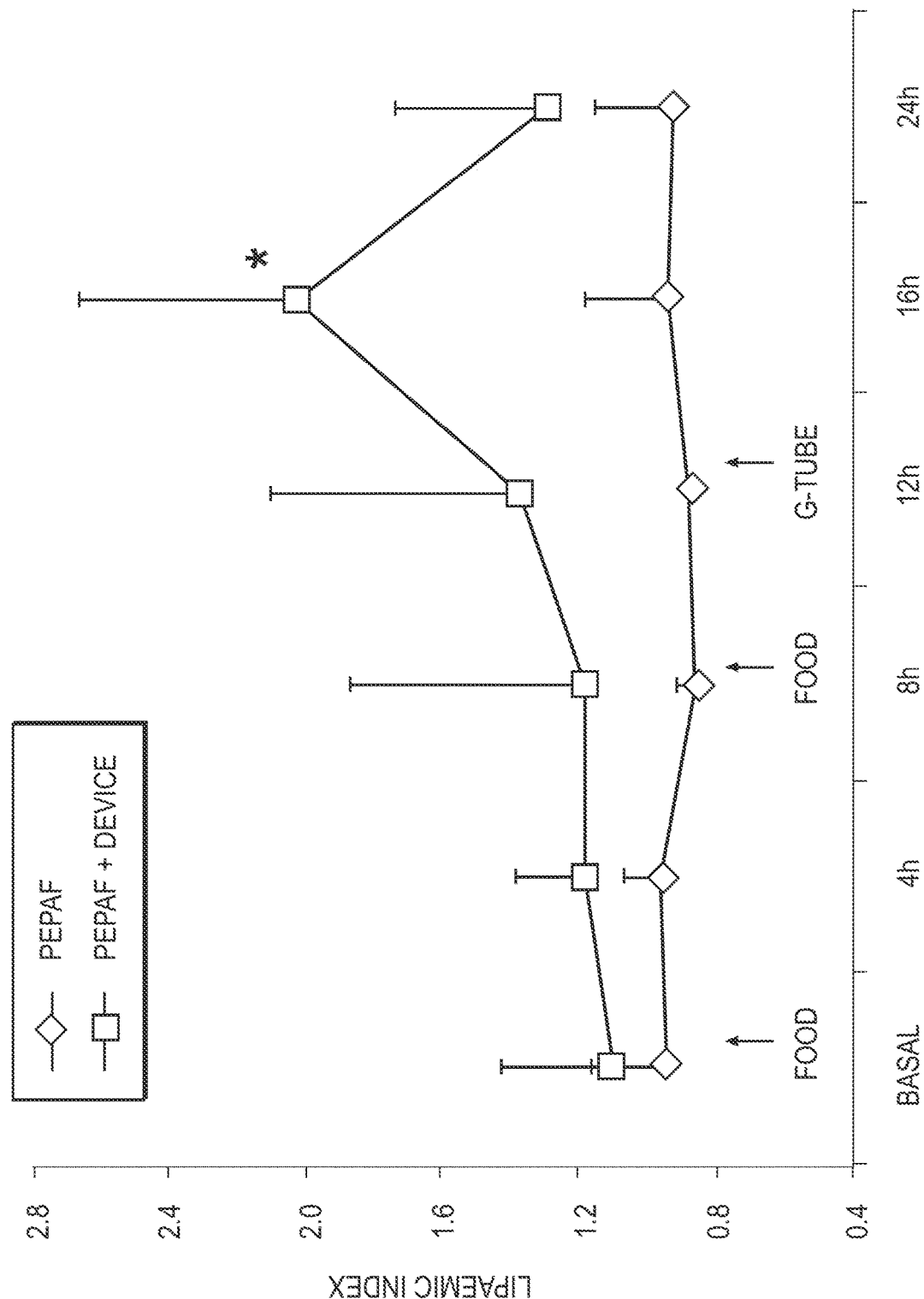
FIG. 45 graphically compares the lipid absorption measured from blood samples before and after solid meals of the control group and before and after G-tube feeding of the test group described in Example 14.

As shown in FIG. 45, total lipid absorption measured as a change in LI increased in pigs from the test group fed with pre-hydrolyzed Peptamen AF® when compared to the control group fed with non-hydrolyzed Peptamen AF®. Calculated $AUC_{t12\text{-}24h}$ values were significantly increased in the test group fed with pre-hydrolyzed formula (11.1±1.29 vs. 20.8±8.6; p<0.05), indicating efficient delivery of easily absorbable fat when using device 200.

Figure 46:
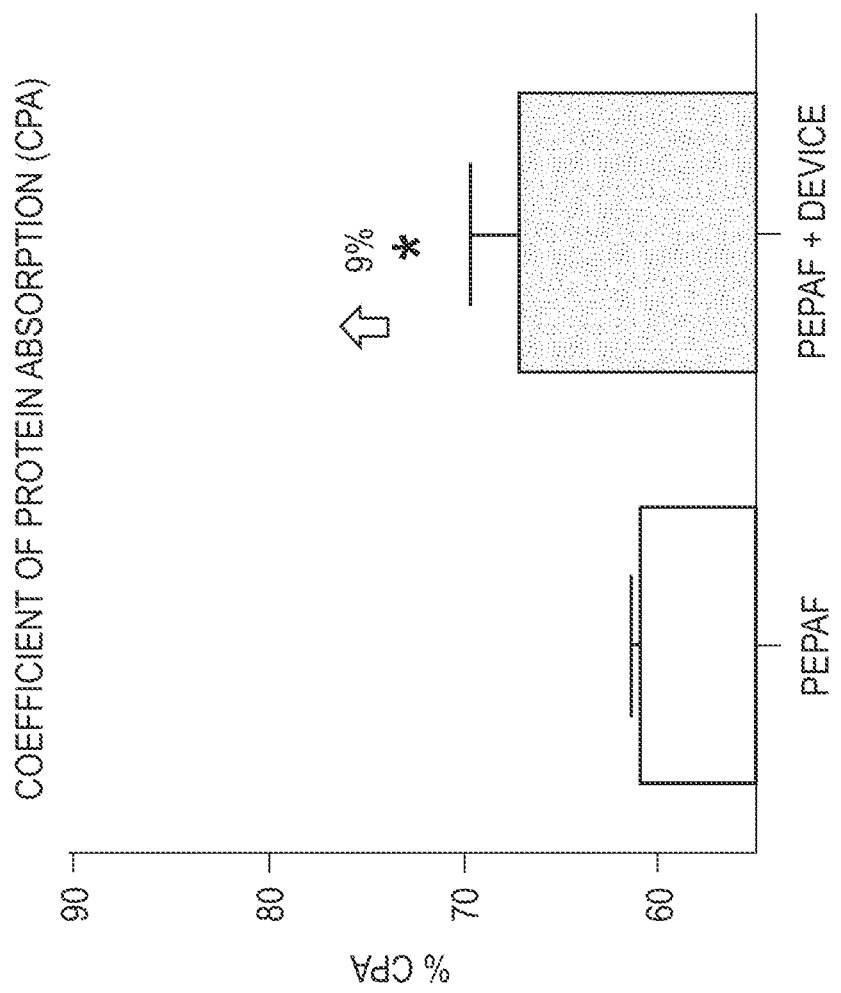
FIG. 46 graphically compares mean coefficient of protein absorption of the control group and the test group described in Example 14.

As shown in FIG. 46, a surprising result in this study was that protein absorption by the pigs of the test group fed with formula pre-hydrolyzed using device 200 (PepAF+Device) improved by 9% compared with the control group fed with non-hydrolyzed formula, as measured by changes in fecal nitrogen levels and expressed as a coefficient of protein absorption (61.2±0.9% vs. 66.9±2.8%, p=0.001). This is surprising, since Peptamen AF® already contains pre-hydrolyzed protein and no difference in protein absorption was expected. It is theoretically hypothesized that pre-hydrolyzed fat from device 200 may lead to less un-hydrolyzed fat in the GI tract, which may reduce inflammation, increase mucosal thickness, improve remodelling capacity of the small intestine, and thus may support enhanced absorption of protein and other nutrients.

As shown in Table 24, another surprising result in this study was that use of device 200 seemed to promote more efficient uptake of fat-soluble vitamins (Vitamins D, E; p<0.05) for the test group. Fat-soluble vitamins (A, D, E, K) have shown to be reduced in people with compromised pancreatic output or fat malabsorption.

TABLE 24

Absorption of vitamins D and E

| Group (n = 5-6) | Vitamin D (ng/mL) | Vitamin E (mcg/mL) |
|---|---|---|
| PepAF + Device (hydrolyzed) | 6.48 ± 2.78* | 0.53 ± 0.26* |
| PepAF (non-hydrolyzed) | 3.82 ± 0.97 | 0.25 ± 0.07 |
| Normal range in healthy pigs | 5-20 | 1-8 |

*p < 0.05 for difference between baseline and day 12

These unexpected results indicate that the test group fed with formula pre-hydrolyzed using device 200 may have better absorption of other nutrients in formula, such as proteins and vitamins, which eventually may be beneficial to the subject in need of the nutrients in the formula.

Example 15: Comparison of 24-Hour Pharmacodynamic Profiles of Total Fat and Free Fatty Acids in EPI Pigs after Single G-Tube Feeding Using Exemplary Device 200 and not Using any Device 200

This study is a pharmacodynamic proof of principle study performed to asses fat absorption from 500 mL Peptamen AF® (750 kcal, about 30% calories from 32 g TG-fat, Nestle Nutrition, EU) after a single G-tube feeding using an exemplary device 200 when compared to standard G-tube feeding. Exemplary device 200 used in this experiment was substantially similar to that used in Example 3. The Peptamen AF® pre-hydrolyzed using an exemplary device 200 (flow rate of 2 mL/min, test group, n=6) and the non-hydrolyzed Peptamen AF® (control group, n=5) were administrated to "naïve" fasted EPI pigs over a period of about 5 hours. The EPI pigs were prepared as described in Example 13. After two days of wash out before the 24-hour treatment period, EPI pigs were returned to baseline levels and then crossed over to the opposite group, and thus each pig served as its own control. After the two days of wash out, a healthy control group of 3 pigs of the same age and breed were enrolled. During this 24-hour test period, the only food provided to the pigs was via G-tube.

The EPI pigs were randomized into the control group ("PepAF") and the test group ("PepAF+Device") based on body weight and health status. The control group was fed with 500 mL of non-hydrolyzed Peptamen AF® via G-tube, the test group was fed with 500 mL of Peptamen AF formula pre-hydrolyzed using device 200 via G-tube, and the healthy control group of pigs was fed with non-hydrolyzed Peptamen AF® via G-tube, during the approximately 5-hour period. The G-tube feeding started at about 10:00 AM, and blood samples were collected before the start of G-tube feeding (basal collection) and at 1, 3, 5, 7, 10, 12, 16, 20, and 24-hour time points.

Ten blood samples of each pig were collected over the 24-hour study period for estimation of the total fat content in Lipaemic Index (LI). Also, changes in the concentrations of DHA and EPA free fatty acids were measured.

Figure 47:
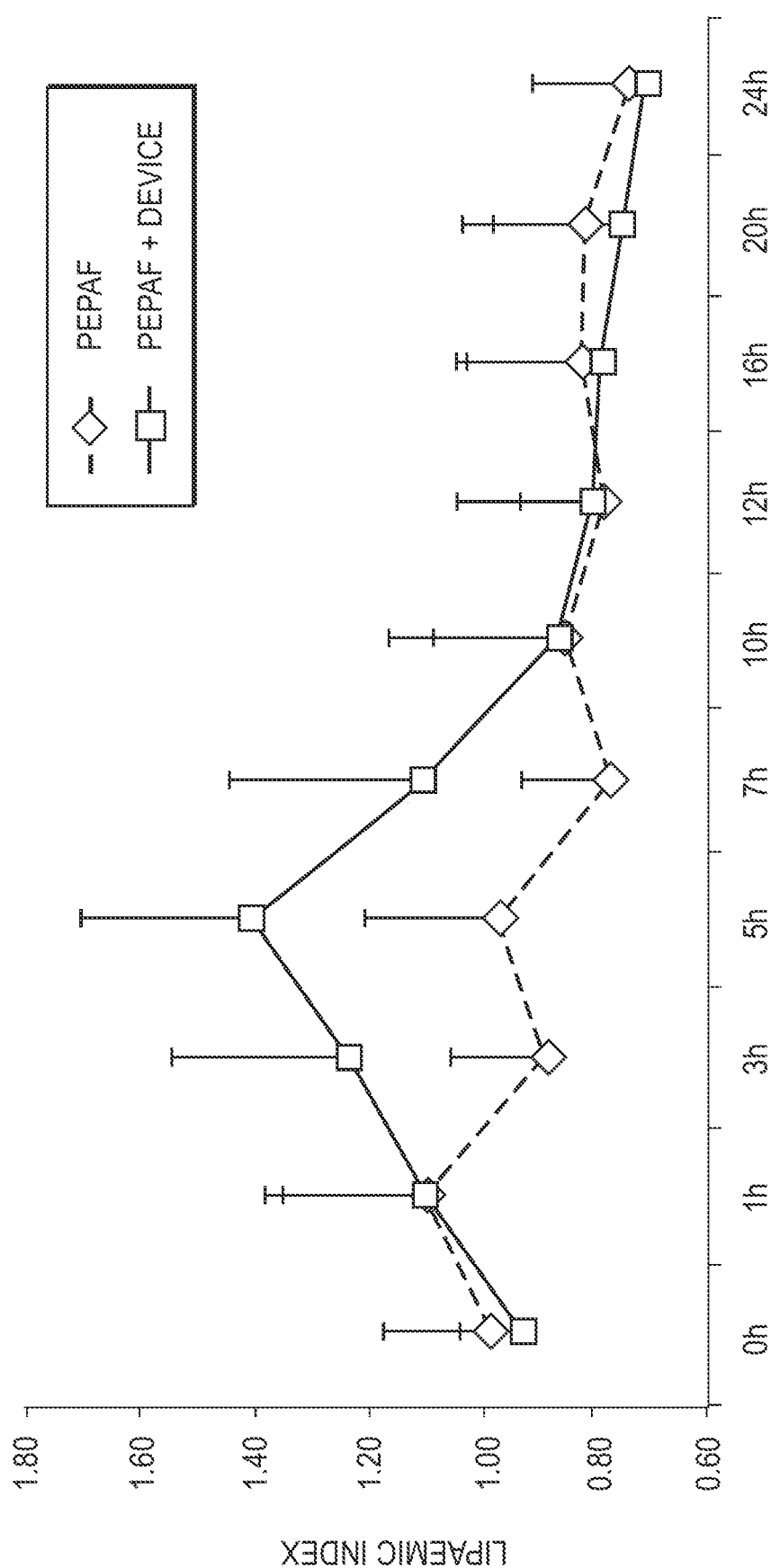
FIG. 47 graphically compares mean fat absorption of EPI pigs of a control group fed non-hydrolyzed nutritional formula and a test group fed nutritional formula pre-hydrolyzed with an exemplary fat hydrolysis device described in Example 14.

As shown in FIG. 47, fat absorption, as measured by lipaemic index (LI), was significantly improved in the PepAF+Device group when compared to the PepAF group fed with non-hydrolyzed Peptamen AF® during and directly after the 5-hour feeding time. Calculated $AUC_{0-10h}$ values were significantly increased in the PepAF+Device group when compared to the PepAF group (11.5±1.99 vs. 9.1±1.63; p=0.023), indicating improved fat absorption with the use of device 200 in the enteral G-tube feeding circuit.

Figures 48A, 48B:
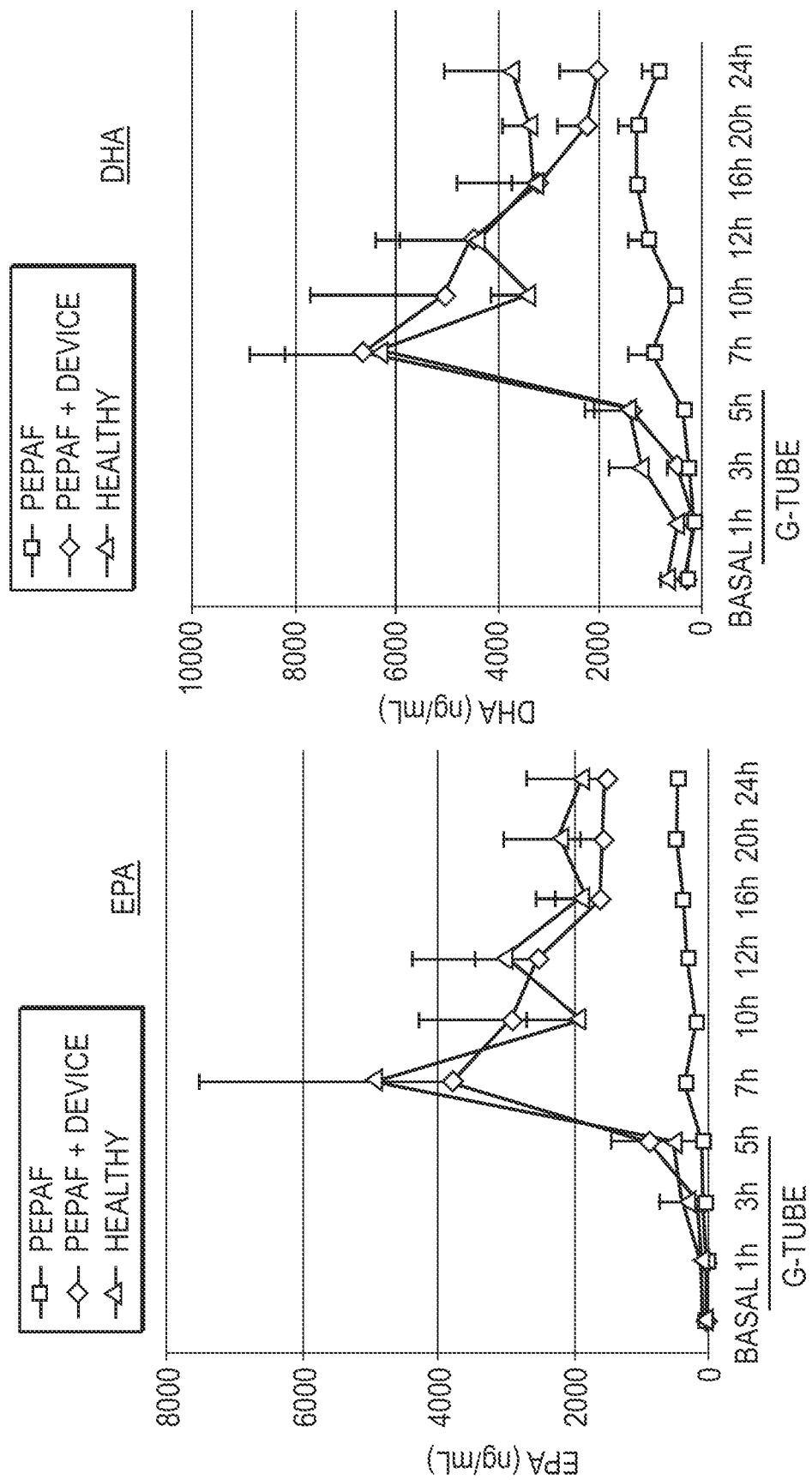
FIG. 48A graphically compares phramacodynamic profiles of EPA of the control group and the test group described in Example 15.
FIG. 48B graphically compares phramacodynamic profiles of DHA of the control group and the test group described in Example 15.

Plasma concentrations of EPA and DHA upon G-tube feeding with pre-hydrolyzed PeptamenAF® were also measured, since these free fatty acids represent one of the most critical biomarkers of LC-PUFA absorption. As shown in FIG. 48A and FIG. 48B, a significant improvement in the absorption of EPA and DHA fatty acid was demonstrated with the use of device 200. Device 200 efficiently hydrolyzed EPA and DHA (the most complex and the longest triglyceride chains) for the test group when compared to the control group. Importantly, the phramacodynamic 24-hour profiles overlapped between healthy pigs and EPI pigs fed with pre-hydrolyzed formula via G-tube using device 200, indicating that absorption of PeptamenAF® pre-hydrolyzed using device 200 was almost normalized compared to that of healthy pigs.

As shown in Table 25, formula hydrolyzed using device 200 was associated with a statistically significant increase in total fat absorption and improvement in uptake of omega-3 fatty acids (DHA and EPA) in plasma levels over 24 hours for the test group compared to the control group fed with non-hydrolyzed formula (p<0.05).

TABLE 25

Changes in total DHA and EPA fatty acids over 24 hours in an exocrine pancreatic insufficiency (EPI) porcine model

| Group | DHA | | | EPA | | |
|---|---|---|---|---|---|---|
| (n = 5-6) | Baseline | 24-h | Change | Baseline | 24-h | Change |
| Pep + Device | 0.9 ± 0.2 | 2.1 ± 0.2 | 1.2* | 1.0 ± 0.1 | 5.5 ± 0.7 | 4.5** |
| PepAF | 1.2 ± 0.2 | 1.6 ± 0.2 | 0.4 | 1.1 ± 0.2 | 2.1 ± 0.2 | 0.9 |
| Healthy control | 1.6 ± 0.0 | 2.3 ± 0.2 | 0.7 | 1.2 ± 0.2 | 3.2 ± 0.1 | 2 |

In Table 25, DHA and EPA are measured as grams of DHA or EPA over 100 g total fatty acids. Results are shown as a mean of the group±SD. The p-values are as follows: *p=0.0005 for the difference between PepAF+Device vs. PepAF over 24 hours for DHA; **p<0.0001 for the difference between PepAF+Device vs. PepAF over 24 hours for EPA.

As shown in Table 26, increased uptake of specific long-chain polyunsaturated fatty acids with use of device 200 resulted in a statistically significant reduction in the omega-6 to omega-3 ratio. Previous studies have demonstrated that a balanced ratio of omega-6 to omega-3 fatty acids is beneficial in maintaining normal development, immunological function, and overall health.

TABLE 26

Change in omega-6 to omega-3 ratio over 24 hours in an exocrine pancreatic insufficiency (EPI) porcine model

| Group (n = 5-6) | Baseline | 24-hours |
|---|---|---|
| PepAF + Device | 10.6 ± 0.4 | 3.6 ± 0.5* |
| PepAF | 10.5 ± 0.8 | 7.0 ± 1.2 |
| Healthy control | 8.7 ± 0.8 | 5.2 ± 0.4 |

In Table 26, DHA and EPA are measured as grams of DHA or EPA over 100 g total fatty acids. Results are shown as a mean of the group±SD. The p-value is *p<0.0001 for difference between baseline and 24 hours for PepAF+Device vs. PepAF.

The single delivery of formula pre-hydrolyzed using device 200 was safe and well tolerated with no vomiting or diarrhea recorded. G-tube feeding of 500 mL of Peptamen AF® pre-hydrolyzed using device 200 resulted in significantly improved total fat absorption and a normalized pharmacodynamic profile of physiologically relevant LC-PUFAs, such as EPA and DHA.

Example 16: Human Study of CF Patients to Evaluate Fat Absorption Using Device 200

A prospective, controlled, randomized, double-blind, cross-over study of human patients with cystic fibrosis (CF) and compromised pancreatic output receiving enteral nutrition was performed to evaluate fat absorption, GI symptoms, and tolerability of nutritional formula using device 200. Device 200 used during this study is described in Device Example 1, below. Like patients with compromised pancreatic output, patients with CF have previously been shown to be deficient in LCPUFAs, including DHA and EPA. People with CF tend to have abnormal fatty acid metabolism, with increased release and high turnover of AA and decreased levels of DHA, EPA, and LA in plasma, erythrocytes, platelets, and tissues.

Plasma measures generally allow for precise assessment of fatty acid absorption, including from enteral feedings of nutritional formulas. Measuring plasma levels of DHA and EPA is believed to provide an accurate assessment of DHA and EPA absorption by the body. Since only a small amount (<1%) of DHA and EPA are internally synthesized, plasma levels of DHA are primarily influenced by dietary intake. In addition, as 20- and 22-carbon-chain polyunsaturated fats, DHA and EPA are poorly absorbed relative to other fatty acids, such as simple medium-chain fatty acids and saturated fat. Therefore, changes in the plasma levels of DHA and EPA after enteral feeding may be a sensitive indicator of fat absorption and may serve as surrogate biomarkers representative of fat absorption from diet in general. Using nutritional formulas containing fixed quantities of certain fatty acids, such as DHA and EPA, also allows for precise measurement of fat absorption following enteral feeding. Accordingly, plasma levels of DHA and EPA were chosen as biomarkers of fat in this study. While previous studies have looked at plasma uptake of fatty acids following ingestion of triglycerides, this study looked at plasma uptake of fatty acids following ingestion of pre-hydrolyzed triglycerides (i.e., free fatty acids and monoglycerides) generated using device 200.

Thirty-three patients with CF, ranging in age from 5 years to 34 years, were recruited as part of the study. The study comprised of a 7-day baseline and run-in period (Period A), an 11-day double-blind crossover period (Period B), and a 9-day open-label safety period (Period C). Each patient received two study treatments (device 200 or a placebo) in a crossover fashion during Period B.

During Period A (Days −7 to −1), baseline evaluations were performed on the patients, enteral nutrition intake was standardized, and patients maintained a 7-day GI symptom diary, a tool developed to asses GI symptoms associated with enteral nutrition administration. At study entry, patients completed an Impact Questionnaire, a study-specific tool developed to assess enteral nutrition use and practice, as well as to assess the impact of enteral nutrition on certain activities of daily living (ADLs). During this period, patients resumed their standard of care, including pancreatic enzyme replacement (PERT) use during the day or with enteral feeding during the night.

On Day 1 of Period B (Days 1 to 11), patients were randomized in a 1:1 ratio to a tube feeding session using Impact® Peptide 1.5 (Nestle Health Science 750 kcal, 32 (g) fat and 2.45 (g) DHA/EPA per 500 mL) with either an active device 200 or a placebo enteral device. The feeding session lasted four hours. Patients returned on Day 9 for the second, crossover treatment. Patients who had received tube feeding with a device 200 on Day 1 received a tube feeding with a placebo device on Day 9, and vice versa. In this way, each patient acted as his or her own control. The feeding session again lasted four hours. Days 1 and 9 were separated by a 7-day washout period. On administration Days 1 and 9, blood samples were collected to assess plasma fatty acid levels at hours 0, 1, 3, 7, 9, 12, and 24. Plasma samples were analyzed for concentrations of DHA and EPA using ultra high performance liquid chromatography (UHPLC).

During Period C (Days 12 to 20), all patients were instructed to use device 200 with standardized nocturnal enteral nutritional formula (Impact Peptide 1.5) from Days 12 to 18. Similar to Period A, patients maintained a GI symptom diary for 7 consecutive days and followed their standard of care. Repeat administration of the Impact Questionnaire was performed on the last day.

Study results indicated that use of device 200 improved tolerability to enteral feedings of nutritional formula and reduced GI symptoms when compared to use of PERTs alone. Use of device 200 with up to 1,000 mL of formula decreased GI symptoms, and during Period C (use of device 200), both the incidence and severity of GI symptoms decreased compared to Period A. At the end of Period C, more patients reported an absence of digestive symptoms and reported that tube feeding did not decrease appetite or ability to eat meals or snacks. Fewer patients skipped breakfast when using device 200 compared to when using just PERTs (33% vs. 48.5%). This may be due to a reduction of GI symptoms (reduced nausea, bloating, fullness), which allowed patients to feel hungry or to be able to eat again. As a result, using device 200 may not only increase caloric intake by increasing the amount of fats a patient's body may absorb, but also by allowing patients to eat more because they have fewer GI symptoms. The number of patients reporting individual symptoms in Period A vs. Period C is shown below in Table 27. One patient did not complete the 7-day GI symptom diary in Period A.

TABLE 27

Number of patients reporting GI symptoms

| Symptom | Period A (n = 32)* | Period C (n = 32) |
| --- | --- | --- |
| Abdominal Pain | 12 (38%) | 9 (27%) |
| Bloating | 7 (22%) | 4 (12%) |
| Constipation | 6 (19%) | 0 |
| Diarrhea | 7 (22%) | 4 (12%) |
| Gas | 11 (34%) | 10 (30%) |
| Indigestion/Heartburn | 7 (22%) | 3 (9%) |
| Nausea | 6 (19%) | 4 (12%) |
| Steatorrhea | 6 (19%) | 3 (9%) |
| Vomiting | 3 (9%) | 3 (9%) |
| Other | 0 | 2 (6%) |

Figure 49A:
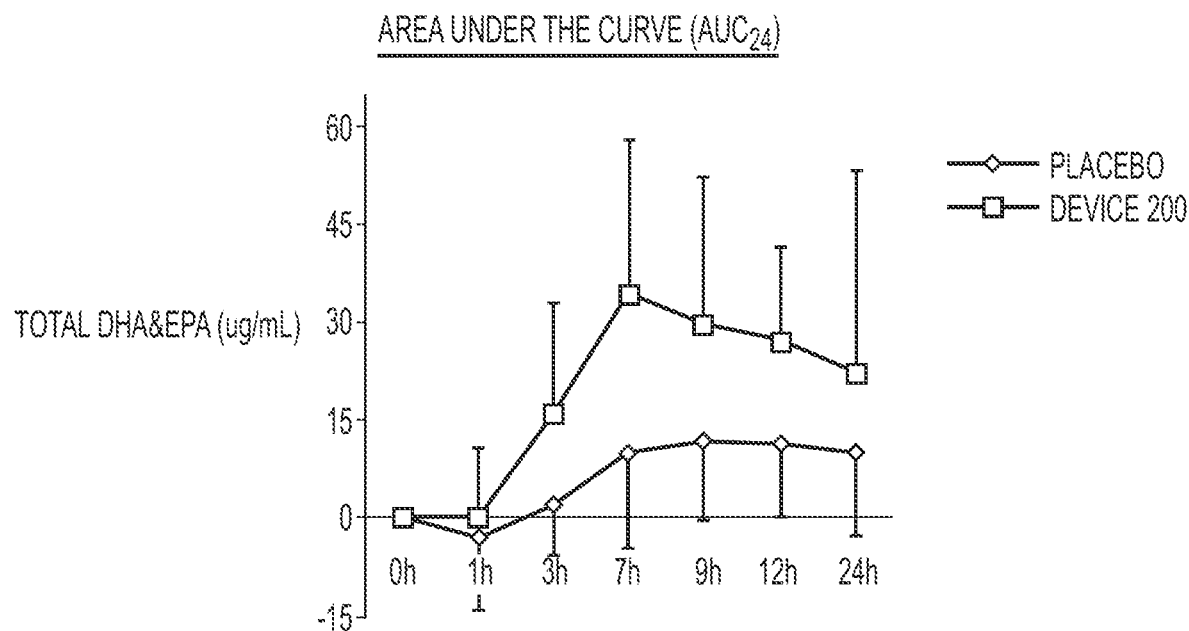
FIG. 49A graphically compares plasma levels over time of DHA and EPA of the control group and the test group described in Example 16.
Figure 49B:
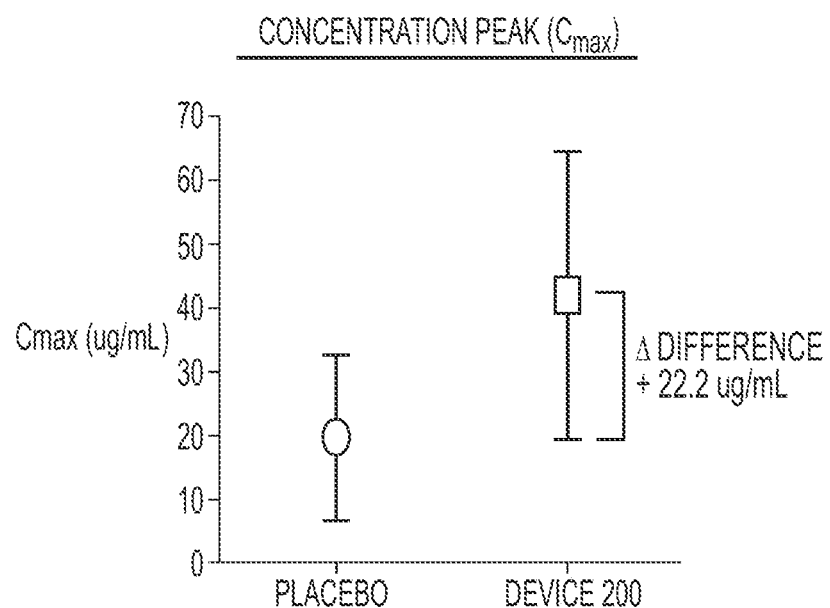
FIG. 49B graphically compares the absolute increase in total DHA and EPA of the control group and the test group described in Example 16.

Plasma levels of both DHA and EPA increased significantly during and after administration of a single enteral tube feeding of 500 mL of a nutritional formula using device 200. The maximum concentration of DHA and EPA in blood plasma occurred at the 7-hour time point and was nearly 300% above baseline, as shown in FIG. 49A. Measurement of bioavailability of DHA and EPA was determined by assessing the area under the curve ($AUC_{24}$), concentration peak ($C_{max}$) and time to max concentration ($T_{max}$) during the 24-hour interval period (T0 to 24 hours) for DHA and EPA (absolute and baseline adjusted). As shown in FIG. 49B, there was an absolute increase in total DHA and EPA concentration in blood plasma. In fact, the increase in plasma concentration achieved using device 200 during this study brought the concentrations of DHA and EPA within range of plasma levels generally seen in normal populations ($p<0.0001$) for $AUC_{24}$.

Use of device 200 showed a statistically significant improvement in absorption of both DHA and EPA ($p<0.01$), as well as LA ($p<0.05$). A 2.4 fold improvement in total EPA and DHA absorption was observed, as measured by $AUC_{24}$, and there was a 2.2 fold improvement in total EPA and DHA absorption, as measured by $C_{max}$. This improvement in EPA and DHA absorption brought the fatty acid profiles of CF patients more in line with the fatty acid profiles of the normal population.

Use of device 200 significantly increased LCPUFA absorption in a pediatric sub-population ($p<0.05$). AUC for plasma concentrations of DHA and EPA were significantly higher with use of device 200 compared with placebo. Similarly, the maximum plasma concentration in 24 hours ($C_{max}$) of DHA and EPA was significantly higher with use of device 200 compared with placebo. Similar results were observed in all age groups, and the results were statistically significant in the child (5-12 years of age) and adolescent (13-21 years of age) study sub-populations, as shown in Table 28, below. Absolute changes seen between age groups in AUC may reflect a dose of DHA and EPA per kg of body weight.

are deficient in people with fat malabsorption, especially those with pancreatic immaturity or deficiency), allowing for increased absorption of the more-complex LCPUFAs. The direct relationship between the complexity of the fat and the magnitude in the increase in fat absorption may have helped change the fatty acid profiles of CF patients in this study, making them look more like the fatty acid profiles of a normal population.

Since people with CF exhibit a deficiency in LCPUFAs, and since plasma uptake of LCPUFAs is slow, there is an initial physiological reduction from baseline for certain fats. Device 200 showed an ability to provide readily absorbable fatty acids, thereby reducing the baseline reduction seen when device 200 was not used.

Use of device 200 resulted in clinically meaningful increases in bioavailability of key physiologically relevant LCPUFAs (DHA, EPA) known to be deficient in people with pancreatic immaturity and/or exocrine pancreatic insufficiency, like CF and fat malabsorption. The magnitude of response in this study exceeded what would be expected in people with CF, since they are known to have not only a deficiency in uptake of DHA and EPA, but also a metabolic defect. However, the study indicates that use of device 200 to pre-hydrolyze LCPUFAs at the point of care allowed CF patients to more readily absorb total fats, but in particular, LCPUFAs, as indicated by increases in plasma content and in reduction of GI symptoms, bringing the fatty acid profiles of the study patients more in line with those of a normal population. The ability to increase LCPUFA uptake into plasma may play a role in inflammation levels in CF patients. The ratio of AA to DHA is directly involved in maintaining a proper inflammatory response, and thus if device 200 is able to improve the AA to DHA ratio, use of

TABLE 28

Mean (SD) AUC and $C_{max}$ for plasma concentrations of DHA and EPA for study population and age group sub-populations, baseline adjusted

|  | All (n = 33) | Ages 5-12 (n = 14) | Ages 13-22 (n = 16) | Ages 22+ (n = 3) |
|---|---|---|---|---|
| AUC (ug/mL/h$_{0-24}$) | | | | |
| Placebo | 251.1 (163.6) | 252.1 (100.4) | 270.1 (212.7) | 144.7 (59.2) |
| Device 200 | 610.8 (307.6) | 722.3 (402.8) | 539.0 (191.6) | 473.8 (165.2) |
| p | <0.001 | <0.001 | <0.0027 | NS |
| $C_{max}$ (ug/mL) | | | | |
| Placebo | 20.1 (13.6) | 22.2 (14.5) | 18.6 (13.9) | 11.6 (8.2) |
| Device 200 | 42.8 (22.9) | 48.1 (10.8) | 48.1 (10.8) | 28.6 (7.0) |
| p | <0.001 | <0.001 | <0.001 | NS |

Patients who rely on nutritional formulas for a large portion of their food intake often have irregular fatty acid profiles. Their fat profiles tend to show over-absorption of some fats, e.g., saturated fats and palmitic acid, and show under-absorption of others, like LCPUFAs, particularly DHA, AA, and EPA. More complex fatty acids, including LCPUFAs like DHA, AA, and EPA, are more difficult for the body to digest and subsequently absorb. The results from this study indicate that as fats become more complex (longer chain length and larger number of double bonds), the magnitude of increase in absorption by the body—as indicated by increased plasma levels—increased with use of device 200. Less complex fats showed nominal increases in absorption with use of device 200. This indicates that device 200 hydrolyzed the more-complex fats effectively (which device 200 may also decrease CF symptoms, because pro-inflammatory products are responsible for increased mucus release and neutrophil influx and activation, resulting in additional inflammation. Pro-inflammatory eicosanoid metabolites of AA (prostaglandins, leukotrienes, lipoxins) correlate with disease severity.

By providing readily absorbable DHA and EPA using device 200, it may be possible to more effectively outline a dose response expectation to promote more effective nutritional management.

Example 17: Evaluation of Device 200 Used to Administer Infant Formula in a Preterm Porcine Model This study tested the use of device 200 during enteral g-tube feeding with Similac Special Care 24 infant nutritional formula. Device 200 used during this study is described in Device Example 1, below.

The study assessed the safety, tolerance, and efficacy of device 200 for enteral feeding of pre-term piglets, an animal model that that approximates human babies born at approximately 30 weeks gestational age. The study was intended to mimic enteral feeding in pre-term babies. The experiment was performed with 15 preterm piglets (8 male and 7 female) delivered by Caesarean section from two sows at 7-8 days prior to full term (day 107/108; full term is 115 days). The study was designed as a parallel 9-day efficacy study with 15 piglets randomized based on body weight and health status into two groups:
  a. Group 1: control group with 7 piglets fed with non-hydrolyzed Similac Special Care 24 with Iron (59 mL, 24 Kcal, 0.25% DHA and 0.40% AA, Abbott Nutrition); and
  b. Group 2: treatment group with 8 piglets fed Similac Special Care 24 with Iron after having been passed through device 200 to pre-hydrolyze the fats.

Nutritional formula was delivered through device 200 at a flow rate of 1 mL/min for the treatment group.

Similac Special Care 24 with Iron is representative of a typical preterm formula. It is an iron-fortified feeding formula for promoting growth in low-birth-weight infants and premature infants. The fat content of the formula is a combination of medium chain triglycerides, soy, and coconut oils, and out of the total fat content, 0.25% is DHA and 0.40% is AA.

Results of the preterm study indicate that use of device 200 for enteral feeding of pre-hydrolyzed fats for a period of 9 days was safe and well tolerated. The treatment group of piglets showed no adverse clinical signs, including no gastrointestinal intolerance, vomiting, diarrhea, or signs of abdominal distension. Feeding volume was adjusted daily, based on growth and feeding tolerance, and was similar between the two groups during the duration of the study (mean formula intake of 127 mL/kg/day for control group and 129 mL/kg/day for treatment group). The treatment group also showed an overall increase in body weight, the development of suckling instinct, and growth of nails, hair, and muscle strength. There were also no histopathology findings in the small or large intestine that could be attributed to the enteral feeding of pre-hydrolyzed fats in the form of free fatty acids and monoglycerides.

Preterm infants often experience suboptimal growth, which may affect organ development, vulnerability to infection, and respiratory or intestinal disorders. Suboptimal growth is generally a result of poor fat digestion and poor nutrient absorption due to immaturity of the pancreas and the intestinal tract, as well as lack of bile-salt-stimulated lipase that is necessary for fat digestion and subsequent fat absorption. Nine days of enteral feeding with nutritional formula hydrolyzed using device 200 significantly improved fat absorption, which resulted in an improved growth velocity of 3.6 g/kg/day in the treatment group when compared to the control group (control group 17.5±6.6 vs. treatment group 21.1±4.6 g/kg/day). Indeed, a 21% increase in the growth velocity was recorded in the treatment group when compared to the control group (p=0.179). It is important to note that daily formula volumes were matched between groups.

To demonstrate the effect of the use of device 200 on blood plasma concentration levels of DHA and AA, blood levels were analyzed at baseline (before use of device 200) and at the end of the treatment period (9$^{th}$ day of treatment). A significant increase of 15% and 22%, respectively, was shown in plasma DHA and AA concentrations in the treatment group after 9 days of use. Increased plasma levels of DHA and AA from baseline through day 9 were as follows:
  i. DHA:
    1. Control: 51.6±7.4 to 51.4±15.8 ug/mL, p=NS
    2. Treatment: 47.4±5.4 to 55.7±6.7 ug/mL, p=0.005
  ii. AA:
    1. Control: 95.4±16.5 to 105.3±32.1 ug/mL, p=NS
    2. Treatment: 87.5±14.9 to 112.2±27.4 ug/mL, p=0.047

As shown above, DHA plasma levels at baseline in the control group were 51.6±7.4 ug/mL and were unchanged at the end of the study (51.4±15.8 ug/mL with a difference of 0.4 ug/mL). In contrast, in the treatment group, DHA plasma levels increased by 8.3 ugL/mL from 47.4±5.4 ug/mL at baseline to 55.7±6.7 ug/mL after 9 days of use (p=0.005).

Similar to the increase in concentration of DHA, plasma levels of AA increased over the nine-day study with use of device 200 in the treatment group by 24.7 ug/mL (a 28% increase) when compared to the control group, which saw an increase of only 9.9 ug/mL (a 10% increase).

There were also significantly reduced fecal fat losses of critical LCPUFAs in the treatment group as compared to the control group, suggesting improved fat absorption when piglets were fed pre-hydrolyzed fats using device 200. This reduction in fecal fat loss corresponds with the improved plasma levels observed in the study. Levels of critical fatty acids (g/100 g fatty acids of % total fat) in stool are shown in Table 29, below.

TABLE 29

| | Fecal LCPUFA content | | | | | |
|---|---|---|---|---|---|---|
| Groups | PUFA | LA | AA | DHA | Omega-6 | Omega-3 |
| | | | (g/100 g FA) | | | |
| Control | 6.61 | 4.53 | 0.779 | 0.481 | 4.99 | 0.85 |
| | (3.26) | (2.98) | (0.248) | (0.199) | (3.47) | (0.34) |
| Treatment | 2.79 | 2.06 | 0.178 | 0.142 | 2.29 | 0.32 |
| | (1.71) | (1.18) | (0.172) | (0.084) | (1.27) | (0.16) |
| % Reduction | 58%↓ | 54%↓ | 77%↓ | 70%↓ | 54%↓ | 63%↓ |
| p value | 0.011 | 0.038 | 0.001 | 0.002 | 0.045 | 0.003 |

Additionally, fecal content of medium chain fatty acids (C8-C12) was also lower by 54.7% with the use of device 200 (control 15.77±7.66 vs. treatment 7.13±4.96 g/100 g FA, p=0.009), indicating efficient hydrolysis of all triglycerides from infant formula.

There was also improved uptake of LCPUFAs into selected tissues, such as enterocytes of small intestine, in the treatment group compared to the control group. Additionally, no negative impact on protein profile, glucose, triglycerides or cholesterol levels was observed in the treatment group (there was no significant difference between the treatment group and the control group, and levels were within normal range for that age in both groups).

In summary, use of device 200 with g-tube enteral feeding with premature infant formula for 9 days was safe and well tolerated. The delivery of pre-hydrolyzed fats resulted in improved body weight (in the targeted clinical range) and increased total and LCPUFA fat absorption, which was demonstrated by significantly increased plasma levels and a decrease in fecal fat content.

Exemplary Devices 200

Device Example 1

An exemplary embodiment of device 200 may include a combination of features, as described below. Device 200 may include a hollow, cylindrical interior region, which may define a chamber 222. Chamber 222 may have an interior diameter of approximately 1.56 cm, a height of approximately 1.94 cm, and a volume of approximately 3.70 mL. The outer surface of device body 210 may also be cylindrical, or may be shaped to facilitate gripping. For example, an outer cross-section of device body 210 may be polygonal, e.g., hexagonal. A length of device body 210 may be approximately 4.42 cm, and a first connector 240 and a second connector 270 may extend from a top and a bottom region of device body 210, respectively. The first and second connectors may be standard, ENFit connectors for use with enteral devices. First connector 240 may be a female connector, and second connector 270 may be a male connector, or vice versa. The female connector may have an interior diameter at an inlet region that is larger than an interior diameter of the male connector at an outlet region, so that the female connector may accommodate the male connector within it. For example, first connector 240 may have an interior diameter at an inlet region of approximately 6.3 mm, or may otherwise be sized to meet the ENFit standard. Second connector 270 may have an interior diameter at an outlet region of approximately 1.9 mm, or may be otherwise sized to meet the ENFit standard. The first and/or second connectors and device body 210 may be formed of a thermoplastic elastomer or rigid plastic, for example, a polycarbonate. In some embodiments, device body 210 may be made of a rigid plastic, such as polycarbonate, which is transparent to allow a user to view the contents of device 200, e.g., particles 300 contained within chamber 222 or formula passing through device 200 during use.

An inlet filter 250 may be located adjacent inlet 212, and an outlet filter 260 may be located adjacent outlet 230 of device 200. The filters may both be tortuous path filters formed of polyethylene. As discussed above, a tortious inlet filter 250 may promote dispersion of incoming nutritional formula more uniformly across chamber 222 or may promote disruption of fat droplets and/or emulsification of the incoming nutritional formula. The outlet filter 270 may be a tortious filter in order to effectively retain particles 300 within chamber 222. The inlet and outlet filters may be the same type of filter in order to simplify manufacturing or supply chain processes. The inlet filter diameter may be approximately 15.0 mm, and inlet filter 250 may have a thickness of approximately 3.2 mm and a pore size of approximately 100 µm. The outlet filter diameter may be approximately 17.1 mm, and inlet filter 260 may also have a thickness of approximately 3.2 mm and a pore size of approximately 100 µm. In some embodiments, the specific sizes of the outlet and inlet filters may depend in part of manufacturing considerations. For example, if press-fitting is used to incorporate the filters into device 200, then the filter inserted first during manufacturing may be smaller in diameter than the filter inserted second into device 200.

Chamber 222 of this exemplary device 200 may contain particles 300 with a mean diameter of approximately 220 µm to approximately 350 µm with a normal particle size distribution, although alternative variations of this embodiment may include particles 300 with a mean diameter of up to about 500 µm, for example, approximately 460 µm. Particles 300 may or may not include fines (much smaller particles, e.g., having diameters of less than approximately 50 um). Particles 300 may generally be spherical and may have a mass density of approximately 0.25 g/mL to approximately 0.36 g/mL and a particle moisture level of <5% when dry. Particles 300 may be porous and may have pore diameters of approximately 10 nm to approximately several hundred nm, which may be located on the surface and within the interior of individual particles 300. Particles 300 may have a mixture of smooth and textured surfaces. Particles 300 may be formed of approximately 58% ethylene glycol dimethacrylate, 41% A butyl methacrylate, and 1% glycidyl methacrylate. In alternative embodiments, particles 300 may be formed of approximately 60% ethylene glycol dimethacrylate, 39% butyl methacrylate, and 1% glycidyl methacrylate. Particles 300 may also include a functional group, e.g., approximately 1% of an epoxy group (e.g., GMA). Exemplary variations of this embodiment may contain epoxide levels (e.g., GMA) of approximately 0%, 0.25%, 2%, or 5%. Particles 300 may also include approximately 7% to 10% of PEG, although, in some variations of this embodiment, less PEG or no PEG may be included on particles 300.

Particles 300 may include *Rhizopus oryzae* lipase immobilized primarily by covalent binding. Approximately 50 mg to approximately 250 mg of *Rhizopus oryzae* lipase per gram of particle (by dry weight) may be bound to particles 300. In some embodiments, a highly purified *Rhizopus oryzae* lipase may be immobilized to particles 300 primarily by covalent binding. The highly purified *Rhizopus oryzae* may have a greater ability to hydrolyze fats as nutritional formula 110 is exposed to device 200. Approximately 5 mg to approximately 250 mg of purified *Rhizopus oryzae* lipase per gram of particle (by dry weight) may be bound to particles 300.

Approximately 90-95% of chamber 222 may be filled with particles 300, leaving a headspace of approximately 5-10% of the chamber volume. Device 200 may be filled by weight to achieve this headspace or may be filled according to volume. Depending on the particle density and size (which may vary slightly even from batch to batch of particles 300), average fill weights for this embodiment may range from approximately 0.9 to 1.1 g to approximately 1.0 to 1.2 g of particles loaded into chamber 222. This weight of particles 300 may be incorporated into chamber 222 to achieve a headspace of approximately 5-10% of chamber 222. In other embodiments, chamber 222 may be filled with only reference to fill volume, rather than fill weight.

Device 200 may be configured for use with a flow rate of from approximately 0.4 to 2.0 mL/min of nutritional formula 110 passing through device 200, and, in some embodiments, may be configured for use with a flow rate of up to approximately 10.0 mL/min. The difference in flow rate between the flow rate set on pump 120 and the flow rate achieved through device 200 may be 10% or less. Device 200 may be designed for delivery of up to approximately 500 mL of nutritional formula per feeding. Device 200 may be designed for delivery of up to approximately 1,000 mL of nutritional formula per feeding. A device 200 according to this embodiment may achieve more than 90% hydrolysis efficiency for most types of nutritional formulas.

Device Example 2

Exemplary embodiments of device 200 may also be configured to accommodate faster flow rates of nutritional formulas passing through the device, e.g., to reduce feed time, or to accommodate greater volumes of nutritional formula per feed without compromising hydrolysis efficiency. For example, chamber 222 may have an increased height compared to Device Example 1, above, to accommodate more particles 300 and/or more nutritional formula 110, and the length of the overall body 210 may be taller to accommodate a taller chamber 222. For example, some embodiments may increase the height of chamber 222 by approximately 5 cm (for a total chamber height of approximately 6.94 cm) or by approximately 2.91 cm (for a total chamber height of approximately 4.85 cm), which may permit incorporation of up to approximately an additional 3 g of particles 300 in chamber 222. In other embodiments, chamber 222 may have similar dimensions to those of Device Example 1 or may have the same dimensions.

Larger particle sizes may be used in devices 200 designed to accommodate a faster flow rate and/or larger quantity of nutritional formula 110 being passed through device 200. For example, particles 300 may have an average diameter of approximately 375 µm or more with a normal particle size distribution. Larger particles may reduce the likelihood of obstruction or clogging that may be more likely to occur when higher flow rates, more viscous nutritional formulas, or larger volumes of nutritional formulas are used. For example, some nutritional formulas may produce semi-solid particles upon hydrolysis, which may collect in device 200. If larger particles are used, then inlet and/or outlet filters with larger pore diameters, for example, approximately 100 µm to approximately 150 µm, may also be used. Otherwise, device 200 of this Device Example 2 may be similar to device 200 of Device Example 1, above.

Device 200 of this example may accommodate use with flow rates of up to approximately 10 mL/minute (600 mL/hour) or for use with volumes of up to 1,000 mL or more of nutritional formula per feed.

Device Example 3

Exemplary embodiments of device 200 may also be configured for use with pre-term babies, full-term babies, neonates, infants, and/or toddlers. For neonate or infant devices, for example, modifications may be made to device 200 in some embodiments. For example, the volume of chamber 222 may be reduced to approximately ½ to ¼ of the volume of the chamber of the device described in Device Example 1, above. Accordingly, the diameter and/or height of chamber 222 and of the overall device body may be reduced to achieve this lower volume.

As described above, delivering nutritional formula 110 pre-hydrolyzed using system 100 with device 200 may allow for direct delivery of hydrolyzed and absorbable fatty acids to the GI tract of a subject prior to ingestion. Also, device 200 may be compatible with a wide range of complex, commercially available nutritional formulas and may not affect negatively other nutrients in the nutritional formula. Further, device 200 may allow normalization of the calorie intake and fatty acid balance and absorption of the subject, which may advantageously provide a more controlled option for healthcare providers to improve their management and treatment of people with compromised pancreatic output or lipid malabsorption.

In some embodiments, a method of supplying nutritional formula 110 using device 200 may include the following steps. Step 1 may include preparing a source of nutritional formula 110. For example, step 1 may include obtaining and/or preparing nutritional formula 110 of a predetermined volume in a container, e.g., a bag, vial, syringe, or bottle. Step 2 may include fluidly connecting the source of nutritional formula 110 to device 200 by using one or more tubes and connectors, such as first tube 122 having tube connectors at its ends. Step 2 may further include connecting a first tube connector of first tube 122 to the source of nutritional formula 110 and connecting a second tube connector of first tube 122 to device 200 or first connector 240 of device 200. Step 3 may include fluidly connecting device 200 to an enteral feeding tube. For example, step 3 may include connecting device 200 or second connector 270 of device 200 to an enteral feeding tube or a connector to an enteral feeding tube. The enteral feeding tube may, for example, have one end temporarily or permanently placed in fluid connection with the GI or nasogastric tract of a subject. Step 4 may include installing pump 120 to system 100 and setting a flow rate of pump 120 for directing nutritional formula 110 through the tubes and device 200. Alternatively, pump 120 may be replace with a syringe. In the gravity feeding embodiments, step 4 may not be needed. Steps 1 to 4 may be performed in any order.

Step 5 may include directing nutritional formula 110 to device 200 using pump 120, a syringe, or by the influence of gravity. Step 5 may further include priming nutritional formula 110 into and through device 200 and the tubes, e.g., first tube 122 and enteral tube 124. Priming may be operated automatically or manually by setting or adjusting pump 120 to fill device 200 and the tubes with nutritional formula 110 before the tubes are connected to the patient. Priming system 100 may reduce the amount of air dispensed into the patient prior to feeding of nutritional formula 110. Pump 120 may operate at a faster speed during priming than during enteral feeding of nutritional formula 110. In such embodiments, device 200 may be designed to ensure that the faster pump rates that occur during priming do not damage or alter the operation of device 200. Step 5 may also include flushing, which may be performed automatically or manually. For example, in reusable embodiments, a pump may be set to a flush mode to purge a solution through the pump tubing to adequately void any residue formula, allowing the tubing to be used more than once.

Step 6 may include directing nutritional formula 110 through inlet 212, inlet filter 250, and particles 300 in chamber 222 of device 200. In some embodiments, step 6 may further include distributing nutritional formula 110 through inlet filter 250 and across particles 300 in chamber 222. Step 7 may include allowing lipase 710 on particles 300 of device 200 to be exposed to and/or to interact with the fat molecules in nutritional formula 110 by directing and/or distributing the flow of nutritional formula 110 across particles 300. Step 7 may further include allowing particles 300 to mix with nutritional formula 110 and to move with the flow dynamics of nutritional formula 110. Step 7 may also include allowing lipase 710 on particles 300 to hydrolyze the triglycerides having LC-PUFAs in nutritional formula 110. In some embodiments, steps 6 and 7 may happen at substantially the same time.

Step 8 may include directing nutritional formula 110 through outlet filter 260 and outlet 282 while retaining particles 300 in device 200. Step 9 may include directing nutritional formula 110 through the enteral feeding tube to the patient. Step 10 may include disconnecting device 200 from system 100, disposing of device 200 and/or particles 300, and/or sterilizing and drying device 200.

In alternative embodiments, multiple devices 200 may be connected to each other in series (tandem) or in parallel. When nutritional formula 110 is flowed through device 200, fats contained in nutritional formula 110 contact the surfaces of particles 300, and the fats may be hydrolyzed from triglyceride form into free fatty acids and monoglycerides via interaction with the lipase on particles 300. The extent of fat hydrolysis may be determined in part by the contact (or residence) time of the formula with particles 300 within chamber 222, as well as the cumulative number of particles 300 to which nutritional formula 110 is exposed. Increasing either the residence time or the number of particles to which nutritional formula 110 is exposed may yield greater fat hydrolysis. Therefore, in cases in which a single device 200 does not alone provide a desired hydrolysis efficiency, the tandem arrangement of two devices 200 may increase hydrolysis, for example, when used with certain nutritional formulas 110.

Connecting multiple devices 200 in series (tandem) may effectively increase the cumulative residence time and the total number of particles to which nutritional formula 110 is exposed. Arranging multiple devices 200 in tandem may, for example, be useful when hydrolyzing larger volumes of nutritional formula 110 or when hydrolyzing nutritional formula 110 at faster rates. To connect multiple devices 200 in series, second connector 270 of a first device 200 may be inserted directly into first connector 240 of a second device 200, or second connector 270 of a first device 200 may connect to tubing, which may then connect to a first connector 240 of a second device 200. The tandem devices may be connected to the source of nutritional formula, tubing, and the patient, and used in a similar manner as described in steps 1-10 above.

A preliminary test assessed the effects of connecting multiple devices 200 in series versus the use of a single device. In the preliminary test, 1,000 mL of Peptamen® was flowed through a single device 200 at a rate of 2 mL/minute, and 1,000 mL of Peptamen® was flowed through two devices 200 connected In tandem at a rate of 2 mL/minute. The mean % hydrolysis of fats in the resulting hydrolyzed nutritional formula was 92% for the single device 200 and 98% for the tandem setup. The test results indicate that the tandem configuration may achieve hydrolysis efficiencies that are as high or higher than the hydrolysis efficiencies achieved by a single device 200.

Alternatively, rather than connecting multiple devices in series, the same formula may be flowed through a single device 200 more than once to effectively increase the total residence time and particle exposure. For example, a device 200 may be connected to a first end of an 'empty' feeding circuit that is not yet attached to a patient. The second end of the 'empty' feeding circuit may be connected to a source of nutritional formula. The 'empty' circuit may then be loaded with nutritional formula 110 by drawing nutritional formula 110 up from the source and through device 200 to a reservoir, which would expose the nutritional formula to one pass through device 200. The circuit would then be disconnected from the source of nutritional formula and instead attached to a patient. The feeding would then proceed as usual, i.e., nutritional formula 110 would be flowed from the reservoir, through chamber 222 of device 200, and to the patient. This would constitute a second pass through device 200.

The impact of this double-pass method on hydrolysis was assessed in preliminary testing comparing a single-pass (regular) method of using device 200 to the double-pass method of using device 200. In the test, two devices 200 were filled with a smaller quantity of particles 300 (375 mg), and 50 mL of Similac® Special Care® 24 Cal infant formula was passed through the devices at a flow rate of 2 mL/minute. For the first device, 50 mL of the formula was passed through once (single-pass). For the second device, 50 mL of the formula was passed through twice (double-pass). To simulate a single-pass method, a syringe was loaded with formula, a device 200 was attached to the syringe, and the nutritional formula was flowed from the syringe through the device. To simulate a double-pass method, a device 200 was attached to an empty syringe. The nutritional formula was then drawn through the device to load the syringe, and then the nutritional formula was flowed out of the syringe and through the device. The percentage of hydrolyzed fats in the formula flowed through using the single-pass method and the formula flowed through using the double-pass method was then measured.

The measured % hydrolysis of the single-pass method was 37%, and the measured % hydrolysis of the double-pass method was 63% in this preliminary trial. The preliminary test data indicates that a multiple-pass method may increase the % hydrolysis of nutritional formulas. Multiple-pass methods may be used for patients generally or may be used in scenarios in which there is a limitation on the total number of particles that may be used each day by a patient, or a limitation on the total number of particles that may be used at the same time. For example, regulatory restrictions may limit the total amount of particles 300 to which a patient may be exposed in a single day. The reduction in particles 300 used per feeding may, however, lower hydrolysis efficiency of device 200. This reduction in hydrolysis efficiency may be offset, or at least partially offset, by using a multi-pass method to boost % hydrolysis by increasing residence time and/or exposures to the particles 300. Thus, multiple-pass methods may be useful during food preparation, for example, to increase % hydrolysis without introducing significant additional steps or changes to the method of using device 200, particularly for infant nutritional formula preparation in a NICU.

The many features and advantages of the present disclosure are apparent from the detailed specification, and thus, it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

We claim:

1. An enteral feeding device comprising:
   a body housing a chamber;
   one or more particles contained within the chamber, wherein lipase is bonded to the one or more particles;
   wherein the one or more particles are configured to transition from a dry configuration to a wet configuration when exposed to a nutritional formula; and
   wherein, in the dry configuration, the one or more particles have a moisture level of 0.1% to 5%, and wherein, in the wet configuration, the one or more particles swell in volume by no more than 15%.

2. The device of claim 1, wherein the one or more particles, when dry, fill at least 50% of the chamber.

3. The device of claim 1, wherein the one or more particles, when dry, fill at least 80% of the chamber.

4. The device of claim 1, wherein the one or more particles, when dry, fill at least 90% of the chamber.

5. The device of claim 1, wherein the one or more particles, when exposed to the nutritional formula, fill at least 80% of the chamber.

6. The device of claim 1, wherein the one or more particles, when exposed to the nutritional formula, fill at least 90% of the chamber.

7. The device of claim 1, wherein the device further comprises an inlet in fluid communication with the chamber for receiving the nutritional formula.

8. The device of claim 1, wherein an outside surface of at least one of the one or more particles is at least partially hydrophobic.

9. The device of claim 1, wherein at least one of the one or more particles is formed of at least one of ethylene glycol dimethacrylate, butyl methacrylate, or glycidyl methacrylate.

10. The device of claim 1, wherein at least one of the one or more particles is formed of 0% to 10% of polyethylene glycol by weight.

11. The device of claim 1, wherein at least one of the one or more particles has a porous cross-section forming internal surfaces within the at least one particle, and wherein the lipase is bonded to the internal surfaces.

12. The device of claim 11, wherein a median or a mean diameter of a pore of the porous cross-section ranges from 10 nm to 250 nm.

13. The device of claim 1, wherein at least one of an outer surface or an internal surface of at least one of the one or more particles includes a functional group.

14. The device of claim 13, wherein the functional group is an epoxy group, and the lipase is bonded to the epoxy group.

15. The device of claim 1, wherein the one or more particles comprises a first group of particles and a second group of particles, wherein the first group of particles has a median or a mean diameter that is different than a median or a mean diameter of the second group of particles.

16. The device of claim 1, wherein an amount of the lipase bonded to the one or more particles falls within a range of 50 mg to 250 mg of lipase per 1 g of the one or more particles.

17. The device of claim 1, further comprising an inlet and an inlet filter, wherein the inlet filter is coated with at least one emulsifier configured to emulsify the nutritional formula.

18. The device of claim 1, wherein the lipase bonded to the one or more particles is a phospholipase.

19. The device of claim 1, wherein the one or more particles have an average diameter of 250 μm to 800 μm.

* * * * *